(12) United States Patent
Leake et al.

(10) Patent No.: US 11,286,479 B2
(45) Date of Patent: Mar. 29, 2022

(54) CHEMICAL METHODS FOR NUCLEIC ACID-BASED DATA STORAGE

(71) Applicant: CATALOG TECHNOLOGIES, INC., Boston, MA (US)

(72) Inventors: Devin Leake, Boston, MA (US); Milena Lazova, Medford, MA (US); Sarah Flickinger, Providence, RI (US); Nathaniel Roquet, Boston, MA (US); Hyunjun Park, Boston, MA (US); Swapnil P. Bhatia, Boston, MA (US)

(73) Assignee: CATALOG TECHNOLOGIES, INC., Charlestown, MA (US)

( * ) Notice: Subject to any disclaimer, the term of this patent is extended or adjusted under 35 U.S.C. 154(b) by 0 days.

(21) Appl. No.: 17/012,909

(22) Filed: Sep. 4, 2020

(65) Prior Publication Data
US 2021/0079382 A1    Mar. 18, 2021

Related U.S. Application Data

(63) Continuation of application No. PCT/US2019/022596, filed on Mar. 15, 2019.
(Continued)

(51) Int. Cl.
*C12N 15/10* (2006.01)
*G06N 3/12* (2006.01)
*G11C 13/02* (2006.01)

(52) U.S. Cl.
CPC ......... *C12N 15/1065* (2013.01); *G06N 3/123* (2013.01); *G11C 13/02* (2013.01); *B01J 2219/00722* (2013.01)

(58) Field of Classification Search
CPC .... C12N 15/1065; G06N 3/123; G11C 13/02; B01J 2219/00722
See application file for complete search history.

(56) References Cited

U.S. PATENT DOCUMENTS 6,187,537 B1   2/2001   Zinn, Jr. et al.
6,221,653 B1   4/2001   Caren et al.
(Continued)

FOREIGN PATENT DOCUMENTS

EP   1512749 A2   3/2005
EP   2329425 A1   6/2011
(Continued)

OTHER PUBLICATIONS

Patrick, et al., DNA Assembly in 3D Printed Fluidics, PLOS One, 10(12): e014636 18 pages (2015).
(Continued)

*Primary Examiner* — Ajay Ojha
(74) *Attorney, Agent, or Firm* — White & Case LLP

(57) ABSTRACT

The present disclosure discloses methods and systems for encoding digital information in nucleic acid (e.g., deoxyribonucleic acid) molecules without base-by-base synthesis, by encoding bit-value information in the presence or absence of unique nucleic acid sequences within a pool, comprising specifying each bit location in a bit-stream with a unique nucleic sequence and specifying the bit value at that location by the presence or absence of the corresponding unique nucleic acid sequence in the pool. Also disclosed are chemical methods for generating unique nucleic acid sequences using combinatorial genomic strategies (e.g., assembly of multiple nucleic acid sequences or enzymatic-based editing of nucleic acid sequences).

28 Claims, 63 Drawing Sheets
Specification includes a Sequence Listing.

Related U.S. Application Data

(60) Provisional application No. 62/644,323, filed on Mar. 16, 2018.

(56) References Cited

U.S. PATENT DOCUMENTS

| | | | |
|---|---|---|---|
| 6,309,828 B1 | 10/2001 | Schleifer et al. | |
| 6,384,210 B1 | 5/2002 | Blanchard | |
| 6,419,883 B1 | 7/2002 | Blanchard | |
| 6,446,642 B1 | 9/2002 | Caren et al. | |
| 6,458,583 B1 | 10/2002 | Bruhn et al. | |
| 6,537,747 B1 | 3/2003 | Mills, Jr. et al. | |
| 6,796,634 B2 | 9/2004 | Caren et al. | |
| 7,176,297 B2 | 2/2007 | Li et al. | |
| 7,306,316 B2 | 12/2007 | Doak | |
| 7,491,422 B2 | 2/2009 | Zhang et al. | |
| 7,600,840 B2 | 10/2009 | Kim et al. | |
| 7,802,517 B2 | 9/2010 | Wessels et al. | |
| 7,833,701 B2 | 11/2010 | Oshima | |
| 7,909,427 B2 | 3/2011 | Kim et al. | |
| 7,951,334 B2 | 5/2011 | Mirkin et al. | |
| 8,071,168 B2 | 12/2011 | Cruchon-Dupeyrat et al. | |
| 8,114,207 B2 | 2/2012 | Josten | |
| 8,136,936 B2 | 3/2012 | Hook et al. | |
| 8,496,326 B2 | 7/2013 | Hook et al. | |
| 8,735,327 B2 | 5/2014 | Macula | |
| 8,769,689 B2 | 7/2014 | Hoglund | |
| 8,806,127 B2 | 8/2014 | Brownell et al. | |
| 8,856,940 B2 | 10/2014 | Kencl et al. | |
| 8,937,564 B2 | 1/2015 | Aloni et al. | |
| 9,061,494 B2 | 6/2015 | Rogers et al. | |
| 9,062,218 B2 | 6/2015 | Oshima et al. | |
| 9,187,777 B2 | 11/2015 | Jacobson et al. | |
| 9,266,370 B2 | 2/2016 | Jung et al. | |
| 9,317,664 B2 | 4/2016 | Ahuja et al. | |
| 9,384,320 B2 | 7/2016 | Church | |
| 9,403,180 B2 | 8/2016 | Ha et al. | |
| 9,487,002 B2 | 11/2016 | Rogers et al. | |
| 9,616,661 B2 | 4/2017 | Pierik et al. | |
| 9,679,030 B2 | 6/2017 | Hatami-Hanza | |
| 9,684,678 B2 | 6/2017 | Hatami-Hanza | |
| 9,774,351 B2 | 9/2017 | Huetter et al. | |
| 9,830,553 B2 | 11/2017 | Chen et al. | |
| 9,904,734 B2 | 2/2018 | Murrah et al. | |
| 9,928,869 B2 | 3/2018 | Church | |
| 9,996,778 B2 | 6/2018 | Church | |
| 10,020,826 B2 | 7/2018 | Gladwin et al. | |
| 10,027,347 B2 | 7/2018 | Le Scouarnec et al. | |
| 10,047,235 B2 | 8/2018 | Wilsher et al. | |
| 10,050,959 B2 | 8/2018 | Soon-Shiong et al. | |
| 10,287,573 B2 | 5/2019 | Macula | |
| 10,289,801 B2 | 5/2019 | Church | |
| 10,370,246 B1 | 8/2019 | Milenkovic et al. | |
| 10,387,301 B2 | 8/2019 | Goldman et al. | |
| 10,417,457 B2 | 9/2019 | Peck | |
| 10,423,341 B1 | 9/2019 | Kermani | |
| 10,438,662 B2 | 10/2019 | Predki | |
| 10,460,220 B2 | 10/2019 | Church | |
| 10,566,077 B1 | 2/2020 | Milenkovic et al. | |
| 10,640,822 B2 | 5/2020 | Predki et al. | |
| 10,650,312 B2 | 5/2020 | Roquet et al. | |
| 10,669,558 B2 | 6/2020 | Ganjam | |
| 10,742,233 B2 | 8/2020 | Erlich | |
| 10,754,994 B2 | 8/2020 | Peck | |
| 10,774,379 B2 | 9/2020 | Chen et al. | |
| 10,787,699 B2 | 9/2020 | Chen et al. | |
| 10,793,897 B2 | 10/2020 | Chen et al. | |
| 10,818,378 B2 | 10/2020 | Hutchison, III et al. | |
| 10,838,939 B2 | 11/2020 | Walder et al. | |
| 10,839,295 B2 | 11/2020 | Shen et al. | |
| 10,853,244 B2 | 12/2020 | Petti et al. | |
| 10,883,140 B2 | 1/2021 | Church et al. | |
| 10,902,939 B2 | 1/2021 | Merriman et al. | |
| 10,917,109 B1 | 2/2021 | Dimopoulou et al. | |
| 10,929,039 B2 | 2/2021 | Kwon et al. | |
| 10,936,953 B2 | 3/2021 | Peck et al. | |
| 10,956,806 B2 | 3/2021 | Masuda et al. | |
| 2003/0116630 A1 | 6/2003 | Carey et al. | |
| 2004/0244623 A1 | 12/2004 | Hayashizaki | |
| 2005/0019760 A1 | 1/2005 | Southern | |
| 2005/0166782 A2 | 8/2005 | Hayashizaki | |
| 2005/0243618 A1 | 11/2005 | Boland et al. | |
| 2006/0263534 A1 | 11/2006 | Laurent et al. | |
| 2008/0252679 A1 | 10/2008 | Pierik et al. | |
| 2008/0269152 A1 | 10/2008 | Verdine et al. | |
| 2008/0303870 A1 | 12/2008 | Verbeek et al. | |
| 2008/0309701 A1 | 12/2008 | Pierik et al. | |
| 2009/0023607 A1 | 1/2009 | Rozhok et al. | |
| 2009/0033690 A1 | 2/2009 | Pierik et al. | |
| 2009/0062129 A1* | 3/2009 | McKernan | C12Q 1/6874 506/3 |
| 2009/0253141 A1 | 10/2009 | Quake | |
| 2010/0029490 A1 | 2/2010 | Pierik et al. | |
| 2010/0056381 A1 | 3/2010 | Kurt et al. | |
| 2011/0195850 A1 | 8/2011 | Rozhok et al. | |
| 2011/0312779 A1 | 12/2011 | Silverbrook et al. | |
| 2011/0312782 A1 | 12/2011 | Azimi et al. | |
| 2011/0312847 A1 | 12/2011 | Silverbrook et al. | |
| 2011/0312851 A1 | 12/2011 | Silverbrook et al. | |
| 2011/0312853 A1 | 12/2011 | Azimi et al. | |
| 2011/0312855 A1 | 12/2011 | Silverbrook et al. | |
| 2011/0312856 A1 | 12/2011 | Silverbrook et al. | |
| 2012/0164396 A1 | 6/2012 | Mirkin et al. | |
| 2012/0329561 A1 | 12/2012 | Evans et al. | |
| 2013/0231254 A1 | 9/2013 | Kawashima et al. | |
| 2013/0233709 A1 | 9/2013 | Dunbar et al. | |
| 2014/0065609 A1 | 3/2014 | Hicks et al. | |
| 2014/0296087 A1 | 10/2014 | Verdine et al. | |
| 2014/0371100 A1 | 12/2014 | Kawashima et al. | |
| 2015/0083797 A1 | 3/2015 | Tran et al. | |
| 2015/0261664 A1 | 9/2015 | Goldman et al. | |
| 2015/0269313 A1 | 9/2015 | Church | |
| 2015/0312212 A1 | 10/2015 | Holmes et al. | |
| 2015/0363550 A1 | 12/2015 | Green, Jr. et al. | |
| 2016/0007893 A1 | 1/2016 | Roberts | |
| 2016/0051985 A1 | 2/2016 | Knight et al. | |
| 2016/0168579 A1 | 6/2016 | Hutchison et al. | |
| 2016/0258939 A1 | 9/2016 | Morin et al. | |
| 2016/0304948 A1* | 10/2016 | Lee | C12Q 1/6844 |
| 2016/0371434 A1 | 12/2016 | Strauss et al. | |
| 2017/0017436 A1 | 1/2017 | Church | |
| 2017/0021611 A1 | 1/2017 | Jung et al. | |
| 2017/0081716 A1 | 3/2017 | Peck | |
| 2017/0093851 A1 | 3/2017 | Allen | |
| 2017/0136452 A1 | 5/2017 | Niles et al. | |
| 2017/0140095 A1 | 5/2017 | Kim | |
| 2017/0218228 A1 | 8/2017 | Jose et al. | |
| 2017/0363953 A1 | 12/2017 | Steinhart et al. | |
| 2018/0068060 A1 | 3/2018 | Ceze et al. | |
| 2018/0086781 A1 | 3/2018 | Liss | |
| 2018/0101487 A1 | 4/2018 | Peck | |
| 2018/0121478 A1 | 5/2018 | Walder et al. | |
| 2018/0137418 A1 | 5/2018 | Roquet et al. | |
| 2018/0173710 A1 | 6/2018 | Maftuleac et al. | |
| 2018/0173738 A1 | 6/2018 | Lopez-Ortiz et al. | |
| 2018/0253563 A1 | 9/2018 | Peck et al. | |
| 2019/0020651 A1 | 1/2019 | Soon-Shiong et al. | |
| 2019/0136307 A1 | 5/2019 | Predki et al. | |
| 2019/0142882 A1* | 5/2019 | Shepherd | C12N 15/65 536/23.1 |
| 2019/0271032 A1 | 9/2019 | Owen | |
| 2019/0344239 A1 | 11/2019 | Efcavitch et al. | |
| 2019/0351673 A1 | 11/2019 | Roquet et al. | |
| 2019/0355442 A1 | 11/2019 | Merriman | |
| 2020/0185057 A1 | 6/2020 | Leake et al. | |
| 2020/0193301 A1 | 6/2020 | Roquet et al. | |
| 2021/0010065 A1* | 1/2021 | Salk | C12N 9/1276 |

FOREIGN PATENT DOCUMENTS

| | | |
|---|---|---|
| EP | 2856375 A2 | 4/2015 |
| EP | 3346404 A1 | 7/2018 |
| JP | 2009244996 | 10/2009 |
| WO | WO-03025123 A2 | 3/2003 |
| WO | WO-2004009844 | 1/2004 |

(56) References Cited

FOREIGN PATENT DOCUMENTS

| WO | WO-2012058638 A2 | 5/2012 |
| --- | --- | --- |
| WO | WO-2014014991 A2 | 1/2014 |
| WO | WO-2015144858 A1 | 10/2015 |
| WO | WO-2016015701 A1 | 2/2016 |
| WO | WO-2016059610 A1 | 4/2016 |
| WO | WO-2016081834 A2 | 5/2016 |
| WO | WO-2016164779 A1 | 10/2016 |
| WO | WO-2016182814 A2 | 11/2016 |
| WO | WO-2017151195 A1 | 9/2017 |
| WO | WO-2017189914 A1 | 11/2017 |
| WO | WO-2017190297 A1 | 11/2017 |
| WO | WO-2017192633 A1 | 11/2017 |
| WO | WO-2018017131 A1 | 1/2018 |
| WO | WO-2018049272 A1 | 3/2018 |
| WO | WO-2018094108 A1 | 5/2018 |
| WO | WO-2018132457 A1 | 7/2018 |
| WO | WO-2018148260 A1 | 8/2018 |
| WO | WO-2018148458 A1 | 8/2018 |
| WO | WO-2018213856 A2 | 11/2018 |
| WO | WO-2019046768 A1 | 3/2019 |
| WO | WO-2019081145 A1 | 5/2019 |
| WO | WO-2019178551 A1 | 9/2019 |
| WO | WO-2020028912 A2 | 2/2020 |
| WO | WO-2020128517 A1 | 6/2020 |

OTHER PUBLICATIONS

De Silva, et al., "New Trends of Digital Data Storage in DNA", BioMed Research International, vol. 2016, Article ID 8072463, 14 pages (Sep. 5, 2016) ps. 14.

Extended European Search Report for EP Application No. 17872172.6 dated Oct. 27, 2020.

Bonnet et al., "Rewritable digital data storage in live cells via engineered control of recombination directionality," Proceeding of the National Academy of Sciences, vol. 109(23): 8884-8889 (2012).

Bornholt et al., "A DNA-Based Archival Storage System," International Conference on Architectural Support for Programming Languages and Operating Systems (ASPLOS), Apr. 2-6, 2016, Atlanta, GA, 637-649.

Buschmann, et al., "Levenshtein Error-Correcting Barcodes for Multiplexed DNA Sequencing", BMC Bioinformatics, vol. 14, No. 1., pp. 1-10 (2013).

Bystrykh, et al., "Generalized DNA Barcode Design Based on Hamming Codes", PLOS One, vol. 7, No. 5, pp. 1-8, (May 2012).

Casini, A. "Advanced DNA assembly strategies and standards for synthetic biology," Thesis, Department of Life Sciences, Imperial College London: 1-178 (2014).

Clarke, et al., "Continuous base identification for single-molecule nanopore DNA sequencing", Nature Nanotechnology, vol. 4, No. 4, pp. 265-270, Feb. 22, 2009.

Deorowicz et al., "Data compression for sequencing data," Algorithms for Molecular Biology, vol. 8(25): 1-13 (2013).

Engler et al., "A One Pot, One Step, Precision Cloning Method with High Throughput Capability," PLoS One, vol. 3(11): E3647 (2008) printed as pp. 1-7.

Engler et al., "Chapter 12: Combinatorial DNA Assembly Using Golden Gate Cloning," Karen M. Polizzi and Cleo Kontoravadi (eds.), Synthetic Biology, Methods in Molecular Biology, vol. 1073, Springer Science+Business Media, New York: 141-156 (2013).

Fogg et al., "New Applications for Phage Integrases," Journal of Molecular Biology, vol. 426(15): 2703-2716 (2014).

Goldman et al., "Towards practical, high-capacity, low-maintenance information storage in synthesized DNA," Nature, vol. 494: 77-80 (2013).

Kivioja et al., "Counting absolute numbers of molecules using unique molecular identifiers," Nature Methods, vol. 9(1): 72-74 (2011), including pp. 1-2 of Online Methods, and pp. 1-14 of Supplementary Information.

Lee, et al, "Enzymatic DNA synthesis for digital information storage", bioRxiv, XP055603868, DOI: 10.1101/348987 Retrieved from the Internet: URL:https://www.biorxiv.org/content/biorxiv/early/2018/06/16/348987.full.pdf [retrieved on Nov. 20, 2019] abstract, pp. 5, 8ff (Jun. 16, 2018).

Leier et al., "Cryptography with DNA binary strands," Biosystems, vol. 57: 13-22 (2000).

Navarro, et al., "Compressed Full-Text Indexes", ACM Computing Surveys, ACM, New York, NY, vol. 39, No. 1 Apr. 12, 2007.

Organick, et al., "Random access in large-scale DNA data storage", Nature Biotechnology, vol. 36, No. 3, pp. 242-248, (Mar. 1, 2018).

PCT/US2017/062098 International Search Report and Written Opinion, dated Mar. 14, 2018.

PCT/US2017/062106 International Search Report and Written Opinion, dated Feb. 22, 2018.

PCT/US2019/022596 International Search Report and Written Opinion, dated Jun. 28, 2019.

PCT/US2019/032756 International Search Report and Written Opinion, dated Sep. 4, 2019.

PCT/US2020/032384 International Search Report and Written Opinion, dated Jul. 30, 2020.

Quetier et al., "The CRISPR-Cas9 technology: Closer to the ultimate toolkit for targeted genome editing," Plant Science, vol. 242: 65-76 (2015).

Roquet et al., "Synthetic recombinase-based state machines in living cells," Science, vol. 353(6297): 363, aad8559-1-aad8559-13 (2016).

Sands, B. and Brent, R., "Overview of Post Cohen-Boyer Methods for Single Segment Cloning and for Multisegment DNA Assembly," Current Protocols in Molecular Biology, vol. 113: 3.26.1-3.26-20 (2016).

Sorek et al., "CRISPR-Mediated Adaptive Immune Systems in Bacteria and Archaea," Annual Review of Biochemistry, vol. 82: 237-266 (2013).

Sun et al., "Recent advances in targeted genome engineering in mammalian systems," Biotechnology Journal, vol. 7: 1074-1087 (2012).

Tulpan, et al., "HyDEn: A Hybrid Steganocryptographic Approach for Data Encryption Using Randomized Error Correcting DNA Codes,", Biomed Research International, vol. 32, No. 4839, pp. 1-11, (2013).

Yang et al., "Permanent genetic memory with >1-byte capacity," Nature Methods, vol. 11(12): 1261-1266 (2014) including pp. 1-3 of Online Methods, and pp. 1-30 of Supplementary Figures and Text.

Yazdi et al., "A Rewritable, Random-Access DNA-Based Storage System," Scientific Reports, vol. 5(14138): 1-10 (2015), including pp. 1-19 of Supplementary Information.

Yazdi et al., "DNA-based storage: Trends and Methods," IEEE Transactions on Molecular, Biological, and Multi-Scale Communications, vol. 1(3): 230-248 (2015).

Yazdi, et al., "Portable and Error-Free DNA-Based Data Storage", bioRxiv preprint doi: https://doi.org/10.1101/079442 (2016).

Yim et al., "The essential component in DNA-based information storage system: robust error-tolerating module," Frontiers in Bioengineering and Biotechnology, vol. 2, Article 49: 1-5 (2014).

Zhu et al., "High-throughput DNA sequence data compression," Briefings in Bioinformatics, 16(1): 1-15 (2015).

PCT/US2020/055351 International Search Report and Written Opinion dated Mar. 31, 2021.

Now U.S. Pat. No. 10,650,312 (U.S. Appl. No. 15/850,112), filed Dec. 21, 2017.

Pending U.S. Appl. No. 16/847,064, filed Apr. 13, 2020.

Pending U.S. Appl. No. 17/007,946, filed Aug. 31, 2020.

Pending U.S. Appl. No. 16/461,774, filed May 16, 2019.

Pending U.S. Appl. No. 16/414,758, filed May 16, 2019.

Pending U.S. Appl. No. 17/206,803, filed Mar. 19, 2021.

Pending U.S. Appl. No. 16/532,077, filed Aug. 5, 2019.

Pending U.S. Appl. No. 17/206,886, filed Mar. 19, 2021.

Pending U.S. Appl. No. 16/872,129, filed May 11, 2020.

Pending U.S. Appl. No. 17/069,420, filed Oct. 13, 2020.

Pending U.S. Appl. No. 17/317,547, filed May 11, 2021.

(56) References Cited

OTHER PUBLICATIONS

Craig et al., "Ordering of cosmid clones covering the Herpes simplex virus type 1 (HSV-1) genome: a test case for fingerprinting by hybridisation," Nucleic Acids Research, vol. 18(9): 2653-2660 (1990).
Lee et al., DNA detection using commercial mobile phones, Biosensors and Bioelectronics, 2011, 26, 4349-4354 (Year: 2011).
PCT/US2019/045160 International Search Report and Written Opinion dated, Jan. 30, 2020.
Craig, et al., "Ordering of Cosmid Clones covering the Herpes Simplex Virus Type 1 (HSV-1) genome: a test case for fingerprinting by hybridisation", Nucleic Acids Research, vol. 18, pp. 2653-2660(1990).

* cited by examiner $C_{xy}$ is the $y_{th}$ component in layer x. For a starting library with M layers, each with N components, the identifiers would have the following architecture:

where a, b, c represent elements in the set {1,2, .., N}

$C_{xy}$ is the yth component in layer x. For a starting library with M layers, each with N components, the identifiers would have the following architecture:

where b, e, h are elements in the set {1, 2, ..., N}, and a, d, f are unique elements in the set {1, 2, ..., M}.

The combinatorial space of possible identifiers is $N^M M!$

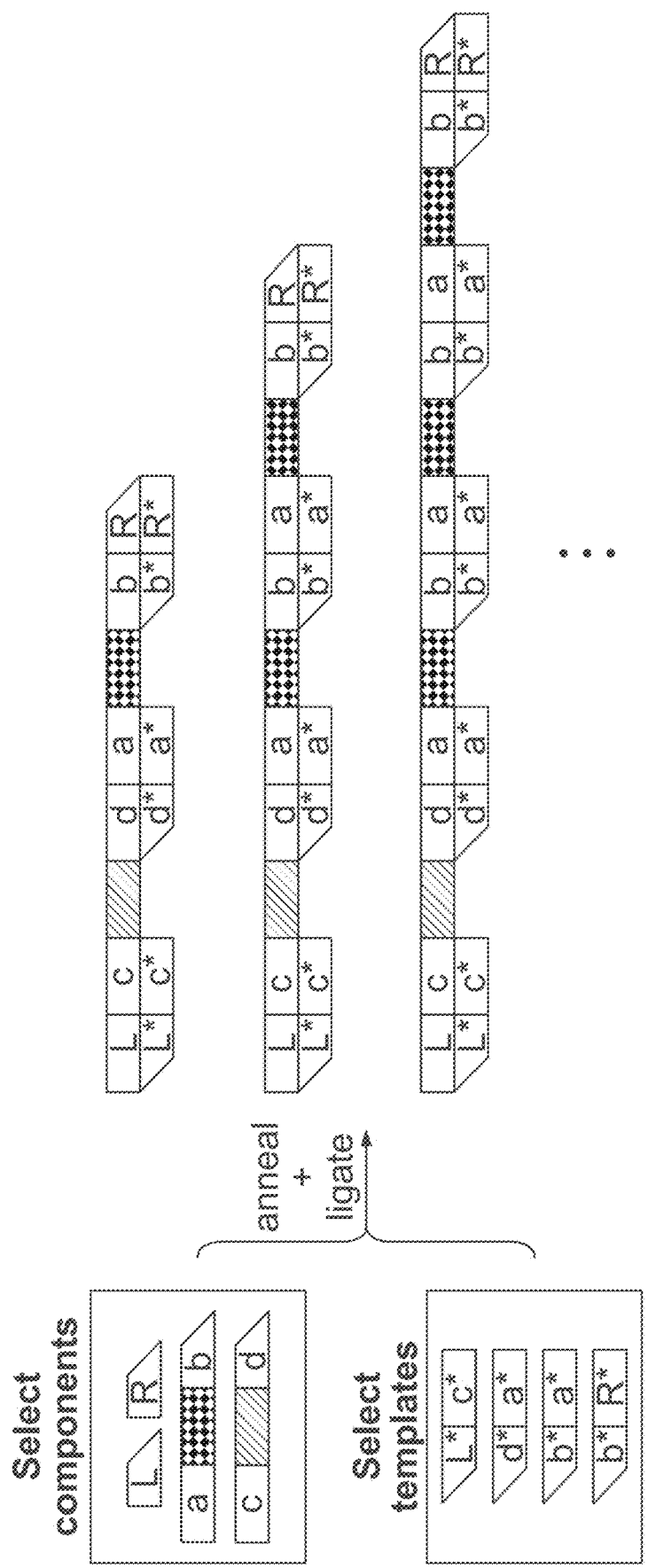

$C_{xy}$ is the yth component in layer x. For a starting library with M layers, each with N components, Identifiers assemble a fixed number of components, k, and have the following architecture:

where b, e, h are elements in the set {1, 2, ..., N}, and a, d, f among k unique, rank-ordered elements in the set {1, 2, ..., M}.

The combinatorial space of possible identifiers is $N^K$ Mchoosek

SEQUENCE LISTING

```
<160> NUMBER OF SEQ ID NOS: 3

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tagtataaga                                                             10
```

```
<210> SEQ ID NO 2
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gagagaggtc                                                              10

<210> SEQ ID NO 3
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
cgccacccac                                                              10
```

CHEMICAL METHODS FOR NUCLEIC ACID-BASED DATA STORAGE

CROSS-REFERENCE

This application is a continuation of International Patent Application No. PCT/US2019/022596 filed Mar. 15, 2019, which claims priority to U.S. Provisional Patent Application No. 62/644,323, filed Mar. 16, 2018, each of which is entirely incorporated herein by reference.

SEQUENCE LISTING

The instant application contains a Sequence Listing, which has been submitted via EFS Web and is hereby incorporated by reference in its entirety. Said ASCII copy, created on Nov. 25, 2020 is named 1885610-0002-004-301.Seq.txt and is 1,046 bytes in size.

BACKGROUND

Nucleic acid digital data storage is a stable approach for encoding and storing information for long periods of time, with data stored at higher densities than magnetic tape or hard drive storage systems. Additionally, digital data stored in nucleic acid molecules that are stored in cold and dry conditions can be retrieved as long as 60,000 years later or longer.

To access digital data stored in nucleic acid molecules, the nucleic acid molecules may be sequenced. As such, nucleic acid digital data storage may be an ideal method for storing data that is not frequently accessed but may have a high volume of information to be stored or archived for long periods of time.

Current methods rely on encoding the digital information (e.g., binary code) into base-by-base nucleic acids sequences, such that the base to base relationship in the sequence directly translates into the digital information (e.g., binary code). Sequencing of digital data stored in base-by-base sequences that can be read into bit-streams or bytes of digitally encoded information can be error prone and costly to encode since the cost of de novo base-by-base nucleic acid synthesis can be expensive. Opportunities for new methods of performing nucleic acid digital data storage may provide approaches for encoding and retrieving data that are less costly and easier to commercially implement.

SUMMARY

Methods and systems for encoding digital information in nucleic acid (e.g., deoxyribonucleic acid, DNA) molecules without base-by-base synthesis, by encoding bit-value information in the presence or absence of unique nucleic acid sequences within a pool, comprising specifying each bit location in a bit-stream with a unique nucleic sequence and specifying the bit value at that location by the presence or absence of the corresponding unique nucleic acid sequence in the pool. But, more generally, specifying unique bytes in a byte stream by unique subsets of nucleic acid sequences. Also disclosed are methods for generating unique nucleic acid sequences without base-to-base synthesis using combinatorial genomic strategies (e.g., assembly of multiple nucleic acid sequences or enzymatic-based editing of nucleic acid sequences).

In an aspect, the present disclosure provides a method for writing information into a nucleic acid sequence, comprising: (a) generating a string of symbols to represent the information; (b) constructing a plurality of components, wherein each individual component of the plurality of components comprises a nucleic acid sequence; (c) generating at least one sticky end of the individual component of the plurality of components; (d) chemically linking together two or more components of the plurality of components via the at least one sticky end of the individual component of the two or more components, thereby generating a plurality of identifiers, wherein each identifier of the plurality of identifiers comprises two or more components, wherein an individual identifier of the plurality of identifiers corresponds to an individual symbol in the string of symbols; and (e) selectively capturing or amplifying an identifier library comprising at least a subset of the plurality of identifiers.

In some embodiments, each symbol of the string of symbols is one of one or more possible symbol values. In some embodiments, each symbol in the string of symbols is one of two possible symbol values. In some embodiments, one symbol value at each position of the string of symbols may be represented by the absence of a distinct identifier in the identifier library. In some embodiments, the two possible symbol values are a bit-value of 0 and 1, wherein the individual symbol with the bit-value of 0 in the string of symbols may be represented by an absence of a distinct identifier in the identifier library, wherein the individual symbol with the bit-value of 1 in the string of symbols may be represented by a presence of the distinct identifier in the identifier library, or vice versa. In some embodiments, (d) comprises chemically linking the two or more components from two or more layers and wherein each layer of the two or more layers comprises a distinct set of components. In some embodiments, the individual identifier from the identifier library comprises one component from each layer of the two or more layers. In some embodiments, the two or more components are assembled in a fixed order. In some embodiments, the two or more components are assembled in any order. In some embodiments, the two or more components are assembled with one or more partitioning components disposed between two components from different layers of the two or more layers. In some embodiments, the individual identifier comprises one component from each layer of a subset of the two or more layers. In some embodiments, the individual identifier comprises at least one component from each of the two or more layers. In some embodiments, (c) comprises using an endonuclease to generate the at least one sticky end of the individual component of the plurality of components. In some embodiments, the at least one sticky end is at a 5' end of the individual component. In some embodiments, the at least one sticky end is at a 3' end of the individual component. In some embodiments, (c) comprises generating two sticky ends of the individual component. In some embodiments, the at least one sticky end is at least one nucleotide in length. In some embodiments, the at least one sticky end is six nucleotides in length. In some embodiments, the at least one sticky end comprises a nucleic acid sequence that is selected from the group consisting of sequences listed in Table 4 or Table 5. In some embodiments, the plurality of nucleic acid sequences stores metadata of the information or conceals the information. In some embodiments, two or more identifier libraries are combined and wherein each identifier library of the two or more identifier libraries is tagged with a distinct barcode. In some embodiments, each individual identifier in the identifier library comprises a distinct barcode or a subset identifiers of the identifier library comprises a distinct barcode. In some embodiments, the plurality of identifiers, or the plurality of components that comprise the identifiers, is selected for ease of read, write, access, copy, and deletion operations. In some embodiments, chemically linking comprises ligating together two or more components of the plurality of components using a reagent comprising a ligase. In some embodiments, the ligase is a T4 ligase, a T7 ligase, a T3 ligase, or an *E. coli* ligase. In some embodiments, the reagent further comprises an additive. In some embodiments, the additive increases efficiency of the ligase. In some embodiments, the additive comprises polyethylene glycol (PEG). In some embodiments, the PEG is PEG400, PEG6000, PEG8000 or any combination thereof. In some embodiments, a final concentration of the PEG molecules is at least about 1% weight per volume (w/v). In some embodiments, a reaction time of the ligating is at least one minute. In some embodiments, the ligating is at 30 degrees Celsius or higher. In some embodiments, a reaction efficiency of the ligating is at least about 20%. In some embodiments, the method further comprises inactivating the ligase using a buffer containing EDTA or guanidine thiocyanate. In some embodiments, final concentration of the ligase is at least about 5 CEU/μL. In some embodiments, the reagent further comprises glycerol molecules. In some embodiments, chemically linking in (d) comprises using overlap-extension polymerase chain reaction (PCR). In some embodiments, the individual component is a deoxyribonucleic acid (DNA) or a ribonucleic acid. In some embodiments, the individual component has been rehydrated. In some embodiments, the individual component is rehydrated from a dehydrated component. In some embodiments, the method further comprises dehydrating the identifier library by dehydrating each individual identifier of at least the subset of the plurality of identifiers. In some embodiments, each individual identifier of at least the subset of the plurality of identifiers is dehydrated. In some embodiments, the method further comprises rehydrating each individual identifier of at least the subset of the plurality of identifiers. In some embodiments, the method further comprises adding a preserving additive to the identifier library to prevent identifier degradation. In some embodiments, the plurality of identifiers is copied with PCR. In some embodiments, the PCR has at least 10 cycles. In some embodiments, the plurality of identifiers is amplified with PCR up to a concentration 10 nanograms per microliter. In some embodiments, the PCR is an emulsion PCR. In some embodiments, the plurality of identifiers is copied with linear amplification. In some embodiments, after the PCR, linear amplification is used to create more copies of the plurality of identifiers. In some embodiments, a subset of the plurality of identifiers is accessed with one or more PCR reactions. In some embodiments, a subset of the plurality of identifiers is accessed with one or more affinity tagged probes. In some embodiments, identifiers of the subset of the plurality of identifiers have a set of components in common. In some embodiments, the identifiers are purified by gel electrophoresis. In some embodiments, the identifiers are purified by affinity tagged probes. In some embodiments, the identifiers are amplified using PCR. In some embodiments, the identifiers are designed to avoid thymine-thymine dinucleotides or cytosine-cytosine dinucleotides.

In another aspect, the present disclosure provides a method for writing information into a nucleic acid sequence, comprising: generating a string of symbols to represent the information; constructing a plurality of components, wherein each individual component of the plurality of components comprises a nucleic acid sequence; generating at least one sticky end of the individual component of the plurality of components, wherein the at least one sticky end is at least six nucleotides in length; chemically linking together two or more components of the plurality of components via the at least one sticky end of the individual component of the two or more components, thereby generating a plurality of identifiers, wherein each identifier of the plurality of identifiers comprises two or more components, wherein an individual identifier of the plurality of identifiers corresponds to an individual symbol in the string of symbols; and selectively capturing or amplifying an identifier library comprising at least a subset of the plurality of identifiers.

In some embodiments, the at least one sticky end is at a 3' end of the individual component. In some embodiments, the linking comprises linking at least 15 or more components of the plurality of components. In some embodiments, the at least one sticky end comprises a nucleic acid sequence that is selected from the group consisting of sequences listed in Table 4 or Table 5.

In another aspect, provided herein is a method for writing information into a nucleic acid sequence, comprising: (a) generating a string of symbols to represent the information; (b) constructing a plurality of sticky-end components, wherein each individual component of the plurality of components comprises a nucleic acid sequence and at least one sticky end; (c) chemically linking together two or more components of the plurality of components via the at least one sticky end of the individual component of the two or more components, thereby generating a plurality of identifiers, wherein each identifier of the plurality of identifiers comprises two or more components, wherein an individual identifier of the plurality of identifiers corresponds to an individual symbol in the string of symbols; and (d) selectively capturing or amplifying an identifier library comprising at least a subset of the plurality of identifiers. In some embodiments, (b) comprises annealing two oligonucleotides to construct each individual component such that each individual component has the at least one sticky end.

In an aspect, the present disclosure provides a method for writing information into nucleic acid sequence(s), comprising: (a) translating the information into a string of symbols; (b) mapping the string of symbols to a plurality of identifiers, wherein an individual identifier of the plurality of identifiers comprises one or more components, wherein an individual component of the one or more components comprises a nucleic acid sequence, and wherein the individual identifier of the plurality of identifiers corresponds to an individual symbol of the string of symbols; and (c) constructing an identifier library comprising at least a subset of the plurality of identifiers.

In some embodiments, each symbol in said string of symbols is one of two possible symbol values. In some embodiments, one symbol value at each position of said string of symbols may be represented by the absence of a distinct identifier in the identifier library. In some embodiments, said two possible symbol values are a bit-value of 0 and 1, wherein said individual symbol with said bit-value of 0 in said string of symbols may be represented by an absence of a distinct identifier in said identifier library, wherein said individual symbol with said bit-value of 1 in said string of symbols may be represented by a presence of said distinct identifier in said identifier library, and vice versa. In some embodiments, each symbol of the string of symbols is one of one or more possible symbol values. In some embodiments, a presence of an individual identifier in the identifier library corresponds to a first symbol value in a binary string and an absence of the individual identifier corresponds to a second symbol value in a binary string. In some embodiments, the first symbol value is a bit value of 1 and the second symbol value is a bit value of 0. In some embodiments, the first symbol value is a bit value of 0 and the second symbol value is a bit value of 1.

In some embodiments, constructing the individual identifier in the identifier library comprises assembling the one or more components from one or more layers and wherein each layer of the one or more layers comprises a distinct set of components. In some embodiments, the individual identifier from the identifier library comprises one component from each layer of the one or more layers. In some embodiments, the one or more components are assembled in a fixed order. In some embodiments, the one or more components are assembled in a random order. In some embodiments, the one or more components are assembled with one or more partitioning components disposed between two components from different layers of the one or more layers. In some embodiments, the individual identifier comprises one component from each layer of a subset of the one or more layers. In some embodiments, the individual identifier comprises at least one component from each of the one or more layers. In some embodiments, the one or more components are assembled using overlap-extension polymerase chain reaction (PCR), polymerase cycling assembly, sticky end ligation, biobricks assembly, golden gate assembly, gibson assembly, recombinase assembly, ligase cycling reaction, or template directed ligation.

In some embodiments, constructing the individual identifier in the identifier library comprises deleting, replacing, or inserting at least one component in a parent identifier by applying nucleic acid editing enzymes to the parent identifier. In some embodiments, the parent identifier comprises a plurality of components flanked by nuclease-specific target sites, recombinase recognition sites, or distinct spacer sequences. In some embodiments, the nucleic acid editing enzymes are selected from the group consisting of CRISPR-Cas, TALENs, Zinc Finger Nucleases, Recombinases, and functional variants thereof.

In some embodiments, the identifier library comprises a plurality of nucleic acid sequences. In some embodiments, the plurality of nucleic acid sequences stores metadata of the information and/or conceals the information. In some embodiments, the metadata comprises secondary information corresponding to a source of the information, an intended recipient of the information, an original format of the information, instrumentation and methods used to encode the information, a date and a time of writing the information into the identifier library, modifications made to the information, and/or a reference to other information.

In some embodiments, one or more identifier libraries are combined and wherein each identifier library of the one or more identifier libraries is tagged with a distinct barcode. In some embodiments, each individual identifier in the identifier library comprises the distinct barcode. In some embodiments, the plurality of identifiers is selected for ease of read, write, access, copy, and deletion operations. In some embodiments, the plurality of identifiers is selected to minimize write errors, mutations, degradation, and read errors.

In another aspect, the present disclosure provides a method for copying information encoded in nucleic acid sequence(s), comprising: (a) providing an identifier library encoding a string of symbols, wherein the identifier library comprises a plurality of identifiers, wherein an individual identifier of the plurality of identifiers comprises one or more components, wherein an individual component of the one or more components comprises a nucleic acid sequence, and wherein the individual identifier of the plurality of identifiers corresponds to an individual symbol of the string of symbols; and (b) constructing one or more copies of the identifier library.

In some embodiments, the plurality of identifiers comprises one or more primer binding sites. In some embodiments, the identifier library is copied using nucleic acid amplification such polymerase chain reaction (PCR) (See Chemical Methods Section D). In some embodiments, the PCR is conventional PCR or linear PCR and wherein a number of copies of the identifier library double or increase linearly, respectively, with each PCR cycle. In some embodiments, the individual identifier in the identifier library is ligated into a circular vector prior to PCR and wherein the circle vector comprises correlated barcodes at each end of the individual identifier, such that if any unintended DNA cross-over events occur during the PCR, the resulting misformed molecules will be detectable in sequencing. In some embodiments, the PCR is isothermal. In some embodiments, the PCR is a form of rolling circle amplification. In some embodiments, the PCR is emulsion PCR (ePCR).

In some embodiments, the identifier library comprises a plurality of nucleic acid sequences. In some embodiments, the plurality of nucleic acid sequences is copied. In some embodiments, one or more identifier libraries are combined prior to copying and wherein each library of the one or more identifier libraries comprises a distinct barcode.

In another aspect, the present disclosure provides a method for accessing information encoded in nucleic acid sequence(s), comprising: (a) providing an identifier library encoding a string of symbols, wherein the identifier library comprises a plurality of identifiers, wherein an individual identifier of the plurality of identifiers comprises one or more components, wherein an individual component of the one or more components comprises a nucleic acid sequence, and wherein the individual identifier of the plurality of identifiers corresponds to an individual symbol of the string of symbols; and (b) extracting a targeted subset of the plurality of identifiers from the identifier library.

In some embodiments, a plurality of probes is combined with the identifier library. In some embodiments, the plurality of probes share complementarity with the targeted subset of the plurality of identifiers from the identifier library. In some embodiments, the plurality of probes hybridizes the targeted subset of the plurality of identifiers in the identifier library. In some embodiments, the plurality of probes comprises one or more affinity tags and wherein the one or more affinity tags is captured by an affinity bead or an affinity column, in a process that may be referred to as nucleic acid capture (see Chemical Methods Section F on nucleic acid capture).

In some embodiments, the identifier library is sequentially combined with one or more subsets of the plurality of probes and wherein a portion of the identifier library binds to the one or more subsets of the plurality of probes. In some embodiments, the portion of the identifier library that binds to the one or more subsets of the plurality of probes is removed prior to the addition of another subset of the plurality of probes to the identifier library. In these embodiments of nucleic acid capture, the captured nucleic acids may be removed from the identifier pool instead of preserved.

In some embodiments, the individual identifier of the plurality of identifiers comprises one or more common primer binding regions, one or more variable primer binding regions, or any combination thereof. In some embodiments, the identifier library is combined with primers that bind to the one or more common primer binding regions or to the one or more variable primer binding regions. In some embodiments, the primers that bind to the one or more variable primer binding regions are used to selectively amplify the targeted subset of the identifier library (see Chemical Methods Section D).

In some embodiments, a portion of identifiers is removed from the identifier library by selective nuclease cleavage. In some embodiments, the identifier library is combined with Cas9 and guide probes and wherein the guide probes guide the Cas9 to remove specified identifiers from the identifier library. In some embodiments, the individual identifiers are single-stranded and wherein the identifier library is combined with a single-strand specific endonuclease(s). In some embodiments, the identifier library is mixed with a complementary set of individual identifiers that protect target individual identifiers from degradation prior to the addition of the single-strand specific endonuclease(s). In some embodiments, the individual identifiers that are not cleaved by the selective nuclease cleavage are separated by size-selective chromatography (see Chemical Methods Section E on nucleic acid size selection). In some embodiments, the individual identifiers that are not cleaved by the selective nuclease cleavage are amplified and wherein the individual identifiers that are cleaved by the selective nuclease cleavage are not amplified (see Chemical Methods Section D on nucleic acid amplification). In some embodiments, the individual identifiers that are not cleaved by the selective nuclease cleavage are captured and wherein the individual identifiers that are cleaved by the selective nuclease cleavage are not captured (see Chemical Methods Section F on nucleic acid capture). In some embodiments, the identifier library comprises a plurality of nucleic acid sequences and wherein the plurality of nucleic acid sequences are extracted with the targeted subset of the plurality of identifiers in the identifier library.

In another aspect, the present disclosure provides a method for reading information encoded in nucleic acid sequence(s), comprising: (a) providing an identifier library comprising a plurality of identifiers, wherein an individual identifier of the plurality of identifiers comprises one or more components, wherein an individual component of the one or more components comprises a nucleic acid sequence; (b) identifying the plurality of identifiers in the identifier library; (c) generating a plurality of symbols from the plurality of identifiers identified in (b), wherein an individual symbol of the plurality of symbols corresponds to the individual identifier of the plurality of identifiers; and (d) compiling the information from the plurality of symbols.

In some embodiments, each symbol in said string of symbols is one of two possible symbol values. In some embodiments, one symbol value at each position of said string of symbols may be represented by the absence of a distinct identifier in the identifier library. In some embodiments, said two possible symbol values are a bit-value of 0 and 1, wherein said individual symbol with said bit-value of 0 in said string of symbols may be represented by an absence of a distinct identifier in said identifier library, wherein said individual symbol with said bit-value of 1 in said string of symbols may be represented by a presence of said distinct identifier in said identifier library, and vice versa. In some embodiments, a presence of an individual identifier in the identifier library corresponds to a first symbol value in a binary string and an absence of the individual identifier in the identifier library corresponds to a second symbol value in a binary string. In some embodiments, the first symbol value is a bit value of 1 and the second symbol value is a bit value of 0. In some embodiments, the first symbol value is a bit value of 0 and the second symbol value is a bit value of 1.

In some embodiments, identifying the plurality of identifiers comprises sequencing the plurality of identifiers in the identifier library. In some embodiments, sequencing comprises digital polymerase chain reaction (PCR), quantitative PCR, a microarray, sequencing by synthesis, or massively-parallel sequencing. In some embodiments, the identifier library comprises a plurality of nucleic acid sequences. In some embodiments, the plurality of nucleic acid sequences store metadata of the information and/or conceal the information. In some embodiments, one or more identifier libraries are combined and wherein each identifier library in the one or more identifier libraries comprises a distinct barcode. In some embodiments, the barcode stores metadata of the information.

In another aspect, the present disclosure provides a method for nucleic acid-based computer data storage, comprising: (a) receiving computer data, (b) synthesizing nucleic acid molecules comprising nucleic acid sequences encoding the computer data, wherein the computer data is encoded in at least a subset of nucleic acid molecules synthesized and not in a sequence of each of the nucleic acid molecules, and (c) storing the nucleic acid molecules having the nucleic acid sequences.

In some embodiments, the at least the subset of the nucleic acid molecules are grouped together. In some embodiments, the method further comprises sequencing the nucleic acid molecule(s) to determine the nucleic acid sequence(s), thereby retrieving the computer data. In some embodiments, (b) is performed in a time period that is less than about 1 day. In some embodiments, (b) is performed at an accuracy of at least about 90%.

In another aspect, the present disclosure provides a method for nucleic acid-based computer data storage, comprising: (a) receiving computer data, (b) synthesizing a nucleic acid molecule comprising at least one nucleic acid sequence encoding the computer data, which synthesizing the nucleic acid molecule is in the absence of base-by-base nucleic acid synthesis, and (c) storing the nucleic acid molecule comprising the at least one nucleic acid sequence.

In some embodiments, the method further comprises sequencing the nucleic acid molecule to determine the nucleic acid sequence, thereby retrieving the computer data. In some embodiments, (b) is performed in a time period that is less than about 1 day. In some embodiments, (b) is performed at an accuracy of at least about 90%.

In another aspect, the present disclosure provides a system for encoding binary sequence data using nucleic acids, comprising: a device configured to construct an identifier library, wherein the identifier library comprises a plurality of identifiers, wherein an individual identifier of the plurality of identifiers comprises one or more components, and wherein an individual component of the one or more components is a nucleic acid sequence; and one or more computer processors operatively coupled to the device, wherein the one or more computer processors are individually or collectively programmed to (i) translate the information into a string of symbols, (ii) map the string of symbols to the plurality of identifiers, wherein the individual identifier of the plurality of identifiers corresponds to an individual symbol of the string of symbols, and (iii) construct an identifier library comprising the plurality of identifiers.

In some embodiments, the device comprises a plurality of partitions and wherein the identifier library is generated in one or more of the plurality of partitions. In some embodiments, the plurality of partitions comprises wells. In some embodiments, constructing the individual identifier in the identifier library comprises assembling the one or more components from one or more layers and wherein each layer of the one or more layers comprises a distinct set of components. In some embodiments, each layer of the one or more layers is stored in a separate portion of the device and wherein the device is configured to combine the one or more components from the one or more layers. In some embodiments, the identifier library comprises a plurality of nucleic acid sequences. In some embodiments, one or more identifier libraries are combined in a single area of the device and wherein each identifier library of the one or more identifier libraries comprises a distinct barcode.

In another aspect, the present disclosure provides a system for reading information encoded in nucleic acid sequence(s), comprising: a database that stores an identifier library comprising a plurality of identifiers, wherein an individual identifier of the plurality of identifiers comprises one or more components, wherein an individual component of the one or more components comprises a nucleic acid sequence; and one or more computer processors operatively coupled to the database, wherein the one or more computer processors are individually or collectively programmed to (i) identify the plurality of identifiers in the identifier library, (ii) generate a plurality of symbols from the plurality of identifiers identified in (i), wherein an individual symbol of the plurality of symbols corresponds to the individual identifier of the plurality of identifiers, and (iii) compile the information from the plurality of symbols.

In some embodiments, the system further comprises a plurality of partitions. In some embodiments, the partitions are wells. In some embodiments, a given partition of the plurality of partitions comprises one or more identifier libraries and wherein each identifier library of the one or more identifier libraries comprises a distinct barcode. In some embodiments, the system further comprises a detection unit configured to identify the plurality of identifiers in the identifier library.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 2A illustrates combining a rank object (or address object) with a byte-value object (or data object) to create an identifier; FIG. 2B illustrates an embodiment of the data at address method wherein the rank objects and byte-value objects are themselves combinatorial concatenations of other objects;

FIG. 3A illustrates encoding digital information using a rank object as an identifier; FIG. 3B illustrates an embodiment of the encoding method wherein the address objects are themselves combinatorial concatenations of other objects;

FIG. 6A illustrates the architecture of identifiers constructed using the product scheme; FIG. 6B illustrates an example of the combinatorial space of identifiers that may be constructed using the product scheme;

FIG. 10A schematically illustrates the use of template directed ligation to construct identifiers (e.g., nucleic acid molecules) from components (e.g., nucleic acid sequences); FIG. 10B shows a histogram of the copy numbers (abundances) of 256 distinct nucleic acid sequences that were each combinatorially assembled from six nucleic acid sequences (e.g., components) in one pooled template directed ligation reaction;

FIG. 11A, FIG. 11B, FIG. 11C, FIG. 11D, FIG. 11E, FIG. 11F, and FIG. 11G schematically illustrate an example method, referred to as the "permutation scheme", for constructing identifiers (e.g., nucleic acid molecules) with permuted components (e.g., nucleic acid sequences); FIG. 11A illustrates the architecture of identifiers constructed using the permutation scheme; FIG. 11B illustrates an example of the combinatorial space of identifiers that may be constructed using the permutation scheme; FIG. 11C shows an example implementation of the permutation scheme with template directed ligation; FIG. 11D shows an example of how the implementation from FIG. 11C may be modified to construct identifiers with permuted and repeated components; FIG. 11E shows how the example implementation from FIG. 11D may lead to unwanted byproducts that may be removed with nucleic acid size selection; FIG. 11F shows another example of how to use template directed ligation and size selection to construct identifiers with permuted and repeated components; FIG. 11G shows an example of when size selection may fail to isolate a particular identifier from unwanted byproducts;

FIG. 12A illustrates the architecture of identifiers constructed using the MchooseK scheme; FIG. 12B illustrates an example of the combinatorial space of identifiers that may be constructed using the MchooseK scheme; FIG. 12C shows an example implementation of the MchooseK scheme using template directed ligation; FIG. 12D shows how the example implementation from FIG. 12C may lead to unwanted byproducts that may be removed with nucleic acid size selection;

FIG. 13A shows an example of the combinatorial space of identifiers that may be constructed using the partition scheme; FIG. 13B shows an example implementation of the partition scheme using template directed ligation;

FIG. 14A shows an example of the combinatorial space of identifiers that may be constructed using the USS scheme; FIG. 14B shows an example implementation of the USS scheme using template directed ligation;

FIG. 15A shows an example of the combinatorial space of identifiers that may be constructed using the component deletion scheme; FIG. 15B shows an example implementation of the component deletion scheme using double stranded targeted cleavage and repair;

FIG. 17A shows example methods for using polymerase chain reaction, affinity tagged probes, and degradation targeting probes to access identifiers containing a specified component; FIG. 17B shows example methods for using polymerase chain reaction to perform 'OR' or 'AND' operations to access identifiers containing multiple specified components; FIG. 17C shows example methods for using affinity tags to perform 'OR' or 'AND' operations to access identifiers containing multiple specified components;

FIG. 18A shows an example of encoding, writing, and reading 5,856 bits of data; FIG. 18b shows an example of encoding, writing, and reading 62,824 bits of data.

DETAILED DESCRIPTION

Figure 1:
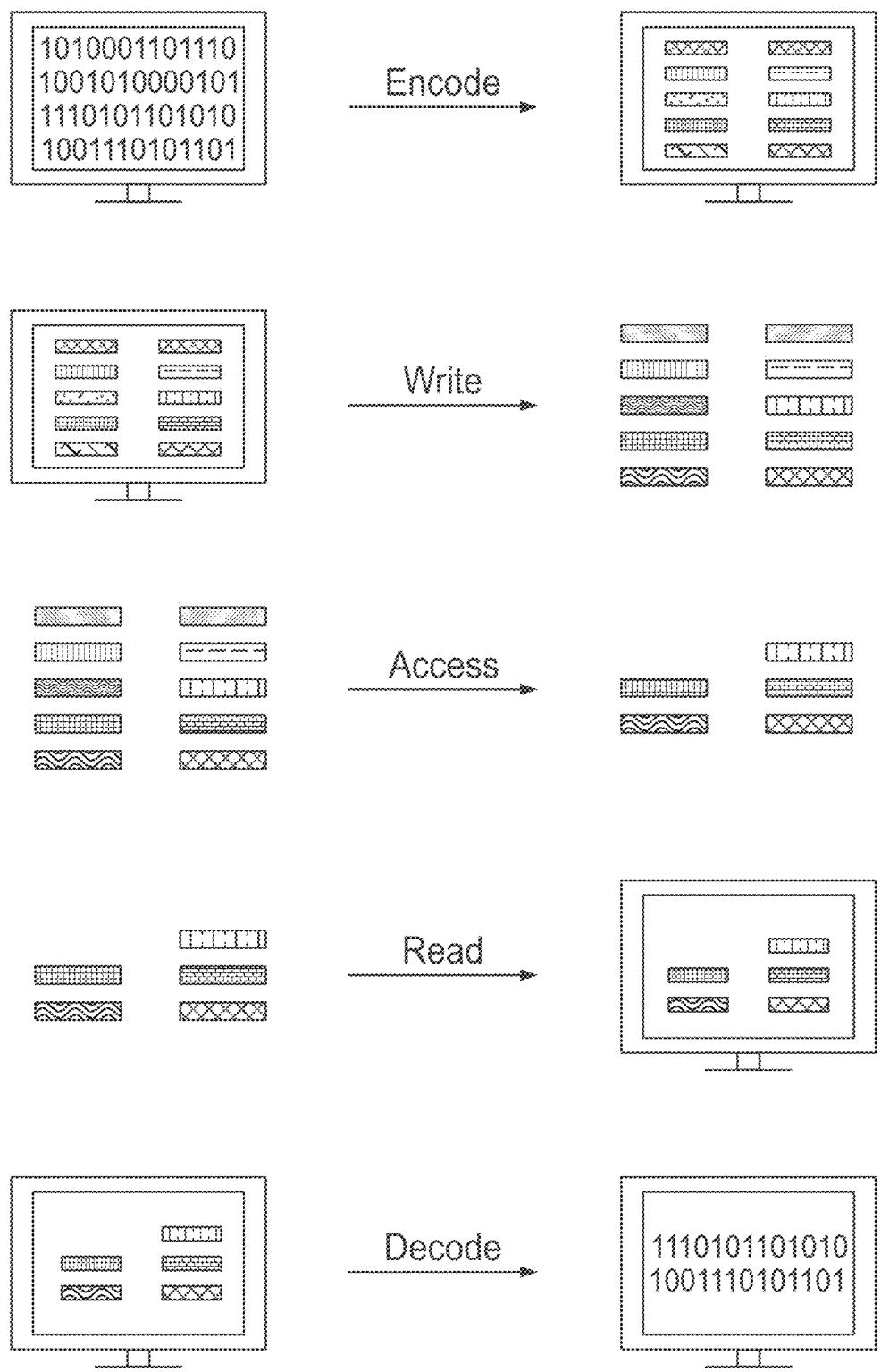
FIG. 1 schematically illustrates an overview of a process for encoding, writing, accessing, reading, and decoding digital information stored in nucleic acid sequences.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "symbol," as used herein, generally refers to a representation of a unit of digital information. Digital information may be divided or translated into a string of symbols. In an example, a symbol may be a bit and the bit may have a value of '0' or '1'.

The term "distinct," or "unique," as used herein, generally refers to an object that is distinguishable from other objects in a group. For example, a distinct, or unique, nucleic acid sequence may be a nucleic acid sequence that does not have the same sequence as any other nucleic acid sequence. A distinct, or unique, nucleic acid molecule may not have the same sequence as any other nucleic acid molecule. The distinct, or unique, nucleic acid sequence or molecule may share regions of similarity with another nucleic acid sequence or molecule.

The term "component," as used herein, generally refers to a nucleic acid sequence. A component may be a distinct nucleic acid sequence. A component may be concatenated or assembled with one or more other components to generate other nucleic acid sequence or molecules.

The term "layer," as used herein, generally refers to group or pool of components. Each layer may comprise a set of distinct components such that the components in one layer are different from the components in another layer. Components from one or more layers may be assembled to generate one or more identifiers.

The term "identifier," as used herein, generally refers to a nucleic acid molecule or a nucleic acid sequence that represents the position and value of a bit-string within a larger bit-string. More generally, an identifier may refer to any object that represents or corresponds to a symbol in a string of symbols. In some embodiments, identifiers may comprise one or multiple concatenated components.

The term "combinatorial space," as used herein generally refers to the set of all possible distinct identifiers that may be generated from a starting set of objects, such as components, and a permissible set of rules for how to modify those objects to form identifiers. The size of a combinatorial space of identifiers made by assembling or concatenating components may depend on the number of layers of components, the number of components in each layer, and the particular assembly method used to generate the identifiers.

The term "identifier rank," as used herein generally refers to a relation that defines the order of identifiers in a set.

The term "identifier library," as used herein generally refers to a collection of identifiers corresponding to the symbols in a symbol string representing digital information. In some embodiments, the absence of a given identifier in the identifier library may indicate a symbol value at a particular position. One or more identifier libraries may be combined in a pool, group, or set of identifiers. Each identifier library may include a unique barcode that identifies the identifier library.

The term "nucleic acid," as used herein, general refers to deoxyribonucleic acid (DNA), ribonucleic acid (RNA), or a variant thereof. A nucleic acid may include one or more subunits selected from adenosine (A), cytosine (C), guanine (G), thymine (T), and uracil (U), or variants thereof. A nucleotide can include A, C, G, T, or U, or variants thereof. A nucleotide can include any subunit that can be incorporated into a growing nucleic acid strand. Such subunit can be A, C, G, T, or U, or any other subunit that may be specific to one of more complementary A, C, G, T, or U, or complementary to a purine (i.e., A or G, or variant thereof) or pyrimidine (i.e., C, T, or U, or variant thereof). In some examples, a nucleic acid may be single-stranded or double stranded, in some cases, a nucleic acid is circular.

The terms "nucleic acid molecule" or "nucleic acid sequence," as used herein, generally refer to a polymeric form of nucleotides, or polynucleotide, that may have various lengths, either deoxyribonucleotides (DNA) or ribonucleotides (RNA), or analogs thereof. The term "nucleic acid sequence" may refer to the alphabetical representation of a polynucleotide; alternatively, the term may be applied to the physical polynucleotide itself. This alphabetical representation can be input into databases in a computer having a central processing unit and used for mapping nucleic acid sequences or nucleic acid molecules to symbols, or bits, encoding digital information. Nucleic acid sequences or oligonucleotides may include one or more non-standard nucleotide(s), nucleotide analog(s) and/or modified nucleotides.

An "oligonucleotide", as used herein, generally refers to a single-stranded nucleic acid sequence, and is typically composed of a specific sequence of four nucleotide bases: adenine (A); cytosine (C); guanine (G), and thymine (T) or uracil (U) when the polynucleotide is RNA.

Examples of modified nucleotides include, but are not limited to diaminopurine, 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, 2,6-diaminopurine and the like. Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone. Nucleic acid molecules may also contain amine-modified groups, such as aminoallyl-dUTP (aa-dUTP) and aminohexylacrylamide-dCTP (aha-dCTP) to allow covalent attachment of amine reactive moieties, such as N-hydroxy succinimide esters (NHS).

The term "primer," as used herein, generally refers to a strand of nucleic acid that serves as a starting point for nucleic acid synthesis, such as polymerase chain reaction (PCR). In an example, during replication of a DNA sample, an enzyme that catalyzes replication starts replication at the 3'-end of a primer attached to the DNA sample and copies the opposite strand. See Chemical Methods Section D for more information on PCR, including details about primer design.

The term "polymerase" or "polymerase enzyme," as used herein, generally refers to any enzyme capable of catalyzing a polymerase reaction. Examples of polymerases include, without limitation, a nucleic acid polymerase. The polymerase can be naturally occurring or synthesized. An example polymerase is a 029 polymerase or derivative thereof. In some cases, a transcriptase or a ligase is used (i.e., enzymes which catalyze the formation of a bond) in conjunction with polymerases or as an alternative to polymerases to construct new nucleic acid sequences. Examples of polymerases include a DNA polymerase, a RNA polymerase, a thermostable polymerase, a wild-type polymerase, a modified polymerase, E. coli DNA polymerase I, T7 DNA polymerase, bacteriophage T4 DNA polymerase Φ29 (phi29) DNA polymerase, Taq polymerase, Tth polymerase, Tli polymerase, Pfu polymerase Pwo polymerase, VENT polymerase, DEEPVENT polymerase, Ex-Taq polymerase, LA-Taw polymerase, Sso polymerase Poc polymerase, Pab polymerase, Mth polymerase ES4 polymerase, Tru polymerase, Tac polymerase, Tne polymerase, Tma polymerase, Tca polymerase, Tih polymerase, Tfi polymerase, Platinum Taq polymerases, Tbr polymerase, Tfl polymerase, Pfutubo polymerase, Pyrobest polymerase, KOD polymerase, Bst polymerase, Sac polymerase, Klenow fragment polymerase with 3' to 5' exonuclease activity, and variants, modified products and derivatives thereof. See Chemical Methods Section D for additional polymerases that may be used with PCR as well as for details on how polymerase characteristics may affect PCR.

Digital information, such as computer data, in the form of binary code can comprise a sequence or string of symbols. A binary code may encode or represent text or computer processor instructions using, for example, a binary number system having two binary symbols, typically 0 and 1, referred to as bits. Digital information may be represented in the form of non-binary code which can comprise a sequence of non-binary symbols. Each encoded symbol can be re-assigned to a unique bit string (or "byte"), and the unique bit string or byte can be arranged into strings of bytes or byte streams. A bit value for a given bit can be one of two symbols (e.g., 0 or 1). A byte, which can comprise a string of N bits, can have a total of $2^N$ unique byte-values. For example, a byte comprising 8 bits can produce a total of $2^8$ or 256 possible unique byte-values, and each of the 256 bytes can correspond to one of 256 possible distinct symbols, letters, or instructions which can be encoded with the bytes. Raw data (e.g., text files and computer instructions) can be represented as strings of bytes or byte streams. Zip files, or compressed data files comprising raw data can also be stored in byte streams, these files can be stored as byte streams in a compressed form, and then decompressed into raw data before being read by the computer.

Methods and systems of the present disclosure may be used to encode computer data or information in a plurality of identifiers, each of which may represent one or more bits of the original information. In some examples, methods and systems of the present disclosure encode data or information using identifiers that each represents two bits of the original information.

Previous methods for encoding digital information into nucleic acids have relied on base-by-base synthesis of the nucleic acids, which can be costly and time consuming. Alternative methods may improve the efficiency, improve the commercial viability of digital information storage by reducing the reliance on base-by-base nucleic acid synthesis for encoding digital information, and eliminate the de novo synthesis of distinct nucleic acid sequences for every new information storage request.

New methods can encode digital information (e.g., binary code) in a plurality of identifiers, or nucleic acid sequences, comprising combinatorial arrangements of components instead of relying on base-by-base or de-novo nucleic acid synthesis (e.g., phosphoramidite synthesis). As such, new strategies may produce a first set of distinct nucleic acid sequences (or components) for the first request of information storage, and can there-after re-use the same nucleic acid sequences (or components) for subsequent information storage requests. These approaches can significantly reduce the cost of DNA-based information storage by reducing the role of de-novo synthesis of nucleic acid sequences in the information-to-DNA encoding and writing process. Moreover, unlike implementations of base-by-base synthesis, such as phosphoramidite chemistry- or template-free polymerase-based nucleic acid elongation, which may use cyclical delivery of each base to each elongating nucleic acid, new methods of information-to-DNA writing using identifier construction from components are highly parallelizable processes that do not necessarily use cyclical nucleic acid elongation. Thus, new methods may increase the speed of writing digital information to DNA compared to older methods.

Methods for Encoding and Writing Information to Nucleic Acid Sequence(s)

In an aspect, the present disclosure provides methods for encoding information into nucleic acid sequences. A method for encoding information into nucleic acid sequences may comprise (a) translating the information into a string of symbols, (b) mapping the string of symbols to a plurality of identifiers, and (c) constructing an identifier library comprising at least a subset of the plurality of identifiers. An individual identifier of the plurality of identifiers may comprise one or more components. An individual component of the one or more components may comprise a nucleic acid sequence. Each symbol at each position in the string of symbols may correspond to a distinct identifier. The individual identifier may correspond to an individual symbol at an individual position in the string of symbols. Moreover, one symbol at each position in the string of symbols may correspond to the absence of an identifier. For example, in a string of binary symbols (e.g., bits) of '0's and '1's, each occurrence of '0' may correspond to the absence of an identifier.

In another aspect, the present disclosure provides methods for nucleic acid-based computer data storage. A method for nucleic acid-based computer data storage may comprise (a) receiving computer data, (b) synthesizing nucleic acid molecules comprising nucleic acid sequences encoding the computer data, and (c) storing the nucleic acid molecules having the nucleic acid sequences. The computer data may be encoded in at least a subset of nucleic acid molecules synthesized and not in a sequence of each of the nucleic acid molecules.

In another aspect, the present disclosure provides methods for writing and storing information in nucleic acid sequences. The method may comprise, (a) receiving or encoding a virtual identifier library that represents information, (b) physically constructing the identifier library, and (c) storing one or more physical copies of the identifier library in one or more separate locations. An individual identifier of the identifier library may comprise one or more components. An individual component of the one or more components may comprise a nucleic acid sequence.

In another aspect, the present disclosure provides methods for nucleic acid-based computer data storage. A method for nucleic acid-based computer data storage may comprise (a) receiving computer data, (b) synthesizing a nucleic acid molecule comprising at least one nucleic acid sequence encoding the computer data, and (c) storing the nucleic acid molecule comprising the at least one nucleic acid sequence. Synthesizing the nucleic acid molecule may be in the absence of base-by-base nucleic acid synthesis.

In another aspect, the present disclosure provides methods for writing and storing information in nucleic acid sequences. A method for writing and storing information in nucleic acid sequences may comprise, (a) receiving or encoding a virtual identifier library that represents information, (b) physically constructing the identifier library, and (c) storing one or more physical copies of the identifier library in one or more separate locations. An individual identifier of the identifier library may comprise one or more components. An individual component of the one or more components may comprise a nucleic acid sequence.

FIG. 1 illustrates an overview process for encoding information into nucleic acid sequences, writing information to the nucleic acid sequences, reading information written to nucleic acid sequences, and decoding the read information. Digital information, or data, may be translated into one or more strings of symbols. In an example, the symbols are bits and each bit may have a value of either '0' or '2'. Each symbol may be mapped, or encoded, to an object (e.g., identifier) representing that symbol. Each symbol may be represented by a distinct identifier. The distinct identifier may be a nucleic acid molecule made up of components. The components may be nucleic acid sequences. The digital information may be written into nucleic acid sequences by generating an identifier library corresponding to the information. The identifier library may be physically generated by physically constructing the identifiers that correspond to each symbol of the digital information. All or any portion of the digital information may be accessed at a time. In an example, a subset of identifiers is accessed from an identifier library. The subset of identifiers may be read by sequencing and identifying the identifiers. The identified identifiers may be associated with their corresponding symbol to decode the digital data.

A method for encoding and reading information using the approach of FIG. 1 can, for example, include receiving a bit stream and mapping each one-bit (bit with bit-value of '1') in the bit stream to a distinct nucleic acid identifier using an identifier rank or a nucleic acid index. Constructing a nucleic acid sample pool, or identifier library, comprising copies of the identifiers that correspond to bit values of 1 (and excluding identifiers for bit values of 0). Reading the sample can comprise using molecular biology methods (e.g., sequencing, hybridization, PCR, etc), determining which identifiers are represented in the identifier library, and assigning bit-values of '1' to the bits corresponding to those identifiers and bit-values of '0' elsewhere (again referring to the identifier rank to identify the bits in the original bit-stream that each identifier corresponds to), thus decoding the information into the original encoded bit stream.

Encoding a string of N distinct bits, can use an equivalent number of unique nucleic acid sequences as possible identifiers. This approach to information encoding may use de-novo synthesis of identifiers (e.g., nucleic acid molecules) for each new item of information (string of N bits) to store. In other instances, the cost of newly synthesizing identifiers (equivalent in number to or less than N) for each new item of information to store can be reduced by the one-time de-novo synthesis and subsequent maintenance of all possible identifiers, such that encoding new items of information may involve mechanically selecting and mixing together pre-synthesized (or pre-fabricated) identifiers to form an identifier library. In other instances, both the cost of (1) de-novo synthesis of up to N identifiers for each new item of information to store or (2) maintaining and selecting from N possible identifiers for each new item of information to store, or any combination thereof, may be reduced by synthesizing and maintaining a number (less than N, and in some cases much less than N) of nucleic acid sequences and then modifying these sequences through enzymatic reactions to generate up to N identifiers for each new item of information to store.

The identifiers may be rationally designed and selected for ease of read, write, access, copy, and deletion operations. The identifiers may be designed and selected to minimize write errors, mutations, degradation, and read errors. See Chemical Methods Section H on the rational design of DNA sequences that comprise synthetic nucleic acid libraries (such as identifier libraries).

Figure 2A:
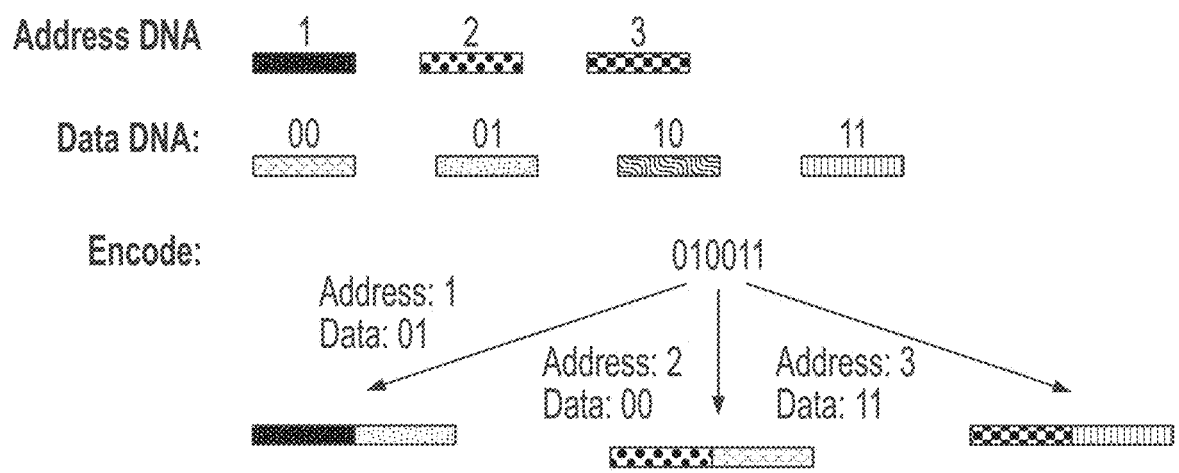
FIG. 2A and FIG. 2B schematically illustrate an example method of encoding digital data, referred to as "data at address", using objects or identifiers (e.g., nucleic acid molecules)
Figure 2B:
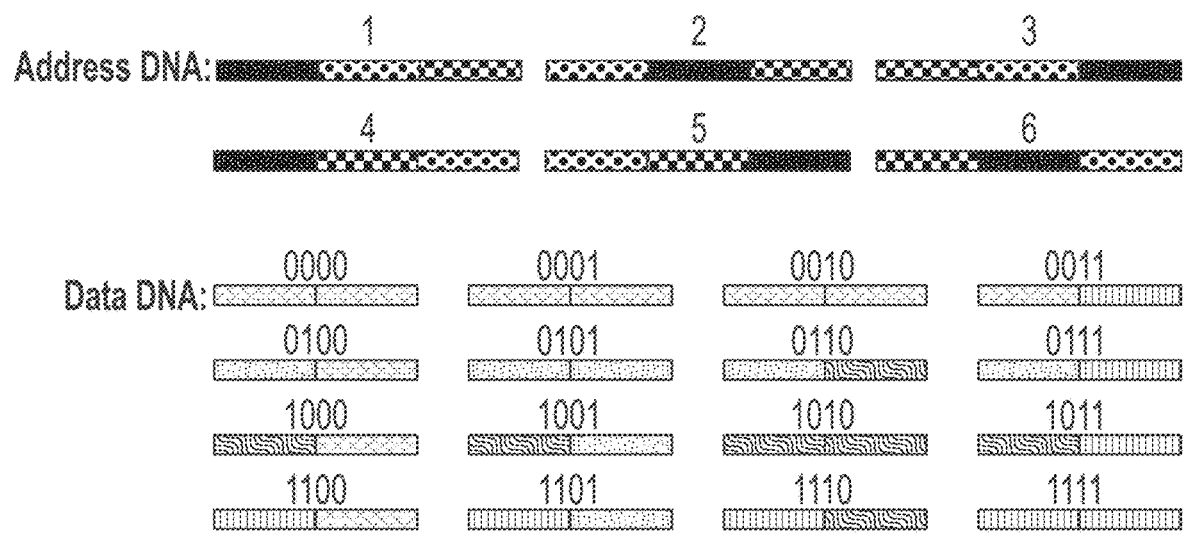

FIGS. 2A and 2B schematically illustrate an example method, referred to as "data at address", of encoding digital data in objects or identifiers (e.g., nucleic acid molecules). FIG. 2A illustrates encoding a bit stream into an identifier library wherein the individual identifiers are constructed by concatenating or assembling a single component that specifies an identifier rank with a single component that specifies a byte-value. In general, the data at address method uses identifiers that encode information modularly by comprising two objects: one object, the "byte-value object" (or "data object"), that identifies a byte-value and one object, the "rank object" (or "address object"), that identifies the identifier rank (or the relative position of the byte in the original bit-stream). FIG. 2B illustrates an example of the data at address method wherein each rank object may be combinatorially constructed from a set of components and each byte-value object may be combinatorially constructed from a set of components. Such combinatorial construction of rank and byte-value objects enables more information to be written into identifiers than if the objects where made from the single components alone (e.g., FIG. 2A).

Figure 3A:
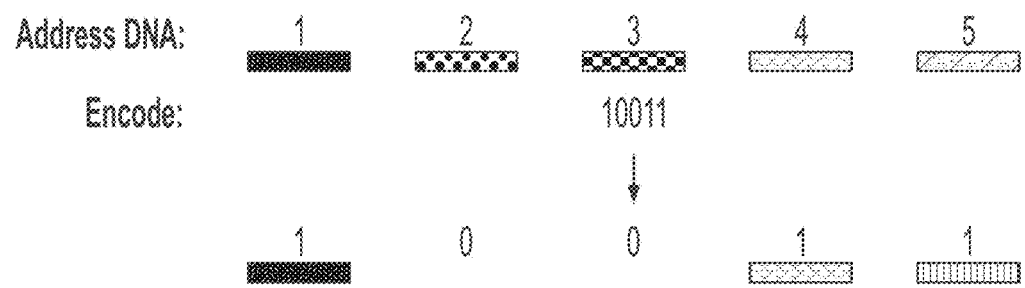
FIG. 3A and FIG. 3B schematically illustrate an example method of encoding digital information using objects or identifiers (e.g., nucleic acid sequences)
Figure 3B:
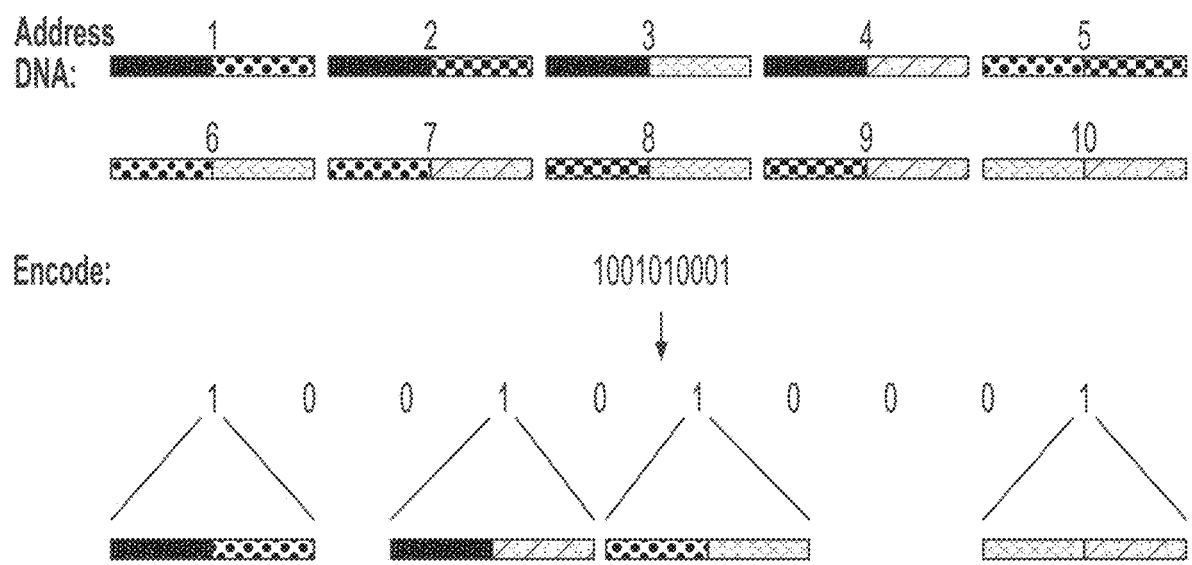

FIGS. 3A and 3B schematically illustrate another example method of encoding digital information in objects or identifiers (e.g., nucleic acid sequences). FIG. 3A illustrates encoding a bit stream into an identifier library wherein identifiers are constructed from single components that specify identifier rank. The presence of an identifier at a particular rank (or address) specifies a bit-value of '1' and the absence of an identifier at a particular rank (or address) specifies a bit-value of '0'. This type of encoding may use identifiers that solely encode rank (the relative position of a bit in the original bit stream) and use the presence or absence of those identifiers in an identifier library to encode a bit-value of '1' or '0', respectively. Reading and decoding the information may include identifying the identifiers present in the identifier library, assigning bit-values of '1' to their corresponding ranks and assigning bit-values of '0' elsewhere. FIG. 3B illustrates an example encoding method where each identifier may be combinatorially constructed from a set of components such that each possible combinatorial construction specifies a rank. Such combinatorial construction enables more information to be written into identifiers than if the identifiers where made from the single components alone (e.g., FIG. 3A). For example, a component set may comprise five distinct components. The five distinct components may be assembled to generate ten distinct identifiers, each comprising two of the five components. The ten distinct identifiers may each have a rank (or address) that corresponds to the position of a bit in a bit stream. An identifier library may include the subset of those ten possible identifiers that corresponds to the positions of bit-value '1', and exclude the subset of those ten possible identifiers that corresponds to the positions of the bit-value '0' within a bit stream of length ten.

Figure 4:
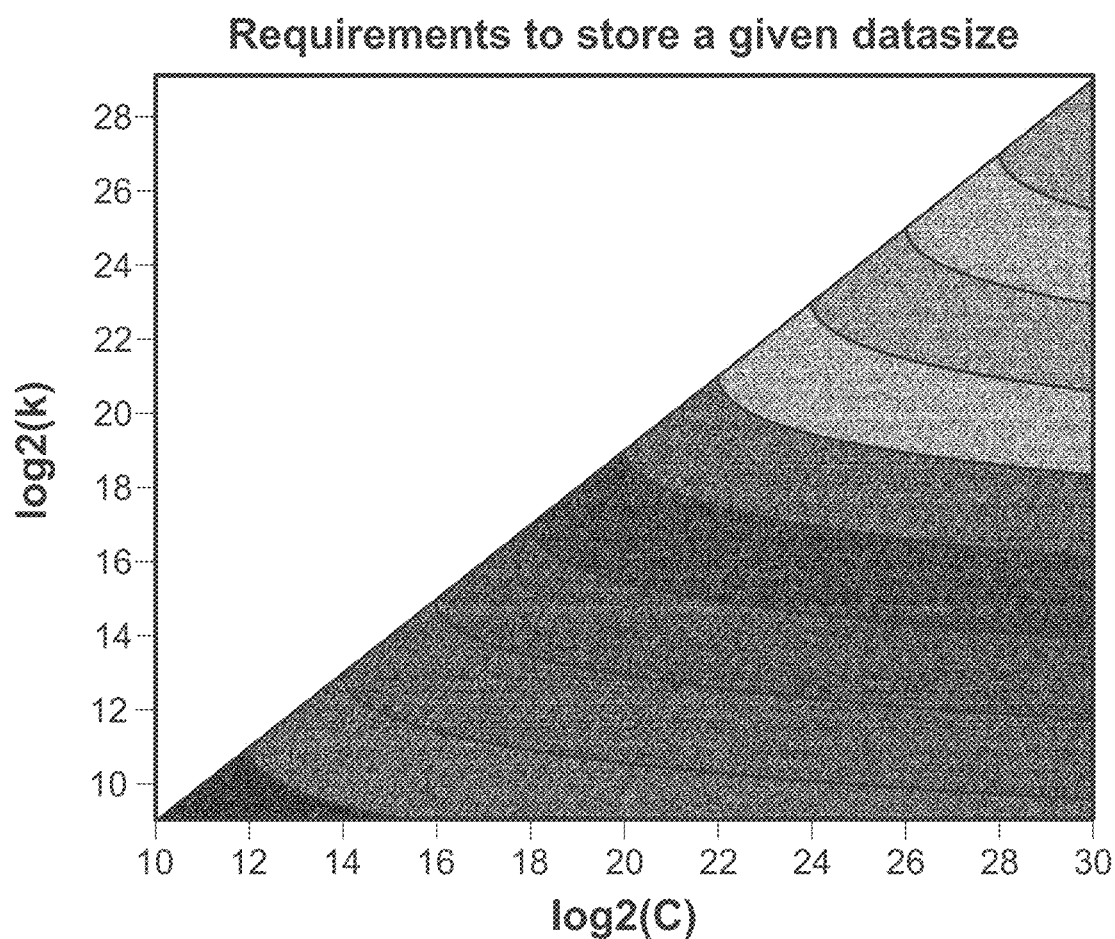
FIG. 4 shows a contour plot, in log space, of a relationship between the combinatorial space of possible identifiers (C, x-axis) and the average number of identifiers (k, y-axis) that may be constructed to store information of a given size (contour lines)

FIG. 4 shows a contour plot, in log space, of a relationship between the combinatorial space of possible identifiers (C, x-axis) and the average number of identifiers (k, y-axis) to be physically constructed in order to store information of a given original size in bits (D, contour lines) using the encoding method shown in FIGS. 3A and 3B. This plot assumes that the original information of size D is re-coded into a string of C bits (where C may be greater than D) where a number of bits, k, has a bit-value of '1'. Moreover, the plot assumes that information-to-nucleic-acid encoding is performed on the re-coded bit string and that identifiers for positions where the bit-value is '1' are constructed and identifiers for positions where the bit-value is '0' are not constructed. Following the assumptions, the combinatorial space of possible identifiers has size C to identify every position in the re-coded bit string, and the number of identifiers used to encode the bit string of size D is such that $D=\log_2(C\text{choose}k)$, where Cchoosek may be the mathematical formula for the number of ways to pick k unordered outcomes from C possibilities. Thus, as the combinatorial space of possible identifiers increases beyond the size (in bits) of a given item of information, a decreasing number of physically constructed identifiers may be used to store the given information.

Figure 5:
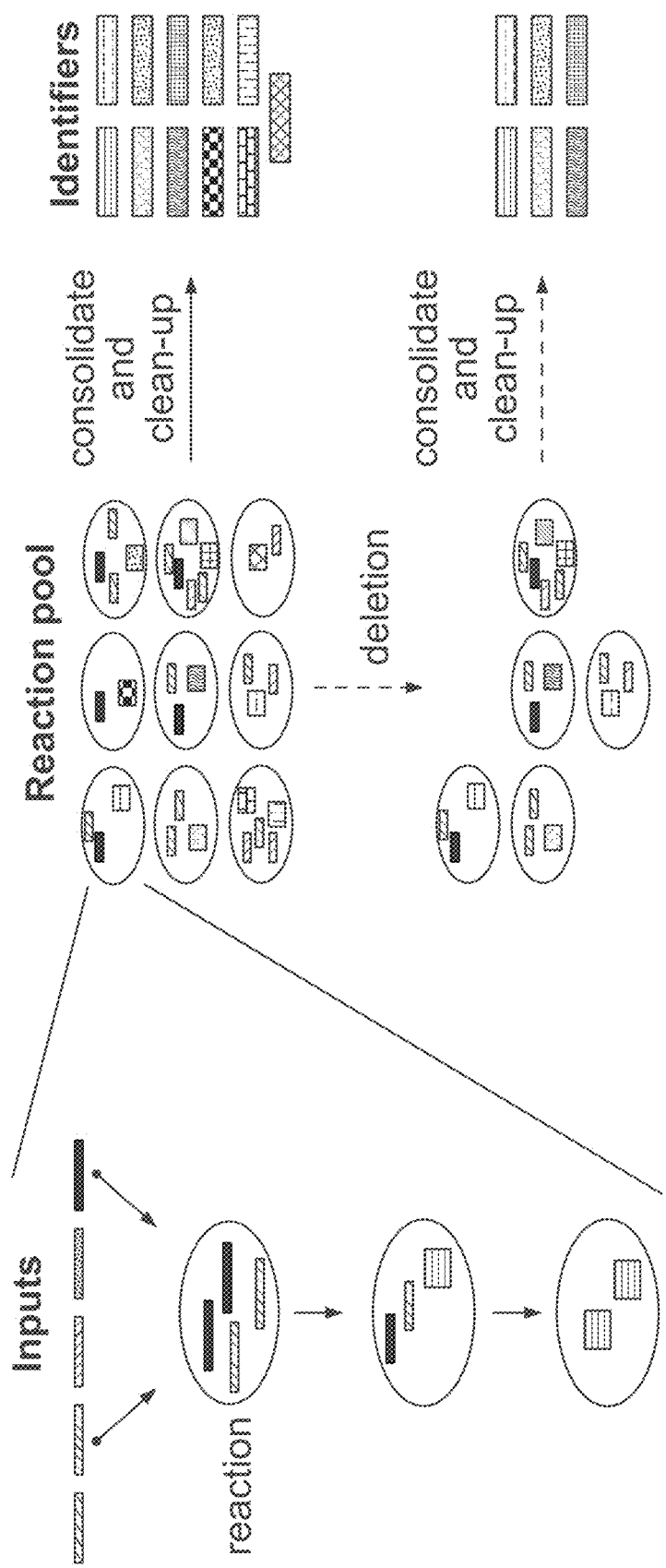
FIG. 5 schematically illustrates an overview of a method for writing information to nucleic acid sequences (e.g., deoxyribonucleic acid)

FIG. 5 shows an overview method for writing information into nucleic acid sequences. Prior to writing the information, the information may be translated into a string of symbols and encoded into a plurality of identifiers. Writing the information may include setting up reactions to produce possible identifiers. A reaction may be set up by depositing inputs into a compartment. The inputs may comprise nucleic acids, components, templates, enzymes, or chemical reagents. The compartment may be a well, a tube, a position on a surface, a chamber in a microfluidic device, or a droplet within an emulsion. Multiple reactions may be set up in multiple compartments. Reactions may proceed to produce identifiers through programmed temperature incubation or cycling. Reactions may be selectively or ubiquitously removed (e.g., deleted). Reactions may also be selectively or ubiquitously interrupted, consolidated, and purified to collect their identifiers in one pool. Identifiers from multiple identifier libraries may be collected in the same pool. An individual identifier may include a barcode or a tag to identify to which identifier library it belongs. Alternatively, or in addition to, the barcode may include metadata for the encoded information. Supplemental nucleic acids or identifiers may also be included in an identifier pool together with an identifier library. The supplemental nucleic acids or identifiers may include metadata for the encoded information or serve to obfuscate or conceal the encoded information.

An identifier rank (e.g., nucleic acid index) can comprise a method or key for determining the ordering of identifiers. The method can comprise a look-up table with all identifiers and their corresponding rank. The method can also comprise a look up table with the rank of all components that constitute identifiers and a function for determining the ordering of any identifier comprising a combination of those components. Such a method may be referred to as lexicographical ordering and may be analogous to the manner in which words in a dictionary are alphabetically ordered. In the data at address encoding method, the identifier rank (encoded by the rank object of the identifier) may be used to determine the position of a byte (encoded by the byte-value object of the identifier) within a bit stream. In an alternative method, the identifier rank (encoded by the entire identifier itself) for a present identifier may be used to determine the position of bit-value of '1' within a bit stream.

A key may assign distinct bytes to unique subsets of identifiers (e.g., nucleic acid molecules) within a sample. For example, in a simple form, a key may assign each bit in a byte to a unique nucleic acid sequence that specifies the position of the bit, and then the presence or absence of that nucleic acid sequence within a sample may specify the bit-value of 1 or 0, respectively. Reading the encoded information from the nucleic acid sample can comprise any number of molecular biology techniques including sequencing, hybridization, or PCR. In some embodiments, reading the encoded dataset may comprise reconstructing a portion of the dataset or reconstructing the entire encoded dataset from each nucleic acid sample. When the sequence may be read the nucleic acid index can be used along with the presence or absence of a unique nucleic acid sequence and the nucleic acid sample can be decoded into a bit stream (e.g., each string of bits, byte, bytes, or string of bytes).

Identifiers may be constructed by combinatorially assembling component nucleic acid sequences. For example, information may be encoded by taking a set of nucleic acid molecules (e.g., identifiers) from a defined group of molecules (e.g., combinatorial space). Each possible identifier of the defined group of molecules may be an assembly of nucleic acid sequences (e.g., components) from a prefabricated set of components that may be divided into layers. Each individual identifier may be constructed by concatenating one component from every layer in a fixed order. For example, if there are M layers and each layer may have n components, then up to $C=n^M$ unique identifiers may be constructed and up to $2^C$ different items of information, or C bits, may be encoded and stored. For example, storage of a megabit of information may use $1\times10^6$ distinct identifiers or a combinatorial space of size $C=1\times10^6$. The identifiers in this example may be assembled from a variety of components organized in different ways. Assemblies may be made from M=2 prefabricated layers, each containing $n=1\times10^3$ components. Alternatively, assemblies may be made from M=3 layers, each containing $n=1\times10^2$ components. As this example illustrates, encoding the same amount of information using a larger number of layers may allow for the total number of components to be smaller. Using a smaller number of total components may be advantageous in terms of writing cost.

In an example, one can start with two sets of unique nucleic acid sequences or layers, X and Y, each with x and y components (e.g., nucleic acid sequences), respectively. Each nucleic acid sequence from X can be assembled to each nucleic acid sequence from Y. Though the total number of nucleic acid sequences maintained in the two sets may be the sum of x and y, the total number of nucleic acid molecules, and hence possible identifiers, that can be generated may be the product of x and y. Even more nucleic acid sequences (e.g., identifiers) can be generated if the sequences from X can be assembled to the sequences of Y in any order. For example, the number of nucleic acid sequences (e.g., identifiers) generated may be twice the product of x and y if the assembly order is programmable. This set of all possible nucleic acid sequences that can be generated may be referred to as XY. The order of the assembled units of unique nucleic acid sequences in XY can be controlled using nucleic acids with distinct 5' and 3' ends, and restriction digestion, ligation, polymerase chain reaction (PCR), and sequencing may occur with respect to the distinct 5' and 3' ends of the sequences. Such an approach can reduce the total number of nucleic acid sequences (e.g., components) used to encode N distinct bits, by encoding information in the combinations and orders of their assembly products. For example, to encode 100 bits of information, two layers of 10 distinct nucleic acid molecules (e.g., component) may be assembled in a fixed order to produce 10*10 or 100 distinct nucleic acid molecules (e.g., identifiers), or one layer of 5 distinct nucleic acid molecules (e.g., components) and another layer of 10 distinct nucleic acid molecules (e.g., components) may be assembled in any order to produce 100 distinct nucleic acid molecules (e.g., identifiers).

Nucleic acid sequences (e.g., components) within each layer may comprise a unique (or distinct) sequence, or barcode, in the middle, a common hybridization region on one end, and another common hybridization region on another other end. The barcode may contain a sufficient number of nucleotides to uniquely identify every sequence within the layer. For example, there are typically four possible nucleotides for each base position within a barcode. Therefore, a three base barcode may uniquely identify $4^3=64$ nucleic acid sequences. The barcodes may be designed to be randomly generated. Alternatively, the barcodes may be designed to avoid sequences that may create complications to the construction chemistry of identifiers or sequencing. Additionally, barcodes may be designed so that each may have a minimum hamming distance from the other barcodes, thereby decreasing the likelihood that base-resolution mutations or read errors may interfere with the proper identification of the barcode. See Chemical Methods Section H on the rational design of DNA sequences.

The hybridization region on one end of the nucleic acid sequence (e.g., component) may be different in each layer, but the hybridization region may be the same for each member within a layer. Adjacent layers are those that have complementary hybridization regions on their components that allow them to interact with one another. For example, any component from layer X may be able to attach to any component from layer Y because they may have complementary hybridization regions. The hybridization region on the opposite end may serve the same purpose as the hybridization region on the first end. For example, any component from layer Y may attach to any component of layer X on one end and any component of layer Z on the opposite end.

Figure 6A:
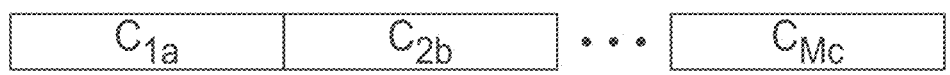
FIG. 6A and FIG. 6B illustrate an example method, referred to as the "product scheme", for constructing identifiers (e.g., nucleic acid molecules) by combinatorially assembling distinct components (e.g., nucleic acid sequences)
Figure 6B:
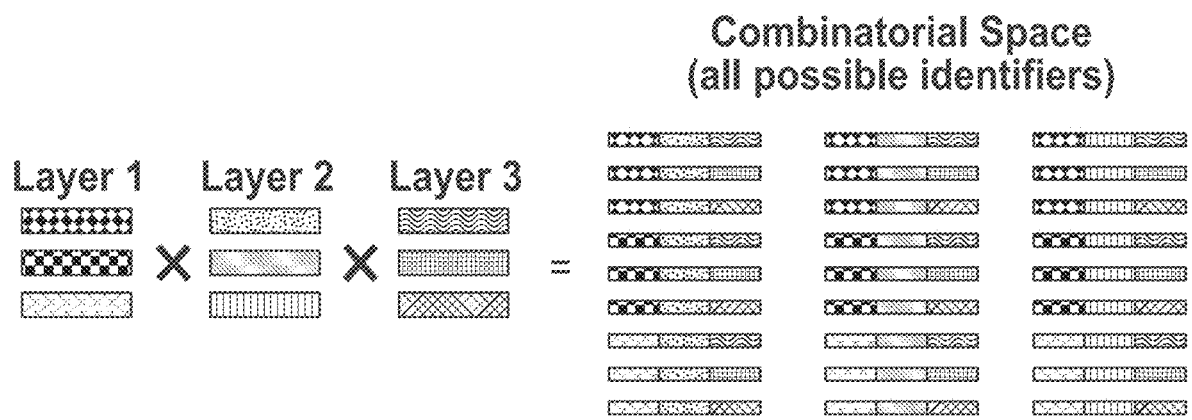

FIGS. 6A and 6B illustrate an example method, referred to as the "product scheme", for constructing identifiers (e.g., nucleic acid molecules) by combinatorially assembling a distinct component (e.g., nucleic acid sequence) from each layer in a fixed order. FIG. 6A illustrates the architecture of identifiers constructed using the product scheme. An identifier may be constructed by combining a single component from each layer in a fixed order. For M layers, each with N components, there are NM possible identifiers. FIG. 6B illustrates an example of the combinatorial space of identifiers that may be constructed using the product scheme. In an example, a combinatorial space may be generated from three layers each comprising three distinct components. The components may be combined such that one component from each layer may be combined in a fixed order. The entire combinatorial space for this assembly method may comprise twenty-seven possible identifiers.

FIGS. 7-10 illustrate chemical methods for implementing the product scheme (see FIG. 6). Methods depicted in FIGS. 7-10, along with any other methods for assembling two or more distinct components in a fixed order may be used, for example, to produce any one or more identifiers in an identifier library. Identifiers may be constructed using any of the implementation methods described in FIGS. 7-10, at any time during the methods or systems disclosed herein. In some instances, all or a portion of the combinatorial space of possible identifiers may be constructed before digital information is encoded or written, and then the writing process may involve mechanically selecting and pooling the identifiers (that encode the information) from the already existing set. In other instances, the identifiers may be constructed after one or more steps of the data encoding or writing process may have occurred (i.e., as information is being written).

Enzymatic reactions may be used to assemble components from the different layers or sets. Assembly can occur in a one pot reaction because components (e.g., nucleic acid sequences) of each layer have specific hybridization or attachment regions for components of adjacent layers. For example, a nucleic acid sequence (e.g., component) X1 from layer X, a nucleic acid sequence Y1 from layer Y, and a nucleic acid sequence Z1 from layer Z may form the assembled nucleic acid molecule (e.g., identifier) X1Y1Z1. Additionally, multiple nucleic acid molecules (e.g., identifiers) may be assembled in one reaction by including multiple nucleic acid sequences from each layer. For example, including both Y1 and Y2 in the one pot reaction of the previous example may yield two assembled products (e.g., identifiers), X1Y1Z1 and X1Y2Z1. This reaction multiplexing may be used to speed up writing time for the plurality of identifiers that are physically constructed. See Chemical Methods Section H for detail about the rational design of DNA sequences as it pertains to assembly efficiency. Assembly of the nucleic acid sequences may be performed in a time period that is less than or equal to about 1 day, 12 hours, 10 hours, 9 hours, 8 hours, 7 hours, 6 hours, 5 hours, 4 hours, 3 hours, 2 hours, or 1 hour. The accuracy of the encoded data may be at least about or equal to about 90%, 95%, 96%, 97%, 98%, 99%, or greater.

Figure 7:
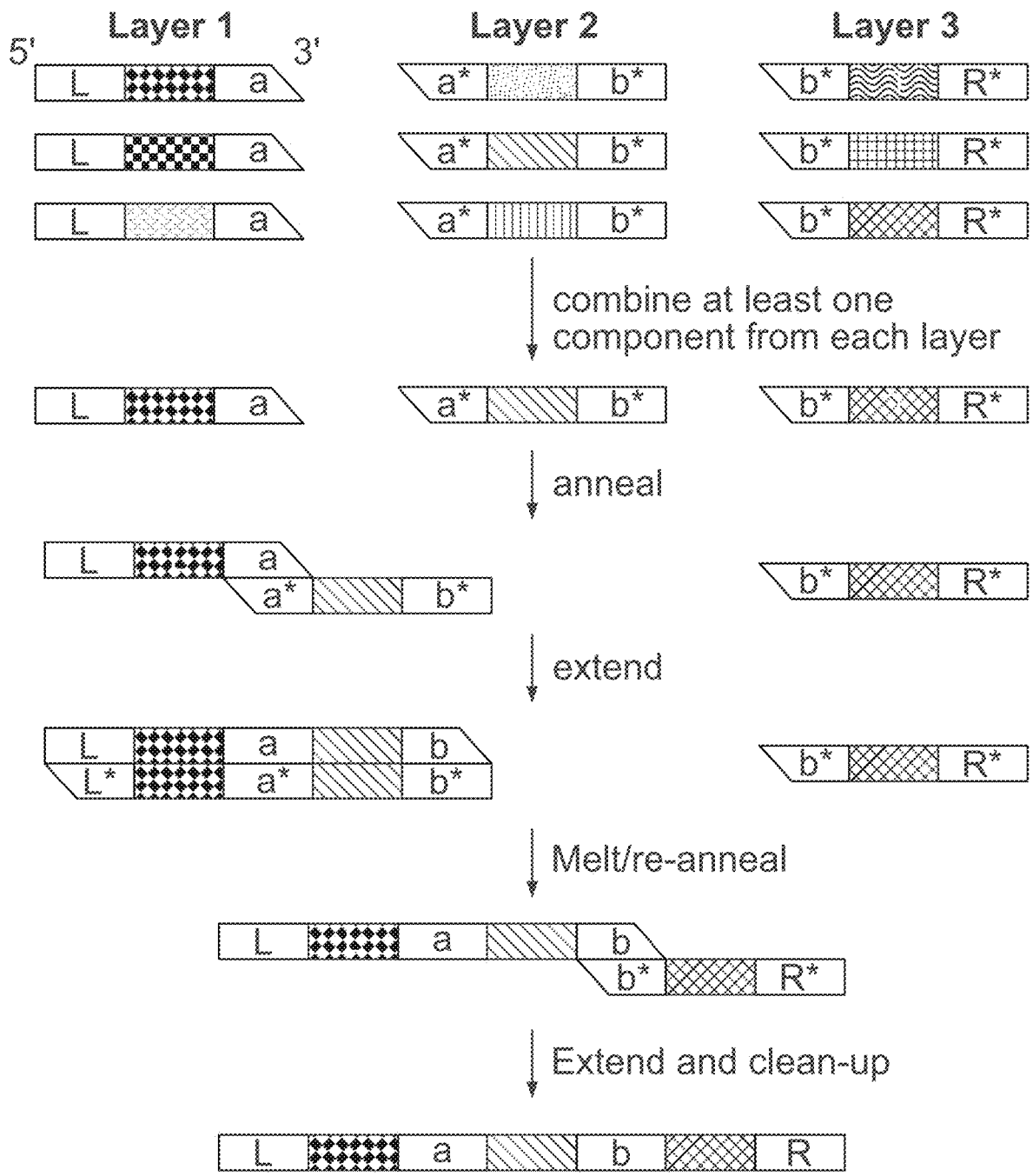
FIG. 7 schematically illustrates the use of overlap extension polymerase chain reaction to construct identifiers (e.g., nucleic acid molecules) from components (e.g., nucleic acid sequences)

Identifiers may be constructed in accordance with the product scheme using overlap extension polymerase chain reaction (OEPCR), as illustrated in FIG. 7. Each component in each layer may comprise a double-stranded or single stranded (as depicted in the figure) nucleic acid sequence with a common hybridization region on the sequence end that may be homologous and/or complementary to the common hybridization region on the sequence end of components from an adjacent layer. An individual identifier may be constructed by concatenating one component (e.g., unique sequence) from a layer X (or layer 1) comprising components $X_1$-$X_A$, a second component (e.g., unique sequence) from a layer Y (or layer 2) comprising $Y_1$-$Y_A$, and a third component (e.g., unique sequence) from layer Z (or layer 3) comprising $Z_1$-$Z_B$. The components from layer X may have a 3' end that shares complementarity with the 3' end on components from layer Y. Thus single-stranded components from layer X and Y may be annealed together at the 3' end and may be extended using PCR to generate a double-stranded nucleic acid molecule. The generated double-stranded nucleic-acid molecule may be melted to generate a 3' end that shares complementarity with a 3' end of a component from layer Z. A component from layer Z may be annealed with the generated nucleic acid molecule and may be extended to generate a unique identifier comprising a single component from layers X, Y, and Z in a fixed order. See Chemical Methods Section A about OEPCR. DNA size selection (e.g., with gel extraction, see Chemical Methods Section E) or polymerase chain reaction (PCR) with primers flanking the outer most layers (see Chemical Methods Section D) may be implemented to isolate fully assembled identifier products from other byproducts that may form in the reaction. Sequential nucleic acid capture with two probes, one for each of the two outermost layers, may also be implemented to isolate fully assembled identifier products from other byproducts that may form in the reaction (see Chemical Methods Section F).

Figure 8:
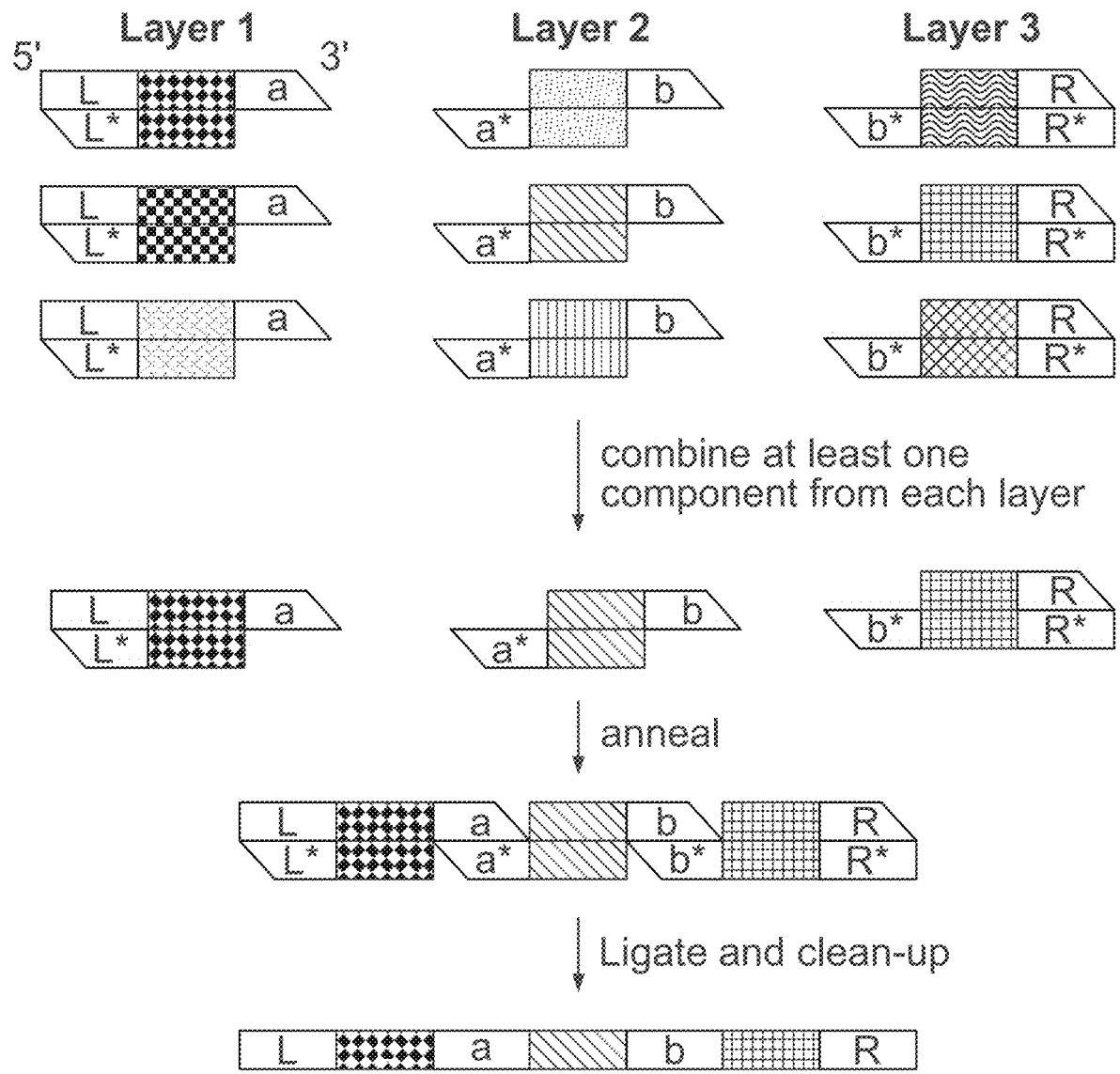
FIG. 8 schematically illustrates the use of sticky end ligation to construct identifiers (e.g., nucleic acid molecules) from components (e.g., nucleic acid sequences)

Identifiers may be assembled in accordance with the product scheme using sticky end ligation, as illustrated in FIG. 8. Three layers, each comprising double stranded components (e.g., double stranded DNA (dsDNA)) with single-stranded 3' overhangs, can be used to assemble distinct identifiers. For example, identifiers comprising one component from the layer X (or layer 1) comprising components $X_1$-$X_A$, a second component from the layer Y (or layer 2) comprising $Y_1$-$Y_B$, and a third component from the layer Z (or layer 3) comprising $Z_1$-$Z_C$. To combine components from layer X with components from layer Y, the components in layer X can comprise a common 3' overhang, FIG. 8 labeled a, and the components in layer Y can comprise a common, complementary 3' overhang, a*. To combine components from layer Y with components from layer Z, the elements in layer Y can comprise a common 3' overhang, FIG. 8 labeled b, and the elements in layer Z can comprise a common, complementary 3' overhang, b*. The 3' overhang in layer X components can be complementary to the 3' end in layer Y components and the other 3' overhang in layer Y components can be complementary to the 3' end in layer Z components allowing the components to hybridize and ligate. As such, components from layer X cannot hybridize with other components from layer X or layer Z, and similarly components from layer Y cannot hybridize with other elements from layer Y. Furthermore, a single component from layer Y can ligate to a single component of layer X and a single component of layer Z, ensuring the formation of a complete identifier. See Chemical Methods Section B about sticky end ligation. DNA size selection (e.g., with gel extraction, see Chemical Methods Section E) or polymerase chain reaction (PCR) with primers flanking the outer most layers (see Chemical Methods Section D) may be implemented to isolate identifier products from other byproducts that may form in the reaction. Sequential nucleic acid capture with two probes, one for each of the two outermost layers, may also be implemented to isolate identifier products from other byproducts that may form in the reaction (see Chemical Methods Section F).

Figure 20:
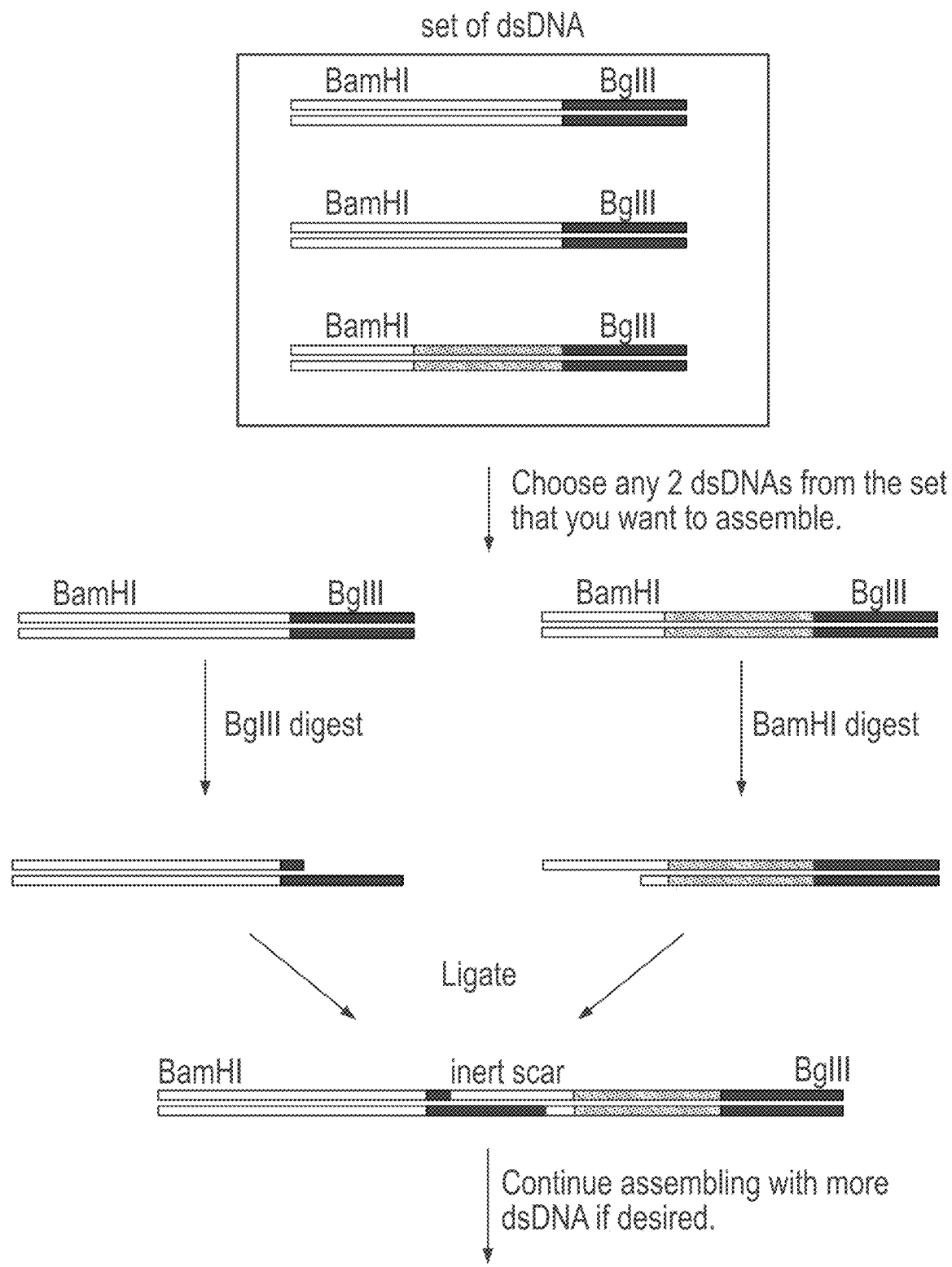
FIG. 20 shows an example scheme of assembly of any two selected double-stranded components from a single parent set of double-stranded components.

The sticky ends for sticky end ligation may be generated by treating the components of each layer with restriction endonucleases (see Chemical Methods Section C for more information about restriction enzyme reactions). In some embodiments, the components of multiple layers may be generated from one "parent" set of components. For example, an embodiment wherein a single parent set of double-stranded components may have complementary restrictions sites on each end (e.g., restriction sites for BamHI and BglII). Any two components may be selected for assembly, and individually digested with one or the other complementary restriction enzymes (e.g., BglII or BamHI) resulting in complementary sticky ends that can be ligated together resulting in an inert scar. The product nucleic acid sequence may comprise the complementary restriction sites on each end (e.g., BamHI on the 5' end and BglII on the 3' end), and can be further ligated to another component from the parent set following the same process. This process may cycle indefinitely (FIG. 20). If the parent comprises N components, then each cycle may be equivalent to adding an extra layer of N components to the product scheme.

A method for using ligation to construct a sequence of nucleic acids comprising elements from set X (e.g., set 1 of dsDNA) and elements from set Y (e.g., set 2 of dsDNA) can comprise the steps of obtaining or constructing two or more pools (e.g., set 1 of dsDNA and set 2 of dsDNA) of double stranded sequences wherein a first set (e.g., set 1 of dsDNA) comprises a sticky end (e.g., a) and a second set (e.g., set 2 of dsDNA) comprises a sticky end (e.g., a*) that is complementary to the sticky end of the first set. Any DNA from the first set (e.g., set 1 of dsDNA) and any subset of DNA from the second set (e.g., set 2 of dsDNA) can me combined and assembled and then ligated together to form a single double stranded DNA with an element from the first set and an element from the second set.

Figure 9:
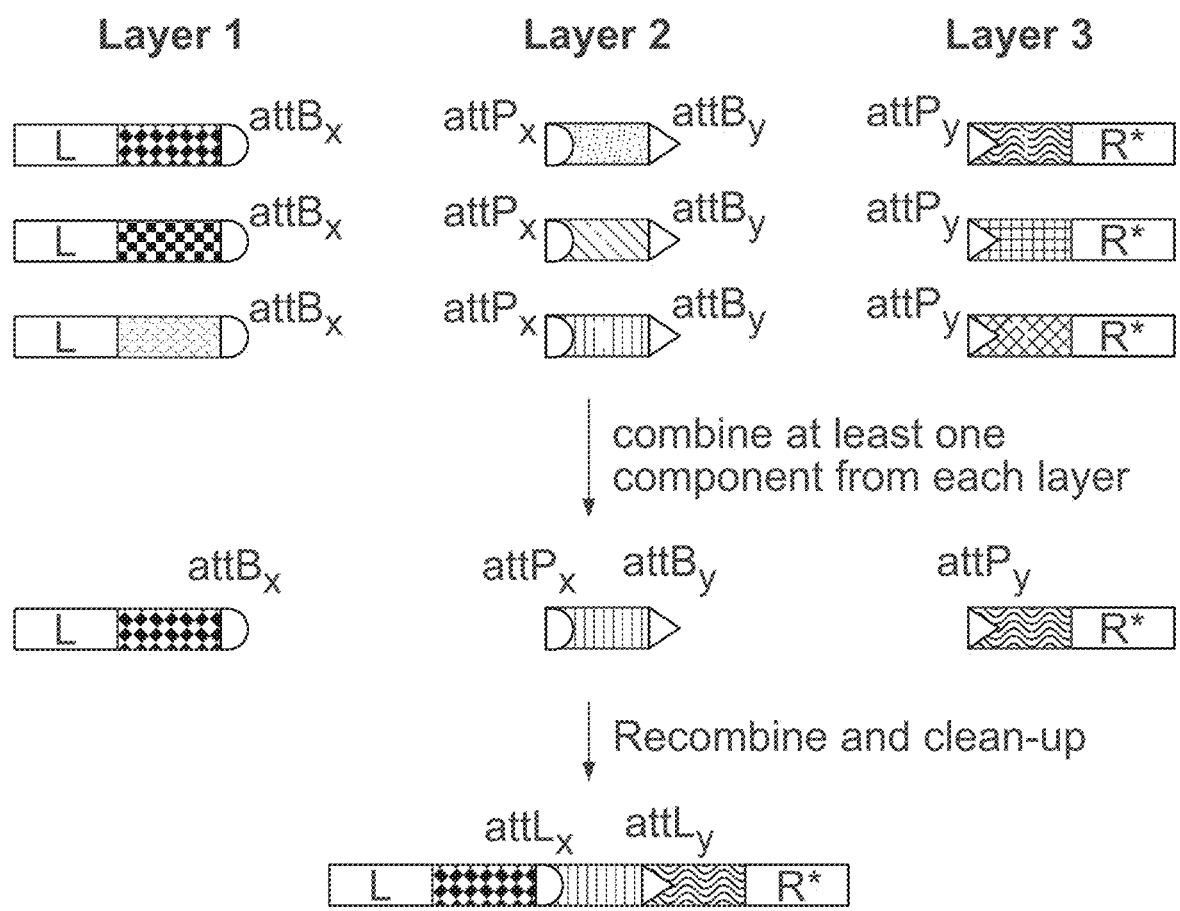
FIG. 9 schematically illustrates the use of recombinase assembly to construct identifiers (e.g., nucleic acid molecules) from components (e.g., nucleic acid sequences)

Identifiers may be assembled in accordance with the product scheme using site specific recombination, as illustrated in FIG. 9. Identifiers may be constructed by assembling components from three different layers. The components in layer X (or layer 1) may comprise double-stranded molecules with an attB$_x$ recombinase site on one side of the molecule, components from layer Y (or layer 2) may comprise double-stranded molecules with an attP$_x$ recombinase site on one side and an attB$_y$ recombinase site on the other side, and components in layer Z (or layer 3) may comprise an attP$_y$ recombinase site on one side of the molecule. attB and attP sites within a pair, as indicate by their subscripts, are capable of recombining in the presence of their corresponding recombinase enzyme. One component from each layer may be combined such that one component from layer X associates with one component from layer Y, and one component from layer Y associates with one component from layer Z. Application of one or more recombinase enzymes may recombine the components to generate a double-stranded identifier comprising the ordered components. DNA size selection (for example with gel extraction) or PCR with primers flanking the outer most layers may be implemented to isolate identifier products from other byproducts that may form in the reaction. In general, multiple orthogonal attB and attP pairs may be used, and each pair may be used to assemble a component from an extra layer. For the large-serine family of recombinases, up to six orthogonal attB and attP pairs may be generated per recombinases, and multiple orthogonal recombinases may be implemented as well. For example, thirteen layers may be assembled by using twelve orthogonal attB and attP pairs, six orthogonal pairs from each of two large serine recombinases, such as BxbI and PhiC31. Orthogonality of attB and attP pairs ensures that an attB site from one pair does not react with an attP site from another pair. This enables components from different layers to be assembled in a fixed order. Recombinase-mediated recombination reactions may be reversible or irreversible depending on the recombinase system implemented. For example, the large serine recombinase family catalyzes irreversible recombination reactions without requiring any high energy cofactors, whereas the tyrosine recombinase family catalyzes reversible reactions.

Figure 10A:
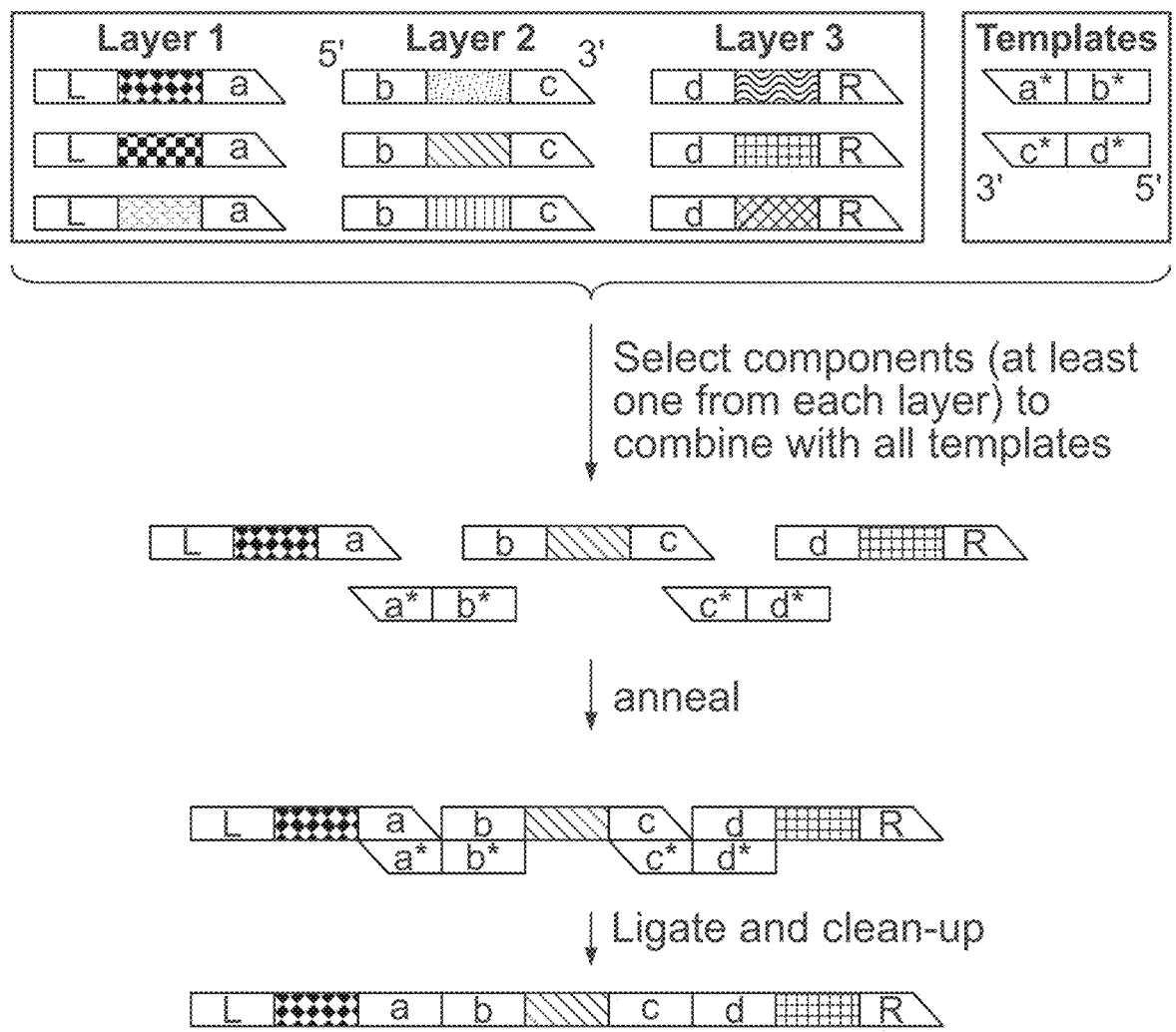
FIG. 10A and FIG. 10B demonstrates template directed ligation.

Identifiers may be constructed in accordance with the product scheme using template directed ligation (TDL), as shown in FIG. 10A. Template directed ligation utilizes single stranded nucleic acid sequences, referred to as "templates" or "staples", to facilitate the ordered ligation of components to form identifiers. The templates simultaneously hybridize to components from adjacent layers and hold them adjacent to each other (3' end against 5' end) while a ligase ligates them. In the example from FIG. 10A, three layers or sets of single-stranded components are combined. A first layer of components (e.g., layer X or layer 1) that share common sequences a on their 3' end, which are complementary to sequences a*; a second layer of components (e.g., layer Y or layer 2) that share common sequences b and c on their 5' and 3' ends respectively, which are complementary to sequences b* and c*; a third layer of components (e.g., layer Z or layer 3) that share common sequence d on their 5' end, which may be complementary to sequences d*; and a set of two templates or "staples" with the first staple comprising the sequence a*b* (5' to 3') and the second staple comprising a sequence c*d* ('5 to 3'). In this example, one or more components from each layer may be selected and mixed into a reaction with the staples, which, by complementary annealing may facilitate the ligation of one component from each layer in a defined order to form an identifier. See Chemical Methods Section B about TDL. DNA size selection (e.g., with gel extraction, see Chemical Methods Section E) or polymerase chain reaction (PCR) with primers flanking the outer most layers (see Chemical Methods Section D) may be implemented to isolate identifier products from other byproducts that may form in the reaction. Sequential nucleic acid capture with two probes, one for each of the two outermost layers, may also be implemented to isolate identifier products from other byproducts that may form in the reaction (see Chemical Methods Section F).

Figure 10B:
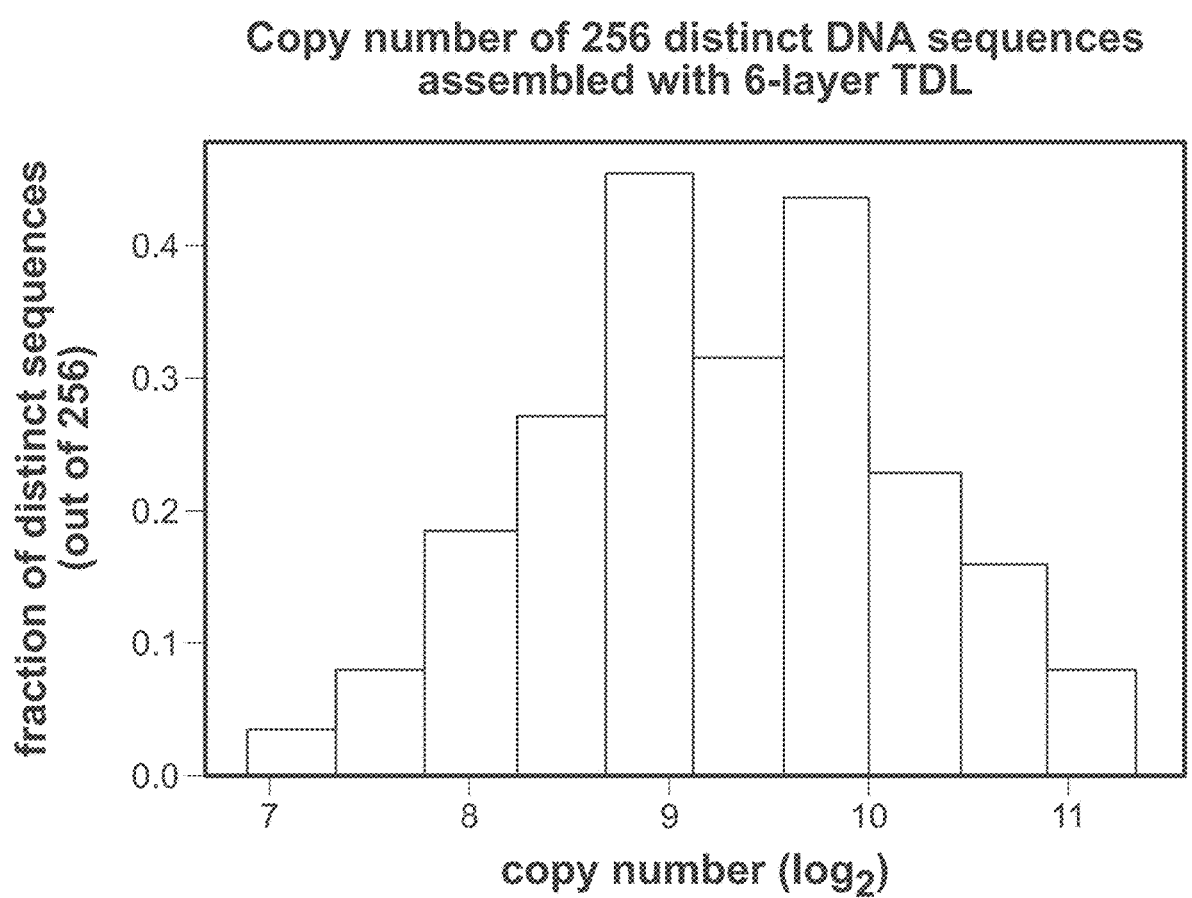

FIG. 10B shows a histogram of the copy numbers (abundances) of 256 distinct nucleic acid sequences that were each assembled with 6-layer TDL. The edge layers (first and final layers) each had one component, and each of the internal layers (remaining 4 four layers) had four components. Each edge layer component was 28 bases including a 10 base hybridization region. Each internal layer component was 30 bases including a 10 base common hybridization region on the 5' end, a 10 base variable (barcode) region, and a 10 base common hybridization region on the 3' end. Each of the three template strands was 20 bases in length. All 256 distinct sequences were assembled in a multiplex fashion with one reaction containing all of the components and templates, T4 Polynucleotide Kinase (for phosphorylating the components), and T4 Ligase, ATP, and other proper reaction reagents. The reaction was incubated at 37 degrees for 30 minutes and then room temperature for 1 hour. Sequencing adapters were added to the reaction product with PCR, and the product was sequenced with an Illumina MiSeq instrument. The relative copy number of each distinct assembled sequence out of 192910 total assembled sequence reads is shown. Other embodiments of this method may use double stranded components, where the components are initially melted to form single stranded versions that can anneal to the staples. Other embodiments or derivatives of this method (i.e., TDL) may be used to construct a combinatorial space of identifiers more complex than what may be accomplished in the product scheme.

Identifiers may be constructed in accordance with the product scheme using various other chemical implementations including golden gate assembly, gibson assembly, and ligase cycling reaction assembly.

Figure 11A:
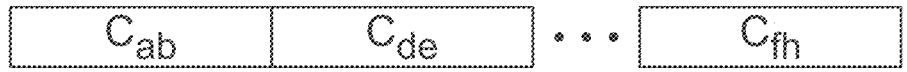
Figure 11B:
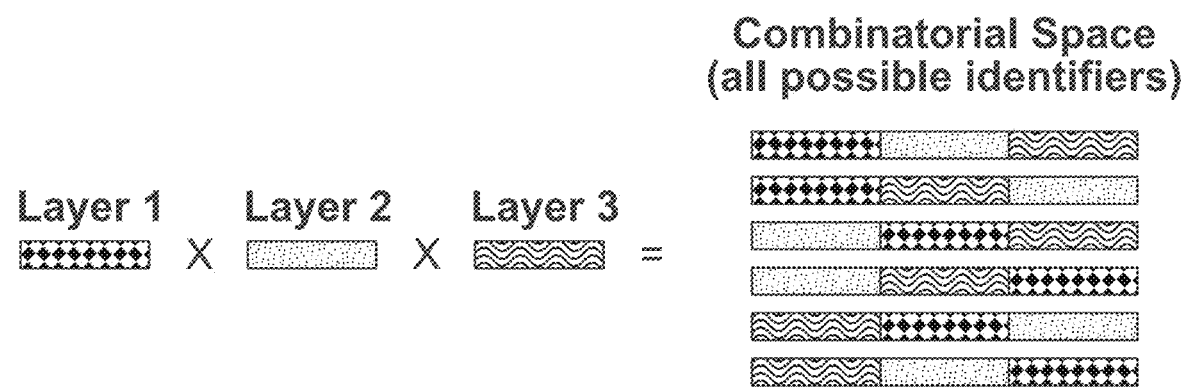

FIGS. 11A and 11B schematically illustrate an example method, referred to as the "permutation scheme", for constructing identifiers (e.g., nucleic acid molecules) with permuted components (e.g., nucleic acid sequences). FIG. 11A illustrates the architecture of identifiers constructed using the permutation scheme. An identifier may be constructed by combining a single component from each layer in a programmable order. FIG. 11B illustrates an example of the combinatorial space of identifiers that may be constructed using the permutation scheme. In an example, a combinatorial space of size six may be generated from three layers each comprising one distinct component. The components may be concatenated in any order. In general, with M layers, each with N components, the permutation scheme enables a combinatorial space of $M^M M!$ total identifiers.

Figure 11C:
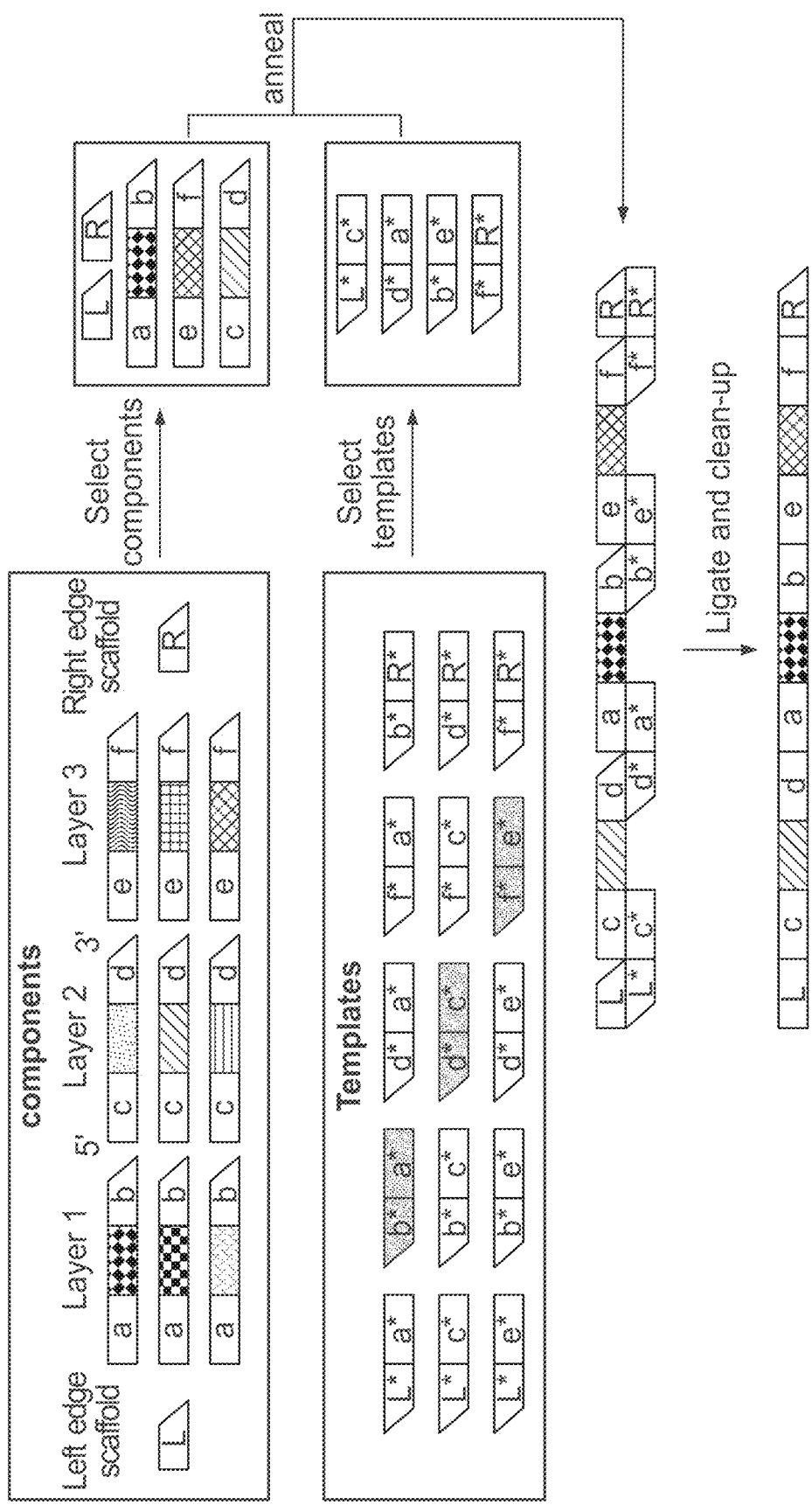

FIG. 11C illustrates an example implementation of the permutation scheme with template directed ligation (TDL, see Chemical Methods Section B). Components from multiple layers are assembled in between fixed left end and right end components, referred to as edge scaffolds. These edge scaffolds are the same for all identifiers in the combinatorial space and thus may be added as part of the reaction master mix for the implementation. Templates or staples exist for any possible junction between any two layers or scaffolds such that the order in which components from different layers are incorporated into an identifier in the reaction depends on the templates selected for the reaction. In order to enable any possible permutation of layers for M layers, there may be $M^2+2M$ distinct selectable staples for every possible junction (including junctions with the scaffolds). M of those templates (shaded in grey) form junctions between layers and themselves and may be excluded for the purposes of permutation assembly as described herein. However, their inclusion can enable a larger combinatorial space with identifiers comprising repeat components as illustrated in FIGS. 11D-G. DNA size selection (e.g., with gel extraction, see Chemical Methods Section E) or polymerase chain reaction (PCR) with primers flanking the outer most layers (see Chemical Methods Section D) may be implemented to isolate identifier products from other byproducts that may form in the reaction. Sequential nucleic acid capture with two probes, one for each of the two outermost layers, may also be implemented to isolate identifier products from other byproducts that may form in the reaction (see Chemical Methods Section F).

Figure 11D:
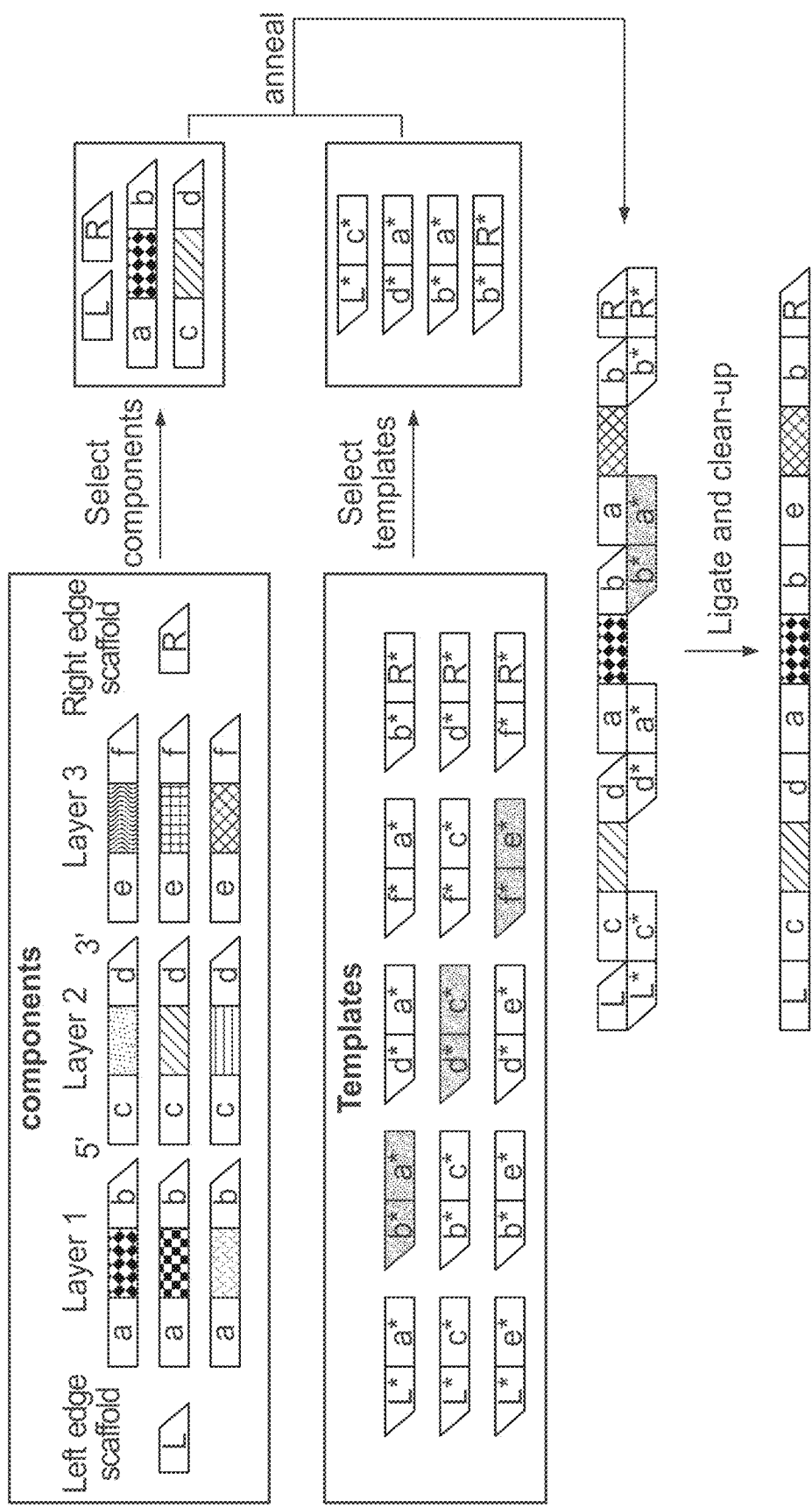
Figure 11F:
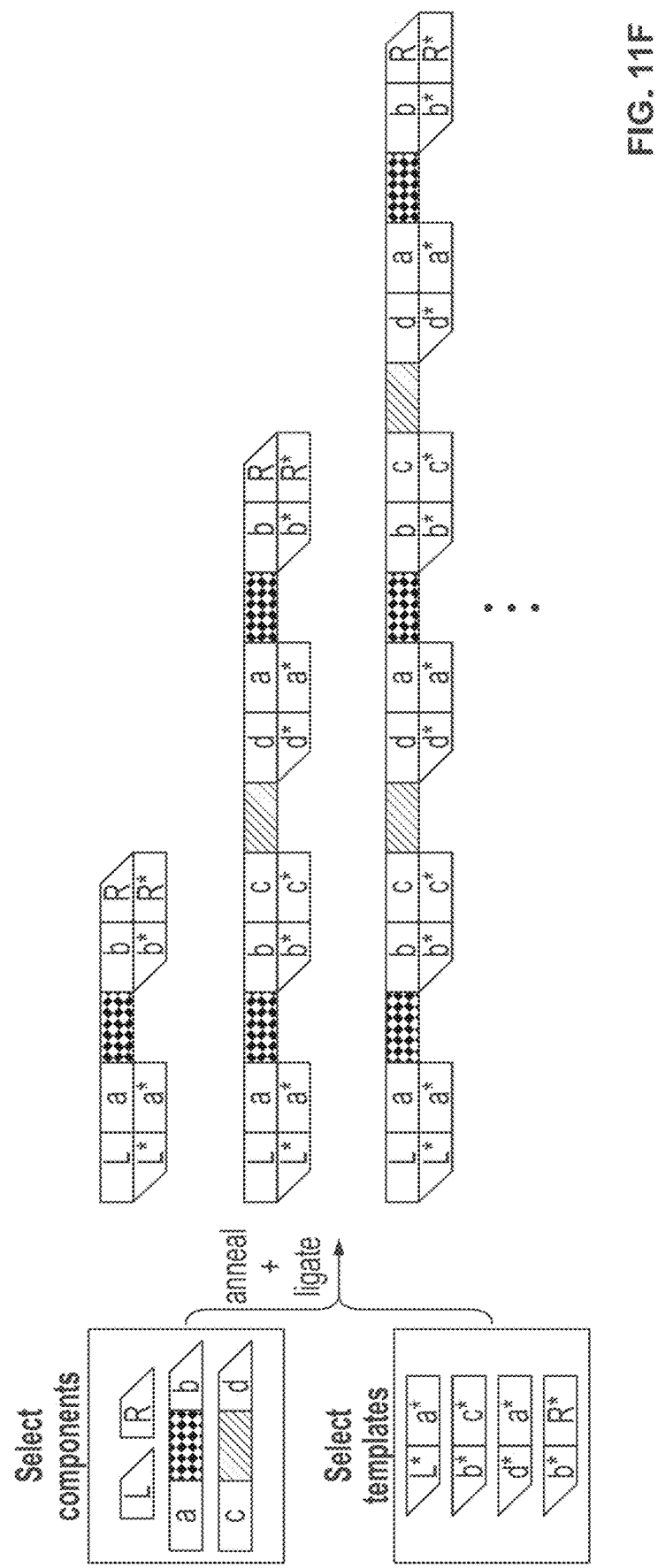
Figure 11G:
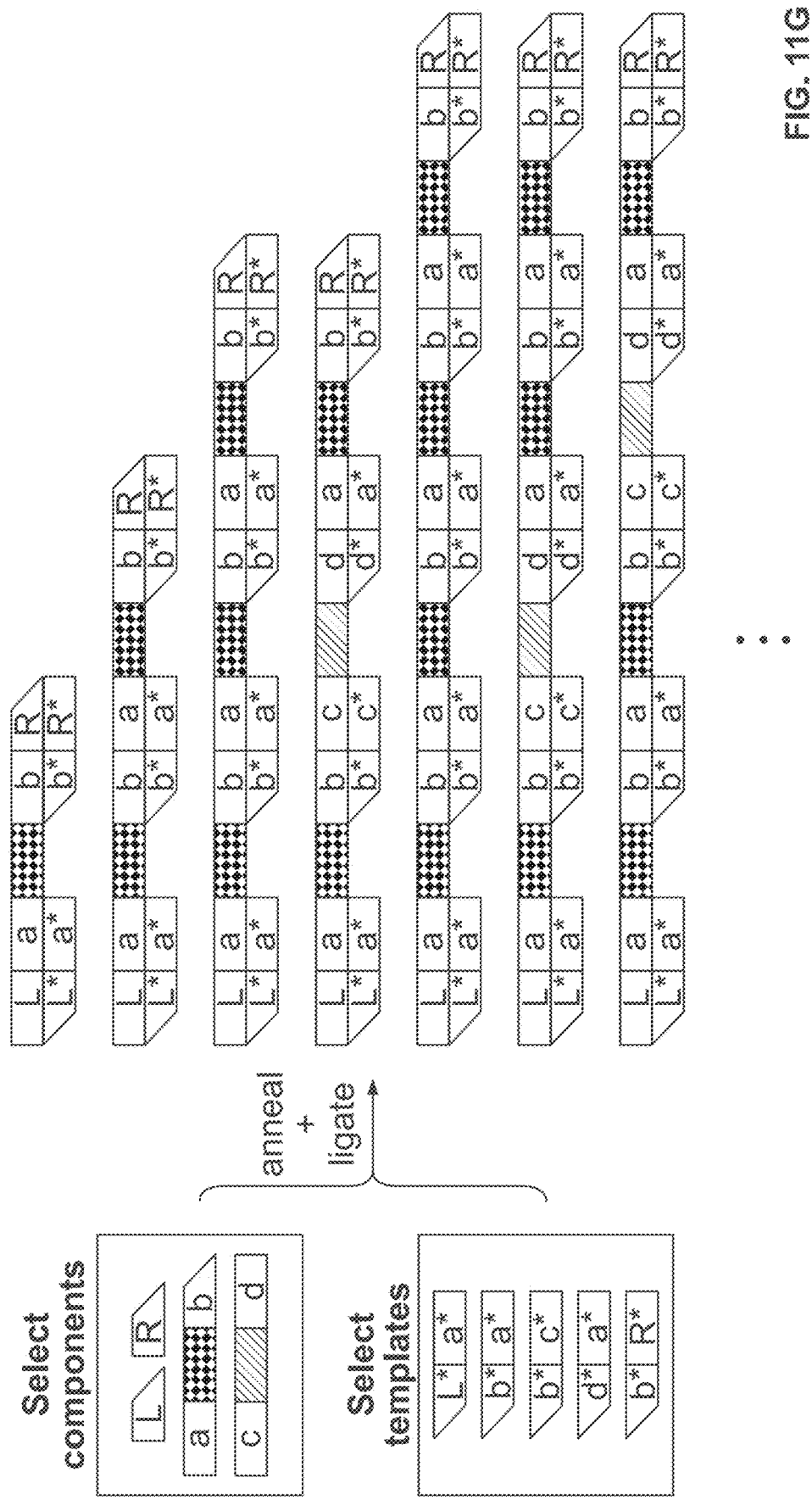

FIGS. 11D-G illustrate example methods of how the permutation scheme may be expanded to include certain instances of identifiers with repeated components. FIG. 11D shows an example of how the implementation form FIG. 11C may be used to construct identifiers with permuted and repeated components. For example, an identifier may comprise three total components assembled from two distinct components. In this example, a component from a layer may be present multiple times in an identifier. Adjacent concatenations of the same component may be achieved by using a staple with adjacent complementary hybridization regions for both the 3' end and 5' end of the same component, such as the a*b* (5' to 3') staple in the figure. In general, for M layers, there are M such staples. Incorporation of repeated components with this implementation may generate nucleic acid sequences of more than one length (i.e., comprising one, two, three, four, or more components) that are assembled between the edge scaffolds, as demonstrated in FIG. 11E. FIG. 11E shows how the example implementation from FIG. 11D may lead to non-targeted nucleic acid sequences, besides the identifier, that are assembled between the edge scaffolds. The appropriate identifier cannot be isolated from non-targeted nucleic acid sequence with PCR because they share the same primer binding sites on the edge. However, in this example, DNA size selection (e.g., with gel extraction) may be implemented to isolate the targeted identifier (e.g., the second sequence from the top) from the non-targeted sequences since each assembled nucleic acid sequence can be designed to have a unique length (e.g., if all components have the same length). See Chemical Methods Section E about size-selection. FIG. 11F shows another example where constructing an identifier with repeated components may generate multiple nucleic acid sequences with equal edge sequences but distinct lengths in the same reaction. In this method, templates that assemble a components in one layer with components in other layers in an alternating pattern may be used. As with the method shown in FIG. 11E, size selection may be used to select identifiers of the designed length. FIG. 11G shows an example where constructing an identifier with repeated components may generate multiple nucleic acid sequences with equal edge sequences and for some nucleic acid sequences (e.g., the third and fourth from the top and the sixth and seventh from the top), equal lengths. In this example, those nucleic acid sequences that share equal lengths may be excluded from both being individual identifiers as it may not be possible to construct one without also constructing the other, even if PCR and DNA size selection are implemented.

Figure 12A:
FIG. 12A, FIG. 12B, FIG. 12C, and FIG. 12D schematically illustrate an example method, referred to as the "MchooseK" scheme, for constructing identifiers (e.g., nucleic acid molecules) with any number, K, of assembled components (e.g., nucleic acid sequences) out of a larger number, M, of possible components.
Figure 12B:
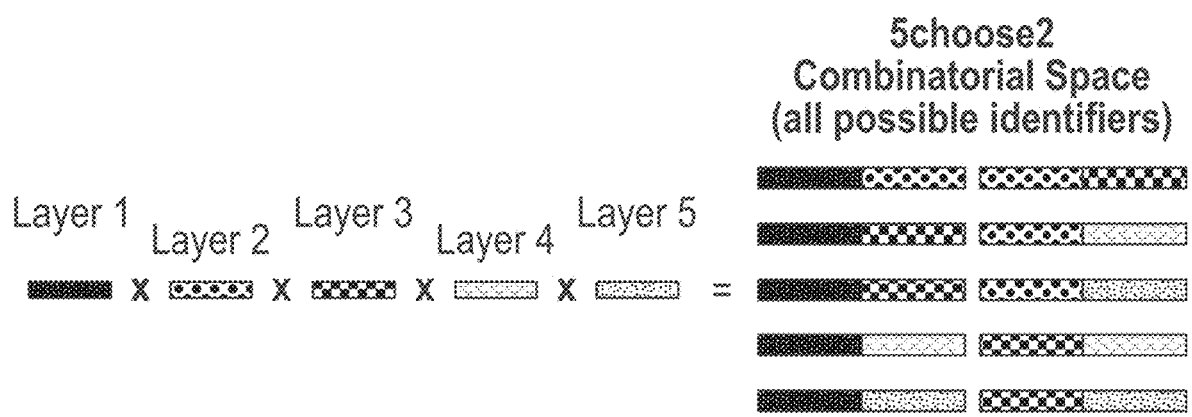

FIGS. 12A-12D schematically illustrate an example method, referred to as the "MchooseK scheme", for constructing identifiers (e.g., nucleic acid molecules) with any number, K, of assembled components (e.g., nucleic acid sequences) out of a larger number, M, of possible components. FIG. 12A illustrates the architecture of identifiers constructed using the MchooseK scheme. Using this method identifiers are constructed by assembling one component form each layer in any subset of all layers (e.g., choose components from k layers out of M possible layers). FIG. 12B illustrates an example of the combinatorial space of identifiers that may be constructed using the MchooseK scheme. In this assembly scheme the combinatorial space may comprise $N^K$MchooseK possible identifiers for M layers, N components per layer, and an identifier length of K components. In an example, if there are five layers each comprising one component, then up to ten distinct identifiers may be assemble comprising two components each.

Figure 12C:
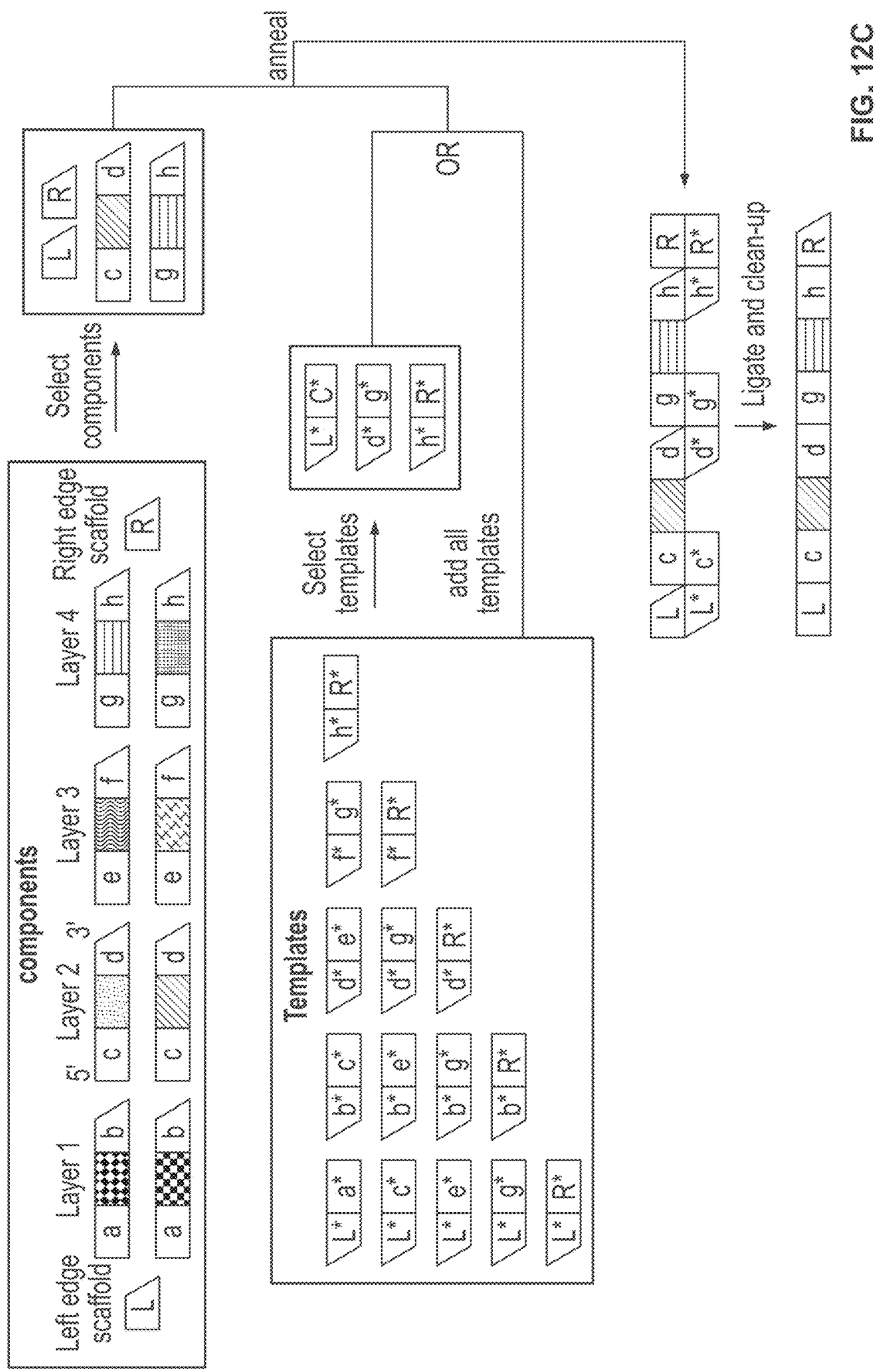
Figure 12D:
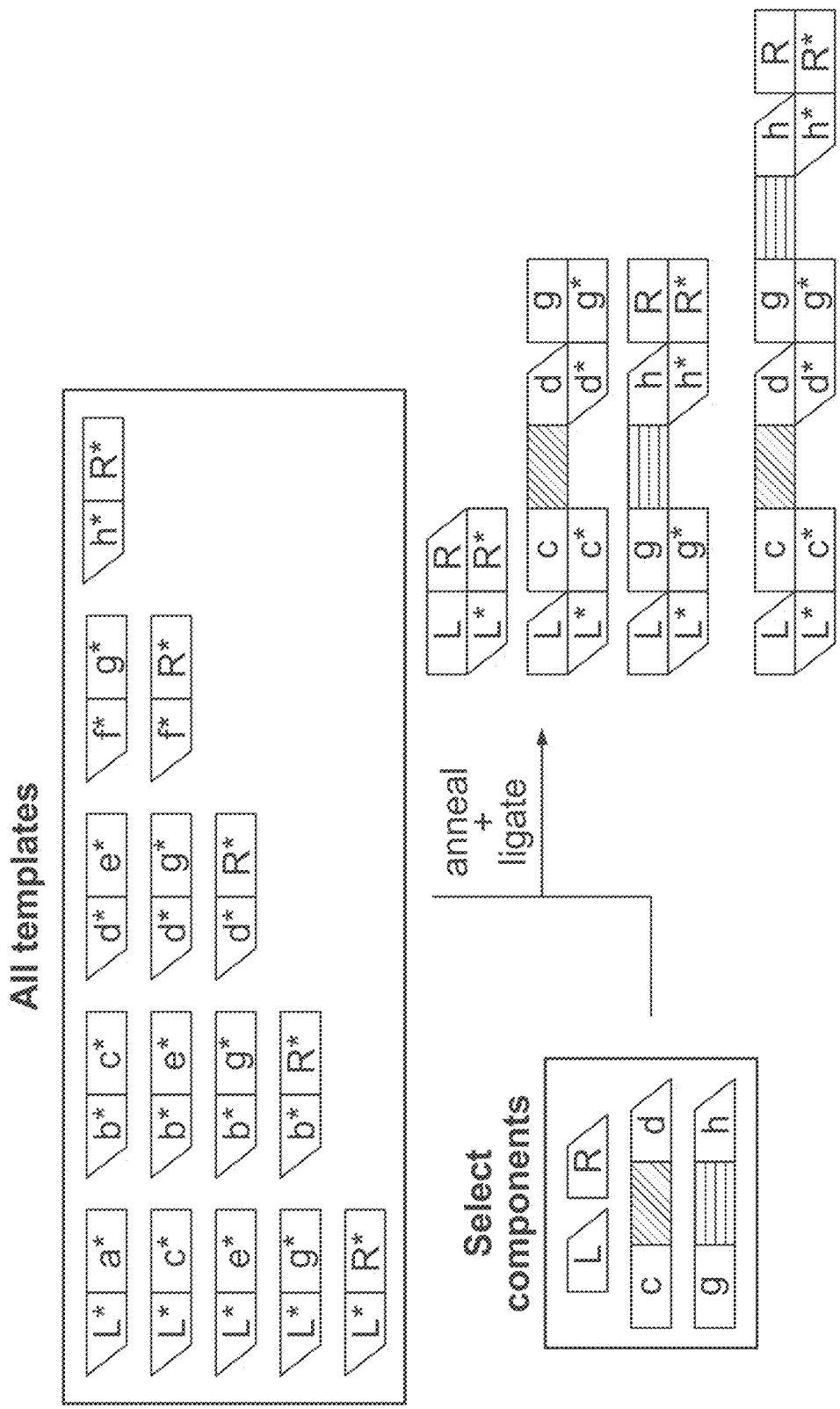

The MchooseK scheme may be implemented using template directed ligation (See Chemical Methods Section B), as shown in FIG. 12C. As with the TDL implementation for the permutation scheme (FIG. 11C), components in this example are assembled between edge scaffolds that may or may not be included in the reaction master mix. Components may be divided into M layers, for example M=4 layers with predefined rank from 2 to M where the left edge scaffold may be rank 1 and the right edge scaffold may be rank M+1. Templates comprise nucleic acid sequences for the 3' to 5' ligation of any two components with lower rank to higher rank, respectively. There are $((M+1)^2+M+1)/2$ such templates. An individual identifier of any K components from distinct layers may be constructed by combining those selected components in a ligation reaction with the corresponding K+1 staples used to bring the K components together with the edge scaffolds in their rank order. Such a reaction set up may yield the nucleic acid sequence corresponding to the target identifier between the edge scaffolds. Alternatively, a reaction mix comprising all templates may be combined with the select components to assemble the target identifier. This alternative method may generate various nucleic acid sequences with the same edge sequences but distinct lengths (if all component lengths are equal), as illustrated in FIG. 12D. The target identifier (bottom) may be isolated from byproduct nucleic acid sequences by size. See Chemical Methods Section E about nucleic acid size-selection.

Figure 13A:
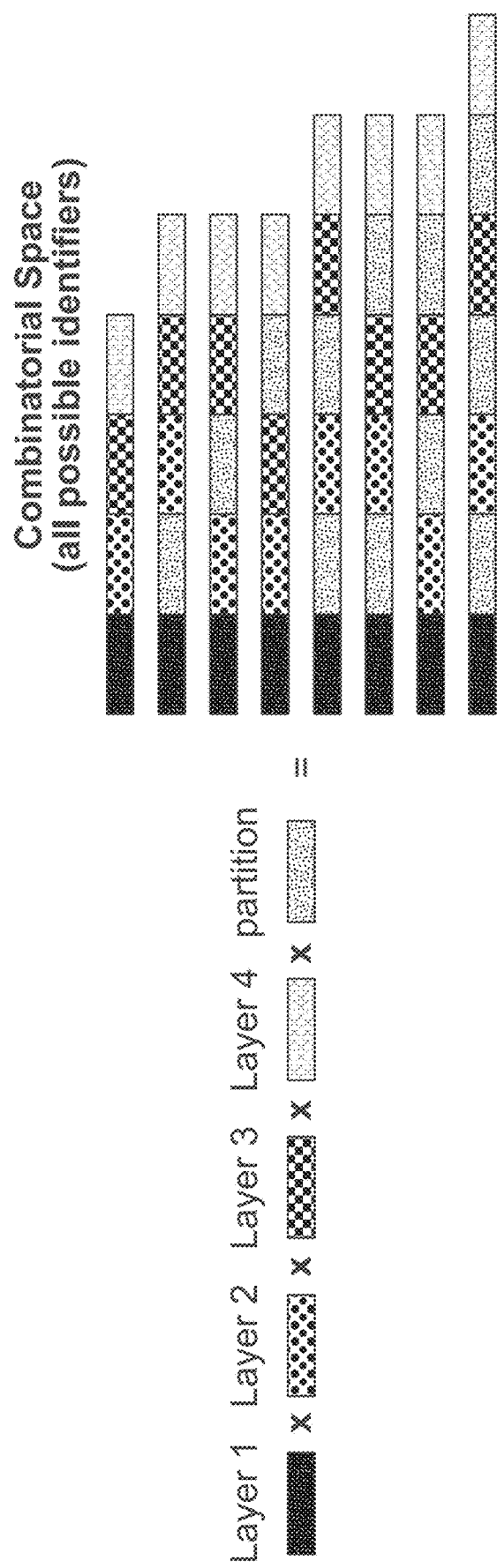
FIG. 13A and FIG. 13B schematically illustrates an example method, referred to as the "partition scheme" for constructing identifiers with partitioned components.
Figure 13B:
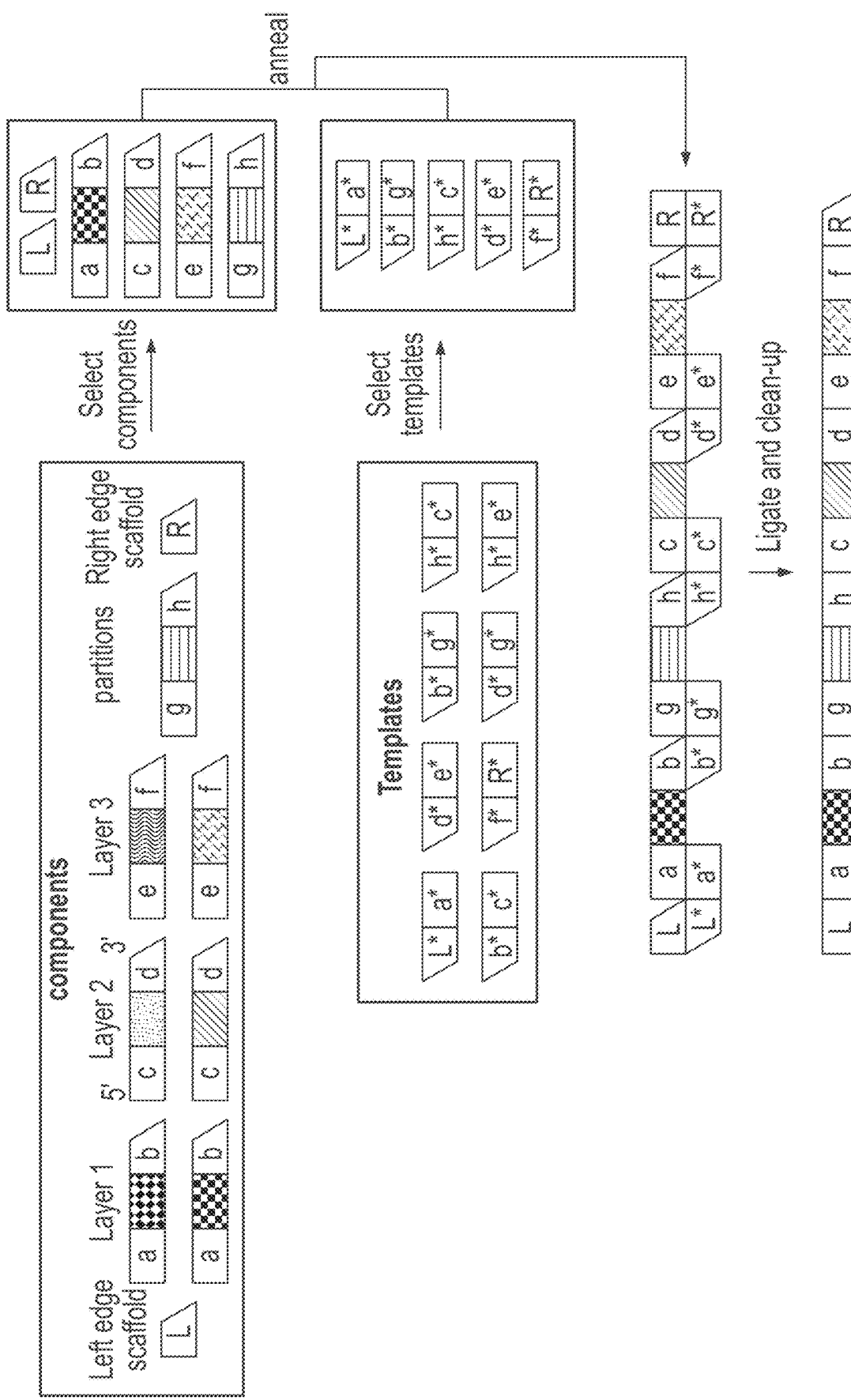

FIGS. 13A and 13B schematically illustrate an example method, referred to as the "partition scheme" for constructing identifiers with partitioned components. FIG. 13A shows an example of the combinatorial space of identifiers that may be constructed using the partition scheme. An individual identifier may be constructed by assembling one component from each layer in a fixed order with the optional placement of any partition (specially classified component) between any two components of different layers. For example, a set of components may be organized into one partition component and four layers containing one component each. A component from each layer may be combined in a fixed order and a single partition component may be assembled in various locations between layers. An identifier in this combinatorial space may comprise no partition components, a partition component between the components from the first and second layer, a partition between the components from the second and third layer, and so on to make a combinatorial space of eight possible identifiers. In general, with M layers, each with N components, and p partition components, there are $N^K(p+1)^{M-1}$ possible identifiers that may be constructed. This method may generate identifiers of various lengths.

FIG. 13B shows an example implementation of the partition scheme using template directed ligation (See Chemical Methods Section B). Templates comprise nucleic acid sequences for ligating together one component from each of M layers in a fixed order. For each partition component, additional pairs of templates exist that enable the partition component to ligate in between the components from any two adjacent layers. For example a pair of templates such that one template (with sequence g*b* (5' to 3') for example) in a pair enables the 3' end of layer 1 (with sequence b) to ligate to the 5' end of the partition component (with sequence g) and such that the second template in the pair (with sequence c*h* (5' to 3') for example) enables the 3' end of the partition component (with sequence h) to ligate to the 5' end of layer 2 (with sequence c). To insert a partition between any two components of adjacent layers, the standard template for ligating together those layers may be excluded in the reaction and the pair of templates for ligating the partition in that position may be selected in the reaction. In the current example, targeting the partition component between layer 1 and layer 2 may use the pair of templates c*h* (5' to 3') and g*b* (5' to 3') to select for the reaction rather than the template c*b* (5' to 3'). Components may be assembled between edge scaffolds that may be included in the reaction mix (along with their corresponding templates for ligating to the first and Mth layers, respectively). In general, a total of around M−1+2*p*(M−1) selectable templates may be used for this method for M layers and p partition components. This implementation of the partition scheme may generate various nucleic acid sequences in a reaction with the same edge sequences but distinct lengths.

The target identifier may be isolated from byproduct nucleic acid sequences by DNA size selection. Specifically, there may be exactly one nucleic acid sequence product with exactly M layer components. If the layer components are designed large enough compared to the partition components, it may be possible to define a universal size selection region whereby the identifier (and none of the non-targeted byproducts) may be selected regardless of the particular partitioning of the components within the identifier, thereby allowing for multiple partitioned identifiers from multiple reactions to be isolated in the same size selection step. See Chemical Methods Section E about nucleic acid size-selection.

Figure 14A:
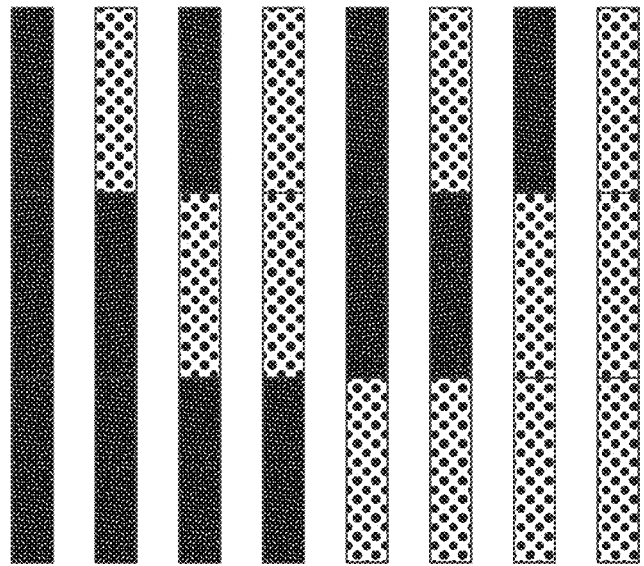
FIG. 14A and FIG. 14B schematically illustrates an example method, referred to as the "unconstrained string" (or USS) scheme, for constructing identifiers made up of any string of components from a number of possible components.
Figure 14A:
Figure 14B:
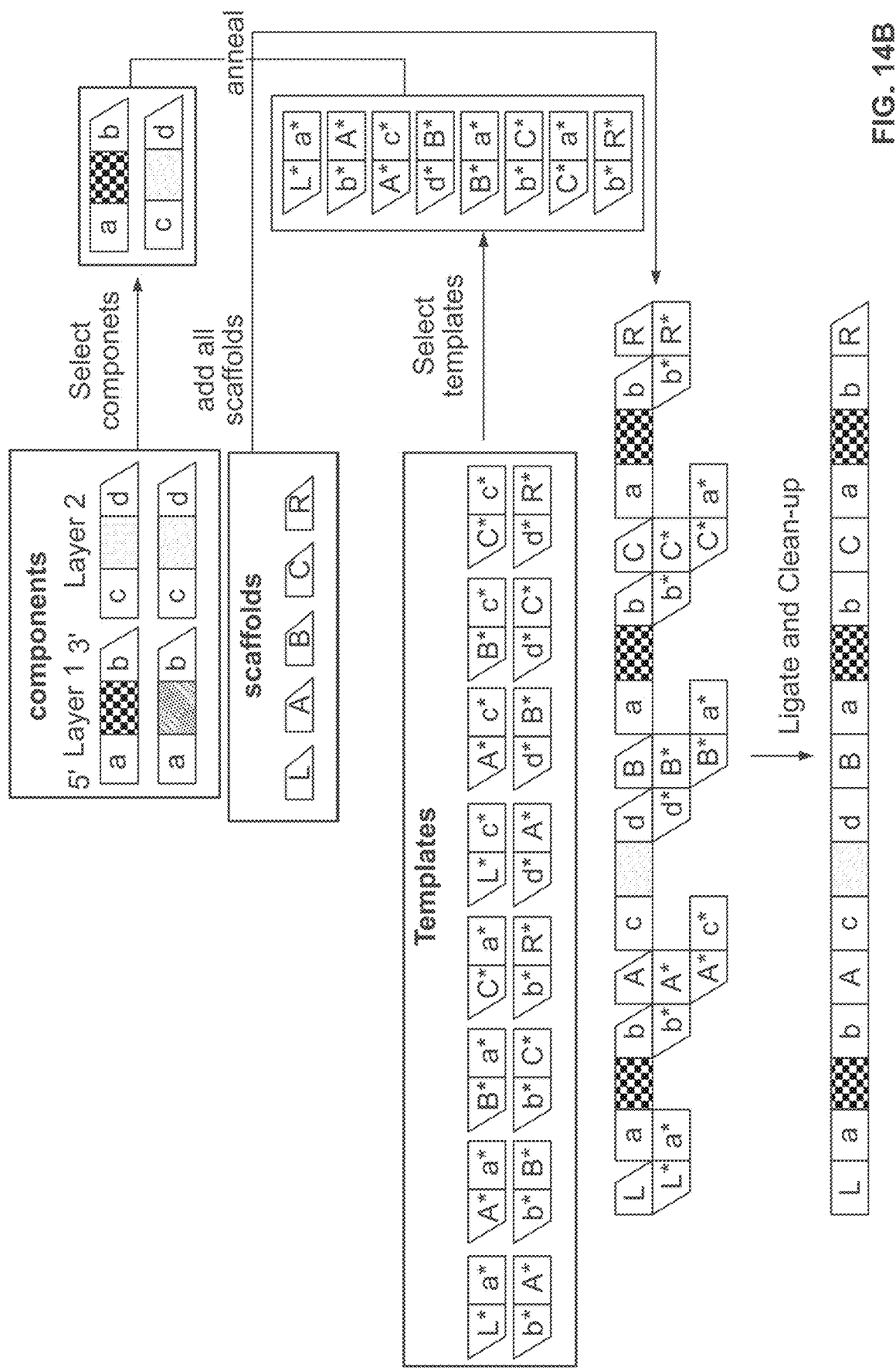

FIGS. 14A and 14B schematically illustrates an example method, referred to as the "unconstrained string scheme" or "USS", for constructing identifiers made up of any string of components from a number of possible components. FIG. 14A shows an example of the combinatorial space of 3-component (or 4-scaffold) length identifiers that may be constructed using the unconstrained string scheme. The unconstrained string scheme constructs an individual identifier of length K components with one or more distinct components each taken from one or more layers, where each distinct component can appear at any of the K component positions in the identifier (allowing for repeats). For example, for two layers, each comprising one component, there are eight possible 3-component length identifiers. In general, with M layers, each with one component, there are MK possible identifiers of length K components. FIG. 14B shows an example implementation of the unconstrained string scheme using template directed ligation (see Chemical Methods Section B). In this method, K+1 single-stranded and ordered scaffold DNA components (including two edge scaffolds and K−1 internal scaffolds) are present in the reaction mix. An individual identifier comprises a single component ligated between every pair of adjacent scaffolds. For example, a component ligated between scaffolds A and B, a component ligated between scaffolds C and D, and so on until all K adjacent scaffold junctions are occupied by a component. In a reaction, selected components from different layers are introduced to scaffolds along with selected pairs of staples that direct them to assemble onto the appropriate scaffolds. For example, the pair of staples a*L* (5' to 3') and A*b* (5' to 3') direct the layer 1 component with a 5' end region 'a' and 3' end region 'b' to ligate in between the L and A scaffolds. In general, with M layers and K+1 scaffolds, 2*M*K selectable staples may be used to construct any USS identifier of length K Because the staples that connect a component to a scaffold on the 5' end are disjoint from the staples that connect the same component to a scaffold on the 3' end, nucleic acid byproducts may form in the reaction with equal edge scaffolds as the target identifier, but with less than K components (less than K+1 scaffolds) or with more than K components (more than K+1 scaffolds). The targeted identifier may form with exactly K components (K+1 scaffolds) and may therefore be selectable through techniques like DNA size selection if all components are designed to be equal in length and all scaffolds are designed to be equal in length. See Chemical Methods Section E on nucleic acid size selection. In certain embodiments of the unconstrained string scheme where there may be one component per layer, that component may solely comprise a single distinct nucleic acid sequence that fulfills all three roles of (1) an identification barcode, (2) a hybridization region for staple-mediated ligation of the 5' end to a scaffold, and (3) a hybridization region for staple mediated ligation of the 3' end to a scaffold.

The internal scaffolds illustrated in FIG. 14B may be designed such that they use the same hybridization sequence for both the staple-mediated 5' ligation of the scaffold to a component and the staple-mediated 3' ligation of the scaffold to another (not necessarily distinct) component. Thus the depicted one-scaffold, two-staple stacked hybridization events in FIG. 14B represent the statistical back-and-forth hybridization events that occur between the scaffold and each of the staples, thus enabling both 5' component ligation and 3' component ligation. In other embodiments of the unconstrained string scheme, the scaffold may be designed with two concatenated hybridization regions—a distinct 3' hybridization region for staple-mediated 3' ligation and a distinct 5' hybridization region for staple-mediated 5' ligation.

Figure 15A:
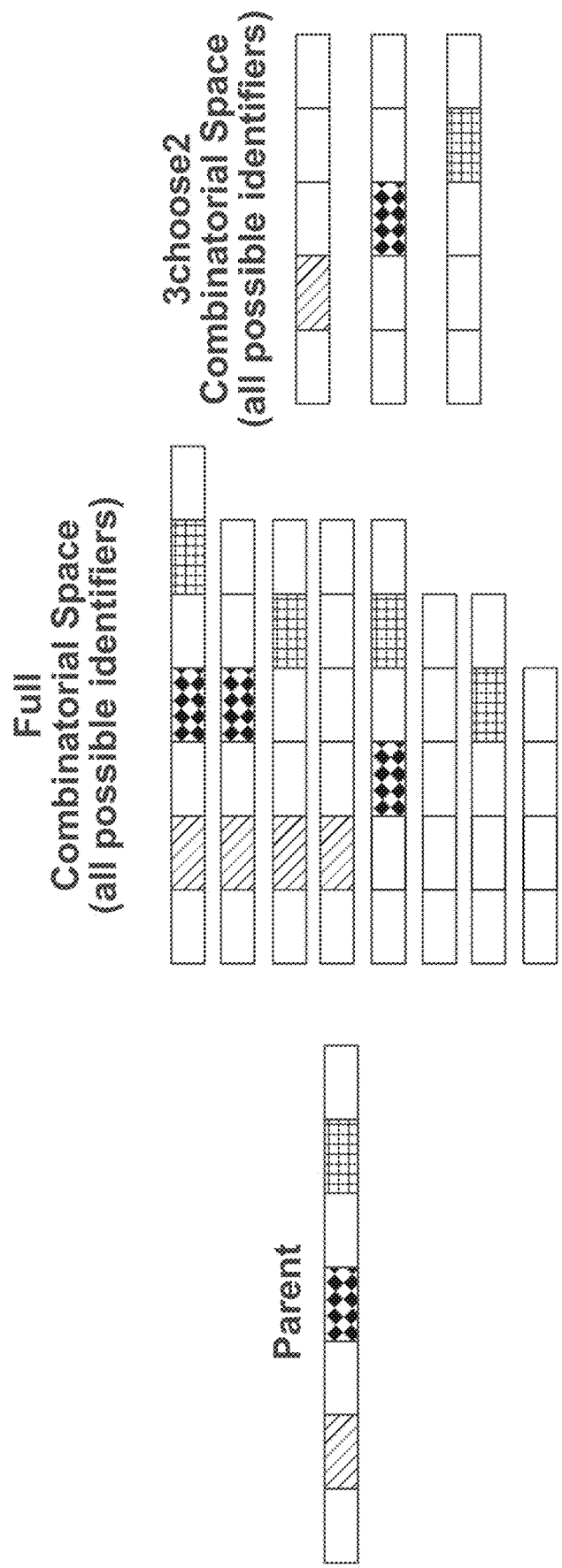
FIG. 15A and FIG. 15B schematically illustrates an example method, referred to as "component deletion" for constructing identifiers by removing components from a parent identifier.
Figure 15B:
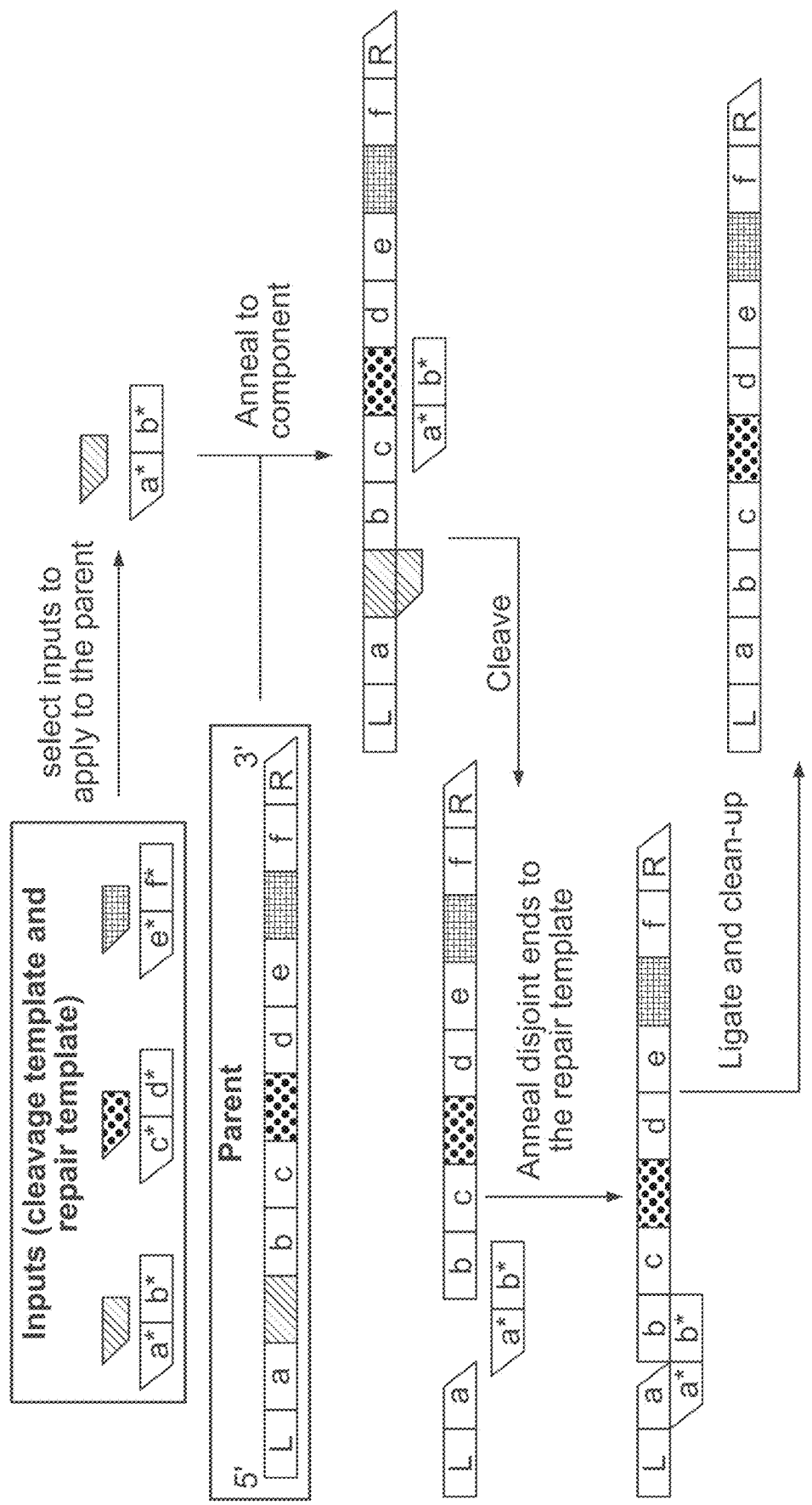

FIGS. 15A and 15B schematically illustrate an example method, referred to as the "component deletion scheme", for constructing identifiers by deleting nucleic acid sequences (or components) from a parent identifier. FIG. 15A shows an example of the combinatorial spaces of possible identifiers that may be constructed using the component deletion scheme. In this example, a parent identifier may comprise multiple components. A parent identifier may comprise more than or equal to about 2, 3, 4, 5, 6, 7, 8, 9, 10, 20, 30, 40, 50 or more components. An individual identifier may be constructed by selectively deleting any number of components from N possible components, leading to a "full" combinatorial space of size 2N, or by deleting a fixed number of K components from N possible components, thus leading to an "NchooseK" combinatorial space of size NchooseK. In an example with a parent identifier with 3 components, the full combinatorial space may be 8 and the 3choose2 combinatorial space may be 3.

FIG. 15B shows an example implementation of the component deletion scheme using double stranded targeted cleavage and repair (DSTCR). The parent sequence may be a single stranded DNA substrate comprising components flanked by nuclease-specific target sites (which can be 4 or less bases in length), and where the parent may be incubated with one or more double-strand-specific nucleases corresponding to the target sites. An individual component may be targeted for deletion with a complementary single stranded DNA (or cleavage template) that binds the component DNA (and flanking nuclease sites) on the parent, thus forming a stable double stranded sequence on the parent that may be cleaved on both ends by the nucleases. Another single stranded DNA (or repair template) hybridizes to the resulting disjoint ends of the parent (between which the component sequence had been) and brings them together for ligation, either directly or bridged by a replacement sequence, such that the ligated sequences on the parent no longer contain active nuclease-targeted sites. We refer to this method as "Double Stranded Targeted Cleavage" (DSTC). Size selection may be used to select for identifiers with a certain number of deleted components. See Chemical Methods Section E about nucleic acid size-selection.

Alternatively, or in addition to, the parent identifier may be a double or single stranded nucleic acid substrate comprising components separated by spacer sequences such that no two components are flanked by the same sequence. The parent identifier may be incubated with Cas9 nuclease. An individual component may be targeted for deletion with guide ribonucleic acids (the cleavage templates) that bind to the edges of the component and enable Cas9-mediated cleavage at its flanking sites. A single stranded nucleic acid (the repair template) may hybridize to the resulting disjoint ends of the parent identifier (e.g., between the ends where the component sequence had been), thus bringing them together for ligation. Ligation may be done directly or by bridging the ends with a replacement sequence, such that the ligated sequences on the parent no longer contain spacer sequences that can be targeted by Cas9. We refer to this method as "sequence specific targeted cleavage and repair" or "SSTCR".

Identifiers may be constructed by inserting components into a parent identifier using a derivative of DSTCR. A parent identifier may be single stranded nucleic acid substrate comprising nuclease-specific target sites (which can be 4 or less bases in length), each embedded within a distinct nucleic acid sequence. The parent identifier may be incubated with one or more double-strand-specific nucleases corresponding to the target sites. An individual target site on the parent identifier may be targeted for component insertion with a complementary single stranded nucleic acid (the cleavage template) that binds the target site and the distinct surrounding nucleic acid sequence on the parent identifier, thus forming a double stranded site. The double-stranded site may be cleaved by a nuclease. Another single stranded nucleic acid (the repair template) may hybridize to the resulting disjoint ends of the parent identifier and bring them together for ligation, bridged by a component sequence, such that the ligated sequences on the parent no longer contain active nuclease-targeted sites. Alternatively a derivative of SSTCR may be used to insert components into a parent identifier. The parent identifier may be a double or single-stranded nucleic acid and the parent may be incubated with a Cas9 nuclease. A distinct site on the parent identifier may be targeted for cleavage with a guide RNA (the cleavage template). A single stranded nucleic acid (the repair template) may hybridize to the disjoint ends of the parent identifier and bring them together for ligation, bridged by a component sequence, such that the ligated sequences on the parent identifier no longer contain active nuclease-targeted sites. Size selection may be used to select for identifiers with a certain number of component insertions.

Figure 16:
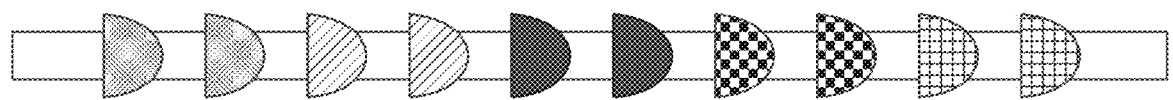
FIG. 16 schematically illustrates a parent identifier with recombinase recognition sites where further identifiers may be constructed by applying recombinases to the parent identifier.

FIG. 16 schematically illustrates a parent identifier with recombinase recognition sites. Recognition sites of different patterns can be recognized by different recombinases. All recognition sites for a given set of recombinases are arranged such that the nucleic acids in between them may be excised if the recombinase is applied. The nucleic acid strand shown in FIG. 16 can adopt $2^5=32$ different sequences depending on the subset of recombinases that are applied to it. In some embodiments, as depicted in FIG. 16, unique molecules can be generated using recombinases to excise, shift, invert, and transpose segments of DNA to create different nucleic acid molecules. In general, with N recombinases there can be $2^N$ possible identifiers built from a parent. In some embodiments, multiple orthogonal pairs of recognition sites from different recombinases may be arranged on a parent identifier in an overlapping fashion such that the application of one recombinase affects the type of recombination event that occurs when a downstream recombinase is applied (see Roquet et al., Synthetic recombinase-based state machines in living cells, Science 353 (6297): aad8559 (2016), which is entirely incorporated herein by reference). Such a system may be capable of constructing a different identifier for every ordering of N recombinases, N!. Recombinases may be of the tyrosine family such as Flp and Cre, or of the large serine recombinase family such as PhiC31, BxbI, TP901, or A118. The use of recombinases from the large serine recombinase family may be advantageous because they facilitate irreversible recombination and therefore may produce identifiers more efficiently than other recombinases.

In some instances, a single nucleic acid sequence can be programmed to become many distinct nucleic acid sequences by applying numerous recombinases in a distinct order. Approximately $\sim e^1 M!$ distinct nucleic acid sequences may be generated by applying M recombinases in different subsets and orders thereof, when the number of recombinases, M, may be less than or equal to 7 for the large serine recombinase family. When the number of recombinases, M, may be greater than 7, the number of sequences that can be produced approximates $3.9^M$, see e.g., Roquet et al., Synthetic recombinase-based state machines in living cells, Science 353 (6297): aad8559 (2016), which is entirely incorporated herein by reference. Additional methods for producing different DNA sequences from one common sequence can include targeted nucleic acid editing enzymes such as CRISPR-Cas, TALENS, and Zinc Finger Nucleases. Sequences produced by recombinases, targeted editing enzymes or the like can be used in conjunction with any of the previous methods, for example methods disclosed in any of the figures and disclosure in the present application.

If the bit-stream of information to be encoded is larger than that which can be encoded by any single nucleic acid molecule, then the information can be split and indexed with nucleic acid sequence barcodes. Moreover, any subset of size k nucleic acid molecules from the set of N nucleic acid molecules can be chosen to produce log 2(Nchoosek) bits of information. Barcodes may be assembled onto the nucleic acid molecules within the subsets of size k to encode even longer bit streams. For example, M barcodes may be used to produce $M*\log_2(Nchoosek)$ bits of information. Given a number, N, of available nucleic acid molecules in a set and a number, M of available barcodes, subsets of size $k=k_0$ may be chosen to minimize the total number of molecules in a pool to encode a piece of information. A method for encoding digital information can comprise steps for breaking up the bit stream and encoding the individual elements. For example, a bit stream comprising 6 bits can be split into 3 components each component comprising two bits. Each two bit component can be barcoded to form an information cassette, and grouped or pooled together to form a hyper-pool of information cassettes.

Barcodes can facilitate information indexing when the amount of digital information to be encoded exceeds the amount that can fit in one pool alone. Information comprising longer strings of bits and/or multiple bytes can be encoded by layering the approach disclosed in FIG. 3, for example, by including a tag with unique nucleic acid sequences encoded using the nucleic acid index. Information cassettes or identifier libraries can comprise nitrogenous bases or nucleic acid sequences that include unique nucleic acid sequences that provide location and bit-value information in addition to a barcode or tag which indicates the component or components of the bit stream that a given sequence corresponds to. Information cassettes can comprise one or more unique nucleic acid sequences as well as a barcode or tag. The barcode or tag on the information cassette can provide a reference for the information cassette and any sequences included in the information cassette. For example, the tag or barcode on an information cassette can indicate which portion of the bit stream or bit component of the bit steam the unique sequence encodes information for (e.g., the bit value and bit position information for).

Using barcodes, more information in bits can be encoded in a pool than the size of the combinatorial space of possible identifiers. A sequence of 10 bits, for example, can be separated into two sets of bytes, each byte comprising 5 bits. Each byte can be mapped to a set of 5 possible distinct identifiers. Initially, the identifiers generated for each byte can be the same, but they may be kept in separate pools or else someone reading the information may not be able to tell which byte a particular nucleic acid sequence belongs to. However each identifier can be barcoded or tagged with a label that corresponds to the byte for which the encoded information applies (e.g., barcode one may be attached to sequences in the nucleic acid pool to provide the first five bits and barcode two may be attached to sequences in the nucleic acid pool to provide the second five bits), and then the identifiers corresponding to the two bytes can be combined into one pool (e.g., "hyper-pool" or one or more identifier libraries). Each identifier library of the one or more combined identifier libraries may comprise a distinct barcode that identifies a given identifier as belonging to a given identifier library. Methods for adding a barcode to each identifier in an identifier library can comprise using PCR, Gibson, ligation, or any other approach that enables a given barcode (e.g., barcode 1) to attach to a given nucleic acid sample pool (e.g., barcode 1 to nucleic acid sample pool 1 and barcode 2 to nucleic acid sample pool 2). The sample from the hyper-pool can be read with sequencing methods, and sequencing information can be parsed using the barcode or tag. A method using identifier libraries and barcodes with a set of M barcodes and N possible identifiers (the combinatorial space) can encode a stream of bits with a length equivalent to the product of M and N.

In some embodiments, identifier libraries may be stored in an array of wells. The array of wells may be defined as having n columns and q rows and each well may comprise two or more identifier libraries in a hyper-pool. The information encoded in each well may constitute one large contiguous item of information of size n×q larger than the information contained in each of the wells. An aliquot may be taken from one or more of the wells in the array of wells and the encoding may be read using sequencing, hybridization, or PCR.

A nucleic acid sample pool, hyper-pool, identifier library, group of identifier libraries, or a well, containing a nucleic acid sample pool or hyper-pool may comprise unique nucleic acid molecules (e.g., identifiers) corresponding to bits of information and a plurality of supplemental nucleic acid sequences. The supplemental nucleic acid sequences may not correspond to encoded data (e.g., do not correspond to a bit value). The supplemental nucleic acid samples may mask or encrypt the information stored in the sample pool. The supplemental nucleic acid sequences may be derived from a biological source or synthetically produced. Supplemental nucleic acid sequences derived from a biological source may include randomly fragmented nucleic acid sequences or rationally fragmented sequences. The biologically derived supplemental nucleic acids may hide or obscure the data-containing nucleic acids within the sample pool by providing natural genetic information along with the synthetically encoded information, especially if the synthetically encoded information (e.g., the combinatorial space of identifiers) is made to resemble natural genetic information (e.g., a fragmented genome). In an example, the identifiers are derived from a biological source and the supplemental nucleic acids are derived from a biological source. A sample pool may contain multiple sets of identifiers and supplemental nucleic acid sequences. Each set of identifiers and supplemental nucleic acid sequences may be derived from different organisms. In an example, the identifiers are derived from one or more organisms and the supplemental nucleic acid sequences are derived from a single, different organism. The supplemental nucleic acid sequences may also be derived from one or more organism and the identifiers may be derived from a single organism that is different from the organism that the supplemental nucleic acids are derived from. Both the identifiers and the supplemental nucleic acid sequences may be derived from multiple different organisms. A key may be used to distinguish the identifiers from the supplemental nucleic acid sequences.

The supplemental nucleic acid sequences may store metadata about the written information. The metadata may comprise extra information for determining and/or authorizing the source of the original information and or the intended recipient of the original information. The metadata may comprise extra information about the format of the original information, the instruments and methods used to encode and write the original information, and the date and time of writing the original information into the identifiers. The metadata may comprise additional information about the format of the original information, the instruments and methods used to encode and write the original information, and the date and time of writing the original information into nucleic acid sequences. The metadata may comprise additional information about modifications made to the original information after writing the information into nucleic acid sequences. The metadata may comprise annotations to the original information or one or more references to external information. Alternatively, or in addition to, the metadata may be stored in one or more barcodes or tags attached to the identifiers.

The identifiers in an identifier pool may have the same, similar, or different lengths than one another. The supplemental nucleic acid sequences may have a length that is less than, substantially equal to, or greater than the length of the identifiers. The supplemental nucleic acid sequences may have an average length that is within one base, within two bases, within three bases, within four bases, within five bases, within six bases, within seven bases, within eight bases, within nine bases, within ten bases, or within more bases of the average length of the identifiers. In an example, the supplemental nucleic acid sequences are the same or substantially the same length as the identifiers. The concentration of supplemental nucleic acid sequences may be less than, substantially equal to, or greater than the concentration of the identifiers in the identifiers library. The concentration of the supplemental nucleic acids may be less than or equal to about 1%, 10%, 20%, 40%, 60%, 80%, 100, %, 125%, 150%, 175%, 200%, 1000%, $1\times10^{4}$%, $1\times10^{5}$%, $1\times10^{6}$%, $1\times10^{7}$%, $1\times10^{8}$% or less than the concentration of the identifiers. The concentration of the supplemental nucleic acids may be greater than or equal to about 1%, 10%, 20%, 40%, 60%, 80%, 100, %, 125%, 150%, 175%, 200%, 1000%, $1\times10^{4}$%, $1\times10^{5}$%, $1\times10^{6}$%, $1\times10^{7}$%, $1\times10^{8}$% or more than the concentration of the identifiers. Larger concentrations may be beneficial for obfuscation or concealing data. In an example, the concentration of the supplemental nucleic acid sequences are substantially greater (e.g., $1\times10^{8}$% greater) than the concentration of identifiers in an identifier pool.

Methods for Copying and Accessing Data Stored in Nucleic Acid Sequences

In another aspect, the present disclosure provides methods for copying (or replicating) information encoded in nucleic acid sequence(s). A method for copying information encoded in nucleic acid sequence(s) may comprise (a) providing an identifier library and (b) constructing one or more copies of the identifier library. An identifier library may comprise a subset of a plurality of identifiers from a larger combinatorial space. Each individual identifier of the plurality of identifiers may correspond to an individual symbol in a string of symbols. An identifier may comprise one or more components. A component may comprise a nucleic acid sequence.

In another aspect, the present disclosure provides methods for accessing information encoded in nucleic acid sequences. A method for accessing information encoded in nucleic acid sequences may comprise (a) providing an identifier library, and (b) extracting a portion or a subset of the identifiers present in the identifier library from the identifier library. An identifier library may comprise a subset of a plurality of identifiers from a larger combinatorial space. Each individual identifier of the plurality of identifiers may correspond to an individual symbol in a string of symbols. An identifier may comprise one or more components. A component may comprise a nucleic acid sequence.

Information may be written into one or more identifier libraries as described elsewhere herein. Identifiers may be constructed using any method described elsewhere herein. Stored data may be copied by generating copies of the individual identifiers in an identifier library or in one or more identifier libraries. A portion of the identifiers may be copied or an entire library may be copied. Copying may be performed by amplifying the identifiers in an identifier library. When one or more identifier libraries are combined, a single identifier library or multiple identifier libraries may be copied. If an identifier library comprises supplemental nucleic acid sequences, the supplemental nucleic acid sequences may or may not be copied.

Identifiers in an identifier library may be constructed to comprise one or more common primer binding sites. The one or more binding sites may be located at the edges of each identifier or interweaved throughout each identifier. The primer binding site may allow for an identifier library specific primer pair or a universal primer pair to bind to and amplify the identifiers. All the identifiers within an identifier library or all the identifiers in one or more identifier libraries may be replicated multiple times by multiple PCR cycles. Conventional PCR may be used to copy the identifiers and the identifiers may be exponentially replicated with each PCR cycle. The number of copies of an identifier may increase exponentially with each PCR cycle. Linear PCR may be used to copy the identifiers and the identifiers may be linearly replicated with each PCR cycle. The number of identifier copies may increase linearly with each PCR cycle. The identifiers may be ligated into a circular vector prior to PCR amplification. The circle vector may comprise a barcode at each end of the identifier insertion site. The PCR primers for amplifying identifiers may be designed to prime to the vector such that the barcoded edges are included with the identifier in the amplification product. During amplification, recombination between identifiers may result in copied identifiers that comprise non-correlated barcodes on each edge. The non-correlated barcodes may be detectable upon reading the identifiers. Identifiers containing non-correlated barcodes may be considered false positives and may be disregarded during the information decoding process. See Chemical Methods Section D.

Information may be encoded by assigning each bit of information to a unique nucleic acid molecule. For example, three sample sets (X, Y, and Z) each containing two nucleic acid sequences may assemble into eight unique nucleic acid molecules and encode eight bits of data:

N1=X1Y1Z1
N2=X1Y1Z2
N3=X1Y2Z1
N4=X1Y2Z2
N5=X2Y1Z1
N6=X2Y1Z2
N7=X2Y2Z1
N8=X2Y2Z2

Each bit in a string may then be assigned to the corresponding nucleic acid molecule (e.g., N1 may specify the first bit, N2 may specify the second bit, N3 may specify the third bit, and so forth). The entire bit string may be assigned to a combination of nucleic acid molecules where the nucleic acid molecules corresponding to bit-values of '1' are included in the combination or pool. For example, in UTF-8 codings, the letter 'K' may be represented by the 8-bit string code 01001011 which may be encoded by the presence of four nucleic acid molecules (e.g., X1Y1Z2, X2Y1Z1, X2Y2Z1, and X2Y2Z2 in the above example).

The information may be accessed through sequencing or hybridization assays. For example, primers or probes may be designed to bind to common regions or the barcoded region of the nucleic acid sequence. This may enable amplification of any region of the nucleic acid molecule. The amplification product may then be read by sequencing the amplification product or by a hybridization assay. In the above example encoding the letter 'K', if the first half of the data is of interest a primer specific to the barcode region of the X1 nucleic acid sequence and a primer that binds to the common region of the Z set may be used to amplify the nucleic acid molecules. This may return the sequence Y1Z2, which may encode for 0100. The substring of that data may also be accessed by further amplifying the nucleic acid molecules with a primer that binds to the barcode region of the Y1 nucleic acid sequence and a primer that binds to the common sequence of the Z set. This may return the Z2 nucleic acid sequence, encoding the substring 01. Alternatively, the data may be accessed by checking for the presence or absence of a particular nucleic acid sequence without sequencing. For example, amplification with a primer specific to the Y2 barcode may generate amplification products for the Y2 barcode, but not for the Y1 barcode. The presence of Y2 amplification product may signal a bit value of '1'. Alternatively, the absence of Y2 amplification products may signal a bit value of '0'.

PCR based methods can be used to access and copy data from identifier or nucleic acid sample pools. Using common primer binding sites that flank the identifiers in the pools or hyper-pools, nucleic acids containing information can be readily copied. Alternatively, other nucleic acid amplification approaches such as isothermal amplification may also be used to readily copy data from sample pools or hyper-pools (e.g., identifier libraries). See Chemical Methods Section D on nucleic acid amplification. In instances where the sample comprises hyper-pools, a particular subset of information (e.g., all nucleic acids relating to a particular barcode) can be accessed and retrieved by using a primer that binds the specific barcode at one edge of the identifier in the forward orientation, along with another primer that binds a common sequence on the opposite edge of the identifier in a reverse orientation. This process can be repeated multiple times to access sub-pools from sub-pools of identifiers (for example, all nucleic acids with two or more particular barcodes). For example, by using nested PCR, first with a primer that bind to a particular barcode on one edge, and then again with a particular primer that binds to a particular barcode one removed from said edge, and then again with a particular primer that binds to a barcode two removed from said edge, and so on. Various read-out methods can be used to pull information from the encoded nucleic acid; for example microarray (or any sort of fluorescent hybridization), digital PCR, quantitative PCR (qPCR), and various sequencing platforms can be further used to read out the encoded sequences and by extension digitally encoded data.

Figure 17A:
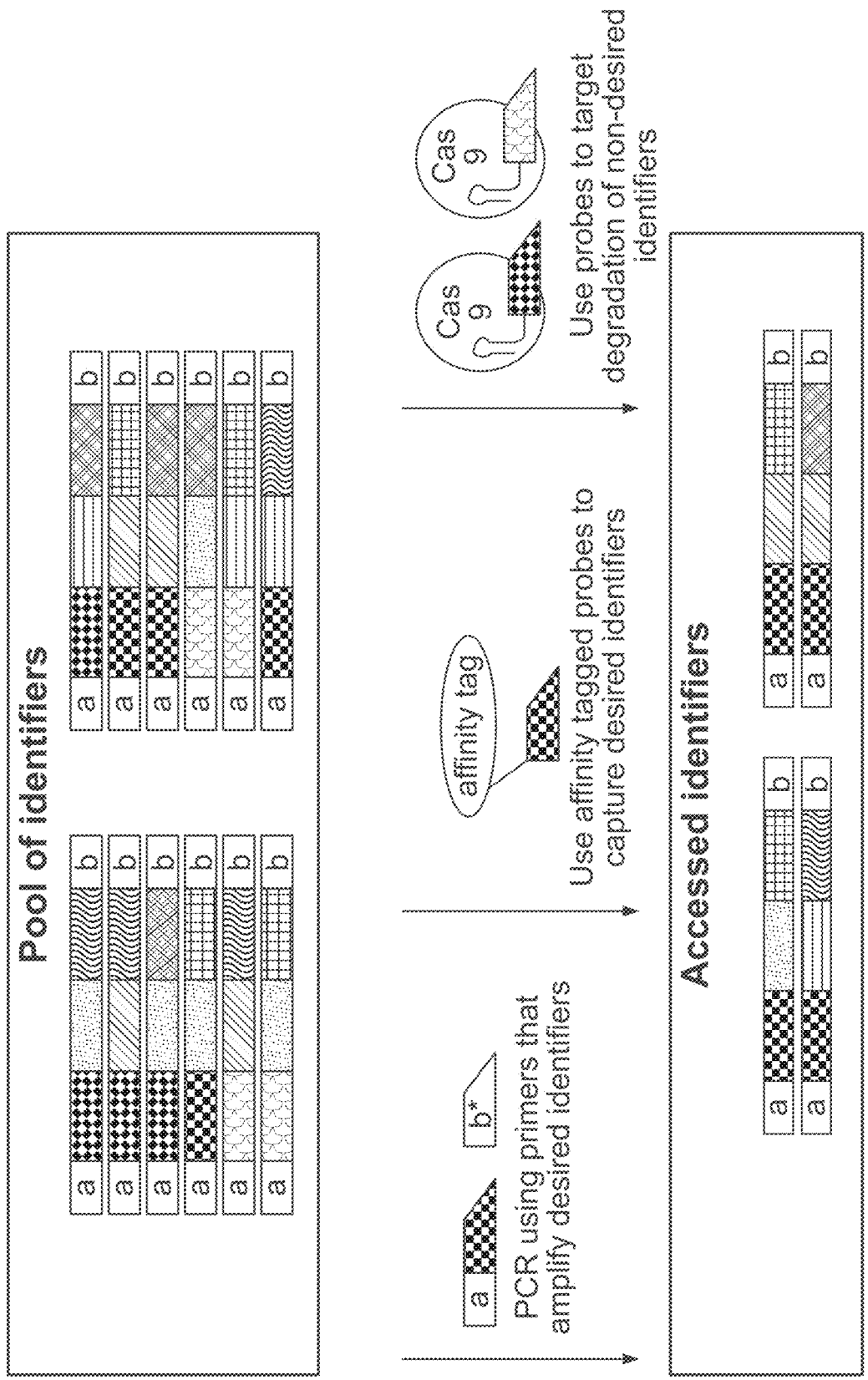
FIG. 17A, FIG. 17B, and FIG. 17C schematically illustrate an overview of example methods for accessing portions of information stored in nucleic acid sequences by accessing a number of particular identifiers from a larger number of identifiers.
Figure 17B:
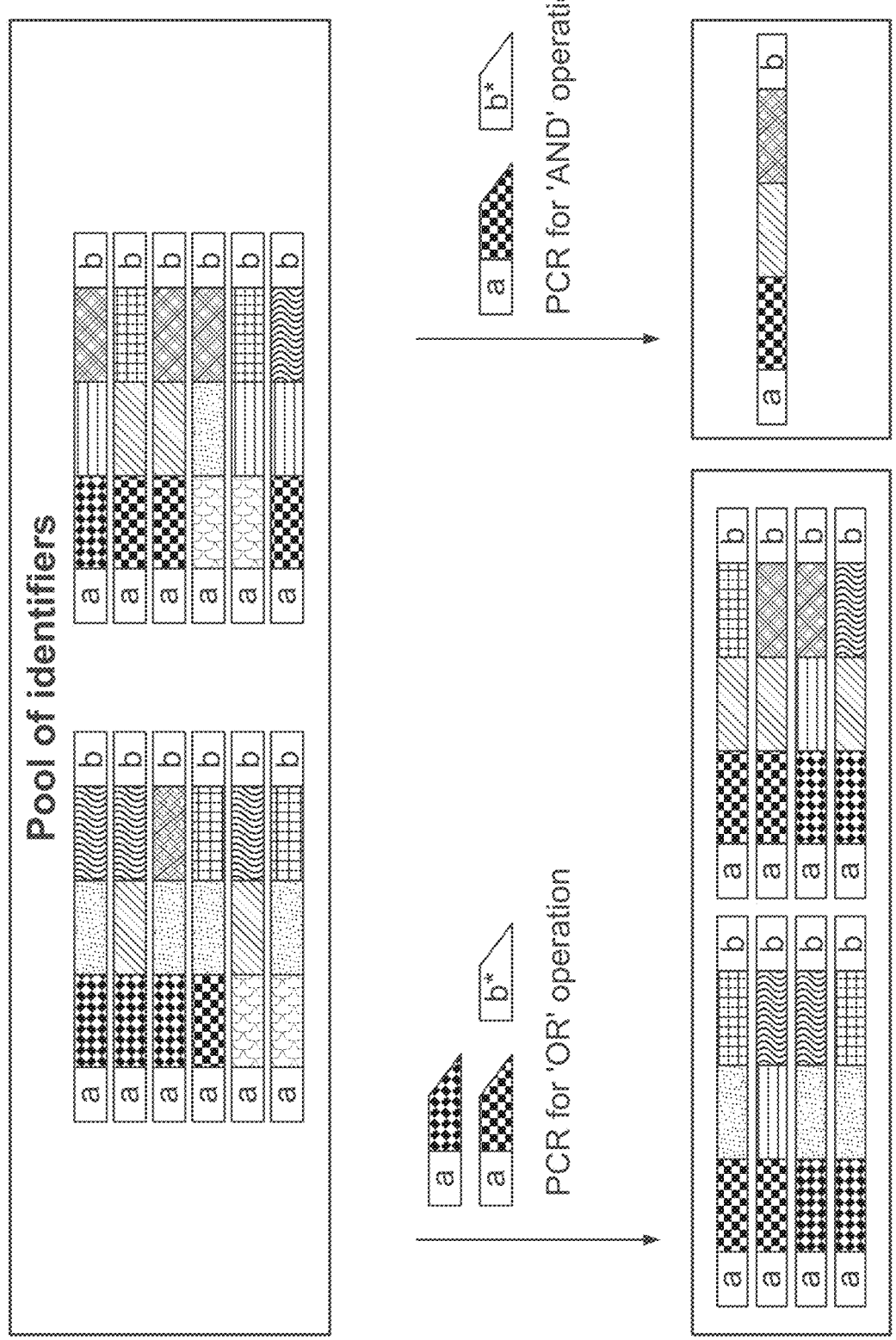
Figure 17C:
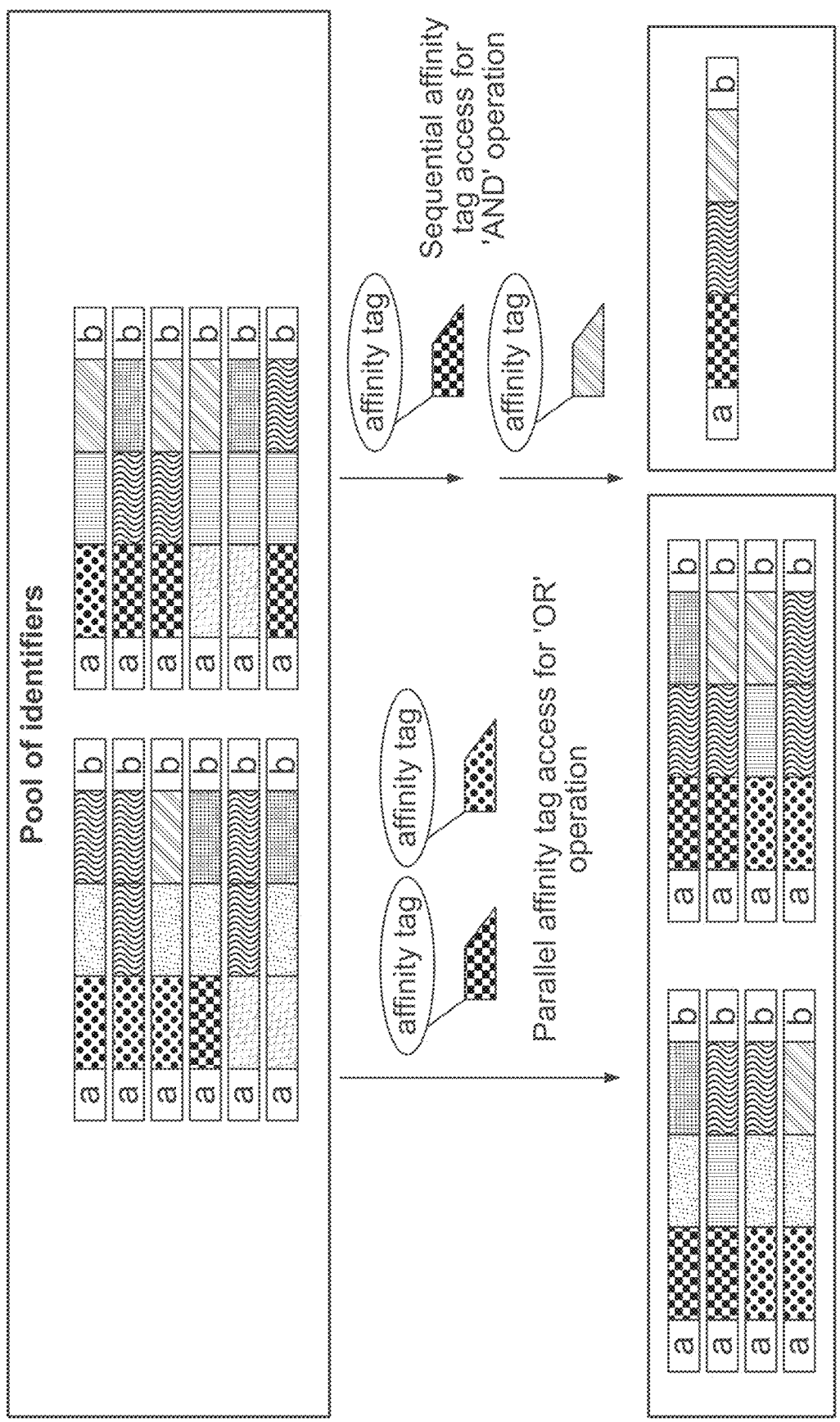

Accessing information stored in nucleic acid molecules (e.g., identifiers) may be performed by selectively removing the portion of non-targeted identifiers from an identifier library or a pool of identifiers or, for example, selectively removing all identifiers of an identifier library from a pool of multiple identifier libraries. Accessing data may also be performed by selectively capturing targeted identifiers from an identifier library or pool of identifiers. The targeted identifiers may correspond to data of interest within the larger item of information. A pool of identifiers may comprise supplemental nucleic acid molecules. The supplemental nucleic acid molecules may contain metadata about the encoded information or may be used to encrypt or mask the identifiers corresponding to the information. The supplemental nucleic acid molecules may or may not be extracted while accessing the targeted identifiers. FIGS. 17A-17C schematically illustrate an overview of example methods for accessing portions of information stored in nucleic acid sequences by accessing a number of particular identifiers from a larger number of identifiers. FIG. 17A shows example methods for using polymerase chain reaction, affinity tagged probes, and degradation targeting probes to access identifiers containing a specified component. For PCR-based access, a pool of identifiers (e.g., identifier library) may comprise identifiers with a common sequence at each end, a variable sequence at each end, or one of a common sequence or a variable sequence at each end. The common sequences or variable sequences may be primer binding sites. One or more primers may bind to the common or variable regions on the identifier edges. The identifiers with primers bound may be amplified by PCR. The amplified identifiers may significantly outnumber the non-amplified identifiers. During reading, the amplified identifiers may be identified. An identifier from an identifier library may comprise sequences on one or both of its ends that are distinct to that library, thus enabling a single library to be selectively accessed from a pool or group of more than one identifier libraries.

For affinity-tag based access, a process which may be referred to as nucleic acid capture, the components that constitute the identifiers in a pool may share complementarity with one or more probes. The one or more probes may bind or hybridize to the identifiers to be accessed. The probe may comprise an affinity tag. The affinity tags may bind to a bead, generating a complex comprising a bead, at least one probe, and at least one identifier. The beads may be magnetic, and together with a magnet, the beads may collect and isolate the identifiers to be accessed. The identifiers may be removed from the beads under denaturing conditions prior to reading. Alternatively, or in addition to, the beads may collect the non-targeted identifiers and sequester them away from the rest of the pool that can get washed into a separate vessel and read. The affinity tag may bind to a column. The identifiers to be accessed may bind to the column for capture. Column-bound identifiers may subsequently be eluted or denatured from the column prior to reading. Alternatively, the non-targeted identifiers may be selectively targeted to the column while the targeted identifiers may flow through the column. Accessing the targeted identifiers may comprise applying one or more probes to a pool of identifiers simultaneously or applying one or more probes to a pool of identifiers sequentially. See Chemical Methods Section F on nucleic acid capture.

For degradation based access, the components that constitute the identifiers in a pool may share complementarity with one or more degradation-targeting probes. The probes may bind to or hybridize with distinct components on the identifiers. The probe may be a target for a degradation enzyme, such as an endonuclease. In an example, one or more identifier libraries may be combined. A set of probes may hybridize with one of the identifier libraries. The set of probes may comprise RNA and the RNA may guide a Cas9 enzyme. A Cas9 enzyme may be introduced to the one or more identifier libraries. The identifiers hybridized with the probes may be degraded by the Cas9 enzyme. The identifiers to be accessed may not be degraded by the degradation enzyme. In another example, the identifiers may be single-stranded and the identifier library may be combined with a single-strand specific endonuclease(s), such as the S1 nuclease, that selectively degrades identifiers that are not to be accessed. Identifiers to be accessed may be hybridized with a complementary set of identifiers to protect them from degradation by the single-strand specific endonuclease(s). The identifiers to be accessed may be separated from the degradation products by size selection, such as size selection chromatography (e.g., agarose gel electrophoresis). Alternatively, or in addition, identifiers that are not degraded may be selectively amplified (e.g., using PCR) such that the degradation products are not amplified. The non-degraded identifiers may be amplified using primers that hybridize to each end of the non-degraded identifiers and therefore not to each end of the degraded or cleaved identifiers.

FIG. 17B shows example methods for using polymerase chain reaction to perform 'OR' or 'AND' operations to access identifiers containing multiple components. In an example, if two forward primers bind distinct sets of identifiers on the left end, then an 'OR' amplification of the union of those sets of identifiers may be accomplished by using the two forward primers together in a multiplex PCR reaction with a reverse primer that binds all of the identifiers on the right end. In another example, if one forward primer binds a set of identifiers on the left end and one reverse primer binds a set of identifiers on the right end, then an 'AND' amplification of the intersection of those two sets of identifiers may be accomplished by using the forward primer and the reverse primer together as a primer pair in a PCR reaction. This process may be repeated in a sequential fashion (e.g., nested PCR) to access identifier sub-pools with any number of components in common.

With each iteration of PCR-based access on an identifier library, the identifiers may become shorter as primers are designed to bind components iteratively further inward from each edge. For example, an identifier library may comprise identifiers of the form A-B-C-D-E-F-G, where A, B, C, D, E, F, and G are layers. Upon amplifying with primers that bind particular components, for example, $A_1$ and $G_1$ in layers A and G respectively, the amplified portion of the identifier library may take on the form $A_1$-B-C-D-E-F-$G_1$. Upon further amplifying with primers that bind particular components, for example, $B_1$ and $F_1$ in layers B and F respectively, the amplified portion of the identifier library may take on the form $B_1$-C-D-E-F-$F_1$, where it may be assumed that these shorter amplified sequences correspond to full identifiers that further comprise component $A_1$ in the position of layer A and $G_1$ in the position of layer G.

FIG. 17C shows example methods for using affinity tags to perform 'OR' or 'AND' operations to access identifiers containing multiple components. In an example, if affinity probe 'P1' captures all identifiers with component 'C1' and another affinity probe 'P2' captures all identifiers with component 'C2', then the set of all identifiers with C1 or C2 can be captured by using P1 and P2 simultaneously (corresponding to an 'OR' operation). In another example with the same components and probes, the set of all identifiers with C1 and C2 can be captures by using P1 and P2 sequentially (corresponding to an 'AND' operation).

Methods for Reading Information Stored in Nucleic Acid Sequences

In another aspect, the present disclosure provides methods for reading information encoded in nucleic acid sequences. A method for reading information encoded in nucleic acid sequences may comprise (a) providing an identifier library, (b) identifying the identifiers present in the identifier library, (c) generating a string of symbols from the identifiers present in the identifier library, and (d) compiling information from the string of symbols. An identifier library may comprise a subset of a plurality of identifiers from a combinatorial space. Each individual identifier of the subset of identifiers may correspond to an individual symbol in a string of symbols. An identifier may comprise one or more components. A component may comprise a nucleic acid sequence.

Information may be written into one or more identifier libraries as described elsewhere herein. Identifiers may be constructed using any method described elsewhere herein. Stored data may be copied and accessed using any method described elsewhere herein.

The identifier may comprise information relating to a location of the encoded symbol, a value of the encoded symbol, or both the location and the value of the encoded symbol. An identifier may include information relating to a location of the encoded symbol and the presence or absence of the identifier in an identifier library may indicate the value of the symbol. The presence of an identifier in an identifier library may indicate a first symbol value (e.g., first bit value) in a binary string and the absence of an identifier in an identifier library may indicate a second symbol value (e.g., second bit value) in a binary string. In a binary system, basing a bit value on the presence or absence of an identifier in an identifier library may reduce the number of identifiers assembled and, therefore, reduce the write time. In an example, the presence of an identifier may indicate a bit value of '1' at the mapped location and the absence of an identifier may indicate a bit value of '0' at the mapped location.

Generating symbols (e.g., bit values) for a piece of information may include identifying the presence or absence of the identifier that the symbol (e.g., bit) may be mapped or encoded to. Determining the presence or absence of an identifier may include sequencing the present identifiers or using a hybridization array to detect the presence of an identifier. In an example, decoding and reading the encoded sequences may be performed using sequencing platforms. Examples of sequencing platforms are described in U.S. patent application Ser. No. 14/465,685 filed Aug. 21, 2014, U.S. patent application Ser. No. 13/886,234 filed May 2, 2013, and U.S. patent application Ser. No. 12/400,593 filed Mar. 9, 2009, each of which is entirely incorporated herein by reference.

In an example, decoding nucleic acid encoded data may be achieved by base-by-base sequencing of the nucleic acid strands, such as Illumina® Sequencing, or by utilizing a sequencing technique that indicates the presence or absence of specific nucleic acid sequences, such as fragmentation analysis by capillary electrophoresis. The sequencing may employ the use of reversible terminators. The sequencing may employ the use of natural or non-natural (e.g., engineered) nucleotides or nucleotide analogs. Alternatively or in addition to, decoding nucleic acid sequences may be performed using a variety of analytical techniques, including but not limited to, any methods that generate optical, electrochemical, or chemical signals. A variety of sequencing approaches may be used including, but not limited to, polymerase chain reaction (PCR), digital PCR, Sanger sequencing, high-throughput sequencing, sequencing-by-synthesis, single-molecule sequencing, sequencing-by-ligation, RNA-Seq (Illumina), Next generation sequencing, Digital Gene Expression (Helicos), Clonal Single MicroArray (Solexa), shotgun sequencing, Maxim-Gilbert sequencing, or massively-parallel sequencing.

Various read-out methods can be used to pull information from the encoded nucleic acid. In an example, microarray (or any sort of fluorescent hybridization), digital PCR, quantitative PCR (qPCR), and various sequencing platforms can be further used to read out the encoded sequences and by extension digitally encoded data.

An identifier library may further comprise supplemental nucleic acid sequences that provide metadata about the information, encrypt or mask the information, or that both provide metadata and mask the information. The supplemental nucleic acids may be identified simultaneously with identification of the identifiers. Alternatively, the supplemental nucleic acids may be identified prior to or after identifying the identifiers. In an example, the supplemental nucleic acids are not identified during reading of the encoded information. The supplemental nucleic acid sequences may be indistinguishable from the identifiers. An identifier index or a key may be used to differentiate the supplemental nucleic acid molecules from the identifiers.

The efficiency of encoding and decoding data may be increased by recoding input bit strings to enable the use of fewer nucleic acid molecules. For example, if an input string is received with a high occurrence of '111' substrings, which may map to three nucleic acid molecules (e.g., identifiers) with an encoding method, it may be recoded to a '000' substring which may map to a null set of nucleic acid molecules. The alternate input substring of '000' may also be recoded to '111'. This method of recoding may reduce the total amount of nucleic acid molecules used to encode the data because there may be a reduction in the number of '1's in the dataset. In this example, the total size of the dataset may be increased to accommodate a codebook that specifies the new mapping instructions. An alternative method for increasing encoding and decoding efficiency may be to recode the input string to reduce the variable length. For example, '111' may be recoded to '00' which may shrink the size of the dataset and reduce the number of '1's in the dataset.

The speed and efficiency of decoding nucleic acid encoded data may be controlled (e.g., increased) by specifically designing identifiers for ease of detection. For example, nucleic acid sequences (e.g., identifiers) that are designed for ease of detection may include nucleic acid sequences comprising a majority of nucleotides that are easier to call and detect based on their optical, electrochemical, chemical, or physical properties. Engineered nucleic acid sequences may be either single or double stranded. Engineered nucleic acid sequences may include synthetic or unnatural nucleotides that improve the detectable properties of the nucleic acid sequence. Engineered nucleic acid sequences may comprise all natural nucleotides, all synthetic or unnatural nucleotides, or a combination of natural, synthetic, and unnatural nucleotides. Synthetic nucleotides may include nucleotide analogues such as peptide nucleic acids, locked nucleic acids, glycol nucleic acids, and threose nucleic acids. Unnatural nucleotides may include dNaM, an artificial nucleoside containing a 3-methoxy-2-naphthyl group, and d5SICS, an artificial nucleoside containing a 6-methylisoquinoline-1-thione-2-yl group. Engineered nucleic acid sequences may be designed for a single enhanced property, such as enhanced optical properties, or the designed nucleic acid sequences may be designed with multiple enhanced properties, such as enhanced optical and electrochemical properties or enhanced optical and chemical properties. See Chemical Methods Section H on DNA design.

Engineered nucleic acid sequences may comprise reactive natural, synthetic, and unnatural nucleotides that do not improve the optical, electrochemical, chemical, or physical properties of the nucleic acid sequences. The reactive components of the nucleic acid sequences may enable the addition of a chemical moiety that confers improved properties to the nucleic acid sequence. Each nucleic acid sequence may include a single chemical moiety or may include multiple chemical moieties. Example chemical moieties may include, but are not limited to, fluorescent moieties, chemiluminescent moieties, acidic or basic moieties, hydrophobic or hydrophilic moieties, and moieties that alter oxidation state or reactivity of the nucleic acid sequence.

A sequencing platform may be designed specifically for decoding and reading information encoded into nucleic acid sequences. The sequencing platform may be dedicated to sequencing single or double stranded nucleic acid molecules. The sequencing platform may decode nucleic acid encoded data by reading individual bases (e.g., base-by-base sequencing) or by detecting the presence or absence of an entire nucleic acid sequence (e.g., component) incorporated within the nucleic acid molecule (e.g., identifier). The sequencing platform may include the use of promiscuous reagents, increased read lengths, and the detection of specific nucleic acid sequences by the addition of detectable chemical moieties. The use of more promiscuous reagents during sequencing may increase reading efficiency by enabling faster base calling which in turn may decrease the sequencing time. The use of increased read lengths may enable longer sequences of encoded nucleic acids to be decoded per read. The addition of detectable chemical moiety tags may enable the detection of the presence or absence of a nucleic acid sequence by the presence or absence of a chemical moiety. For example, each nucleic acid sequence encoding a bit of information may be tagged with a chemical moiety that generates a unique optical, electrochemical, or chemical signal. The presence or absence of that unique optical, electrochemical, or chemical signal may indicate a '0' or a '1' bit value. The nucleic acid sequence may comprise a single chemical moiety or multiple chemical moieties. The chemical moiety may be added to the nucleic acid sequence prior to use of the nucleic acid sequence to encode data. Alternatively or in addition to, the chemical moiety may be added to the nucleic acid sequence after encoding the data, but prior to decoding the data. The chemical moiety tag may be added directly to the nucleic acid sequence or the nucleic acid sequence may comprise a synthetic or unnatural nucleotide anchor and the chemical moiety tag may be added to that anchor.

Unique codes may be applied to minimize or detect encoding and decoding errors. Encoding and decoding errors may occur from false negatives (e.g., a nucleic acid molecule or identifier not included in a random sampling). An example of an error detecting code may be a checksum sequence that counts the number of identifiers in a contiguous set of possible identifiers that is included in the identifier library. While reading the identifier library, the checksum may indicate how many identifiers from that contiguous set of identifiers to expect to retrieve, and identifiers can continue to be sampled for reading until the expected number is met. In some embodiments, a checksum sequence may be included for every contiguous set of R identifiers where R can be equal in size or greater than 1, 2, 5, 10, 50, 100, 200, 500, or 1000 or less than 1000, 500, 200, 100, 50, 10, 5, or 2. The smaller the value of R, the better the error detection. In some embodiments, the checksums may be supplemental nucleic acid sequences. For example, a set comprising seven nucleic acid sequences (e.g., components) may be divided into two groups, nucleic acid sequences for constructing identifiers with a product scheme (components X1-X3 in layer X and Y1-Y3 in layer Y), and nucleic acid sequences for the supplemental checksums (X4-X7 and Y4-Y7). The checksum sequences X4-X7 may indicate whether zero, one, two, or three sequences of layer X are assembled with each member of layer Y. Alternatively, the checksum sequences Y4-Y7 may indicate whether zero, one, two, or three sequences of layer Y are assembled with each member of layer X. In this example, an original identifier library with identifiers {X1Y1, X1Y3, X2Y1, X2Y2, X2Y3} may be supplemented to include checksums to become the following pool: {X1Y1, X1Y3, X2Y1, X2Y2, X2Y3, X1Y6, X2Y7, X3Y4, X6Y1, X5Y2, X6Y3}. The checksum sequences may also be used for error correction. For example, absence of X1Y1 from the above dataset and the presence of X1Y6 and X6Y1 may enable inference that the X1Y1 nucleic acid molecule is missing from the dataset. The checksum sequences may indicate whether identifiers are missing from a sampling of the identifier library or an accessed portion of the identifier library. In the case of a missing checksum sequence, access methods such as PCR or affinity tagged probe hybridization may amplify and/or isolate it. In some embodiments, the checksums may not be supplemental nucleic acid sequences. They checksums may be coded directly into the information such that they are represented by identifiers.

Noise in data encoding and decoding may be reduced by constructing identifiers palindromically, for example, by using palindromic pairs of components rather than single components in the product scheme. Then the pairs of components from different layers may be assembled to one another in a palindromic manner (e.g., YXY instead of XY for components X and Y). This palindromic method may be expanded to larger numbers of layers (e.g., ZYXYZ instead of XYZ) and may enable detection of erroneous cross reactions between identifiers.

Adding supplemental nucleic acid sequences in excess (e.g., vast excess) to the identifiers may prevent sequencing from recovering the encoded identifiers. Prior to decoding the information, the identifiers may be enriched from the supplemental nucleic acid sequences. For example, the identifiers may be enriched by a nucleic acid amplification reaction using primers specific to the identifier ends. Alternatively, or in addition to, the information may be decoded without enriching the sample pool by sequencing (e.g., sequencing by synthesis) using a specific primer. In both decoding methods, it may be difficult to enrich or decode the information without having a decoding key or knowing something about the composition of the identifiers. Alternative access methods may also be employed such as using affinity tag based probes.

Systems for Encoding Binary Sequence Data

A system for encoding digital information into nucleic acids (e.g., DNA) can comprise systems, methods and devices for converting files and data (e.g., raw data, compressed zip files, integer data, and other forms of data) into bytes and encoding the bytes into segments or sequences of nucleic acids, typically DNA, or combinations thereof.

In an aspect, the present disclosure provides systems for encoding binary sequence data using nucleic acids. A system for encoding binary sequence data using nucleic acids may comprise a device and one or more computer processors. The device may be configured to construct an identifier library. The one or more computer processors may be individually or collectively programmed to (i) translate the information into a sting of symbols, (ii) map the string of symbols to the plurality of identifiers, and (iii) construct an identifier library comprising at least a subset of a plurality of identifiers. An individual identifier of the plurality of identifiers may correspond to an individual symbol of the string of symbols. An individual identifier of the plurality of identifiers may comprise one or more components. An individual component of the one or more components may comprise a nucleic acid sequence.

In another aspect, the present disclosure provides systems for reading binary sequence data using nucleic acids. A system for reading binary sequence data using nucleic acids may comprise a database and one or more computer processors. The database may store an identifier library encoding the information. The one or more computer processors may be individually or collectively programmed to (i) identify the identifiers in the identifier library, (ii) generate a plurality of symbols from identifiers identified in (i), and (iii) compile the information from the plurality of symbols. The identifier library may comprise a subset of a plurality of identifiers. Each individual identifier of the plurality of identifiers may correspond to an individual symbol in a string of symbols. An identifier may comprise one or more components. A component may comprise a nucleic acid sequence.

Non-limiting embodiments of methods for using the system to encode digital data can comprise steps for receiving digital information in the form of byte streams. Parsing the byte streams into individual bytes, mapping the location of a bit within the byte using a nucleic acid index (or identifier rank), and encoding sequences corresponding to either bit values of 1 or bit values of 0 into identifiers. Steps for retrieving digital data can comprise sequencing a nucleic acid sample or nucleic acid pool comprising sequences of nucleic acid (e.g., identifiers) that map to one or more bits, referencing an identifier rank to confirm if the identifier is present in the nucleic acid pool and decoding the location and bit-value information for each sequence into a byte comprising a sequence of digital information.

Systems for encoding, writing, copying, accessing, reading, and decoding information encoded and written into nucleic acid molecules may be a single integrated unit or may be multiple units configured to execute one or more of the aforementioned operations. A system for encoding and writing information into nucleic acid molecules (e.g., identifiers) may include a device and one or more computer processors. The one or more computer processors may be programmed to parse the information into strings of symbols (e.g., strings of bits). The computer processor may generate an identifier rank. The computer processor may categorize the symbols into two or more categories. One category may include symbols to be represented by a presence of the corresponding identifier in the identifier library and the other category may include symbols to be represented by an absence of the corresponding identifiers in the identifier library. The computer processor may direct the device to assemble the identifiers corresponding to symbols to be represented to the presence of an identifier in the identifier library.

The device may comprise a plurality regions, sections, or partitions. The reagents and components to assemble the identifiers may be stored in one or more regions, sections, or partitions of the device. Layers may be stored in separate regions of section of the device. A layer may comprise one or more unique components. The component in one layer may be unique from the components in another layer. The regions or sections may comprise vessels and the partitions may comprise wells. Each layer may be stored in a separate vessel or partition. Each reagent or nucleic acid sequence may be stored in a separate vessel or partition. Alternatively, or in addition to, reagents may be combined to form a master mix for identifier construction. The device may transfer reagents, components, and templates from one section of the device to be combined in another section. The device may provide the conditions for completing the assembly reaction. For example, the device may provide heating, agitation, and detection of reaction progress. The constructed identifiers may be directed to undergo one or more subsequent reactions to add barcodes, common sequences, variable sequences, or tags to one or more ends of the identifiers. The identifiers may then be directed to a region or partition to generate an identifier library. One or more identifier libraries may be stored in each region, section, or individual partition of the device. The device may transfer fluid (e.g., reagents, components, templates) using pressure, vacuum, or suction.

The identifier libraries may be stored in the device or may be moved to a separate database. The database may comprise one or more identifier libraries. The database may provide conditions for long term storage of the identifier libraries (e.g., conditions to reduce degradation of identifiers). The identifier libraries may be stored in a powder, liquid, or solid form. Aqueous solutions of identifiers may be lyophilized for more stable storage (see Chemical Methods Section G for more information about lyophilization). The database may provide UltraViolet light protection, reduced temperature (e.g., refrigeration or freezing), and protection from degrading chemicals and enzymes. Prior to being transferred to a database, the identifier libraries may be lyophilized or frozen. The identifier libraries may include ethylenediaminetetraacetic acid (EDTA) to inactivate nucleases and/or a buffer to maintain the stability of the nucleic acid molecules.

The database may be coupled to, include, or be separate from a device that writes the information into identifiers, copies the information, accesses the information, or reads the information. A portion of an identifier library may be removed from the database prior to copying, accessing or reading. The device that copies the information from the database may be the same or a different device from that which writes the information. The device that copies the information may extract an aliquot of an identifier library from the device and combine that aliquot with the reagents and constituents to amplify a portion of or the entire identifier library. The device may control the temperature, pressure, and agitation of the amplification reaction. The device may comprise partitions and one or more amplification reaction may occur in the partition comprising the identifier library. The device may copy more than one pool of identifiers at a time.

The copied identifiers may be transferred from the copy device to an accessing device. The accessing device may be the same device as the copy device. The access device may comprise separate regions, sections, or partitions. The access device may have one or more columns, bead reservoirs, or magnetic regions for separating identifiers bound to affinity tags (see Chemical Methods Section F about nucleic acid capture). Alternatively, or in addition to, the access device may have one or more size selection units. A size selection unit may include agarose gel electrophoresis or any other method for size selecting nucleic acid molecules (see Chemical Methods Section E for more information about nucleic acid size-selection). Copying and extraction may be performed in the same region of a device or in different regions of a device (see Chemical Methods Section D about nucleic acid amplification).

The accessed data may be read in the same device or the accessed data may be transferred to another device. The reading device may comprise a detection unit to detect and identify the identifiers. The detection unit may be part of a sequencer, hybridization array, or other unit for identifying the presence or absence of an identifier. A sequencing platform may be designed specifically for decoding and reading information encoded into nucleic acid sequences. The sequencing platform may be dedicated to sequencing single or double stranded nucleic acid molecules. The sequencing platform may decode nucleic acid encoded data by reading individual bases (e.g., base-by-base sequencing) or by detecting the presence or absence of an entire nucleic acid sequence (e.g., component) incorporated within the nucleic acid molecule (e.g., identifier). Alternatively, the sequencing platform may be a system such as Illumina® Sequencing or fragmentation analysis by capillary electrophoresis. Alternatively or in addition to, decoding nucleic acid sequences may be performed using a variety of analytical techniques implemented by the device, including but not limited to, any methods that generate optical, electrochemical, or chemical signals.

Information storage in nucleic acid molecules may have various applications including, but not limited to, long term information storage, sensitive information storage, and storage of medical information. In an example, a person's medical information (e.g., medical history and records) may be stored in nucleic acid molecules and carried on his or her person. The information may be stored external to the body (e.g., in a wearable device) or internal to the body (e.g., in a subcutaneous capsule). When a patient is brought into a medical office or hospital, a sample may be taken from the device or capsule and the information may be decoded with the use of a nucleic acid sequencer. Personal storage of medical records in nucleic acid molecules may provide an alternative to computer and cloud based storage systems. Personal storage of medical records in nucleic acid molecules may reduce the instance or prevalence of medical records being hacked. Nucleic acid molecules used for capsule-based storage of medical records may be derived from human genomic sequences. The use of human genomic sequences may decrease the immunogenicity of the nucleic acid sequences in the event of capsule failure and leakage.

Computer Systems

Figure 19:
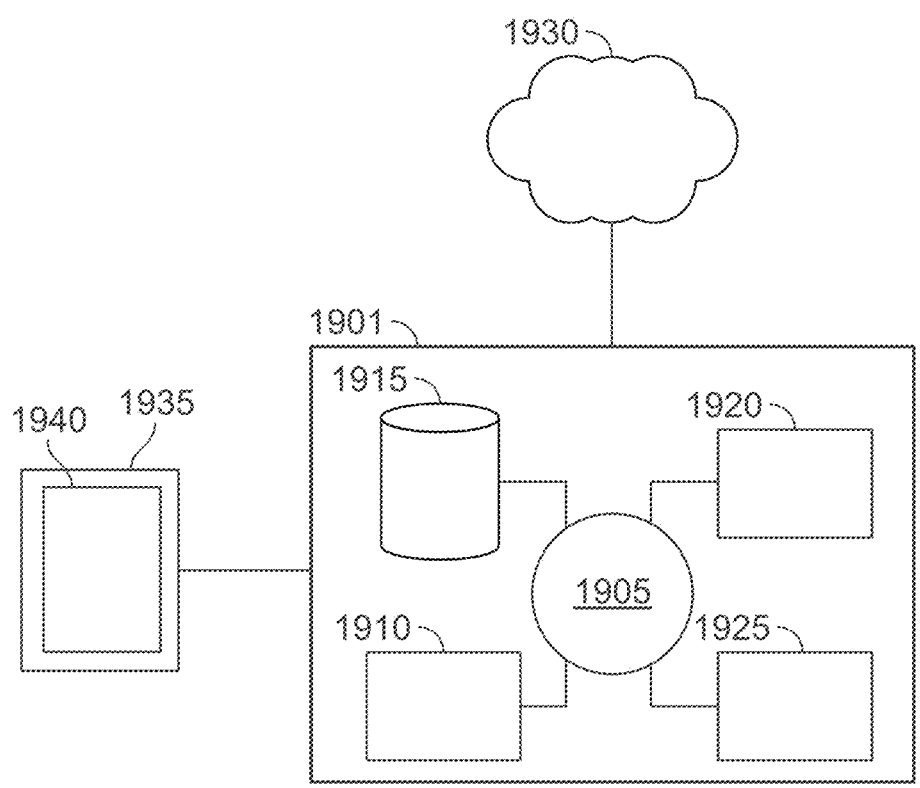
FIG. 19 shows a computer system that is programmed or otherwise configured to implement methods provided herein.

The present disclosure provides computer systems that are programmed to implement methods of the disclosure. FIG. 19 shows a computer system 1901 that is programmed or otherwise configured to encode digital information into nucleic acid sequences and/or read (e.g., decode) information derived from nucleic acid sequences. The computer system 1901 can regulate various aspects of the encoding and decoding procedures of the present disclosure, such as, for example, the bit-values and bit location information for a given bit or byte from an encoded bitstream or byte stream.

The computer system 1901 includes a central processing unit (CPU, also "processor" and "computer processor" herein) 1905, which can be a single core or multi core processor, or a plurality of processors for parallel processing. The computer system 1901 also includes memory or memory location 1910 (e.g., random-access memory, read-only memory, flash memory), electronic storage unit 1915 (e.g., hard disk), communication interface 1920 (e.g., network adapter) for communicating with one or more other systems, and peripheral devices 1925, such as cache, other memory, data storage and/or electronic display adapters. The memory 1910, storage unit 1915, interface 1920 and peripheral devices 1925 are in communication with the CPU 1905 through a communication bus (solid lines), such as a motherboard. The storage unit 1915 can be a data storage unit (or data repository) for storing data. The computer system 1901 can be operatively coupled to a computer network ("network") 1930 with the aid of the communication interface 1920. The network 1930 can be the Internet, an internet and/or extranet, or an intranet and/or extranet that is in communication with the Internet. The network 1930 in some cases is a telecommunication and/or data network. The network 1930 can include one or more computer servers, which can enable distributed computing, such as cloud computing. The network 1930, in some cases with the aid of the computer system 1901, can implement a peer-to-peer network, which may enable devices coupled to the computer system 1901 to behave as a client or a server.

The CPU 1905 can execute a sequence of machine-readable instructions, which can be embodied in a program or software. The instructions may be stored in a memory location, such as the memory 1910. The instructions can be directed to the CPU 1905, which can subsequently program or otherwise configure the CPU 1905 to implement methods of the present disclosure. Examples of operations performed by the CPU 1905 can include fetch, decode, execute, and writeback.

The CPU 1905 can be part of a circuit, such as an integrated circuit. One or more other components of the system 1901 can be included in the circuit. In some cases, the circuit is an application specific integrated circuit (ASIC).

The storage unit 1915 can store files, such as drivers, libraries and saved programs. The storage unit 1915 can store user data, e.g., user preferences and user programs. The computer system 1901 in some cases can include one or more additional data storage units that are external to the computer system 1901, such as located on a remote server that is in communication with the computer system 1901 through an intranet or the Internet.

The computer system 1901 can communicate with one or more remote computer systems through the network 1930. For instance, the computer system 1901 can communicate with a remote computer system of a user or other devices and or machinery that may be used by the user in the course of analyzing data encoded or decoded in a sequence of nucleic acids (e.g., a sequencer or other system for chemically determining the order of nitrogenous bases in a nucleic acid sequence). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1901 via the network 1930.

Methods as described herein can be implemented by way of machine (e.g., computer processor) executable code stored on an electronic storage location of the computer system 1901, such as, for example, on the memory 1910 or electronic storage unit 1915. The machine executable or machine readable code can be provided in the form of software. During use, the code can be executed by the processor 1905. In some cases, the code can be retrieved from the storage unit 1915 and stored on the memory 1910 for ready access by the processor 1905. In some situations, the electronic storage unit 1915 can be precluded, and machine-executable instructions are stored on memory 1910.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 1901, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1901 can include or be in communication with an electronic display 1935 that comprises a user interface (UI) 1940 for providing, for example, sequence output data including chromatographs, sequences as well as bits, bytes, or bit streams encoded by or read by a machine or computer system that is encoding or decoding nucleic acids, raw data, files and compressed or decompressed zip files to be encoded or decoded into DNA stored data. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 1905. The algorithm can, for example, be used with a DNA index and raw data or zip file compressed or decompressed data, to determine a customized method for coding digital information from the raw data or zip file compressed data, prior to encoding the digital information.

Chemical Methods Section

A. Overlap Extension PCR (OEPCR) Assembly

In OEPCR, components are assembled in a reaction comprising polymerase and dNTPs (deoxynucleotide tri phosphates comprising dATP, dTTP, dCTP, dGTP or variants or analogs thereof). Components can be single stranded or double stranded nucleic acids. Components to be assembled adjacent to each other may have complementary 3' ends, complementary 5' ends, or homology between one component's 5' end and the adjacent component's 3' end. These end regions, termed "hybridization regions", are intended to facilitate the formation of hybridized junctions between the components during OEPCR, wherein the 3' end of one input component (or the complement thereof) is hybridized to the 3' end of its intended adjacent component (or the complement thereof). An assembled double-stranded product is then formed by polymerase extension. This product may then be assembled to more components through subsequent hybridization and extension. FIG. 7 illustrates an example schematic of OEPCR for assembling three nucleic acids.

In some embodiments, the OEPCR may comprise cycling between three temperatures: a melting temperature, an annealing temperature, and an extension temperature. The melting temperature is intended to turn double stranded nucleic acids into single stranded nucleic acids, as well as remove the formation of secondary structures or hybridizations within a component or between components. Typically the melting temperature is high, for example above 95 degrees Celsius. In some embodiments the melting temperature may be at least 96, 97, 98, 99, 100, 101, 102, 103, 104, or 105 degrees Celsius. In other embodiments the melting temperature may be at most 95, 94, 93, 92, 91, or 90 degrees Celsius. A higher melting temperature will improve dissociation of nucleic acids and their secondary structures, but may also cause side effects such as the degradation of nucleic acids or the polymerase. Melting temperatures may be applied to the reaction for at least 1, 2, 3, 4, 5 seconds, or above, such as 30 seconds, 1 minute, 2 minutes, or 3 minutes.

The annealing temperature is intended to facilitate the formation of hybridization between complementary 3' ends of intended adjacent components (or their complements). In some embodiments, the annealing temperature may match the calculated melting temperature of the intended hybridized nucleic acid formation. In other embodiments, the annealing temperature may be within 10 degrees Celsius or more of said melting temperature. In some embodiments, the annealing temperature may be at least 25, 30, 50, 55, 60, 65, or 70 degrees Celsius. The melting temperature may depend on the sequence of the intended hybridization region between components. Longer hybridization regions have higher melting temperatures, and hybridization regions with higher percent content of Guanine or Cytosine nucleotides may have higher melting temperatures. It may therefore be possible to design components for OEPCR reactions intended to assemble optimally at particular annealing temperatures. Annealing temperatures may be applied to the reaction for at least 1, 5, 10, 15, 20, 25, or 30 seconds, or above.

The extension temperature is intended to initiate and facilitate the nucleic acid chain elongation of hybridized 3' ends catalyzed by one or more polymerase enzymes. In some embodiments, the extension temperature may be set at the temperature in which the polymerase functions optimally in terms of nucleic acid binding strength, elongation speed, elongation stability, or fidelity. In some embodiments, the extension temperature may be at least 30, 40, 50, 60, or 70 degrees Celsius, or above. Annealing temperatures may be applied to the reaction for at least 1, 5, 10, 15, 20, 25, 30, 40, 50, or 60 seconds or above. Recommended extension times may be around 15 to 45 seconds per kilobase of expected elongation.

In some embodiments of OEPCR, the annealing temperature and the extension temperature may be the same. Thus a 2-step temperature cycle may be used instead of a 3-step temperature cycle. Examples of combined annealing and extension temperatures include 60, 65, or 72 degrees Celsius.

In some embodiments, OEPCR may be performed with one temperature cycle. Such embodiments may involve the intended assembly of just two components. In other embodiments, OEPCR may be performed with multiple temperature cycles. Any give nucleic acid in OEPCR may only assemble to at most one other nucleic acid in one cycle. This is because assembly (or extension or elongation) may only occur at the 3' end of a nucleic acid and each nucleic acid may only have one 3' end. Therefore, the assembly of multiple components may require multiple temperature cycles. For example, assembling four components may involve 3 temperature cycles. Assembling 6 components may involve 5 temperature cycles. Assembling 10 components may involve 9 temperature cycles. In some embodiments, using more temperature cycles than the minimum required may increase assembly efficiency. For example using four temperature cycles to assemble two components may yield more product than only using one temperature cycle. This is because the hybridization and elongation of components is a statistical event that occurs with a fraction of the total number of components in each cycle. So the total fraction of assembled components may increase with increased cycles.

In addition to temperature cycling considerations, the design of the nucleic acid sequences in OEPCR may influence the efficiency of their assembly to one another. Nucleic acids with long hybridization regions may hybridize more efficiently at a given annealing temperature compared with nucleic acids with short hybridization regions. This is because a longer hybridized product contains a larger number of stable base-pairs and may therefore be a more stable overall hybridized product than a shorter hybridized product. Hybridization regions may have a length of at least 1, 2, 3 4, 5, 6, 7, 8, 9, 10, or more bases.

Hybridization regions with high guanine or cytosine content may hybridize more efficiently at a given temperature than hybridization regions with low guanine or cytosine content. This is because guanine forms a more stable base-pair with cytosine than adenine does with thymine. Hybridization regions may have a guanine or cytosine content (also known as GC content) of anywhere between 0% and 100%.

In addition to hybridization region length and GC content, there are many more aspects of the nucleic acid sequence design that may affect the efficiency of the OEPCR. For example, the formation of undesired secondary structures within a component may interfere with its ability to form a hybridization product with its intended adjacent component. These secondary structures may include hairpin loops. The types of possible secondary structures and their stability (for example meting temperature) for a nucleic acid may be predicted based on the sequence. Design space search algorithms may be used to determine nucleic acid sequences that meet proper length and GC content criteria for efficient OEPCR, while avoiding sequences with potentially inhibitory secondary structures. Design space search algorithms may include genetic algorithms, heuristic search algorithms, meta-heuristic search strategies like tabu search, branch-and-bound search algorithms, dynamic programming-based algorithms, constrained combinatorial optimization algorithms, gradient descent-based algorithms, randomized search algorithms, or combinations thereof.

Likewise, the formation of homodimers (nucleic acid molecules that hybridize with nucleic acid molecules of the same sequence) and unwanted heterodimers (nucleic acid sequences that hybridize with other nucleic acid sequences aside from their intended assembly partner) may interfere with OEPCR. Similar to secondary structures within a nucleic acid, the formation of homodimers and heterodimers may be predicted and accounted for during nucleic acid design using computation methods and design space search algorithms.

Longer nucleic acid sequences or higher GC content may create increased formation of unwanted secondary structures, homodimers, and heterodimers with the OEPCR. Therefore, in some embodiments, the use of shorter nucleic acid sequences or lower GC content may lead to higher assembly efficiency. These design principles may counteract the design strategies of using long hybridization regions or high GC content for more efficient assembly. As such, in some embodiments, OEPCR may be optimized by using long hybridization regions with high GC content but short non-hybridization regions with low GC content. The overall length of nucleic acids may be at least 10, 20, 30, 40, 50, 60, 70, 80, 90, or 100 bases, or above. In some embodiments, there may be an optimal length and optimal GC content for the hybridization regions of nucleic acids where the assembly efficiency is optimized.

A larger number of distinct nucleic acids in an OEPCR reaction may interfere with the expected assembly efficiency. This is because a larger number of distinct nucleic acid sequences may create a higher probability for undesirable molecular interactions, particularly in the form of heterodimers. Therefore in some embodiments of OEPCR that assemble large numbers of components, nucleic acid sequence constraints may become more stringent for efficient assembly.

Primers for amplifying the anticipated final assembled product may be included in an OEPCR reaction. The OEPCR reaction may then be performed with more temperature cycles to improve the yield of the assembled product, not just by creating more assemblies between the constituent components, but also by exponentially amplifying the full assembled product in the manner of conventional PCR (see Chemical Methods Section D).

Additives may be included in the OEPCR reaction to improve assembly efficiency. For example, the addition of Betaine, Dimethyl sulfoxide (DMSO), non-ionic detergents, Formamide, Magnesium, Bovine Serum Albumin (BSA), or combinations thereof. Additive content (weight per volume) may be at least 0%, 1%, 5%, 10%, 20%, or more.

Various polymerases may be used for OEPCR. The polymerase can be naturally occurring or synthesized. An example polymerase is a Φ29 polymerase or derivative thereof. In some cases, a transcriptase or a ligase is used (i.e., enzymes which catalyze the formation of a bond) in conjunction with polymerases or as an alternative to polymerases to construct new nucleic acid sequences. Examples of polymerases include a DNA polymerase, a RNA polymerase, a thermostable polymerase, a wild-type polymerase, a modified polymerase, *E. coli* DNA polymerase I, T7 DNA polymerase, bacteriophage T4 DNA polymerase Φ29 (phi29) DNA polymerase, Taq polymerase, Tth polymerase, Tli polymerase, Pfu polymerase Pwo polymerase, VENT polymerase, DEEPVENT polymerase, Ex-Taq polymerase, LA-Taw polymerase, Sso polymerase Poc polymerase, Pab polymerase, Mth polymerase ES4 polymerase, Tru polymerase, Tac polymerase, Tne polymerase, Tma polymerase, Tca polymerase, Tih polymerase, Tfi polymerase, Platinum Taq polymerases, Tbr polymerase, Phusion polymerase, KAPA polymerase, Q5 polymerase, Tfl polymerase, Pfutubo polymerase, Pyrobest polymerase, KOD polymerase, Bst polymerase, Sac polymerase, Klenow fragment polymerase with 3' to 5' exonuclease activity, and variants, modified products and derivatives thereof. Different polymerases may be stable and function optimally at different temperatures. Moreover, different polymerases have different properties. For example, some polymerases, such a Phusion polymerase, may exhibit 3' to 5' exonuclease activity, which may contribute to higher fidelity during nucleic acid elongation. Some polymerases may displace leading sequences during elongation, while others may degrade them or halt elongation. Some polymerases, like Taq, incorporate an adenine base at the 3' end of nucleic acid sequences. This process is referred to as A-tailing and may be inhibitory to OEPCR as the addition of an Adenine base may disrupt the designed 3' complementarity between intended adjacent components.

OEPCR may also be referred to as polymerase cycling assembly (or PCA).

B. Ligation Assembly

In ligation assembly, separate nucleic acids are assembled in a reaction comprising one or more ligase enzymes and additional co-factors. Co-factors may include Adenosine Tri-Phosphate (ATP), Dithiothreitol (DTT), or Magnesium ion (Mg2+). During ligation, the 3'-end of one nucleic acid strand is covalently linked to the 5' end of another nucleic acid strand, thus forming an assembled nucleic acid. Components in a ligation reaction may be blunt-ended double stranded DNA (dsDNA), single stranded DNA (ssDNA), or partially hybridized single-stranded DNA. Strategies that bring the ends of nucleic acids together increase the frequency of viable substrate for ligase enzymes, and thus may be used for improving the efficiency of ligase reactions. Blunt-ended dsDNA molecules tend to form hydrophobic stacks on which ligase enzymes may act, but a more successful strategy for bringing nucleic acids together may be to use nucleic acid components with either 5' or 3' single-stranded overhangs that have complementarity for the overhangs of components to which they are intended to assemble. In the latter instance, more stable nucleic acid duplexes may form due to base-base hybridization.

When a double stranded nucleic acid has an overhang strand on one end, the other strand on the same end may be referred to as a "cavity". Together, a cavity and overhang form a "sticky end", also known as a "cohesive-end". A sticky end may be either a 3' overhang and a 5' cavity, or a 5' overhang and a 3' cavity. The sticky-ends between two intended adjacent components may be designed to have complementarity such that the overhang of both sticky ends hybridize such that each overhang ends directly adjacent to the beginning of the cavity on the other component. This forms a "nick" (a double stranded DNA break) that may be "sealed" (covalently linked through a phosphodiester bond) by the action of a ligase. See FIG. 8 for an example schematic of sticky end ligation for assembling three nucleic acids. Either the nick on one strand or the other, or both, may be sealed. Thermodynamically, the top and bottom strand of a molecule that forms a sticky end may move between associated and dissociated states, and therefore the sticky end may be a transient formation. Once, however, the nick along one strand of a sticky end duplex between two components is sealed, that covalent linkage remains even if the members of the opposite strand dissociate. The linked strand may then become a template to which the intended adjacent members of the opposite strand can bind and once again form a nick that may be sealed.

Sticky ends may be created by digesting dsDNA with one or more endonucleases. Endonucleases (that may be referred to as restriction enzymes) may target specific sites (that may be referred to as restriction sites) on either or both ends of dsDNA molecule, and create a staggered cleavage (sometimes referred to as a digestion) thus leaving a sticky end. See Chemical Methods Section C on restriction digests. The digest may leave a palindromic overhang (an overhang with a sequence that is the reverse complement of itself). If so, then two components digested with the same endonuclease may form complementary sticky ends along which they may be assembled with a ligase. The digestion and ligation may occur together in the same reaction if the endonuclease and ligase are compatible. The reaction may occur at a uniform temperature, such as 4, 10, 16, 25, or 37 degrees Celsius. Or the reaction may cycle between multiple temperatures, such as between 16 degrees Celsius and 37 degrees Celsius. Cycling between multiple temperatures may enable the digestion and ligation to each proceed at their respective optimal temperatures during different parts of the cycle.

It may be beneficial to perform the digestion and ligation in separate reactions. For example, if the desired ligases and the desired endonucleases function optimally at different conditions. Or, for example, if the ligated product forms a new restriction site for the endonuclease. In these instances, it may be better to perform the restriction digest and then the ligation separately, and perhaps it may be further beneficial to remove the restriction enzyme prior to ligation. Nucleic acids may be separated from enzymes through phenol-chloroform extraction, ethanol precipitation, magnetic bead capture, and/or silica membrane adsorption, washing, and elution. Multiple endonucleases may be used in the same reaction, though care should be taken to ensure that the endonucleases do not interfere with each other and function under similar reaction conditions. Using two endonucleases, one may create orthogonal (non-complementary) sticky ends on both ends of a dsDNA component.

Endonuclease digestion can leave sticky ends with phosphorylated 5' ends. Ligases may only function on phosphorylated 5' ends, and not on non-phosphorylated 5' ends. As such, there may not be any need for an intermediate 5' phosphorylation step in between digestion and ligation. A digested dsDNA component with a palindromic overhang on its sticky end may ligate to itself. To prevent self-ligation, it may be beneficial to dephosphorylate said dsDNA component prior to ligation.

Multiple endonucleases may target different restriction sites, but leave compatible overhangs (overhangs that are the reverse complement of each other). The product of ligation of sticky ends created with two such endonucleases may result in an assembled product that does not contain a restriction site for either endonuclease at the site of ligation. Such endonucleases form the basis of assembly methods, such as biobricks assembly, that may programmably assemble multiple components using just two endonucleases by performing repetitive digestion-ligation cycles. FIG. 20 illustrates an example of a digestion-ligation cycle using endonucleases BamHI and BglII with compatible overhangs.

In some embodiments, the endonucleases used to create sticky ends may be type IIS restriction enzymes. These enzymes cleave a fixed number of bases away from their restriction sites in a particular direction, therefore the sequence of the overhangs that they generate may be customized. The overhang sequences need not be palindromic. The same type IIS restriction enzyme may be used to create multiple different sticky ends in the same reaction, or in multiple reactions. Moreover, one or multiple type IIS restriction enzymes may be used to create components with compatible overhangs in the same reaction, or in multiple reactions. The ligation site between two sticky ends generated by type IIS restriction enzymes may be designed such that it does not form a new restriction site. In addition, the type IIS restriction enzyme sites may be placed on a dsDNA such that the restriction enzyme cleaves off its own restriction site when it generates a component with a sticky end. Therefore the ligation product between multiple components generated from type IIS restriction enzymes may not contain any restriction sites.

Type IIS restriction enzymes may be mixed in a reaction together with ligase to perform the component digestion and ligation together. The temperature of the reaction may be cycled between two or more values to promote optimal digestion and ligation. For example, the digestion may be performed optimally at 37 degrees Celsius and the ligation may be performed optimally at 16 degrees Celsius. More generally, the reaction may cycle between temperature values of at least 0, 5, 10, 15, 20, 25, 30, 35, 40, 45, 50, 55, 60, or 65 degrees Celsius or above. A combined digestion and ligation reaction may be used to assemble at least 2, 3, 4, 5, 6, 7, 8, 9, 10, 11, 12, 13, 14, 15, 16, 17, 18, 19, or 20 components, or more. Examples of assembly reactions that leverage Type IIS restriction enzymes to create sticky ends include Golden Gate Assembly (also known as Golden Gate Cloning) or Modular Cloning (also known as MoClo).

In some embodiments of ligation, exonucleases may be used to create components with sticky ends. 3' exonucleases may be used to chew back the 3' ends from dsDNA, thus creating 5' overhangs. Likewise, 5' exonucleases may be used to chew back the 5' ends from dsDNA thus creating 3' overhangs. Different exonucleases may have different properties. For example, exonucleases may differ in the direction of their nuclease activity (5' to 3' or 3' to 5'), whether or not they act on ssDNA, whether they act on phosphorylated or non-phosphorylated 5' ends, whether or not they are able to initiate on a nick, or whether or not they are able to initiate their activity on 5' cavities, 3' cavities, 5' overhangs, or 3' overhangs. Different types of exonucleases include Lambda exonuclease, RecJ$_f$, Exonuclease III, Exonuclease I, Exonuclease T, Exonuclease V, Exonuclease VIII, Exonuclease VII, Nuclease BAL_31, T5 Exonuclease, and T7 Exonuclease.

Exonuclease may be used in a reaction together with ligase to assemble multiple components. The reaction may occur at a fixed temperature or cycle between multiple temperatures, each ideal for the ligase or the exonuclease, respectively. Polymerase may be included in an assembly reaction with ligase and a 5'-to-3' exonuclease. The components in such a reaction may be designed such that components intended to assemble adjacent to each other share homologous sequences on their edges. For example, a component X to be assembled with component Y may have a 3' edge sequence of the form 5'-z-3', and the component Y may have a 5' edge sequence of the form 5'-z-3', where z is any nucleic acid sequence. Homologous edge sequences of such a form can be referred to as 'gibson overlaps'. As the 5' exonuclease chews back the 5' end of dsDNA components with gibson overlaps it creates compatible 3' overhangs that hybridize to each other. The hybridized 3' ends may then be extended by the action of polymerase to the end of the template component, or to the point where the extended 3' overhang of one component meets the 5' cavity of the adjacent component, thereby forming a nick that may be sealed by a ligase. Such an assembly reaction where polymerase, ligase, and exonuclease are used together is often referred to as "Gibson assembly". Gibson assembly may be performed by using T5 exonuclease, Phusion polymerase, and Taq ligase, and incubating the reaction at 50 degrees Celsius. In said instance, the use of the thermophilic ligase, Taq, enables the reaction to proceed at 50 degrees Celsius, a temperature suitable for all three types of enzymes in the reaction.

The term "Gibson assembly" may generally refer to any assembly reaction involving polymerase, ligase, and exonuclease. Gibson assembly may be used to assemble at least 2, 3, 4, 5, 6, 7, 8, 9, 10, or more components. Gibson assembly may occur as a one-step, isothermal reaction or as a multi-step reaction with one or more temperature incubations. For example, Gibson assembly may occur at temperatures of at least 30, 40, 50, 60, or 70 degrees, or less. The incubation time for a Gibson assembly may be at least 1, 5, 10, 20, 40, or 80 minutes.

Gibson assembly reactions may occur optimally when gibson overlaps between intended adjacent components are a certain length and have sequence features, such as sequences that avoid undesirable hybridization events such as hairpins, homodimers, or unwanted heterodimers. Generally, gibson overlaps of at least 20 bases are recommended. But Gibson overlaps may be at least 1, 2, 3, 5, 10, 20, 30, 40, 50, 60, 100, or more bases in length. The GC content of a gibson overlap may be anywhere from 0% to 100%.

Though Gibson assembly is commonly described with a 5' exonuclease, the reaction may also occur with a 3' exonuclease. As the 3' exonuclease chews back the 3' end of dsDNA components, the polymerase counteracts the action by extending the 3' end. This dynamic process may continue until the 5' overhang (created by the exonuclease) of two components (that share a gibson overlap) hybridize and the polymerase extends the 3' end of one component far enough to meet the 5' end of its adjacent component, thus leaving a nick that may be sealed by a ligase.

Figure 21:
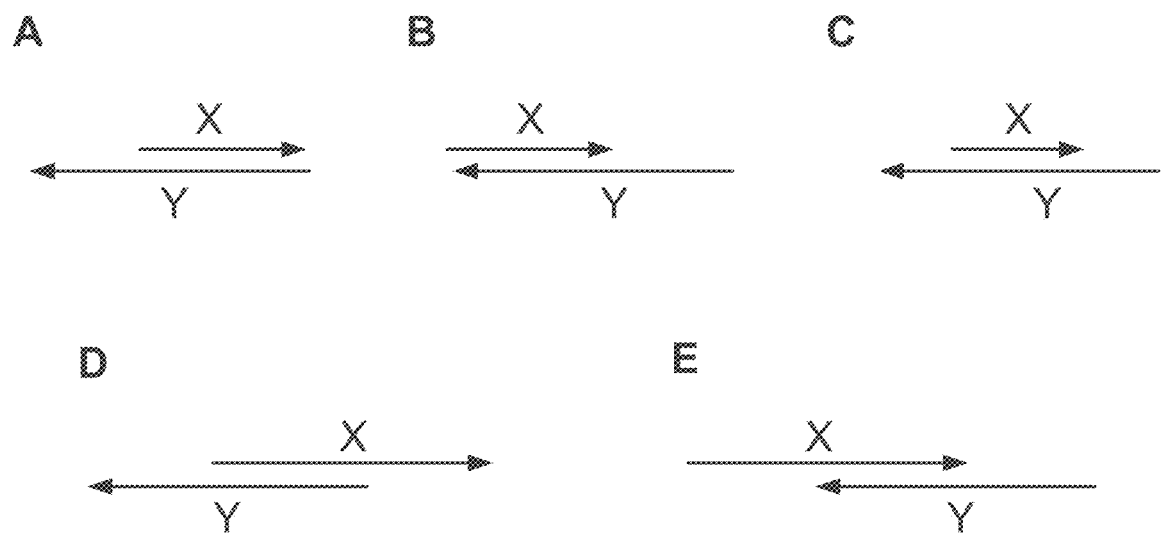
FIG. 21 shows possible sticky-end component structures made from two oligos, X and Y.

In some embodiments of ligation, components with sticky ends may be created synthetically, as opposed to enzymatically, by mixing together two single stranded nucleic acids, or oligos, that do not share full complementarity. For example, two oligos, oligo X and oligo Y, may be designed to only fully hybridize along a contiguous string of complementary bases that form a substring of a larger string of bases that make up the entirety of either one or both oligos. This complementary string of bases is referred to as the "index region". If the index region occupies the entirety of oligo X and only the 5' end of oligo Y, then the oligos together form a component with a blunt end on one side and a sticky end on the other with a 3' overhang from oligo Y (FIG. 21A). If the index region occupies the entirety of oligo X and only the 3' end of oligo Y, then the oligos together form a component with a blunt end on one side and a sticky end on the other with a 5' overhang from oligo Y (FIG. 21B). If the index region occupies the entirety of oligo X and neither end of oligo Y (implying that the index region is embedded within the middle of oligo Y), then the oligos together form a component with a sticky end on one side with a 3' overhang from oligo Y and on the other side with a 5' overhang from oligo Y (FIG. 21C). If the index region occupies only the 5' end of oligo X and only the 5' end of oligo Y, then the oligos together form a component with a sticky end on one side with a 3' overhang from oligo Y and on the other side with a 3' overhang from oligo X (FIG. 21D). If the index region occupies only the 3' end of oligo X and only the 3' end of oligo Y, then the oligos together form a component with a sticky end on one side with a 5' overhang from oligo Y and on the other side with a 5' overhang from oligo X (FIG. 21E). In the aforementioned examples, the sequences of the overhangs are defined by the oligo sequences outside of the index region. These overhang sequences may be referred to as hybridization regions as they are the regions along which components hybridize for ligation.

The index region and hybridization region(s) of oligos in sticky-end ligation may be designed to facilitate the proper assembly of components. Components with long overhangs may hybridize more efficiently with each other at a given annealing temperature compared with components with short overhangs. Overhangs may have a length of at least 1, 2, 3 4, 5, 6, 7, 8, 9, 10, 15, 20, 30, or more bases.

Components with overhangs that contain high guanine or cystosine content may hybridize more efficiently to their complementary component at a given temperature than components with overhangs that contain low guanine or cytosine content. This is because guanine forms a more stable base-pair with cytosine than adenine does with thymine. Overhangs may have a guanine or cytosine content (also known as GC content) of anywhere between 0% and 100%.

As with overhang sequences, the GC content and length of the index region of an oligo may also affect ligation efficiency. This is because sticky-end components may assemble more efficiently if the top and bottom strand of each component are stably bound. Therefore, index regions may be designed with higher GC content, longer sequences, and other features that promote higher melting temperatures. However, there are many more aspects of the oligo design, for both the index region and overhang sequence(s), that may affect the efficiency of the ligation assembly. For example, the formation of undesired secondary structures within a component may interfere with its ability to form an assembled product with its intended adjacent component. This may occur due to either secondary structures in the index region, in the overhang sequence, or in both. These secondary structures may include hairpin loops. The types of possible secondary structures and their stability (for example meting temperature) for an oligo may be predicted based on the sequence. Design space search algorithms may be used to determine oligo sequences that meet proper length and GC content criteria for the formation of effective components, while avoiding sequences with potentially inhibitory secondary structures. Design space search algorithms may include genetic algorithms, heuristic search algorithms, meta-heuristic search strategies like tabu search, branch-and-bound search algorithms, dynamic programming-based algorithms, constrained combinatorial optimization algorithms, gradient descent-based algorithms, randomized search algorithms, or combinations thereof.

Likewise, the formation of homodimers (oligos that hybridize with oligos of the same sequence) and unwanted heterodimers (oligos that hybridize with other oligos aside from their intended assembly partner) may interfere with ligation. Similar to secondary structures within a component, the formation of homodimers and heterodimers may be predicted and accounted for during oligo design using computation methods and design space search algorithms.

Longer oligo sequences or higher GC content may create increased formation of unwanted secondary structures, homodimers, and heterodimers within the ligation reaction. Therefore, in some embodiments, the use of shorter oligos or lower GC content may lead to higher assembly efficiency. These design principles may counteract the design strategies of using long oligos or high GC content for more efficient assembly. As such, there may be an optimal length and optimal GC content for the oligos that make up each component such that the ligation assembly efficiency is optimized. The overall length of oligos to be used in ligation may be at least 10, 20, 30, 40, 50, 60, 70, 80, 90, or 100 bases, or above. The overall GC content of oligos to be used in ligation may be anywhere between 0% and 100%.

In addition to sticky end ligation, ligation may also occur between single-stranded nucleic acids using staple (or template or bridge) strands. This method may be referred to as staple strand ligation (SSL), template directed ligation (TDL), or bridge strand ligation. See FIG. 10A for an example schematic of TDL for assembling three nucleic acids. In TDL, two single stranded nucleic acids hybridize adjacently onto a template, thus forming a nick that may be sealed by a ligase. The same nucleic acid design considerations for sticky end ligation also apply to TDL. Stronger hybridization between the templates and their intended complementary nucleic acid sequences may lead to increased ligation efficiency. Therefore sequence features that improve the hybridization stability (or melting temperature) on each side of the template may improve ligation efficiency. These features may include longer sequence length and higher GC content. The length of nucleic acids in TDL, including templates, may be at least 5, 10, 20, 30, 40, 50, 60, 70, 80, 90, or 100 bases, or above. The GC content of nucleic acids, including templates, may be anywhere between 0% and 100%.

In TDL, as with sticky end ligation, care may be taken to design component and template sequences that avoid unwanted secondary structures by using nucleic acid structure-predicting software with sequence space search algorithms. As the components in TDL may be single stranded instead of double stranded, there may be higher incidence of unwanted secondary structures (as compared to sticky end ligation) due to the exposed bases.

TDL may also be performed with blunt-ended dsDNA components. In such reactions, in order for the staple strand to properly bridge two single-stranded nucleic acids, the staple may first need to displace or partially displace the full single-stranded complements. To facilitate the TDL reaction with dsDNA components, the dsDNA may initially be melted with incubation at a high temperature. The reaction may then be cooled thus allowing staple strands to anneal to their proper nucleic acid complements. This process may be made even more efficient by using a relatively high concentration of template compared to dsDNA components, thus enabling the templates to outcompete the proper full-length ssDNA complements for binding. Once two ssDNA strands get assembled by their template and a ligase, that assembled nucleic acid may then become a template for the opposite full-length ssDNA complements. Therefore, ligation of blunt-ended dsDNA with TDL may be improved through multiple rounds of melting (incubation at higher temperatures) and annealing (incubation at lower temperatures). This process may be referred to as Ligase Cycling Reaction, or LCR. Proper melting and annealing temperatures depend on the nucleic acid sequences. Melting and annealing temperatures may be at least 4, 10, 20, 20, 30, 40, 50, 60, 70, 80, 90, or 100 degrees Celsius. The number of temperature cycles may be at least 1, 5, 10, 15, 20, 15, 30, or more.

All ligations may be performed in fixed temperature reactions or in multi-temperature reactions. Ligation temperatures may be at least 0, 4, 10, 20, 20, 30, 40, 50, or 60 degrees Celsius or above. The optimal temperature for ligase activity may differ depending on the type of ligase. Moreover, the rate at which components adjoin or hybridize in the reaction may differ depending on their nucleic acid sequences. Higher incubation temperatures may promote faster diffusion and therefore increase the frequency with which components temporarily adjoin or hybridize. However increased temperature may also disrupt basepair bonds and therefore decrease the stability of those adjoined or hybridized component duplexes. The optimal temperature for ligation may depend on the number of nucleic acids to be assembled, the sequences of those nucleic acids, the type of ligase, as well as other factors such as reaction additives. For example, two sticky end components with 4-base complementary overhangs may assembled faster at 4 degrees Celsius with T4 ligase than at 25 degrees Celsius with T4 ligase. But two sticky-end components with 25-base complementary overhangs may assemble faster at 25 degrees Celsius with T4 ligase than at 4 degrees Celsius with T4 ligase, and perhaps faster than ligation with 4-base overhangs at any temperature. In some embodiments of ligation, it may be beneficial to heat and slowly cool the components for annealing prior to ligase addition.

Ligation may be used to assembled at least 2, 3, 4, 5, 6, 7, 8, 9, 10, 11, 12, 13, 14, 15, 16, 17, 18, 19, 20, or more nucleic acids. Ligation incubation times may be at most 30 seconds, 1 minute, 2 minutes, 5 minutes, 10 minutes, 20 minutes, 30 minutes, 1 hour, or longer. Longer incubation times may improve ligation efficiency.

Ligation may require nucleic acids with 5' phosphorylated ends. Nucleic acid components without 5' phosphorylated ends may be phosphorylated in a reaction with polynucleotide kinase, such as T4 polynucleotide kinase (or T4 PNK). Other co-factors may be present in the reaction such as ATP, magnesium ion, or DTT. Polynucleotide kinase reactions may occur at 37 degrees Celsius for 30 minutes. Polynucleotide kinase reaction temperatures may be at least 4, 10, 20, 20, 30, 40, 50, or 60 degrees Celsius. Polynucleotide kinase reaction incubation times may be at most, 1 minute, 5 minutes, 10 minutes, 20 minutes, 30 minutes, 60 minutes, or more. Alternatively, the nucleic acid components may be synthetically (as opposed to enzymatically) designed and manufactured with a modified 5' phosphorylation. Only nucleic acids being assembled on their 5' ends may require phosphorylation. For example, templates in TDL may not be phosphorylated as they are not intended to be assembled.

Additives may be included in a ligation reaction to improve ligation efficiency. For example, the addition of Dimethyl sulfoxide (DMSO), polyethylene glycol (PEG), 1,2-Propanediol (1,2-Prd), glycerol, Tween-20 or combinations thereof. PEG6000 may be a particularly effective ligation enhancer. PEG6000 may increase ligation efficiency by acting as a crowding agent. For example, the PEG6000 may form aggregated nodules that take up space in the ligase reaction solution and bring the ligase and components to closer proximity. Additive content (weight per volume) may be at least 0%, 1%, 5%, 10%, 20%, or more.

Various ligases may be used for ligation. The ligases can be naturally occurring or synthesized. Examples of ligases include T4 DNA Ligase, T7 DNA Ligase, T3 DNA Ligase, Taq DNA Ligase, 9°N™ DNA Ligase, *E. coli* DNA Ligase, and SplintR DNA Ligase. Different ligases may be stable and function optimally at different temperatures. For example, Taq DNA Ligase is thermostable and T4 DNA Ligase is not. Moreover, different ligases have different properties. For example, T4 DNA Ligase may ligate blunt-ended dsDNA while T7 DNA Ligase may not.

Ligation may be used to attach sequencing adapters to a library of nucleic acids. For example, the ligation may be performed with common sticky ends or staples at the ends of each member of the nucleic acid library. If the sticky end or staple at one end of the nucleic acids is distinct from that of the other end, then the sequencing adapters may be ligated asymmetrically. For example, a forward sequencing adapter may be ligated to one end of the members of the nucleic acid library and a reverse sequencing adapter may be ligate to the other end of the members of the nucleic acid library. Alternatively, blunt-ended ligation may be used to attach adapters to a library of blunt-ended double-stranded nucleic acids. Fork adapters may be used to asymmetrically attach adapters to a nucleic acid library with either blunt ends or sticky ends that are equivalent at each end (such as A-tails).

Ligation may be inhibited by heat inactivation (for example incubation at 65 degrees Celsius for at least 20 minutes), addition of a denaturant, or addition of a chelator such as EDTA.

C. Restriction Digest

Restriction digests are reactions in which restriction endonucleases (or restriction enzymes) recognize their cognate restriction site on nucleic acids and subsequently cleave (or digest) the nucleic acids containing said restriction site. Type I, type II, type III, or type IV restriction enzymes may be used for restriction digests. Type II restriction enzymes may be the most efficient restriction enzymes for nucleic acid digestions. Type II restriction enzymes may recognize palindromic restriction sites and cleave nucleic acids within the recognition site. Examples of said restriction enzymes (and their restriction sites) include AatII (GACGTC), AfeI (AGCGCT), ApaI (GGGCCC), DpnI (GATC), EcoRI (GAATTC), NgeI (GCTAGC), and many more. Some restriction enzymes, such as DpnI and AfeI, may cut their restriction sites in the center, thus leaving blunt-ended dsDNA products. Other restriction enzymes, such as EcoRI and AatII, cut their restriction sites off-center, thus leaving dsDNA products with sticky ends (or staggered ends). Some restriction enzymes may target discontinuous restriction sites. For example, the restriction enzyme AlwNI recognizes the restriction site CAGNNNCTG, where N may be either A, T, C, or G. Restriction sites may be at least 2, 4, 6, 8, 10, or more bases long.

Some Type II restriction enzymes cleave nucleic acids outside of their restriction sites. The enzymes may be sub-classified as either Type IIS or Type IIG restriction enzymes. Said enzymes may recognize restriction sites that are non-palindromic. Examples of said restriction enzymes include BbsI, that recognizes GAAAC and creates a staggered cleavage 2 (same strand) and 6 (opposite strand) bases further downstream. Another example includes BsaI, that recognizes GGTCTC and creates a staggered cleavage 1 (same strand) and 5 (opposite strand) bases further downstream. Said restriction enzymes may be used for golden gate assembly or modular cloning (MoClo). Some restriction enzymes, such as BcgI (a Type IIG restriction enzyme) may create a staggered cleavage on both ends of its recognition site. Restriction enzymes may cleave nucleic acids at least 1, 5, 10, 15, 20, or more bases away from their recognition sites. Because said restriction enzymes may create staggered cleavages outside of their recognitions sites, the sequences of the resulting nucleic acid overhangs may be arbitrarily designed. This is as opposed to restriction enzymes that create staggered cleavages within their recognition sites, where the sequence of a resulting nucleic acid overhang is coupled to the sequence of the restriction site. Nucleic acid overhangs created by restriction digests may be at least 1, 2, 3, 4, 5, 6, 7, 8, or more bases long. When restriction enzymes cleave nucleic acids, the resulting 5' ends contain a phosphate.

One or more nucleic acid sequences may be included in a restriction digest reaction. Likewise, one or more restriction enzymes may be used together in a restriction digest reaction. Restriction digests may contain additives and cofactors including potassium ion, magnesium ion, sodium ion, BSA, S-Adenosyl-L-methionine (SAM), or combinations thereof. Restriction digest reactions may be incubated at 37 degrees Celsius for one hour. Restriction digest reactions may be incubated in temperatures of at least 0, 10, 20, 30, 40, 50, or 60 degrees Celsius. Optimal digest temperatures may depend on the enzymes. Restriction digest reactions may be incubated for at most 1, 10, 30, 60, 90, 120, or more minutes. Longer incubation times may result in increased digestion.

D. Nucleic Acid Amplification

Nucleic acid amplification may be executed with polymerase chain reaction, or PCR. In PCR, a starting pool of nucleic acids (referred to as the template pool or template) may be combined with polymerase, primers (short nucleic acid probes), nucleotide tri phosphates (such as dATP, dTTP, dCTP, dGTP, and analogs or variants thereof), and additional cofactors and additives such as betaine, DMSO, and magnesium ion. The template may be single stranded or double stranded nucleic acids. The primer may be a short nucleic acid sequence built synthetically to complement and hybridize to a target sequence in the template pool. Typically, there are two primers in a PCR reaction, one to complement a primer binding site on the top strand of a target template, and another to complement a primer binding site on the bottom strand of the target template downstream of the first binding site. The 5'-to-3' orientation in which these primers bind their target must be facing each other in order to successfully replicate and exponentially amplify the nucleic acid sequence in between them. Though "PCR" may typically refer to reactions specifically of said form, it may also be used more generally to refer to any nucleic acid amplification reaction.

In some embodiments, PCR may comprise cycling between three temperatures: a melting temperature, an annealing temperature, and an extension temperature. The melting temperature is intended to turn double stranded nucleic acids into single stranded nucleic acids, as well as remove the formation of hybridization products and secondary structures. Typically the melting temperature is high, for example above 95 degrees Celsius. In some embodiments the melting temperature may be at least 96, 97, 98, 99, 100, 101, 102, 103, 104, or 105 degrees Celsius. In other embodiments the melting temperature may be at most 95, 94, 93, 92, 91, or 90 degrees Celsius. A higher melting temperature will improve dissociation of nucleic acids and their secondary structures, but may also cause side effects such as the degradation of nucleic acids or the polymerase. Melting temperatures may be applied to the reaction for at least 1, 2, 3, 4, 5 seconds, or above, such as 30 seconds, 1 minute, 2 minutes, or 3 minutes. A longer initial melting temperature step may be recommended for PCR with complex or long template.

The annealing temperature is intended to facilitate the formation of hybridization between the primers and their target templates. In some embodiments, the annealing temperature may match the calculated melting temperature of the primer. In other embodiments, the annealing temperature may be within 10 degrees Celsius or more of said melting temperature. In some embodiments, the annealing temperature may be at least 25, 30, 50, 55, 60, 65, or 70 degrees Celsius. The melting temperature may depend on the sequence of the primer. Longer primers may have higher melting temperatures, and primers with higher percent content of Guanine or Cystosine nucleotides may have higher melting temperatures. It may therefore be possible to design primers intended to assemble optimally at particular annealing temperatures. Annealing temperatures may be applied to the reaction for at least 1, 5, 10, 15, 20, 25, or 30 seconds, or above. To help ensure annealing, the primer concentrations may be at high or saturating amounts. Primer concentrations may be 500 nanomolar (nM). Primer concentrations may be at most 1 nM, 10 nM, 100 nM, 1000 nM, or more.

The extension temperature is intended to initiate and facilitate the 3' end nucleic acid chain elongation of primers catalyzed by one or more polymerase enzymes. In some embodiments, the extension temperature may be set at the temperature in which the polymerase functions optimally in terms of nucleic acid binding strength, elongation speed, elongation stability, or fidelity. In some embodiments, the extension temperature may be at least 30, 40, 50, 60, or 70 degrees Celsius, or above. Annealing temperatures may be applied to the reaction for at least 1, 5, 10, 15, 20, 25, 30, 40, 50, or 60 seconds or above. Recommended extension times may be approximately 15 to 45 seconds per kilobase of expected elongation.

In some embodiments of PCR, the annealing temperature and the extension temperature may be the same. Thus a 2-step temperature cycle may be used instead of a 3-step temperature cycle. Examples of combined annealing and extension temperatures include 60, 65, or 72 degrees Celsius.

In some embodiments, PCR may be performed with one temperature cycle. Such embodiments may involve turning targeted single stranded template nucleic into double stranded nucleic acid. In other embodiments, PCR may be performed with multiple temperature cycles. If the PCR is efficient, it is expected that the number of target nucleic acid molecules will double each cycle, thereby creating an exponential increase in the number of targeted nucleic acid templates from the original template pool. The efficiency of PCR may vary. Therefore, the actual percent of targeted nucleic acid that is replicated each round may be more or less than 100%. Each PCR cycle may introduce undesirable artifacts such as mutated and recombined nucleic acids. To curtail this potential detriment, a polymerase with high fidelity and high processivity may be used. In addition, a limited number of PCR cycles may be used. PCR may involve at most 1, 5, 10, 15, 20, 25, 30, 35, 40, 45, or more cycles.

In some embodiments, multiple distinct target nucleic acid sequences may amplified together in one PCR. If each target sequence has common primer binding sites, then all nucleic acid sequences may be amplified with the same set of primers. Alternatively, PCR may comprise multiple primers intended to each target distinct nucleic acids. Said PCR may be referred to as multiplex PCR. PCR may involve at most 1, 2, 3, 4, 5, 6, 7, 8, 9, 10, or more distinct primers. In PCR with multiple distinct nucleic acid targets, each PCR cycle may change the relative distribution of the targeted nucleic acids. For example, a uniform distribution may become skewed or non-uniformly distributed. To curtail this potential detriment, optimal polymerases (e.g., with high fidelity and sequence robustness) and optimal PCR conditions may be used. Factors such as annealing and extension temperature and time may be optimized. In addition, a limited number of PCR cycles may be used.

In some embodiments of PCR, a primer with base mismatches to its targeted primer binding site in the template may be used to mutate the target sequence. In some embodiments of PCR, a primer with an extra sequence on its 5' end (known as an overhang) may be used to attach a sequence to its targeted nucleic acid. For example, primers containing sequencing adapters on their 5' ends may be used to prepare and/or amplify a nucleic acid library for sequencing. Primers that target sequencing adapters may be used to amplify nucleic acid libraries to sufficient enrichment for certain sequencing technologies.

In some embodiments, linear-PCR (or asymmetric-PCR) is used wherein primers only target one strand (not both strands) of a template. In linear-PCR the replicated nucleic acid from each cycle is not complemented to the primers, so the primers do not bind it. Therefore, the primers only replicate the original target template with each cycle, hence the linear (as opposed to exponential) amplification. Though the amplification from linear-PCR may not be as fast as conventional (exponential) PCR, the maximal yield may be greater. Theoretically, the primer concentration in linear-PCR may not become a limiting factor with increased cycles and increased yield as it would with conventional PCR. Linear-After-The-Exponential-PCR (or LATE-PCR) is a modified version of linear-PCR that may be capable of particularly high yields.

In some embodiments of nucleic acid amplification, the process of melting, annealing, and extension may occur at a single temperature. Such PCR may be referred to as isothermal PCR. Isothermal PCR may leverage temperature-independent methods for dissociating or displacing the fully-complemented strands of nucleic acids from each other in favor of primer binding. Strategies include loop-mediated isothermal amplification, strand displacement amplification, helicase-dependent amplification, and nicking enzyme amplification reaction. Isothermal nucleic acid amplification may occur at temperatures of at most 20, 30, 40, 50, 60, or 70 degrees Celsius or more.

In some embodiments, PCR may further comprise a fluorescent probe or dye to quantify the amount of nucleic acid in a sample. For example, the dye may interpolate into double stranded nucleic acids. An example of said dye is SYBR Green. A fluorescent probe may also be a nucleic acid sequence attached to a fluorescent unit. The fluorescent unit may be release upon hybridization of the probe to a target nucleic acid and subsequent modification from an extending polymerase unit. Examples of said probes include Taqman probes. Such probes may be used in conjunction with PCR and optical measurement tools (for excitation and detection) to quantify nucleic acid concentration in a sample. This process may be referred to as quantitative PCR (qPCR) or real-time PCR (rtPCR).

In some embodiments, a PCR may be performed on single a molecule template (in a process that may be referred to as single-molecule PCR), rather than on a pool of multiple template molecules. For example, emulsion-PCR (ePCR) may be used to encapsulate single nucleic acid molecules within water droplets within an oil emulsion. The water droplets may also contain PCR reagents, and the water droplets may be held in a temperature-controlled environment capable of requisite temperature cycling for PCR. This way, multiple self-contained PCR reactions may occur simultaneously in high throughput. The stability of oil emulsions may be improved with surfactants. The movement of droplets may be controlled with pressure through microfluidic channels. Microfluidic devices may be used to create droplets, split droplets, merge droplets, inject material intro droplets, and to incubate droplets. The size of water droplets in oil emulsions may be at least 1 picoliter (pL), 10 pL, 100 pL, 1 nanoliter (nL), 10 nL, 100 nL, or more.

In some embodiments, single-molecule PCR may be performed one a solid-phase substrate. Examples include the Illumina solid-phase amplification method or variants thereof. The template pool may be exposed to a solid-phase substrate, wherein the solid phase substrate may immobilize templates at a certain spatial resolution. Bridge amplification may then occur within the spatial neighborhood of each template thereby amplifying single molecules in a high throughput fashion on the substrate.

High-throughput, single-molecule PCR may be useful for amplifying a pool of distinct nucleic acids that may interfere with each other. For example, if multiple distinct nucleic acids share a common sequence region, then recombination between the nucleic acids along this common region may occur during the PCR reaction, resulting in new, recombined nucleic acids. Single-molecule PCR would prevent this potential amplification error as it compartmentalizes distinct nucleic acid sequences from each other so they may not interact. Single-molecule PCR may be particularly useful for preparing nucleic acids for sequencing. Single-molecule PCR mat also be useful for absolute quantitation of a number of targets within a template pool. For example, digital PCR (or dPCR), uses the frequency of distinct single-molecule PCR amplification signals to estimate the number of starting nucleic acid molecules in a sample.

In some embodiments of PCR, a group of nucleic acids may be non-discriminantly amplified using primers for primer binding sites common to all nucleic acids. For example, primers for primer binding sites flanking all nucleic acids in a pool. Synthetic nucleic acid libraries may be created or assembled with these common sites for general amplification. However, in some embodiments, PCR may be used to selectively amplify a targeted subset of nucleic acids from a pool. For example, by using primers with primer binding sites that only appear on said targeted subset of nucleic acids. Synthetic nucleic acid libraries may be created or assembled such that nucleic acids belonging to potential sub-libraries of interest all share common primer binding sites on their edges (common within the sub-library but distinct from other sub-libraries) for selective amplification of the sub-library from the more general library. In some embodiments, PCR may be combined with nucleic acid assembly reactions (such as ligation or OEPCR) to selectively amplify fully assembled or potentially fully assembled nucleic acids from partially assembled or mis-assembled (or unintended or undesirable) bi-products. For example, the assembly may involve assembling a nucleic acid with a primer binding site on each edge sequence such that only a full assembled nucleic product would contain the requisite two primer binding sites for amplification. In said example, a partially assembled product may contain neither or only one of the edge sequences with the primer binding sites, and therefore should not be amplified. Likewise a mis-assembled (or unintended or undesirable) product may contain neither or only one of the edge sequences, or both edge sequences but in the incorrect orientation or separated by an incorrect amount of bases. Therefore said mis-assembled product should either not amplify or amplify to create a product of incorrect length. In the latter case the amplified mis-assembled product of incorrect length may be separated from the amplified fully assembled product of correct length by nucleic acid size selection methods (see Chemical Methods Section E), such as DNA electrophoresis in an agarose gel followed by gel extraction.

Additives may be included in the PCR to improve the efficiency of nucleic acid amplification. For example, the addition of Betaine, Dimethyl sulfoxide (DMSO), non-ionic detergents, Formamide, Magnesium, Bovine Serum Albumin (BSA), or combinations thereof. Additive content (weight per volume) may be at least 0%, 1%, 5%, 10%, 20%, or more.

Various polymerases may be used for PCR. The polymerase can be naturally occurring or synthesized. An example polymerase is a Φ29 polymerase or derivative thereof. In some cases, a transcriptase or a ligase is used (i.e., enzymes which catalyze the formation of a bond) in conjunction with polymerases or as an alternative to polymerases to construct new nucleic acid sequences. Examples of polymerases include a DNA polymerase, a RNA polymerase, a thermostable polymerase, a wild-type polymerase, a modified polymerase, E. coli DNA polymerase I, T7 DNA polymerase, bacteriophage T4 DNA polymerase Φ29 (phi29) DNA polymerase, Taq polymerase, Tth polymerase, Tli polymerase, Pfu polymerase Pwo polymerase, VENT polymerase, DEEPVENT polymerase, Ex-Taq polymerase, LA-Taw polymerase, Sso polymerase Poc polymerase, Pab polymerase, Mth polymerase ES4 polymerase, Tru polymerase, Tac polymerase, Tne polymerase, Tma polymerase, Tca polymerase, Tih polymerase, Tfi polymerase, Platinum Taq polymerases, Tbr polymerase, Phusion polymerase, KAPA polymerase, Q5 polymerase, Tfl polymerase, Pfutubo polymerase, Pyrobest polymerase, KOD polymerase, Bst polymerase, Sac polymerase, Klenow fragment polymerase with 3' to 5' exonuclease activity, and variants, modified products and derivatives thereof. Different polymerases may be stable and function optimally at different temperatures. Moreover, different polymerases have different properties. For example, some polymerases, such a Phusion polymerase, may exhibit 3' to 5' exonuclease activity, which may contribute to higher fidelity during nucleic acid elongation. Some polymerases may displace leading sequences during elongation, while others may degrade them or halt elongation. Some polymerases, like Taq, incorporate an adenine base at the 3' end of nucleic acid sequences. Additionally, some polymerases may have higher fidelity and processivity than others and may be more suitable to PCR applications, such as sequencing preparation, where it is important for the amplified nucleic acid yield to have minimal mutations and where it is important for the distribution of distinct nucleic acids to maintain uniform distribution throughout amplification.

E. Size Selection

Nucleic acids of a particular size may be selected from a sample using size-selection techniques. In some embodiments, size-selection may be performed using gel electrophoresis or chromatography. Liquid samples of nucleic acids may be loaded onto one terminal of a stationary phase or gel (or matrix). A voltage difference may be placed across the gel such that the negative terminal of the gel is the terminal at which the nucleic acid samples are loaded and the positive terminal of the gel is the opposite terminal. Since the nucleic acids have a negatively charged phosphate backbone, they will migrate across the gel to the positive terminal. The size of the nucleic acid will determine it's relative speed of migration through the gel. Therefore nucleic acids of different sizes will resolve on the gel as they migrate. Voltage differences may be 100V or 120V. Voltage differences may be at most 50V, 100V, 150V, 200V, 250V, or more. Larger voltage differences may increase the speed of nucleic acid migration and size resolution. However, larger voltage differences may also damage the nucleic acids or the gel. Larger voltage differences may be recommended for resolving nucleic acids of larger sizes. Typical migration times may be between 15 minutes and 60 minutes. Migration times may be at most 10 minutes, 30 minutes, 60 minutes, 90 minutes, 120 minutes, or more. Longer migration times, similar to higher voltage, may lead to better nucleic acid resolution but may lead to increased nucleic acid damage. Longer migration times may be recommended for resolving nucleic acids of larger sizes. For example, a voltage difference of 120V and a migration time of 30 minutes may be sufficient for resolving a 200-base nucleic acid from a 250-base nucleic acid.

The properties of the gel, or matrix, may affect the size-selection process. Gels typically comprise a polymer substance, such as agarose or polyacrylamide, dispersed in a conductive buffer such as TAE (Tris-acetate-EDTA) or TBE (Tris-borate-EDTA). The content (weight per volume) of the substance (e.g. agarose or acrylamide) in the gel may be at most 0.5%, 1%, 2%, 3%, 5%, 10%, 15%, 20%, 25%, or higher. Higher content may decrease migration speed. Higher content may be preferable for resolving smaller nucleic acids. Agarose gels may be better for resolving double stranded DNA (dsDNA). Polyacrylamide gels may be better for resolving single stranded DNA (ssDNA). The preferred gel composition may depend on the nucleic acid type and size, the compatibility of additives (e.g., dyes, stains, denaturing solutions, or loading buffers) as well as the anticipate downstream applications (e.g., gel extraction then ligation, PCR, or sequencing). Agarose gels may be simpler for gel extraction than polyacrylamide gels. TAE, though not as good a conductor as TBE, may also be better for gel extraction because borate (an enzyme inhibitor) carry-over in the extraction process may inhibit downstream enzymatic reactions.

Gels may further comprise a denaturing solution such as SDS (sodium dodecyl sulfate) or urea. SDS may be used, for example, to denature proteins or to separate nucleic acids from potentially bound proteins. Urea may be used to denature secondary structures in DNA. For example, urea may convert dsDNA into ssDNA, or urea may convert a folded ssDNA (for example a hairpin) to a non-folded ssDNA. Urea-polyacrylamide gels (further comprising TBE) may be used for accurately resolving ssDNA.

Samples may be incorporate into gels with different formats. In some embodiments, gels may contain wells in which samples may be loaded manually. One gel may have multiple wells for running multiple nucleic acids samples. In other embodiments, the gels may be attached to microfluidic channels that automatically load the nucleic acid sample(s). Each gel may be downstream of several microfluidic channels, or the gels themselves may each occupy separate microfluidic channels. The dimensions of the gel may affect the sensitivity of nucleic acid detection (or visualization). For example, thin gels or gels inside of microfluidic channels (such as in bioanalyzers or tapestations) may improve the sensitivity of nucleic acid detection. The nucleic acid detection step may be important for selecting and extracting a nucleic acid fragment of the correct size.

A ladder may be loaded into a gel for nucleic acid size reference. The ladder may contain markers of different sizes to which the nucleic acid sample may be compared. Different ladders may have different size ranges and resolutions. For example a 50 base ladder may have markers at 50, 100, 150, 200, 250, 300, 350, 400, 450, 500, 550, and 600 bases. Said ladder may be useful for detecting and selecting nucleic acids within the size range of 50 and 600 bases. The ladder may also be used as a standard for estimating the concentration of nucleic acids of different sizes in a sample.

Nucleic acid samples and ladders may be mixed with loading buffer to facilitate the gel electrophoresis (or chromatography) process. Loading buffer may contain dyes and markers to help track the migration of the nucleic acids. Loading buffer may further comprise reagents (such as glycerol) that are denser than the running buffer (e.g., TAE or TBE), to ensure that nucleic acid samples sink to the bottom of the sample loading wells (which may be submerged in the running buffer). Loading buffer may further comprise denaturing agents such as SDS or urea. Loading buffer may further comprise reagents for improving the stability of nucleic acids. For example, loading buffer may contain EDTA to protect nucleic acids from nucleases.

In some embodiments, the gel may comprise a stain that binds the nucleic acid and that may be used to optically detect nucleic acids of different sizes. Stains may be specific for dsDNA, ssDNA, or both. Different stains may be compatible with different gel substances. Some stains may require excitation from a source light (or electromagnetic wave) in order to visualize. The source light may be UV (ultraviolet) or blue light. In some embodiments, stains may be added to the gel prior to electrophoresis. In other embodiments, stains may be added to the gel after electrophoresis. Examples of stains include Ethidium Bromide (EtBr), SYBR Safe, SYBR Gold, silver stain, or methylene blue. A reliable method for visualizing dsDNA of a certain size, for example, may be to use an agarose TAE gel with a SYBR Safe or EtBr stain. A reliable method for visualizing ssDNA of a certain size, for example, may be to use a urea-polyacrylamide TBE gel with a methylene blue or silver stain.

In some embodiments, the migration of nucleic acids through gels may be driven by other methods besides electrophoresis. For example, gravity, centrifugation, vacuums, or pressure may be used to drive nucleic acids through gels so that they may resolve according to their size.

Nucleic acids of a certain size may be extracted from gels using a blade or razor to excise the band of gel containing the nucleic acid. Proper optical detection techniques and DNA ladders may be used to ensure that the excision occurs precisely at a certain band and that the excision successfully excludes nucleic acids that may belong to different, undesirable size bands. The gel band may be incubated with buffer to dissolve it, thus releasing the nucleic acids into the buffer solution. Heat or physical agitation may speed the dissolution. Alternatively, the gel band may be incubated in buffer long enough to allow diffusion of the DNA into the buffer solution without requiring gel dissolution. The buffer may then be separated from the remaining solid-phase gel, for example by aspiration or centrifugation. The nucleic acids may then be purified from the solution using standard purification or buffer-exchange techniques, such as phenol-chloroform extraction, ethanol precipitation, magnetic bead capture, and/or silica membrane adsorption, washing, and elution. Nucleic acids may also be concentrated in this step.

As an alternative to gel excision, nucleic acids of a certain size may be separated from a gel by allowing them to run off the gel. Migrating nucleic acids may pass through a basin (or well) either embedded in the gel or at the end of the gel. The migration process may be timed or optically monitored such that when the nucleic acid group of a certain size enters the basin, the sample is collected from the basin. The collection may occur, for example, by aspiration. The nucleic acids may then be purified from the collected solution using standard purification or buffer-exchange techniques, such as phenol-chloroform extraction, ethanol precipitation, magnetic bead capture, and/or silica membrane adsorption, washing, and elution. Nucleic acids may also be concentrated in this step.

Other methods for nucleic acid size selection may include mass-spectrometry or membrane-based filtration. In some embodiments of membrane-based filtration, nucleic acids are passed through a membrane (for example a silica membrane) that may preferentially bind to either dsDNA, ssDNA, or both. The membrane may be designed to preferentially capture nucleic acids of at least a certain size. For example, membranes may be designed to filter out nucleic acids of less than 20, 30, 40, 50, 70, 90, or more bases. Said membrane-based, size-selection techniques may not be as stringent as gel electrophoresis or chromatography, F. Nucleic Acid Capture Affinity-tagged nucleic acids may be used as sequence specific probes for nucleic acid capture. The probe may be designed to complement a target sequence within a pool of nucleic acids. Subsequently, the probe may be incubated with the nucleic acid pool and hybridized to its target. The incubation temperature may be below the melting temperature of the probe to facilitate hybridization. The incubation temperature may be up to 5, 10, 15, 20, 25, or more degrees Celsius below the melting temperature of the probe. The hybridized target may be captured to a solid-phase substrate that specifically binds the affinity tag. The solid-phase substrate may be a membrane, a well, a column, or a bead. Multiple rounds of washing may remove all non-hybridized nucleic acids from the targets. The washing may occur at a temperature below the melting temperature of the probe to facilitate stable immobilization of target sequences during the wash. The washing temperature may be up to 5, 10, 15, 20, 25, or more degrees Celsius below the melting temperature of the probe. A final elution step may recover the nucleic acid targets from the solid phase-substrate, as well as from the affinity tagged probes. The elution step may occur at a temperature above the melting temperature of the probe to facilitate the release of nucleic acid targets into an elution buffer. The elution temperature may be up to 5, 10, 15, 20, 25, or more degrees Celsius above the melting temperature of the probe.

In some embodiments, biotin may be used as an affinity tag that is immobilized by streptavidin on a solid-phase substrate. Biotinylated oligos, for use as nucleic acid capture probes, may be designed and manufactured. Oligos may be biotinylated on the 5' or 3' end. They may also be biotinylated internally on thymine residues. Increased biotin on an oligo may lead to stronger capture on the streptavidin substrate. A biotin on the 3' end of an oligo may block the oligo from extending during PCR. The biotin tag may be a variant of standard biotin. For example, the biotin variant may be biotin-TEG (triethylene glycol), dual biotin, PC biotin, DesthioBiotin-TEG, and biotin Azide. Dual biotin may increase the biotin-streptavidin affinity. Biotin-TEG attaches the biotin group onto a nucleic acid separated by a TEG linker. This may prevent the biotin from interfering with the function of the nucleic acid probe, for example its hybridization to the target. A nucleic acid biotin linker may also be attached to the probe. The nucleic acid linker may comprise nucleic acid sequences that are not intended to hybridize to the target.

The biotinylated nucleic acid probe may be designed with consideration for how well it may hybridize to its target. Nucleic acid probes with higher designed melting temperatures may hybridize to their targets more strongly. Longer nucleic acid probes, as well as probes with higher GC content, may hybridize more strongly due to increased melting temperatures. Nucleic acid probes may have a length of a least 5, 10, 15, 20, 30, 40, 50, or 100 bases, or more. Nucleic acid probes may have a GC content anywhere between 0 and 100%. Care may be taken to ensure that the melting temperature of the probe does not exceed the temperature tolerance of the streptavidin substrate. Nucleic acid probes may be designed to avoid inhibitory secondary structures such as hairpins, homodimers, and heterodimers with off-target nucleic acids. There may be a tradeoff between probe melting temperature and off-target binding. There may be an optimal probe length and GC content at which melting temperature is high and off-target binding is low. A synthetic nucleic acid library may be designed such that its nucleic acids comprise efficient probe binding sites.

The solid-phase streptavidin substrate may be magnetic beads. Magnetic beads may be immobilized using a magnetic strip or plate. The magnetic strip or plate may be brought into contact with a container to immobilize the magnetic beads to the container. Conversely, the magnetic strip or plate may be removed from a container to release the magnetic beads from the container wall into a solution. different bead properties may affect their application. Beads may have varying sizes. For example beads may be anywhere between 1 and 3 micrometers (um) in diameter. Beads may have a diameter of at most 1, 2, 3, 4, 5, 10, 15, 20, or more micrometers. Bead surfaces may be hydrophobic or hydrophilic. Beads may be coated with blocking proteins, for example BSA. Prior to use, beads may be washed or pre-treated with additives, such as blocking solution to prevent them from non-specifically binding nucleic acids.

A Biotinylated probe may be coupled to the magnetic streptavidin beads prior to incubation with the nucleic acid sample pool. This process may be referred to as direct capture. Alternatively, the biotinylated probe may be incubated with the nucleic acid sample pool prior to the addition of magnetic streptavidin beads. This process may be referred to as indirect capture. The indirect capture method may improve target yield. shorter nucleic acid probes may require a shorter amount of time to couple to the magnetic beads.

Optimal incubation of the nucleic acid probe with the nucleic acid sample may occur at a temperature that is 1 to 10 degrees Celsius or more below the melting temperature of the probe. Incubation temperatures may be at most 5, 10, 20, 30, 40, 50, 60, 70, 80, or more degrees Celsius. The recommended incubation time may be 1 hour. The incubation time may be at most 1, 5, 10, 20, 30, 60, 90, 120, or more minutes. Longer incubation times may lead to better capture efficiency. An additional 10 minutes of incubation may occur after the addition of the streptavidin beads to allow biotin-streptavidin coupling. This additional time may be at most 1, 5, 10, 20, 30, 60, 90, 120, or more minutes. Incubation may occur in buffered solution with additives such as sodium ion.

Hybridization of the probe to its target may be improved if the nucleic acid pool is single-stranded nucleic acid (as opposed to double-stranded). Preparing a ssDNA pool from a dsDNA pool may entail performing linear-PCR with one primer that commonly binds the edge of all nucleic acid sequences in the pool. If the nucleic acid pool is synthetically created or assembled, then this common primer binding site may be included in the synthetic design. The product of the linear-PCR will be ssDNA. More starting ssDNA template for the nucleic acid capture may be generated with more cycles of linear-PCR. See Chemical Methods Section D on PCR.

After the nucleic acid probes are hybridized to their targets and coupled to magnetic streptavidin beads, the beads may be immobilized by a magnet and several rounds of washing may occur. Three to five washes may be sufficient to remove non-target nucleic acids, but more or less rounds of washing may be used. Each incremental wash may further decrease non-targeted nucleic acids, but it may also decrease the yield of target nucleic acids. To facilitate proper hybridization of the target nucleic acids to the probe during the wash step, a low incubation temperature may be used. Temperatures as low as 60, 50, 40, 30, 20, 10, or 5 degrees Celsius or less may be used. The washing buffer may comprise Tris buffered solution with sodium ion.

Optimal elution of the hybridized targets from the magnetic bead-coupled probes may occur at a temperature that is equivalent to or more than the melting temperature of the probe. Higher temperatures will facilitate the dissociation of the target to the probe. Elution temperatures may be at most 30, 40, 50, 60, 70, 80, or 90 degrees Celsius, or more. Elution incubation time may be at most 1, 2, 5, 10, 30, 60 or more minutes. Typical incubation times may be approximately 5 minutes, but longer incubation times may improve yield. Elution buffer may be water or tris-buffered solution with additives such as EDTA.

Nucleic acid capture of target sequences containing at least one or more of a set of distinct sites may be performed in one reaction with multiple distinct probes for each of those sites. Nucleic acid capture of target sequences containing every member of a set of distinct sites may be performed in a series of capture reactions, one reaction for each distinct site using a probe for that particular site. The target yield after a series of capture reactions may be low, but the captured targets may subsequently be amplified with PCR. If the nucleic acid library is synthetically designed, then the targets may be designed with common primer binding sites for PCR.

Synthetic nucleic acid libraries may be created or assembled with common probe binding sites for general nucleic acid capture. These common sites may be used to selectively capture fully assembled or potentially fully assembled nucleic acids from assembly reactions, thereby filtering out partially assembled or mis-assembled (or unintended or undesirable) bi-products. For example, the assembly may involve assembling a nucleic acid with a probe binding site on each edge sequence such that only a fully assembled nucleic product would contain the requisite two probe binding sites necessary to pass through a series of two capture reactions using each probe. In said example, a partially assembled product may contain neither or only one of the probe sites, and therefore should not ultimately be captured. Likewise a mis-assembled (or unintended or undesirable) product may contain neither or only one of the edge sequences. Therefore said mis-assembled product may not ultimately be captured. For increased stringency, common probe binding sites may be included on each component of an assembly. A subsequent series of nucleic acid capture reactions using a probe for each component may isolate only fully assembled product (containing each component) from any bi-products of the assembly reaction. Subsequent PCR may improve target enrichment, and subsequent size-selection may improve target stringency.

In some embodiments, nucleic acid capture may be used to selectively capture a targeted subset of nucleic acids from a pool. For example, by using probes with binding sites that only appear on said targeted subset of nucleic acids. Synthetic nucleic acid libraries may be created or assembled such that nucleic acids belonging to potential sub-libraries of interest all share common probe binding sites (common within the sub-library but distinct from other sub-libraries) for the selective capture of the sub-library from the more general library.

G. Lyophilization

Lyophilization is a dehydration process. Both nucleic acids and enzymes may be lyophilized. Lyophilized substances may have longer lifetimes. Additives such as chemical stabilizers may be used to maintain functional products (e.g., active enzymes) through the lyophilization process. Disaccharides, such as sucrose and trehalose, may be used as chemical stabilizers.

H. DNA Design

The sequences of nucleic acids (e.g., components) for building synthetic libraries (e.g., identifier libraries) may be designed to avoid synthesis, sequencing, and assembly complications. Moreover, they may be designed to decrease the cost of building the synthetic library and to improve the lifetime over which the synthetic library may be stored.

Nucleic acids may be designed to avoid long strings of homopolymers (or repeated base sequences) that may be difficult to synthesize. Nucleic acids may be designed to avoid homopolymers of length greater than 2, 3, 4, 5, 6, 7 or more. Moreover, nucleic acids may be designed to avoid the formation of secondary structures, such as hairpin loops, that may inhibit their synthesis process. For example, predictive software may be used to generate nucleic acid sequence that do not form stable secondary structures. Nucleic acids for building synthetic libraries may be designed to be short. Longer nucleic acids may be more difficult and expensive to synthesize. Longer nucleic acids may also have a higher chance of mutations during synthesis. Nucleic acids (e.g., components) may be at most 5, 10, 15, 20, 25, 30, 40, 50, 60 or more bases.

Nucleic acids to become components in an assembly reaction may be designed to facilitate that assembly reaction. See Appendices A and B for more information on nucleic acid sequence considerations for OEPCR and ligation-based assembly reactions, respectively. Efficient assembly reactions typically involve hybridization between adjacent components. Sequences may be designed to promote these on-target hybridization events while avoiding potential off-target hybridizations. Nucleic acid base modifications, such as locked nucleic acids (LNAs), may be used to strengthen on-target hybridization. These modified nucleic acids may be used, for example, as staples in staple strand ligation or as sticky ends in sticky-strand ligation. Other modified bases that may be used for building synthetic nucleic acid libraries (or identifier libraries) include 2,6-Diaminopurine, 5-Bromo dU, deoxyUridine, inverted dT, inverted diDeoxy-T, Dideoxy-C, 5-Methyl dC, deoxyInosine, Super T, Super G, or 5-Nitroindole. Nucleic acids may contain one or multiple of the same or different modified bases. Some of the said modified bases are natural base analogs (for example, 5-Methyl dC and 2,6-Diaminopurine) that have higher melting temperatures and may therefore be useful for facilitating specific hybridization events in assembly reactions. Some of the said modified bases are universal bases (for example, 5-Nitroindole) that can bind to all natural bases and may therefore be useful for facilitating hybridization with nucleic acids that may have variable sequences within desirable binding sites. In addition to their beneficial roles in assembly reactions, these modified bases may be useful in primers (e.g., for PCR) and probes (e.g., for nucleic acid capture) as they may facilitate the specific binding of primers and probes to their target nucleic acids within a pool of nucleic acids. See Chemical Methods Section D and F for more nucleic acid design considerations with regard to nucleic acid amplification (or PCR) and nucleic acid capture, respectively.

Nucleic acids may be designed to facilitate sequencing. For example, nucleic acids may be designed to avoid typical sequencing complications such as secondary structure, stretches of homopolymers, repetitive sequences, and sequences with too high or too low of a GC content. Certain sequencers or sequencing methods may be error prone. Nucleic acid sequences (or components) that make up synthetic libraries (e.g., identifier libraries) may be designed with certain hamming distances from each other. This way, even when base resolution errors occur at a high rate in sequencing, the stretches of error-containing sequences may still be mapped back to their most likely nucleic acid (or component). Nucleic acid sequences may be designed with hamming distances of at least 1, 2, 3, 4, 5, 6, 7, 8, 9, 10, 11, 12, 13, 14, 15 or more base mutations. Alternative distance metrics from hamming distance may also be used to define a minimum requisite distance between designed nucleic acids.

Some sequencing methods and instruments may require input nucleic acids to contain particular sequences, such as adapter sequences or primer-binding sites. These sequences may be referred to as "method-specific sequences". Typical preparatory workflows for said sequencing instruments and methods may involve assembling the method-specific sequences to the nucleic acid libraries. However, if it is known ahead of time that a synthetic nucleic acid library (e.g., identifier library) will be sequenced with a particular instrument or method, then these method-specific sequences may be designed into the nucleic acids (e.g., components) that comprise the library (e.g., identifier library). For example, sequencing adapters may be assembled onto the members of a synthetic nucleic acid library in the same reaction step as when the members of a synthetic nucleic acid library are themselves assembled from individual nucleic acid components.

Nucleic acids may be designed to avoid sequences that may facilitate DNA damage. For example, sequences containing sites for site-specific nucleases may be avoided. As another example, UVB (ultraviolet-B) light may cause adjacent thymines to form pyrimidine dimers which may then inhibit sequencing and PCR. Therefore, if a synthetic nucleic acid library is intended to be stored in an environment exposed to UVB, then it may be beneficial to design its nucleic acid sequences to avoid adjacent thymines (i.e., TT) or adjacent cytosines (i.e., CC).

All information contained within the Chemical Methods section is intended to support and enable the aforementioned technologies, methods, protocols, systems, and processes

EXAMPLES

Example 1: Encoding, Writing and Reading a Single Poem in DNA Molecules

Data to be encoded is a textfile containing a poem. The data is encoded manually with pipettes to mix together DNA components from two layers of 96 components to construct identifiers using the product scheme implemented with overlap extension PCR. The first layer, X, comprises 96 total DNA components. The second layer, Y, also comprises 96 total components. Prior to writing the DNA, the data is mapped to binary and then recoded to a uniform weight format where every contiguous (adjacent disjoint) string of 61 bits of the original data is translated to a 96 bit string with exactly 17 bit-values of 1. This uniform weight format may have natural error checking qualities. The data is then hashed into a 96 by 96 table to form a reference map.

Figure 18A:
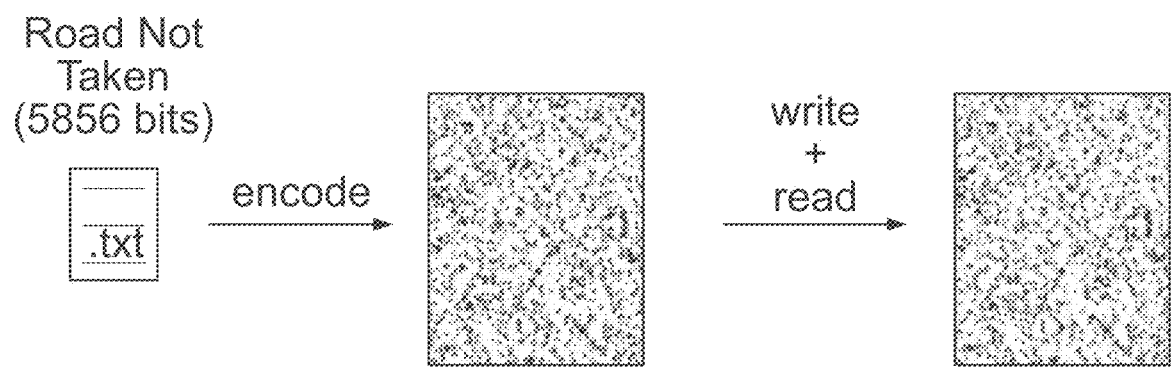
FIG. 18A and FIG. 18B show examples of encoding, writing, and reading data encoded in nucleic acid molecules.

The middle panel of FIG. 18A shows the two-dimensional reference map of a 96 by 96 table encoding the poem into a plurality of identifiers. Dark points correspond to a '1' bit-value and white points corresponded to a '0' bit-value. The data is encoded into identifiers using two layers of 96 components. Each X value and Y value of the table is assigned a component and the X and Y components are assembled into an identifier using overlap extension PCR for each (X,Y) coordinate with a '1' value. The data was read back (e.g., decoded) by sequencing the identifier library to determine the presence or absence of each possible (X,Y) assembly.

The right panel of figure FIG. 18A shows a two-dimensional heat map of the abundances of sequences present in the identifier library as determined by sequencing. Each pixel represents a molecule comprising the corresponding X and Y components, and the greyscale intensity at that pixel represents the relative abundance of that molecule compared to other molecules. Identifiers are taken as the top 17 most abundant (X, Y) assemblies in each row (as the uniform weight encoding guarantees that each contiguous string of 96 bits may have exactly 17 '1' values, and hence 17 corresponding identifiers).

Example 2: Encoding a 62824 Bit Textfile

Data to be encoded is a textfile of three poems totaling 62824 bits. The data is encoded using a Labcyte Echo®

Liquid Handler to mix together DNA components from two layers of 384 components to construct identifiers using the product scheme implemented with overlap extension PCR. The first layer, X, comprises 384 total DNA components. The second layer, Y, also comprises 384 total components. Prior to writing the DNA, the data is mapped to binary and then recoded to decrease the weight (number of bit-values of '1') and include checksums. The checksums are established so that there is an identifier that corresponds to a checksum for every contiguous string of 192 bits of data. The re-coded data has a weight of approximately 10,100, which corresponds to the number of identifiers to be constructed. The data may then be hashed into a 384 by 384 table to form a reference map.

Figure 18B:
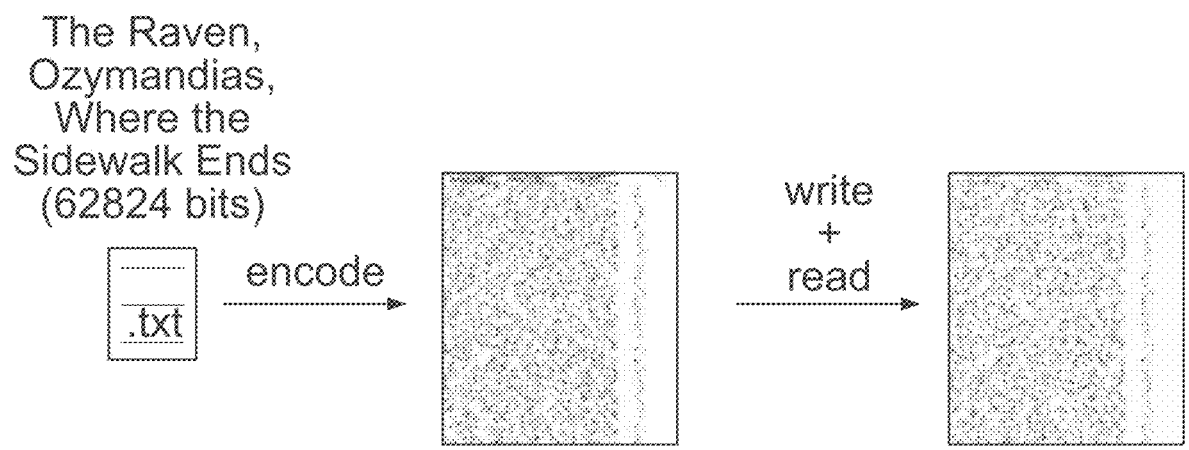

The middle panel of FIG. 18B shows a two-dimensional reference map of a 384 by 384 table encoding the textfile into a plurality of identifiers. Each coordinate (X,Y) corresponds to the bit of data at position X+(Y−1)*192. Black points correspond to a bit value of '1' and white points correspond to a bit value of '0'. The black points on the right side of the figure are the checksums and the pattern of black points on the top of the figure is the codebook (e.g., dictionary for de-coding the data). Each X value and Y value of the table may be assigned a component and the X and Y components are assembled into an identifier using overlap extension PCR for each (X, Y) coordinate with a '1' value. The data was read back (e.g., decoded) by sequencing the identifier library to determine the presence or absence of each possible (X, Y) assembly.

The right panel of FIG. 18B shows a two-dimensional heat map of the abundances of sequences present in the identifier library as determined by sequencing. Each pixel represents a molecule comprising the corresponding X and Y components, and the greyscale intensity at that pixel represents the relative abundance of that molecule compared to other molecules. Identifiers are taken as the top S most abundant (X, Y) assemblies in each row, where S for each row may be the checksum value.

Example 3: A Comparison of 5' Versus 3' Overhangs and 4-Base Versus 6-Base Overhangs on a 15-Piece, Sticky-End Ligation Table 1 presents the measured ligation efficiency of 4 different sets of 15-DNA components labeled the following: 6/24/6 3', 6/24/6 5', 4/24/4 3', and 4/24/4 5'. The first 3 numbers in the label, X/Y/Z, indicates the form of each DNA component in the set with an X-base overhang on one end, a Y-base duplex (or barcode) region in the middle, and a Z-base overhang on the other end. The final number in each label (preceding the apostrophe) indicates whether the overhangs in the set are 5' or 3'. Ligation was performed at 37° C. with 0.067 µM each DNA component, 5 CEU/µL of T4 Ligase (CEU=Cohesive End Unit), 7.5% w/v PEG6000, 20% v/v glycerol, and standard T4 ligase buffer parts. Ligation time was 2.5 minutes. Efficiency was measured with qPCR relative to a full length control (FLC) representing the fully ligated product for each possible set.

TABLE 1

| 15-component set | Measured ligation efficiency | | |
|---|---|---|---|
| | Average ligation efficiency | Sandard deviation | |
| 6/24/6 5' | 0.2471% | 0.0750% | |
| 6/24/6 5' | 0.7237% | 0.1059% | |
| 6/24/6 5' | 0.0275% | 0.0047% | |

TABLE 1-continued

| 15-component set | Measured ligation efficiency | |
|---|---|---|
| | Average ligation efficiency | Sandard deviation |
| 6/24/6 3' | 0.2221% | 0.0470% |
| 6/24/6 3' | 0.0490% | 0.0068% |
| 6/24/6 3' | 0.0398% | 0.0077% |
| 4/24/4 5' | 0.0008% | 0.0001% |
| 4/24/4 5' | 0.0008% | 0.0002% |
| 4/24/4 5' | 0.0003% | 0.0000% |
| 4/24/4 3' | 0.0014% | 0.0003% |
| 4/24/4 3' | 0.0047% | 0.0005% |
| 4/24/4 3' | 0.0008% | 0.0002% |

Figure 22:
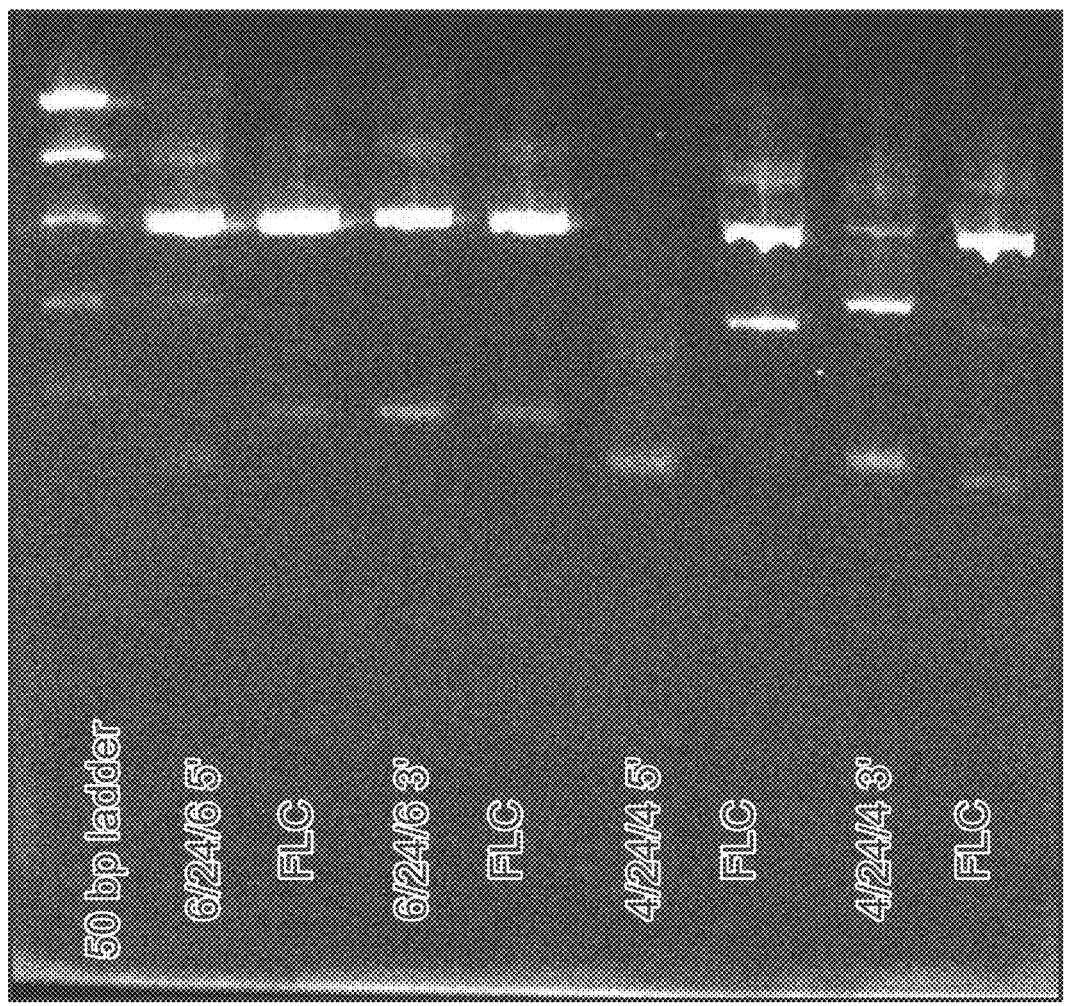
FIG. 22 shows an exemplary gel electrophoresis image of qPCR products from 15-piece, sticky-ended DNA component ligations.

FIG. 22 presents a gel electrophoresis image of the qPCR products from one of each of the 4 different experimental ligation reactions alongside their respective FLCs, which have a length of around 450 bases. Together with Table 1, results indicate that 6-base overhangs led to higher ligation efficiency and specificity of full length product than 4-base overhangs. No obvious pattern in efficiency is observed regarding the use of 5' overhangs versus 3' overhangs.

Figure 23A:
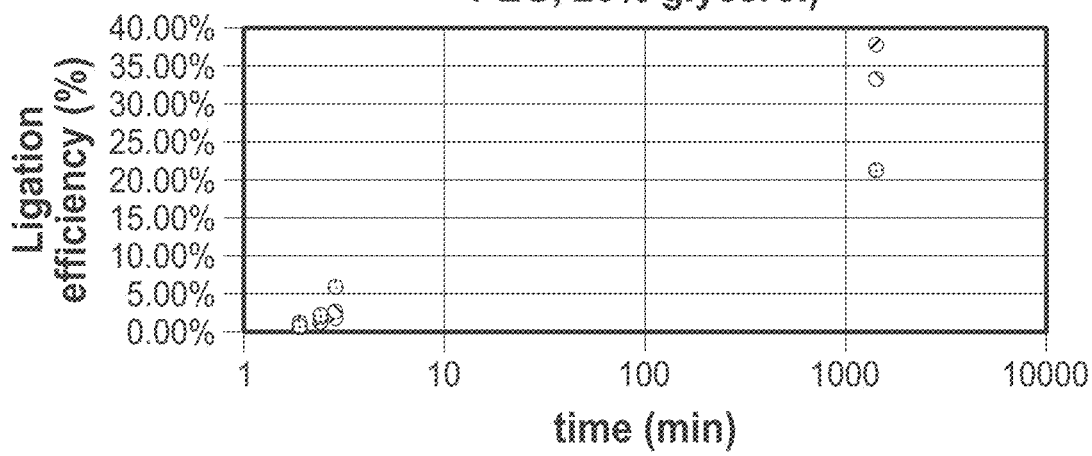
FIG. 23A shows exemplary data for ligation efficiency of 15-piece, 6-base 5' overhang DNA component sets ligated for 2, 2.5, 3, and 1440 minutes.
Figure 23B:
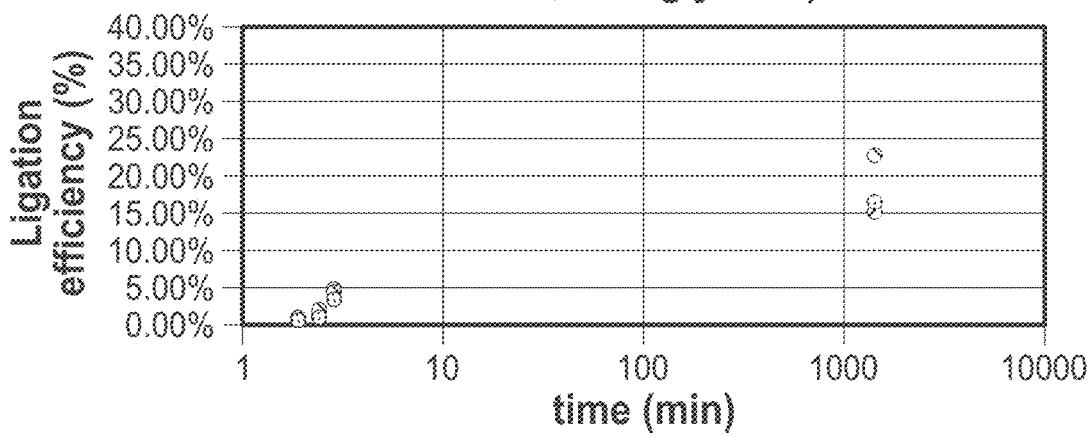
FIG. 23B shows exemplary data for ligation efficiency of 15-piece, 6-base 3' DNA component sets ligated for 2, 2.5, 3, and 1440 minutes.
Figure 23C:
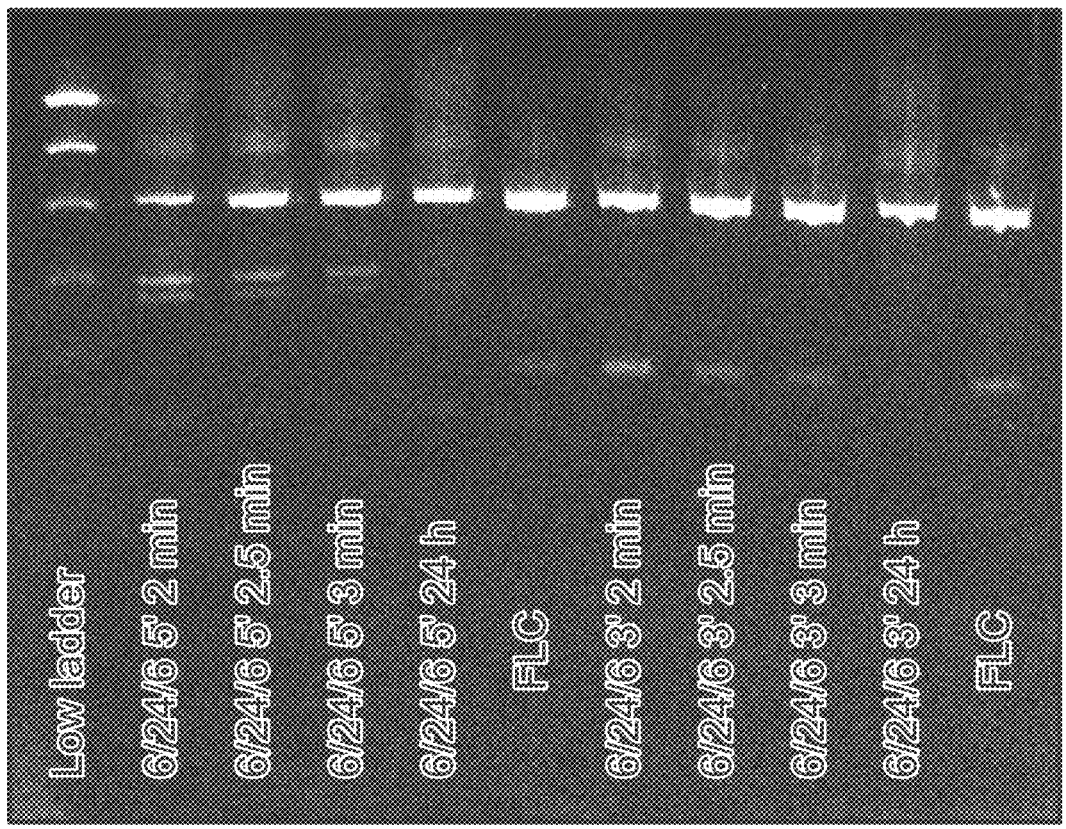
FIG. 23C shows an exemplary gel electrophoresis image of the qPCR products.

FIGS. 23A and 23B present data for ligation efficiency of 6/24/6 3' (FIG. 23B) and 6/24/6 5' (FIG. 23A) DNA component sets ligated for 2, 2.5, 3, and 1440 minutes. FIGS. 23A and 23B show ligation efficiency as measured by qPCR relative to the FLC for each set. FIG. 23C shows a gel electrophoresis image of the qPCR products alongside their FLCs, which have a length of around 450 bases. Results also indicate that the 3' overhang set may have higher specificity than the 5' overhang set.

Example 4: Testing the Effect of Overhang Length, Overhang Melting Temperature, and Overhang GC Content on Sticky-End Ligation Efficiency Table 2 presents the characteristics of 9 different sticky-ended (with 3' overhang) DNA component pairs designed to have different length overhangs (short=6-base, medium=8-base, and long=10-base), different GC contents (low, medium, and high), and different melting temperatures (Tm). The overhangs themselves are given in the cells of the table along with their predicted melting temperatures in degrees Celsius. Ligation was performed on each DNA component pair at 37° C. with 0.067 µM each DNA component, 5 CEU/µL of T4 Ligase, 7.5% w/v PEG6000, 20% v/v glycerol, and standard T4 ligase buffer parts. Ligation was performed at 2.5 minutes and 60 minutes. Efficiency was measured using qPCR relative to a full length control representing the fully ligated product for each pair.

TABLE 2

Characteristics of different sticky-ended (with 3' overhang) DNA component pairs

| | ShortLength (6) | MedLength (8) | HighLength (10) |
|---|---|---|---|
| LowGC | Pair 1<br>Tm = −4.3, CAAGAA | Pair 4<br>Tm = 8.4,<br>TAGATAAG | Pair 7<br>Tm = 21.4,<br>TAGTATAAGA |
| MedGC | Pair 2<br>Tm = 9.0, CCTCGA | Pair 5<br>Tm = 20.8,<br>CCAATACC | Pair 8<br>Tm = 37.4,<br>GAGAGAGGTC |

TABLE 2-continued

Characteristics of different sticky-ended
(with 3' overhang) DNA component pairs

|  | ShortLength (6) | MedLength (8) | HighLength (10) |
|---|---|---|---|
| HighGC | Pair 3<br>Tm = 20.7, GCCCCC | Pair 6<br>Tm = 37.4,<br>CGAACGCC | Pair 9<br>Tm = 51.2,<br>CGCCACCCAC |

Figure 24A:
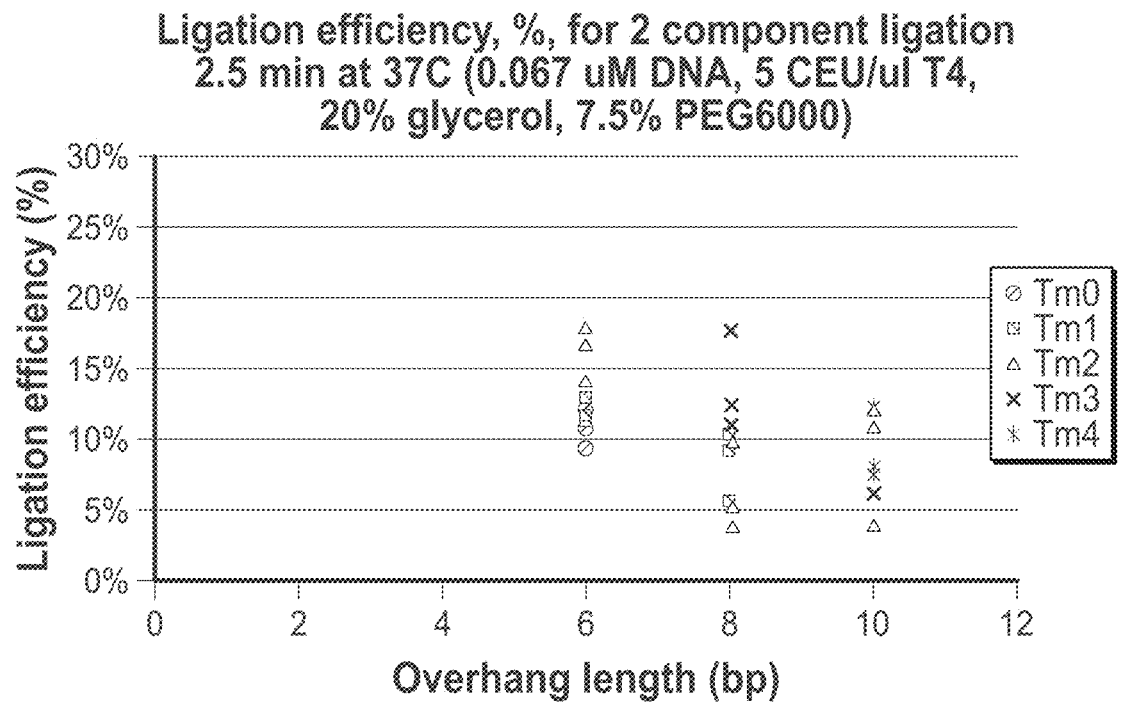
FIG. 24A shows exemplary data presenting the ligation efficiency for DNA component pairs grouped by overhang lengths.
Figure 24B:
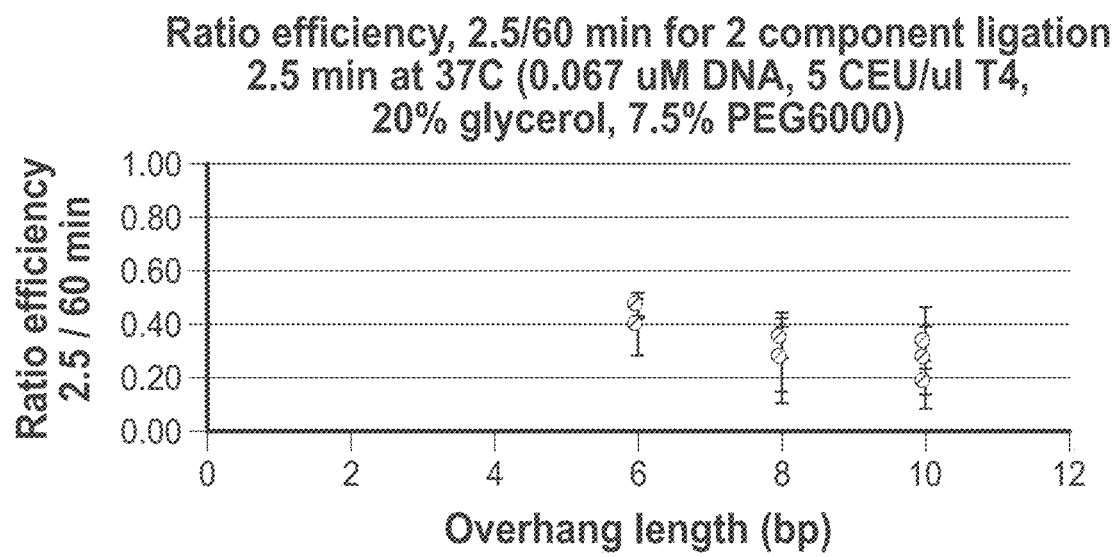
FIG. 24B shows exemplary data presenting the ligation efficiency for DNA component pairs grouped by overhang lengths.

FIGS. 24A and 24B present the ligation efficiency for these DNA component pairs grouped by overhang lengths. FIG. 24A shows the 2.5 minute ligation efficiencies and FIG. 24B shows the ratio of efficiencies between the 2.5 and 60 minute timepoints. Results indicate that ligation rate may be higher when shorter overhangs are used.

Figure 25A:
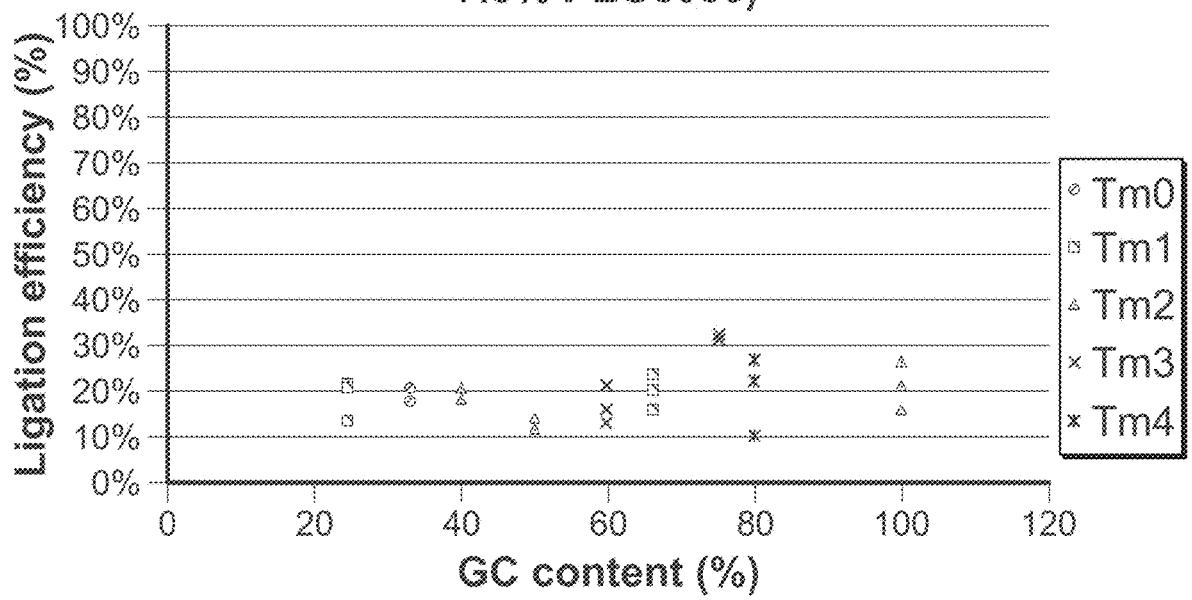
FIG. 25A shows exemplary data presenting the ligation efficiency for DNA component pairs grouped by GC content.
Figure 25B:
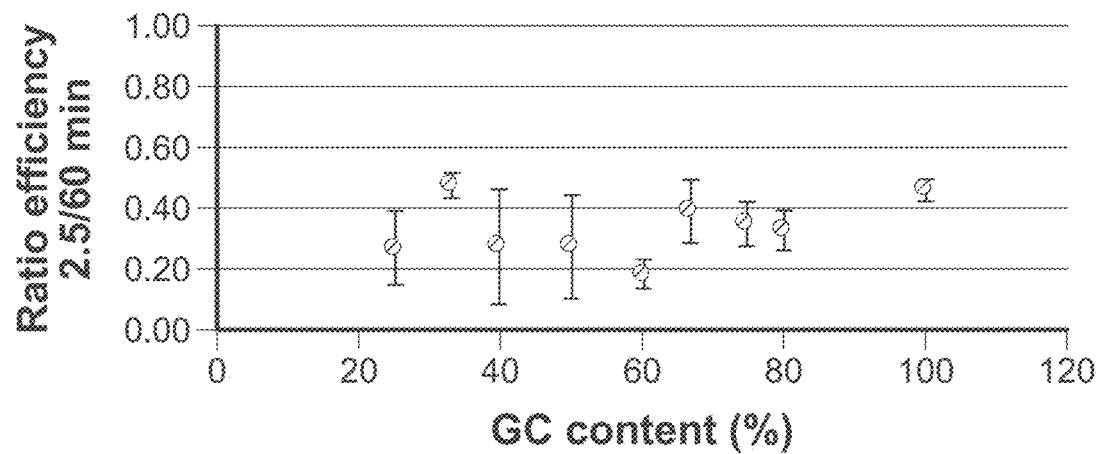
FIG. 25B shows exemplary data presenting the ligation efficiency for DNA component pairs grouped by GC content.

FIGS. 25A and 25B present the ligation efficiency for these DNA component pairs grouped by GC content. FIG. 25A shows the 2.5 minute ligation efficiencies and FIG. 25B shows the ratio of efficiencies between the 2.5 and 60 minute timepoints. Results indicate that there may not be large differences in ligation rate for overhangs of different GC contents (or melting temperatures), but that there may be a slightly higher ligation rate when overhangs with higher GC content (or melting temperature) are used. The melting temperatures correlate with GC content.

Example 5: Testing the Effect of Temperature on Ligation Efficiency

Figure 26:
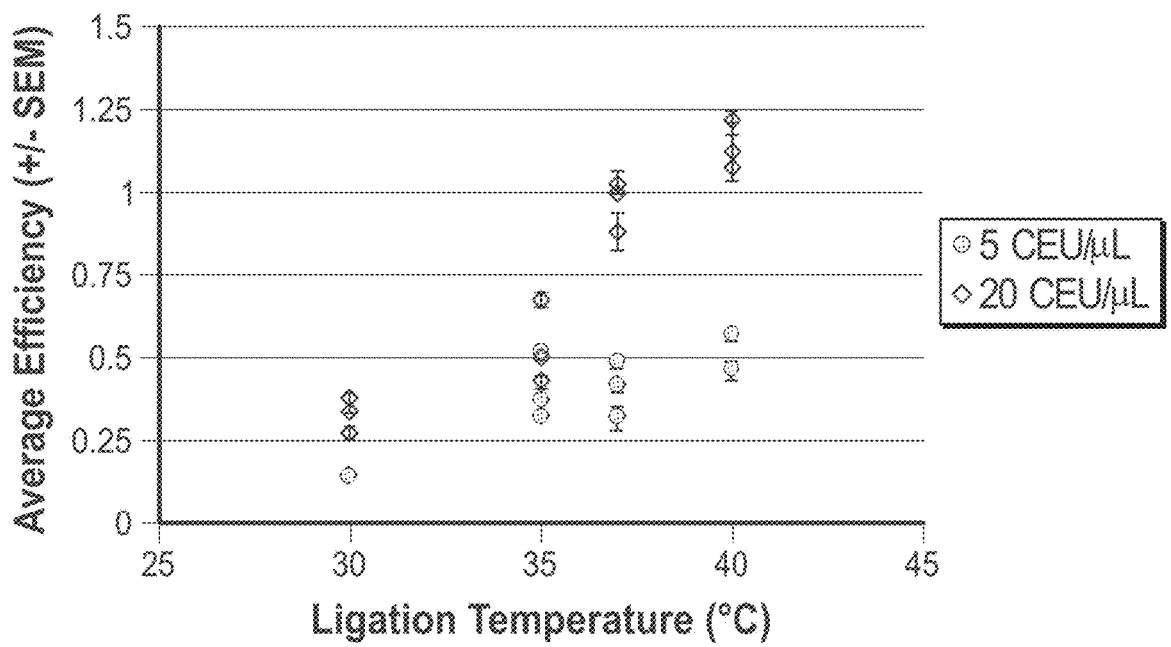
FIG. 26 shows exemplary data from the ligation of 4 sticky-ended (with 6-base, 3' overhangs) DNA components, ligated together with T4 ligase at various temperatures.

FIG. 26 presents data from the ligation of 4 sticky-ended (with 6-base, 3' overhangs) DNA components, ligated together with T4 ligase at various temperatures. Ligation was performed with 0.25 µM each DNA component, 5 CEU/µL or 20 CEU/µL of T4 Ligase, 7.5% w/v PEG6000, 20% v/v glycerol, and standard T4 ligase buffer parts. Ligation time was 2.5 minutes. Efficiency was measured using qPCR relative to a full length control representing the fully ligated product. Results indicate that higher temperatures and higher ligase concentrations may increase ligation efficiency with T4 ligase.

Figure 27:
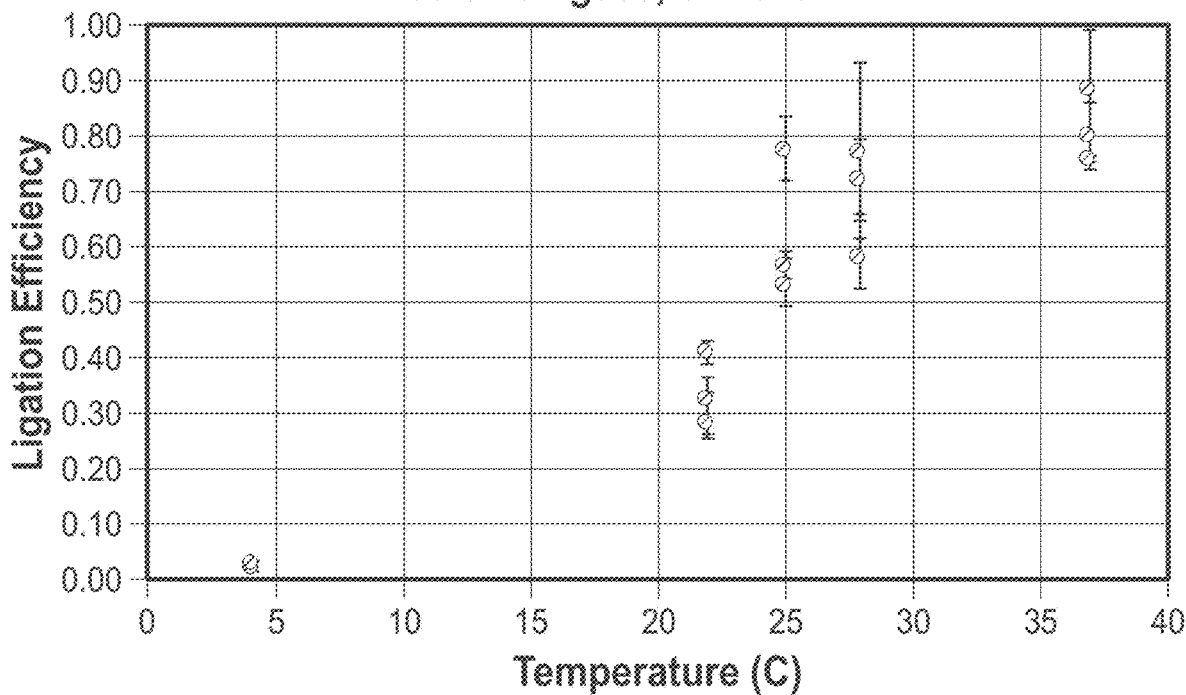
FIG. 27 shows exemplary data from the ligation of 4 sticky-ended (with 6-base, 3' overhangs) DNA components, ligated together with T4 ligase at various temperatures

FIG. 27 presents data from the ligation of 4 sticky-ended (with 6-base, 3' overhangs) DNA components, ligated together with T4 ligase at various temperatures. Ligation was performed with 0.125 µM each DNA component, 5 CEU/µL T4 Ligase (in 20 µL, so 100 CEU total), 7.5% w/v PEG6000, 20% v/v glycerol, and standard T4 ligase buffer parts. Ligation time was 2.5 minutes. Efficiency was measured using qPCR relative to a full length control representing the fully ligated product. Results indicate that higher temperatures and higher ligase concentrations may increase ligation efficiency with T4 ligase. Results indicate a similar trend as observed in FIG. 26.

Example 6: Testing the Effect of Ligase Type on Ligation Efficiency

Figure 28A:
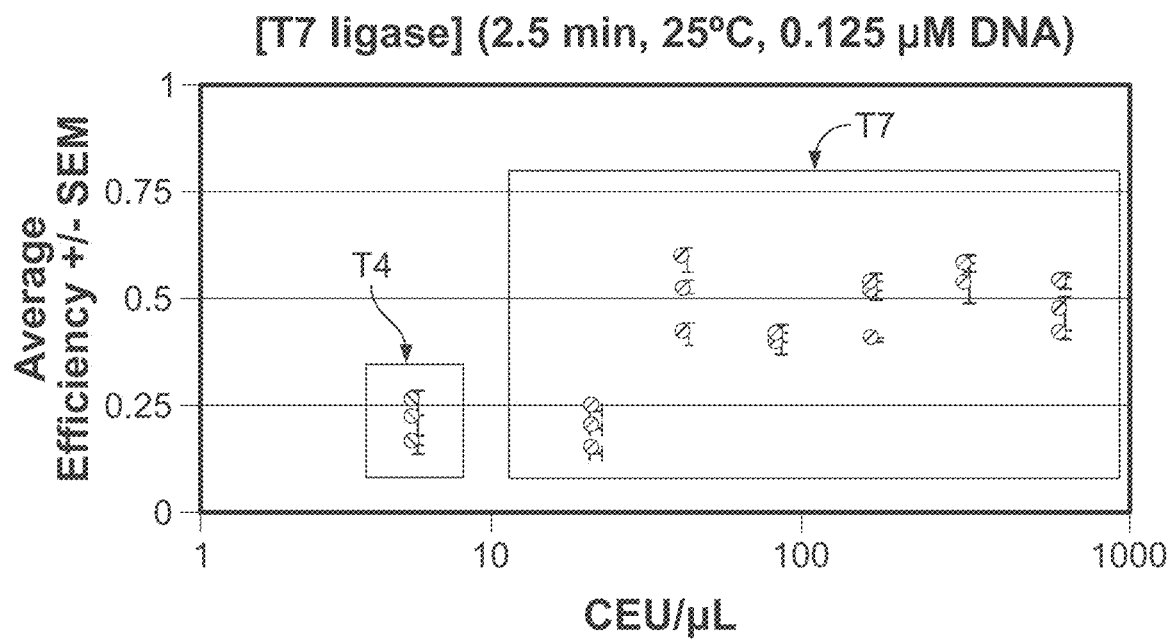
FIG. 28A shows exemplary data for ligation efficiencies of T7 DNA ligase, as compared to T4 DNA ligase.
Figure 28B:
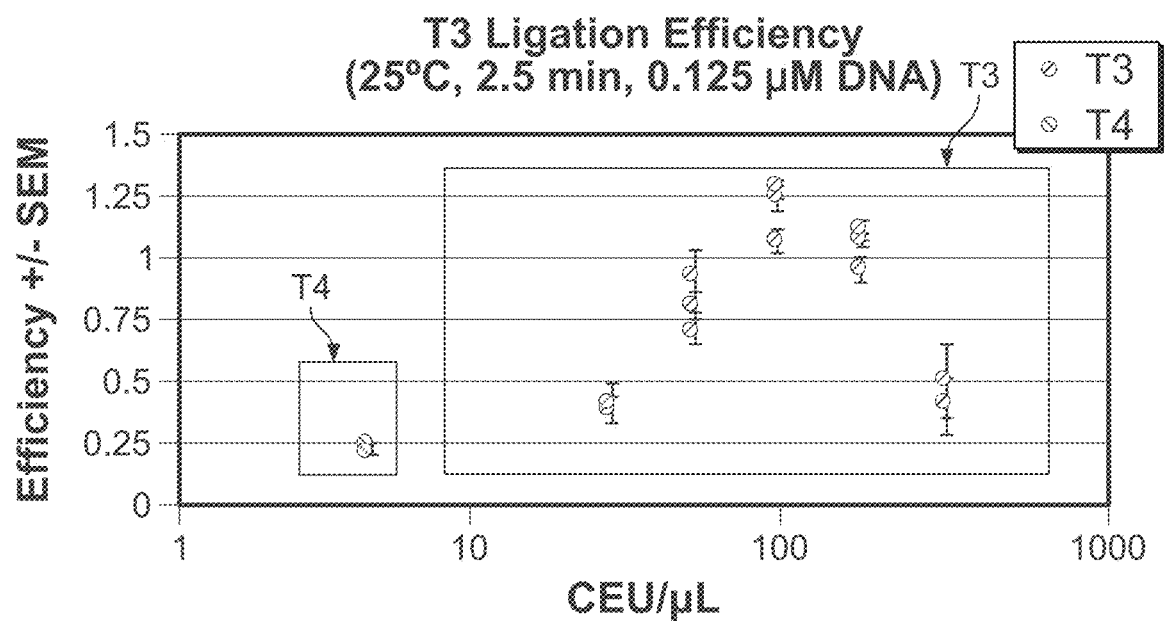
FIG. 28B shows exemplary data for ligation efficiencies of T3 DNA ligase, as compared to T4 DNA ligase.

FIGS. 28A and 28B present data for ligation efficiencies of T7 (FIG. 28A) and T3 (FIG. 28B) DNA ligase, as compared to T4 DNA ligase. Ligation was performed on 4 sticky-ended (with 6-base, 3' overhangs) DNA components at 25° C. with 0.125 µM each DNA component. Ligation time was 2.5 minutes. Efficiency was measured using qPCR relative to a full length control representing the fully ligated product. Ligase concentrations varied between 10 and 100 CEU/µL. Within each plot, efficiencies are compared to the same ligation performed with T4 DNA ligase at 5 CEU/µL. Results indicate that T3 ligase at a concentration of around 100 CEU/uL may be the optimal ligase for room temperature ligations.

Figure 29:
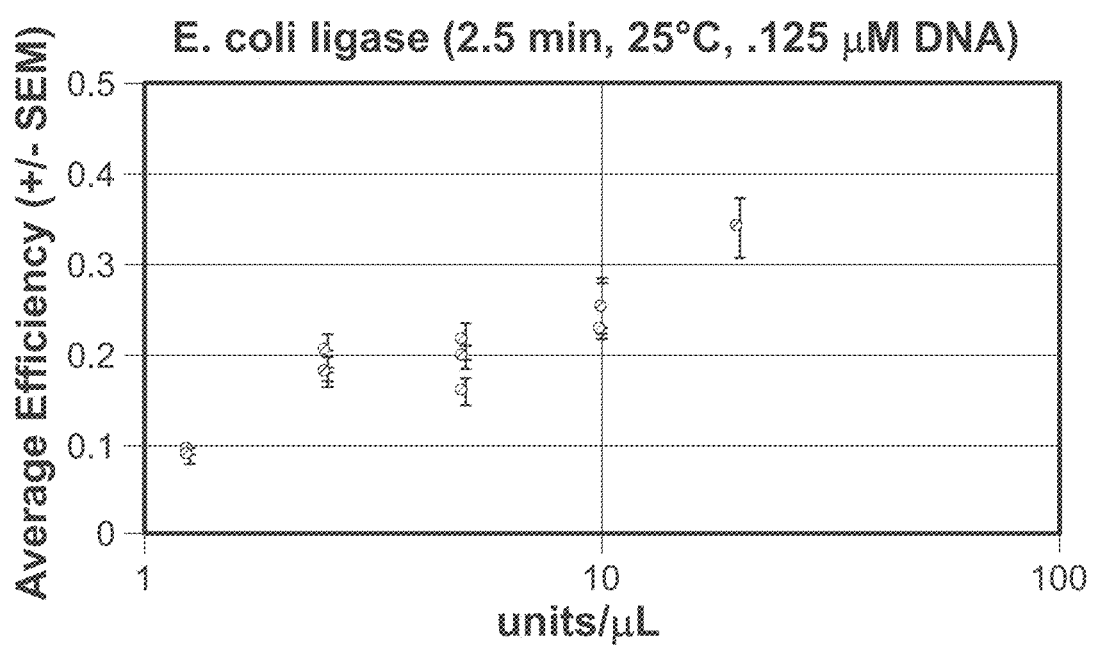
FIG. 29 shows exemplary data for ligation efficiencies of E. coli DNA Ligase at various concentrations.

FIG. 29 presents data for ligation efficiencies of E. coli DNA Ligase at various concentrations. Ligation was performed on 4 sticky-ended (with 6-base, 3' overhangs) DNA components at 25° C. with 0.125 µM each DNA component. Ligation time was 2.5 minutes. Efficiency was measured using qPCR relative to a full length control representing the fully ligated product. Ligase concentrations varied between 1 and 100 CEU/µL.

Table 3 presents average ligation efficiency measurements for 4 different types of ligase. Ligation was performed on 15 sticky-ended (with 6-base, 3' overhangs) DNA components at 25° C. with 0.268 µM each DNA component. Ligation time was 2.5 minutes. Efficiency was measured using qPCR relative to a full length control representing the fully ligated product. T4 was at 20 CEU/µL, and T3 and T7 were each at 150 CEU/µL.

TABLE 3

Average ligation efficiency measurements

|  | Ligation Efficiency | StDev |
|---|---|---|
| T4 | 0.039% | 0.004% |
| T4 + 7.5% PEG600 | 0.298% | 0.012% |
| T7 | 0.419% | 0.043% |
| T3 | 0.804% | 0.237% |

Figure 30A:
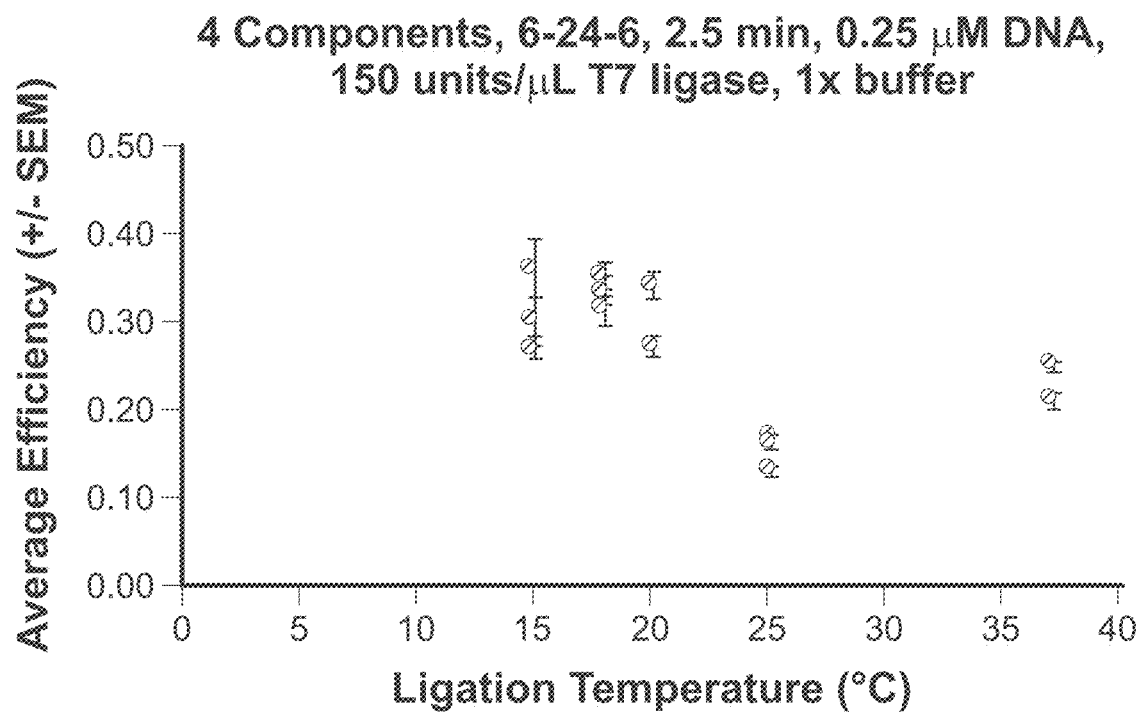
FIG. 30A shows exemplary data from the ligation of 4 sticky-ended (with 6-base, 3' overhangs) DNA components, ligated together with T7 DNA ligase at various temperatures.
Figure 30B:
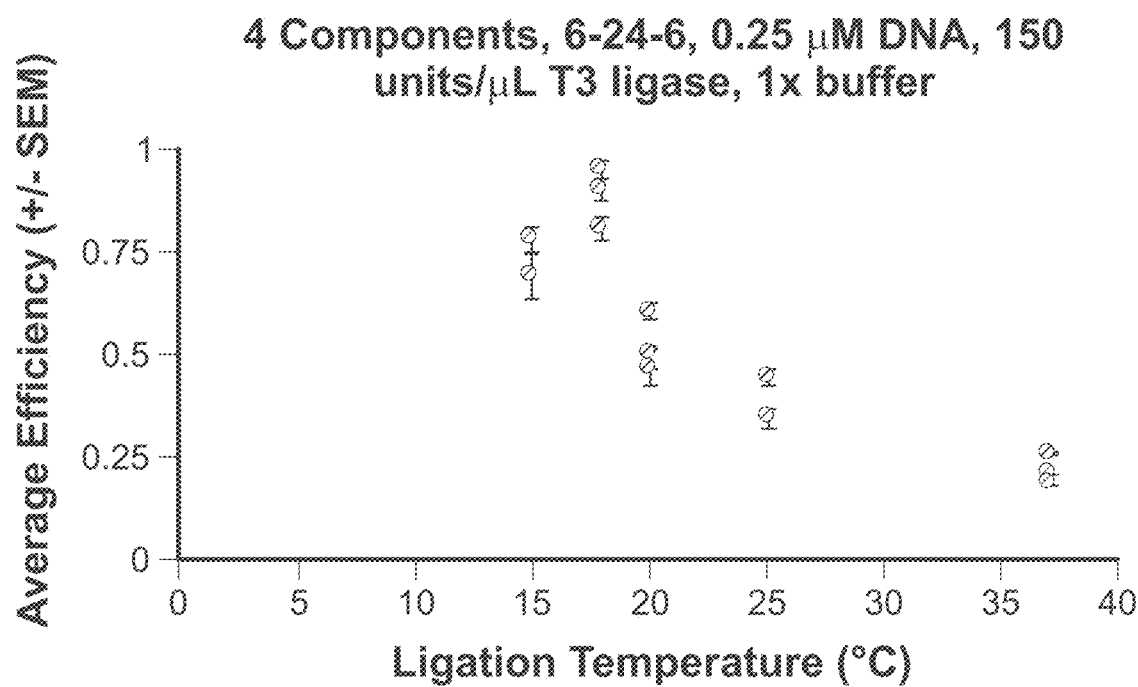
FIG. 30B shows exemplary data from the ligation of 4 sticky-ended (with 6-base, 3' overhangs) DNA components, ligated together with T3 DNA ligase at various temperatures.

FIGS. 30A and 30B present data from the ligation of 4 sticky-ended (with 6-base, 3' overhangs) DNA components, ligated together with T7 DNA ligase (FIG. 30A) or T3 DNA ligase (FIG. 30B) at various temperatures. Ligation was performed with 0.125 µM each DNA component and 150 CEU/µL T7 or T3 DNA Ligase. Ligation time was 2.5 minutes. Efficiency was measured using qPCR relative to a full length control representing the fully ligated product. Results indicate that T3 and T7 may lose efficiency between 20° C. and 40° C., with T3 dropping faster, but having a higher efficiency at lower temperatures (e.g., 15 to 20° C.). This indicates that at higher temperature incubations (e.g., 37° C.), T4 DNA ligase (see, e.g., FIG. 26 and FIG. 27) may perform better than T3 and T7 DNA ligase.

Figure 31A:
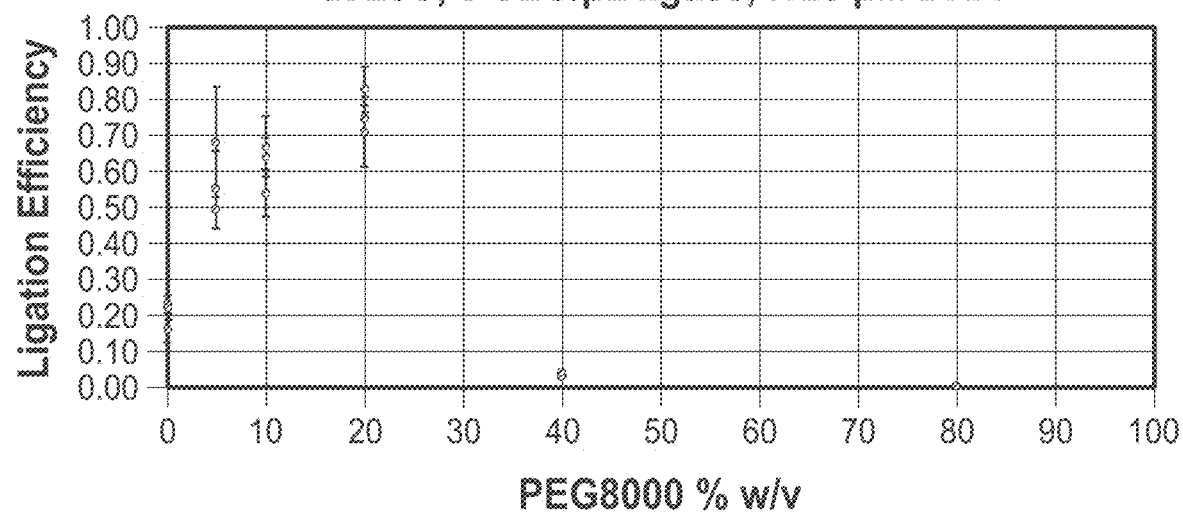
FIG. 31A shows exemplary data of effects of PEG8000 on ligation efficiency.
Figure 31B:
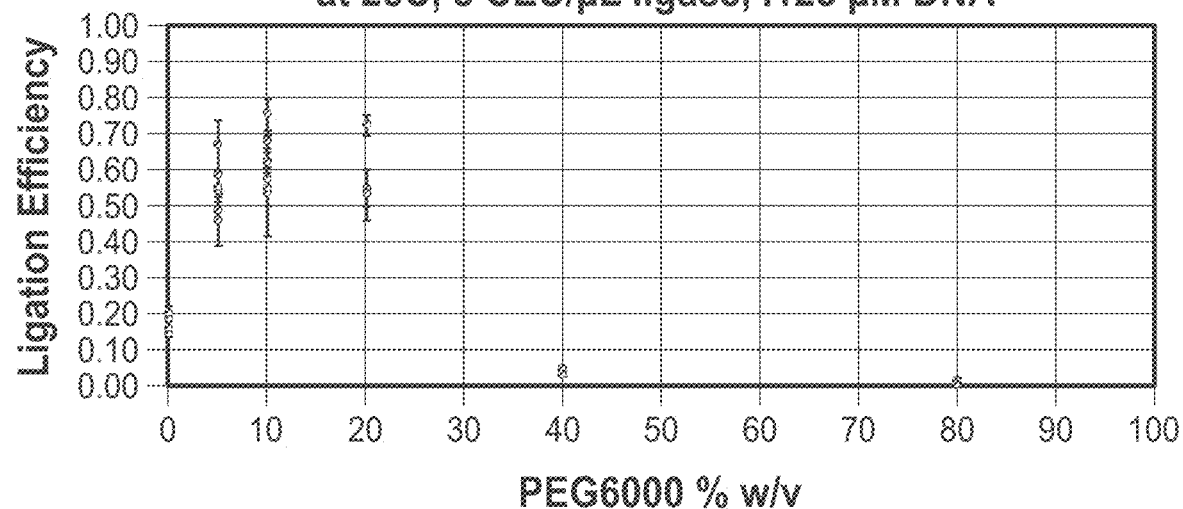
FIG. 31B shows exemplary data of effects of PEG6000 on ligation efficiency.
Figure 31C:
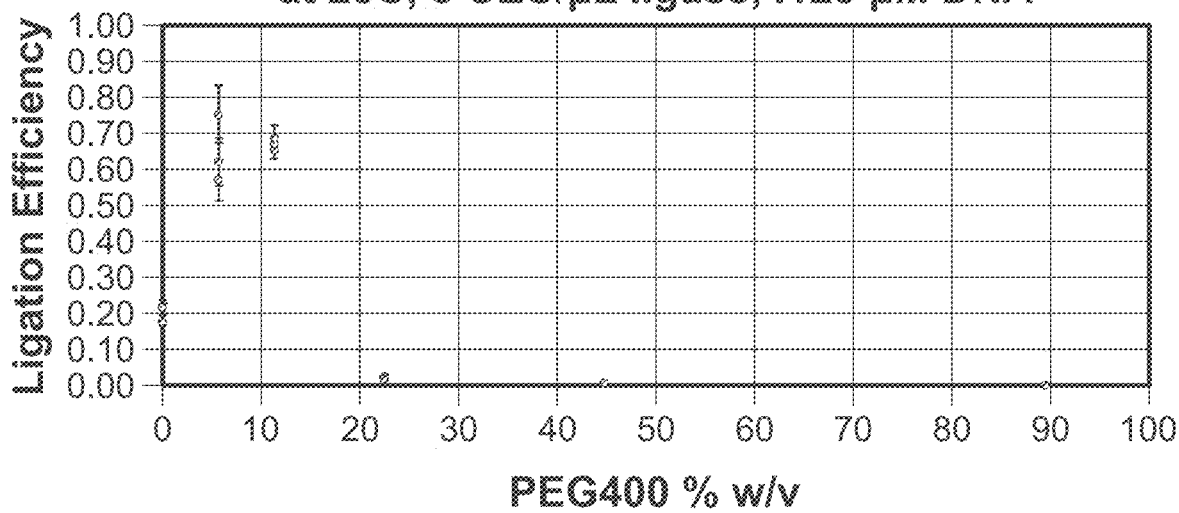
FIG. 31C shows exemplary data of effects of PEG400 on ligation efficiency.

Example 7: Testing the Effect of Polyethyleneglycol (PEG) on Ligation Efficiency FIG. 31A-C present data from ligation of 4 sticky-ended (with 10-base, 3' overhangs) DNA components ligated together with various amounts (in terms of percent weight-per-volume) of PEG8000 (FIG. 31A), PEG6000 (FIG. 31B), and PEG400 (FIG. 31C). Ligation was performed with 0.125 µM each DNA component and 5 CEU/µL T4 ligase at 25° C. Ligation time was 2.5 minutes. Efficiency was measured using qPCR relative to a full length control representing the fully ligated product. Results indicate that adding PEG up to a particular amount to a ligation may improve efficiency, but then inhibit efficiency beyond a certain amount. The amount of PEG that may be added to a ligation reaction to improve efficiency depends on the molecular weight of the PEG.

Figure 32:
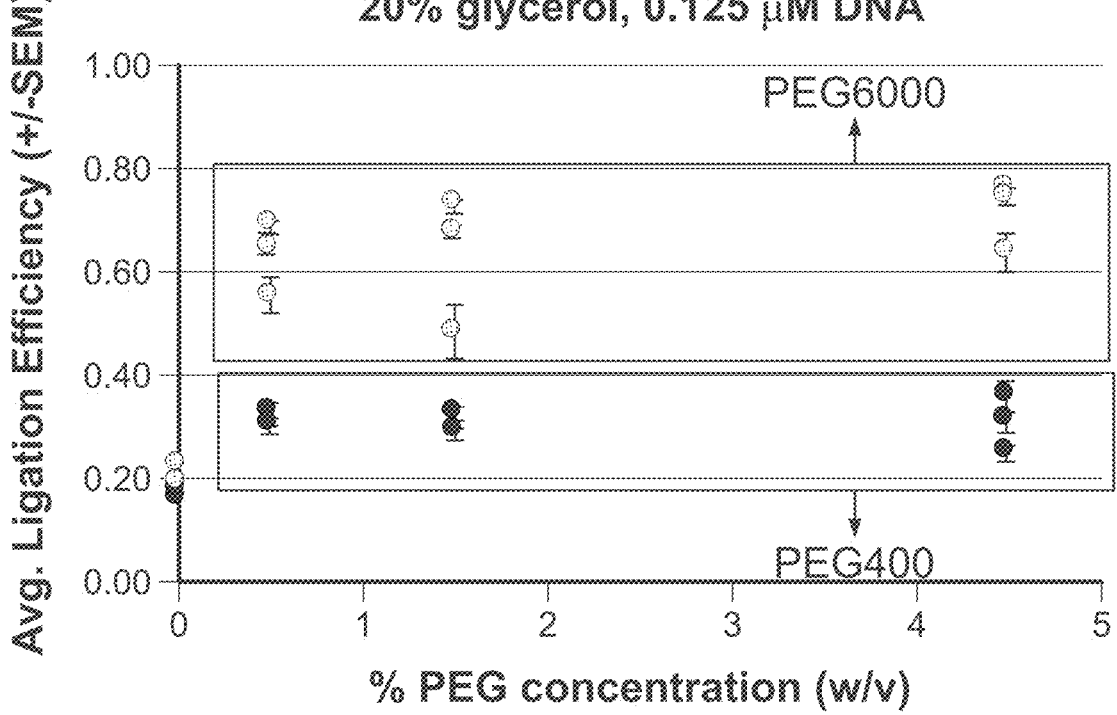
FIG. 32 shows exemplary data from ligation of four sticky-ended (with 10-base, 3' overhangs) DNA components ligated together in the presence of PEG400 or PEG6000.

FIG. 32 presents data from ligation of 4 sticky-ended (with 10-base, 3' overhangs) DNA components ligated together in the presence of either PEG400 or PEG6000 at low weight-per-volume concentrations. Ligation was performed with 0.125 µM each DNA component, 5 CEU/µL T4 DNA ligase, 20% v/v glycerol, and standard T4 ligase buffer parts at 37° C. Ligation time was 2.5 minutes. Efficiency was measured using qPCR relative to a full length control representing the fully ligated product. Results indicate that under these conditions, adding PEG6000 may improve ligation efficiency more than adding and equivalent amount (by weight) of PEG400.

Example 8: A Comparison of Ligation Deactivation Methods

Figure 33:
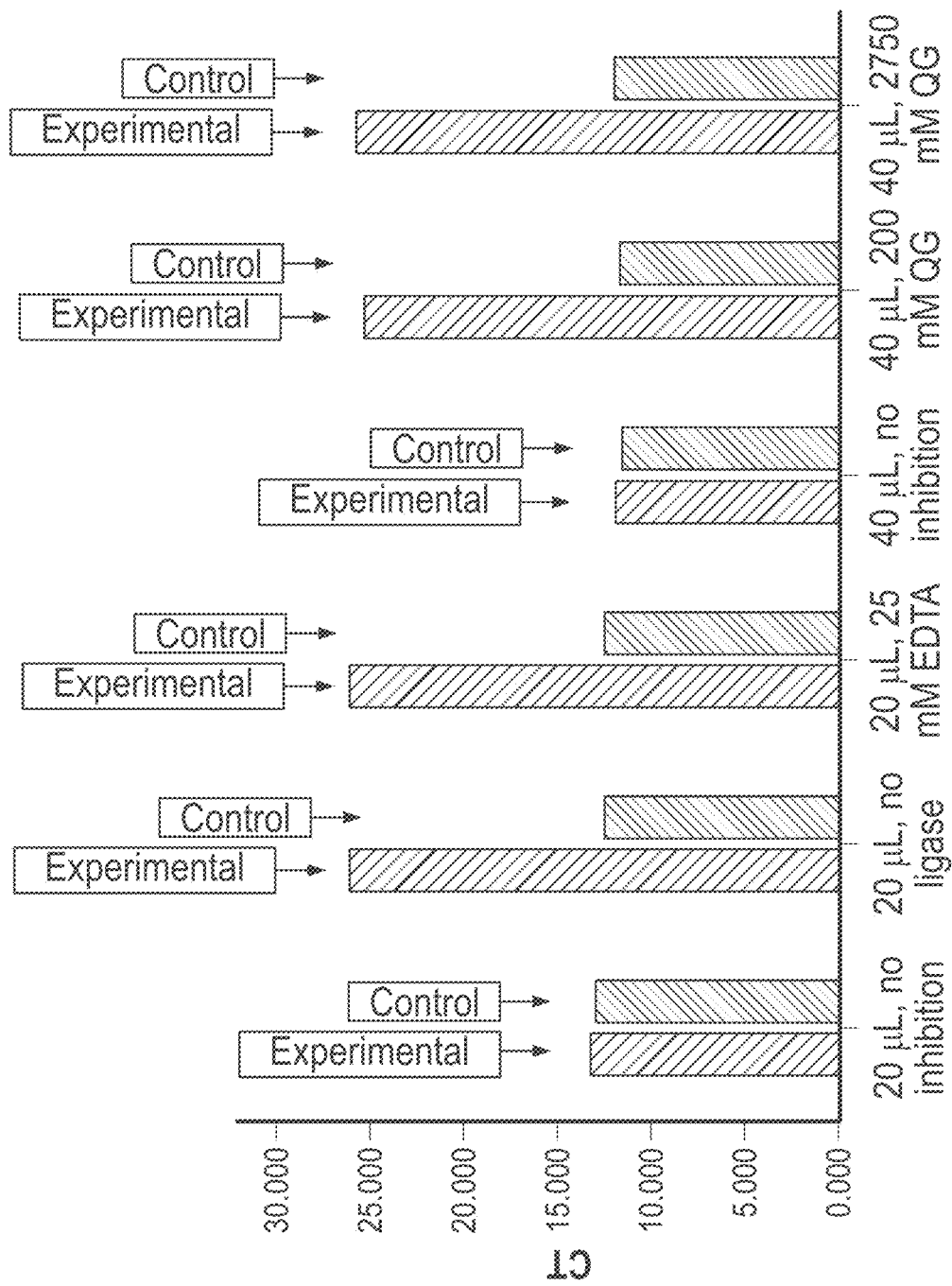
FIG. 33 shows exemplary qPCR data of effects of buffer QG or EDTA on ligase.

FIG. 33 presents data on using buffer QG or EDTA to inactivate ligase. Ligation was performed on 4 sticky-ended DNA components. The buffer QG refers to buffer QG manufactured by Qiagen or a buffer with similar components (e.g., 5.5 M guanidine thiocyanate (GuSCN), 20 mM Tris HCl pH 6.6). In the control group, T4 ligase was used under standard buffer conditions at room temperature in the given volume indicated on the horizontal axis. In the experimental group, the T4 ligase reaction mix was treated with the indicated additive prior to being added to the DNA components to make a reaction of the given volume. Ligation time was 2.5 minutes. The vertical axis shows Ct results obtained from qPCR on the full length product of each ligation. Note that Ct represents a Log base-2 scale for concentration. Results indicate that using EDTA or buffer QG may deactivate ligase. The results of the ligation groups with EDTA and buffer QG deactivated ligase look similar to the results of the no ligase group.

Example 9: A Study of DNA Replication

Figure 34:
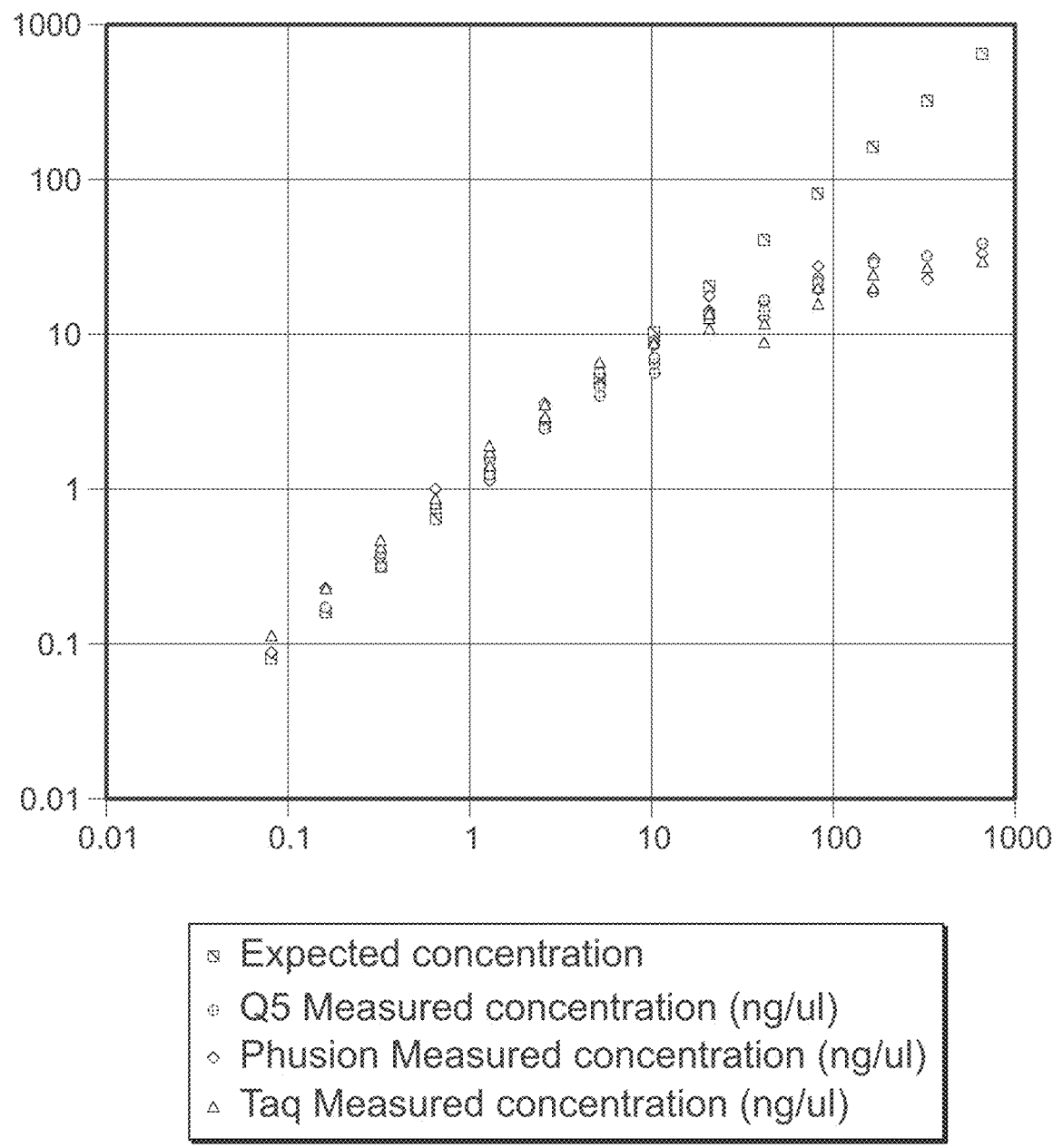
FIG. 34 shows exemplary data on the linearity of replication using Q5, Phusion, and Taq DNA polymerase.

FIG. 34 presents data on the linearity of replication using Q5, Phusion, and Taq DNA polymerase. The horizontal axis represents theoretical target DNA concentration (ng/µL), and the vertical axis represents measured target DNA concentration (ng/µL) using qPCR relative to a standard. Measurements were taken at different cycles of PCR reaction. The dots on the full diagonal represent full linearity (theoretical). Other dots represent experimental data points from different ligases. Results indicate that standard PCR reactions (regardless of ligase) may be linear up to or beyond 10 ng/µL of target. In this example, the target DNA used was ~450 bases.

Example 10: A Study of Different Methods for Drying DNA

Figure 35:
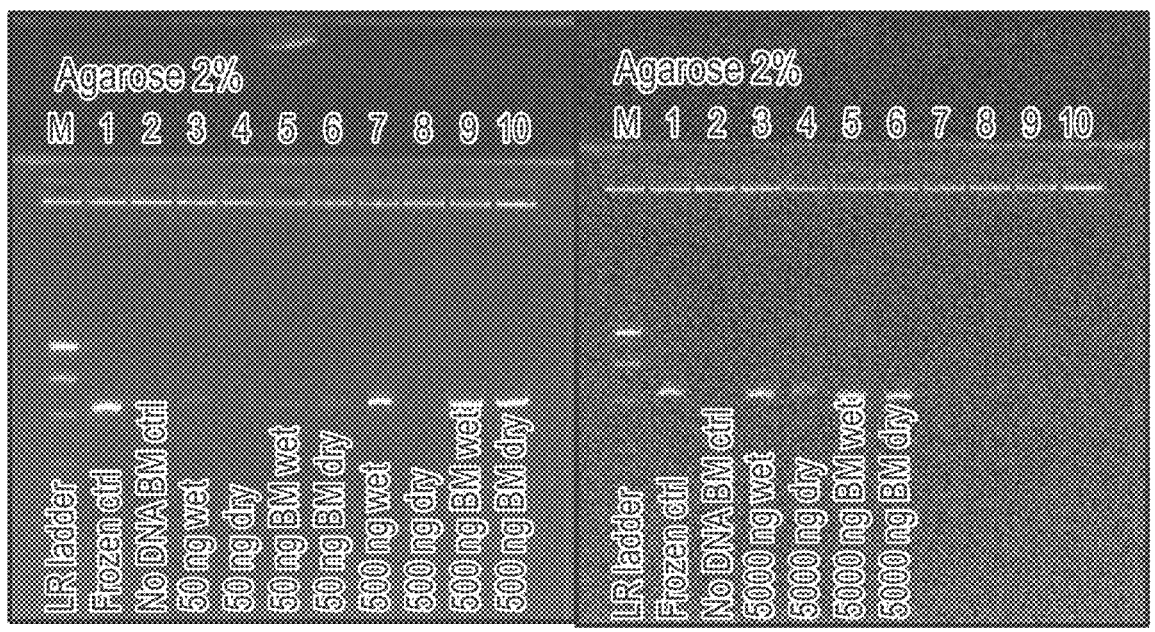
FIG. 35 shows an exemplary gel image of different DNA samples stored at room temperature for 4 days.

FIG. 35 presents data for DNA samples stored at room temperature for 4 days. Different amounts of DNA samples containing DNA of about 450 bases in length were stored (50 ng, 500 ng, and 5000 ng). The DNA samples were stored in different conditions: wet or dry, and with or without preserving additive (e.g., BM represents biostabilizing material). Results were compared to the same DNA samples containing DNA of about 450 bases in length stored in frozen water during those 4 days. Results indicate that minimal DNA degradation may take place at room temperature and that the use of preserving additive, like BM (biostabilizing material), may contribute to decreased degradation. The drying process may lead to DNA degradation without the presence of DNA preserving additive.

Figure 36:
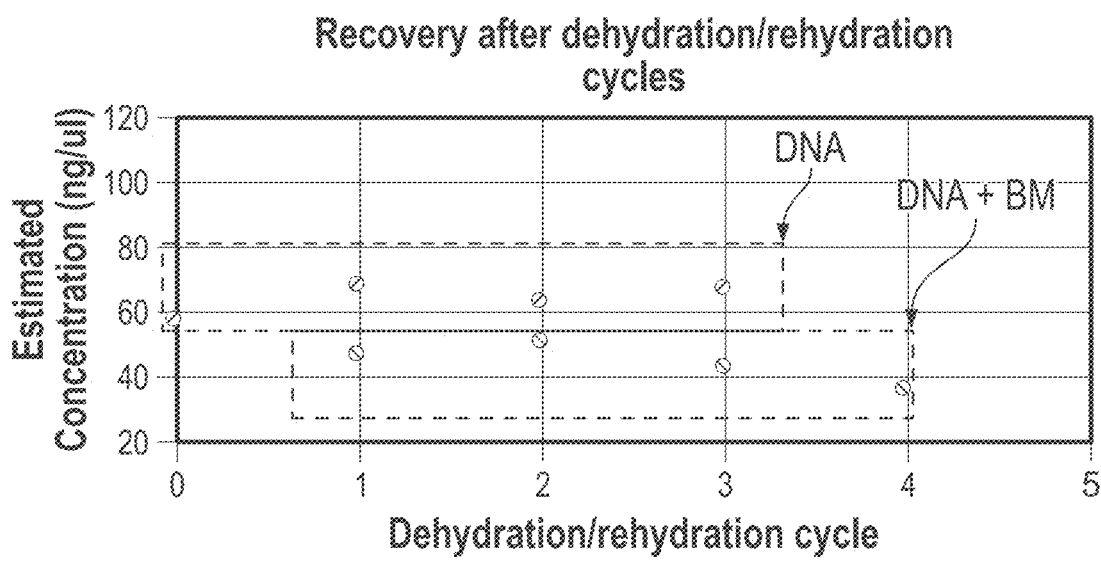
FIG. 36 shows exemplary data for DNA repeatedly being dried and re-hydrated at room temperature.

FIG. 36 presents data for DNA repeatedly being dried and re-hydrated at room temperature. Results are shown for DNA with and without preserving additive (e.g., BM represents biostabilizing material). Results indicate that Drying/rehydration of DNA samples 3-4 times with and without preserving additive can be achieved without losing substantial amounts of DNA.

Example 11: Designing and Testing 6 Base Overhangs for Ligation

Table 4 presents a set of 32 computationally designed 3' overhangs. The overhangs (and their reverse complements) were designed to have a length of 6 bases, no homopolymers of more than 3 bases, no hamming distances less than 3 bases between each other, no equivalent substrings of more than 3 bases between each other, and no equivalent substring of more than 2 bases from each other for substrings on either edge of the overhang.

TABLE 4

A set of 32 computationally designed 3' overhangs

| ID | sequence |
|---|---|
| 1 | GAGAAC |
| 2 | TCTATC |
| 3 | CCATCT |
| 4 | TTTACT |
| 5 | TGTGTA |
| 6 | ACCCAC |
| 7 | CCTTTG |
| 8 | TCGTGC |
| 9 | CTCGCC |
| 10 | GCCTAA |
| 11 | AGGGTC |
| 12 | CAGCGT |
| 13 | CTACAT |
| 14 | GTCATG |
| 15 | CGTCGC |
| 16 | GAATAT |
| 17 | ATTTGA |
| 18 | AAACTA |
| 19 | TGCCGG |
| 20 | TGACCC |
| 21 | CTGATA |
| 22 | AGCAGC |
| 23 | GGAATT |
| 24 | GGTTAC |
| 25 | CTTGGG |
| 26 | TGGAGT |
| 27 | ATCCTT |

TABLE 4-continued

A set of 32 computationally designed 3' overhangs

| ID | sequence |
|---|---|
| 28 | CGGCAA |
| 29 | TCCGTT |
| 30 | CACTCG |
| 31 | TAAGAA |
| 32 | CGCTGT |

Table 5 presents another set of 32 computationally designed 3' overhangs. This set of 6-base overhangs (and their reverse complements) were designed to be overall less stringently constrained than those of Table 4, but to contain subsets of 16 overhangs within that met the equivalent constraints to those in Table 4. The two bolded sequences were designed to be reverse complements of each other, as a control for a combinatorial experiment.

TABLE 5

A set of 32 computationally designed 3' overhangs

| ID | sequence |
|---|---|
| 1 | CGTTAC |
| 2 | GTCTCG |
| 3 | GTTGAC |
| 4 | ACTGAG |
| 5 | TACCAC |
| 6 | CATCCA |
| 7 | CCTTCA |
| 8 | TCTACG |
| 9 | TCGAAA |
| 10 | TGTTCC |
| 11 | GCATAG |
| 12 | CCAAAG |
| 13 | CGAGAC |
| 14 | CAATCG |
| 15 | CAAGAC |
| 16 | GTTAGG |
| 17 | TAGGCC |
| 18 | TTAGCT |
| 19 | TCATTC |
| 20 | AGGCGG |
| 21 | TTGCTT |
| 22 | GAGTTT |
| 23 | TCCTGT |
| 24 | TAAGTG |

TABLE 5-continued

A set of 32 computationally designed 3' overhangs

| ID | sequence |
|---|---|
| 25 | CGCCAT |
| 26 | ATCGGC |
| 27 | TGCACT |
| 28 | GCGACC |
| 29 | GGGAAT |
| 30 | AATAGC |
| 31 | AACTCT |
| 32 | GATCAG |

Figure 37:
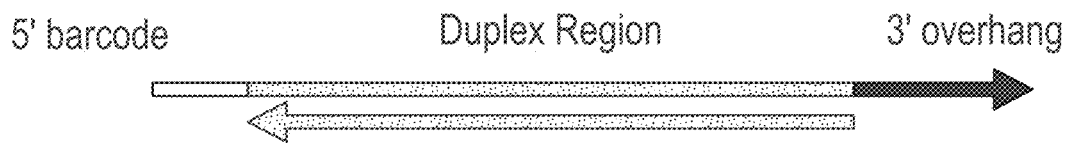
FIG. 37 shows an exemplary scheme of constructed sticky end sequences.

Sticky-end DNA sequences for each overhang and their reverse complements in Table 4 and Table 5 were constructed. Each sequence for each overhang (and reverse complement) in each table had the same proximal duplex region but was uniquely barcoded on its distal end with a distinct 3-base 5' overhang. See FIG. 37 for the scheme of the constructed sticky end sequences. In total, with reverse complements, 64 sequences were constructed for each table. Those sequences were pooled in equimolar concentration and ligated with T4 ligase at 37° C. in standard ligase buffer. Ligation was performed for 2.5 minutes prior to being quenched with EDTA. Ligated sequences were purified through gel extraction and then 5' ends were filled and dA-tailed using Klenow Polymerase. Sequencing adapters were subsequently ligated to the ends of the products, and amplified and purified to prepare for sequencing on the Illumina iSeq. The relative copy number of each possible ligated product was inferred by counting the number of sequence reads for each possible combination of barcodes. There were 64×(64+1)/2=2080 possible products in total for each set of overhangs (Table 4 and Table 5), 64 of which in each correspond to overhangs ligated to their correct reverse complement partners.

Figure 38A:
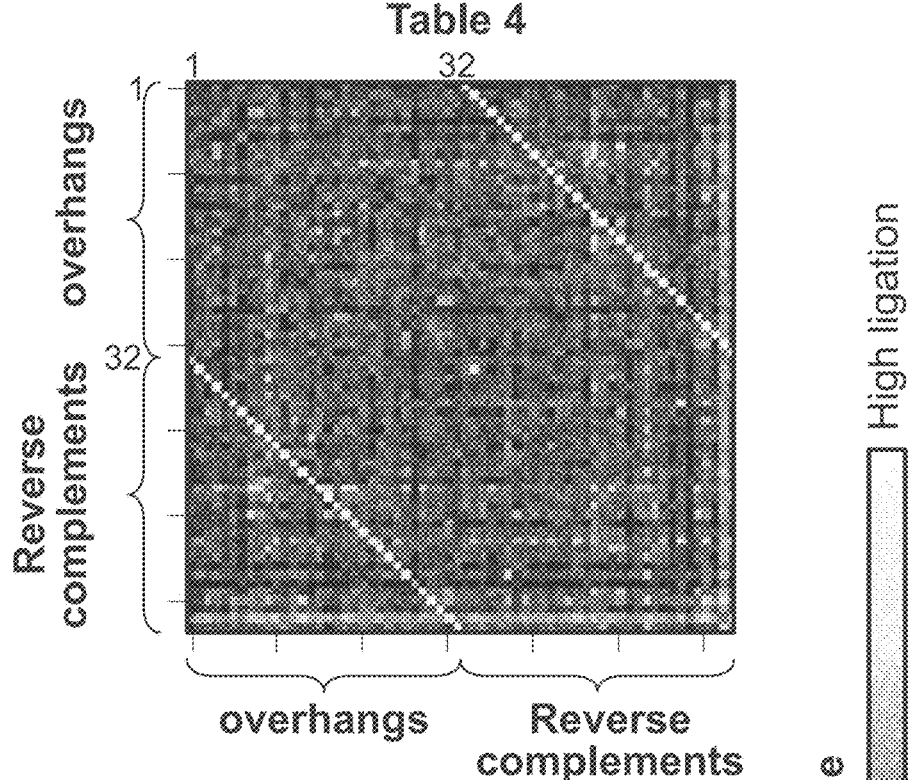
FIG. 38A shows exemplary data from the ligation of different pairs of overhang sequences listed in Table 4.
Figure 38B:
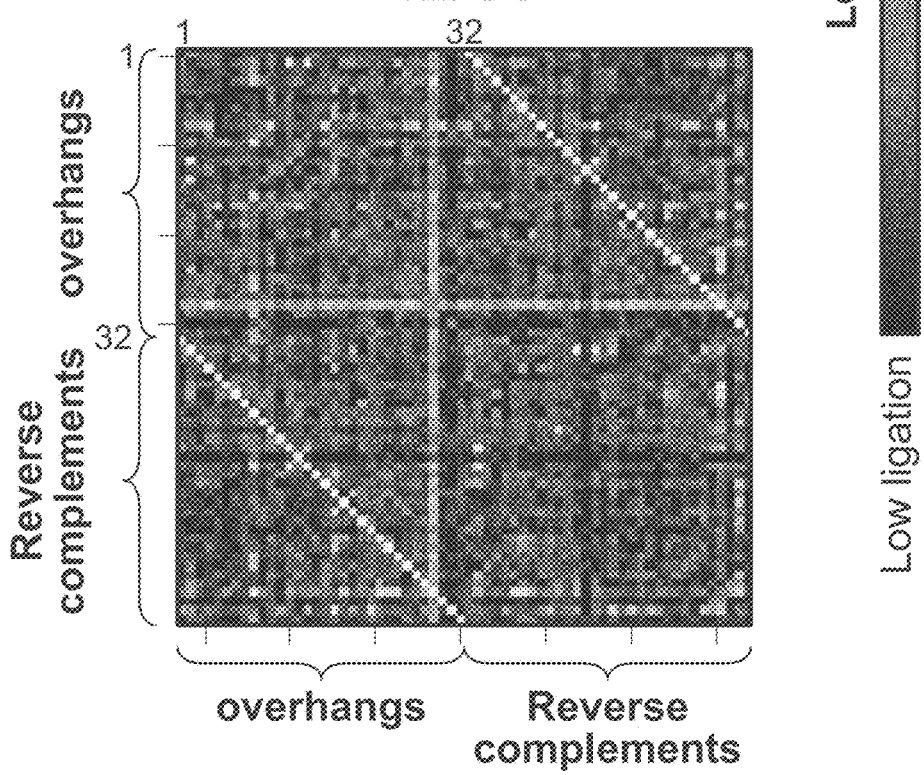
FIG. 38B shows exemplary data from the ligation of different pairs of overhang sequences listed in Table 5.

FIG. 38 presents the data from the ligation of the set of overhang sequences in Table 4 (FIG. 38A) and Table 5 (FIG. 38B). Each pixel in each heatmap corresponds to the ligation product formed by the overhangs that represent the row and column of that pixel. The greyscale (or "heat") of the pixel represents the relative amount of that ligation product (in log base-2 scale). Each row and column corresponds to an overhang 1-32 from either Table 4 (FIG. 38A) or Table 5 (FIG. 38B) and then the reverse complements of those overhangs. Results suggest that each overhang ligates most strongly with its reverse complement, but that multiple non-specific products may also be formed in a ligation.

These data were used to calculate penalty scores for subsets of overhangs from each set of 32 overhangs. For a subset of overhangs, penalty scores were calculated by adding the relative amount of off-target product formed for each possible overhang in the subset (compared to the amount of correct product) in the data set.

Figure 39:
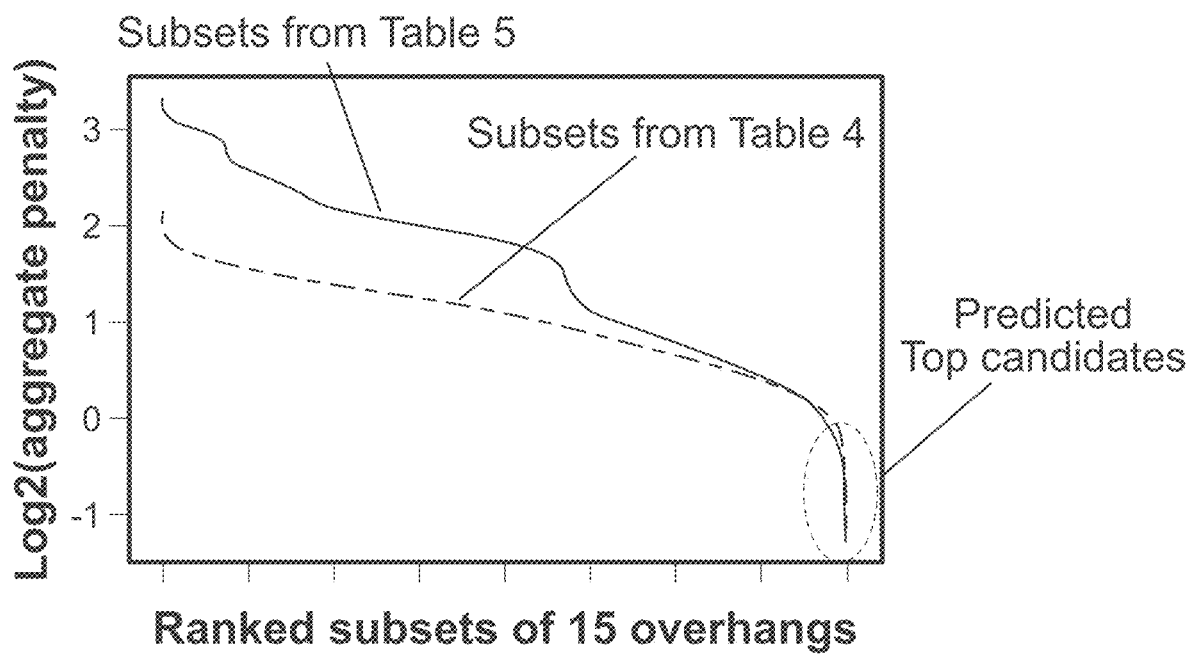
FIG. 39 shows penalty scores from 2 million subsets of 15 overhangs from each set of overhangs listed in Table 4 and Table 5.

FIG. 39 presents penalty scores from 2M subsets of 15 overhangs from each the set of overhangs in Table 4 and Table 5. Penalty scores may be used to predict high-efficiency, high-specificity sets of 15 overhangs to be used in 16 component ligation. Top candidates may be found with the lowest penalty score. Similar analysis may be done with subsets of X overhangs to find top overhang candidates for ligating together X+1 overhangs. Based on this analysis, Table 6 presents putative high-efficiency, high-specificity subsets of 15 overhangs (taken from the set in Table 4) for ligating together 16 DNA components. Likewise, Table 7 presents putative subsets of 15 overhangs (taken from the set in Table 5) for ligating together 16 DNA components.

TABLE 6

Putative high-efficiency, high-specificity subsets of 15 overhangs

| Penalty score | Overhang IDs from Table 4 |
|---|---|
| 0.51 | [3, 5, 7, 8, 9, 11, 13, 14, 17, 21, 23, 24, 25, 28, 30] |
| 0.52 | [3, 4, 7, 11, 12, 13, 17, 21, 23, 24, 25, 26, 28, 30, 32] |
| 0.54 | [3, 4, 7, 11, 12, 13, 14, 15, 23, 24, 25, 26, 28, 30, 32] |
| 0.58 | [6, 7, 8, 9, 11, 12, 14, 17, 18, 20, 21, 23, 25, 28, 30] |

TABLE 7

Putative subsets of 15 overhangs

| Penalty score | Overhang IDs from Table 5 |
|---|---|
| 0.42 | [1, 4, 6, 15, 17, 19, 20, 21, 22, 24, 25, 26, 28, 30, 32] |
| 0.43 | [4, 6, 8, 15, 17, 19, 20, 21, 22, 23, 24, 25, 27, 30, 32] |
| 0.44 | [4, 5, 6, 15, 16, 17, 20, 21, 22, 24, 25, 27, 28, 30, 32] |
| 0.45 | [4, 5, 6, 7, 8, 15, 17, 19, 20, 21, 24, 25, 27, 30, 32] |
| 2.1 | [1, 2, 3, 4, 5, 7, 8, 9, 10, 11, 12, 14, 15, 16, 17] |

Figure 40:
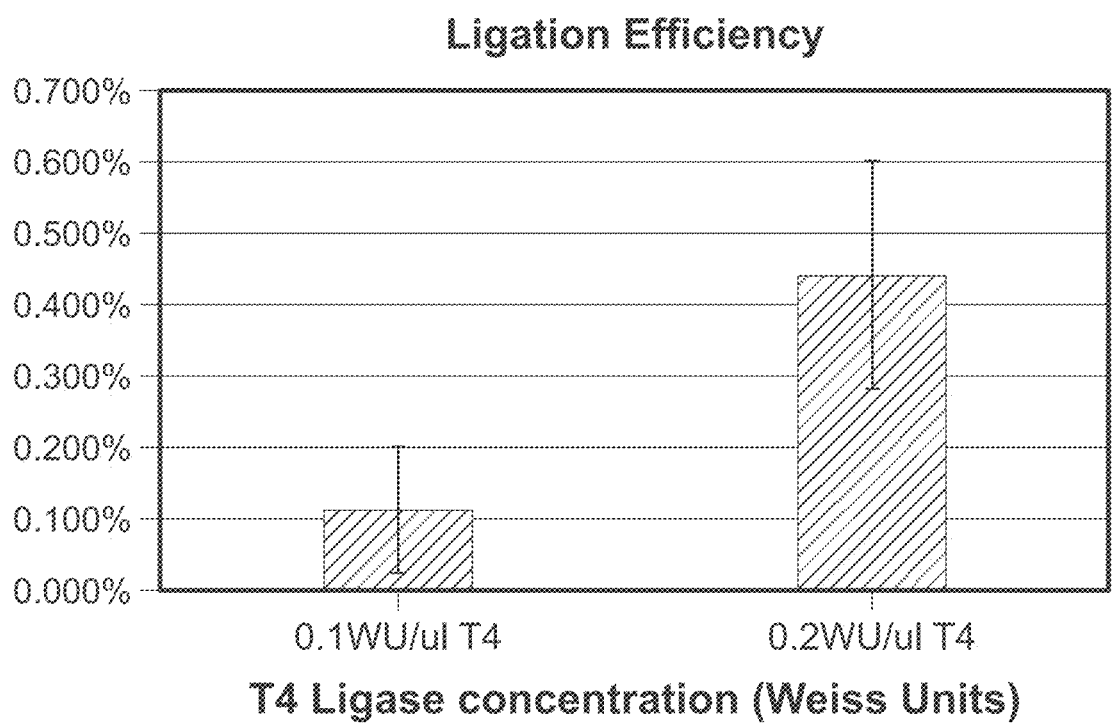
FIG. 40 shows exemplary data for ligation efficiency of 16 DNA components using the overhangs from the final row of Table 7.

FIG. 40 presents data for the ligation efficiency of 16 DNA components using the overhangs from the final (bold) row of Table 7 and a particular formulation of ligation mix that may be optimized for dispensing out of a printhead. The mix contains humectant in the form of glycerol, dye in the form of Orange G, and biocide in the form of Nipacide. Ligation was performed at two ligase concentrations—0.1 Weiss units/µL and 0.2 Weiss units/µL. Moreover, ligation was performed with 0.0625 µM each DNA component, 22.5% v/v glycerol, 3.1% w/v PEG6000, 1.25% w/v orange G dye, 0.1% w/v Nipacide, and standard T4 ligase buffer parts at 37° C. Ligation time was 2.5 minutes. Efficiency was measured using qPCR relative to a full length control representing the fully ligated product.

Example 12: Encoding to, Replicating, and Accessing from 60 kb of Digital Information A digitized audio clip ("message") of length 68,800 bits (73,440 bits after error protection) was encoded using a component library of 372 DNA components in an eight-layer product scheme (see FIG. 16B for product scheme overview). There were 7 layers of 3 components (the "base layers") and one layer (the "multiplex layer") of 351 components, and therefore 767637 possible identifiers, but the encoded message only used 119353 identifiers from the combinatorial space. The writing was performed on the Labcyte Echo 555 Access System. The process was repeated twice. DNA components were designed computationally and constructed by duplexing manufactured oligos.

The writing process occurred in 4 phases: (1) computational encoding, (2) DNA component collocation, (3) ligation, and (4) consolidation. During (1) computational encoding, the error corrected message was encoded into contiguous codewords of length 13 and weight 3. Hence codewords were represented by 13 lexicographically ordered identifiers, 3 of which were intended to be present ("true identifiers"), and the other 10 intended not to be present ("false identifiers"). There were 9181 codewords in total. In (2) DNA collocation, the 372 DNA components were mixed together in 341 reaction wells (of a 384-well plate) using the Labcyte Echo 555. Each reaction was intended to create 27 contiguous codewords (81 true identifiers total), except for one reaction, which was intended to create only one codeword (3 true identifiers total). Reactions were setup to contain one DNA component from each of the base layers and multiple components from the multiplex layer (3 for each codeword). Additionally, sequencing adapters to ligate onto each end of the fully formed identifiers were added to reaction wells. In (3) ligation, 4 uL of T4 ligase reaction mix (containing 5 CEU/µL of T4 ligase, and 7.5% PEG6000) was added to each reaction well and incubated at 37° C. for 1 hour. Concentrations were set up such that each reaction contained approximately 4 nM of aggregate DNA components from each layer. Subsequently, in (4) consolidation, approximately 50 nL of every reaction was consolidated into one container with EDTA solution to deactivate the ligase activity. The consolidated pool of identifiers (the identifier library) was amplified using PCR and gel purified to extract full length identifiers for sequencing.

Figures 41A, 41B:
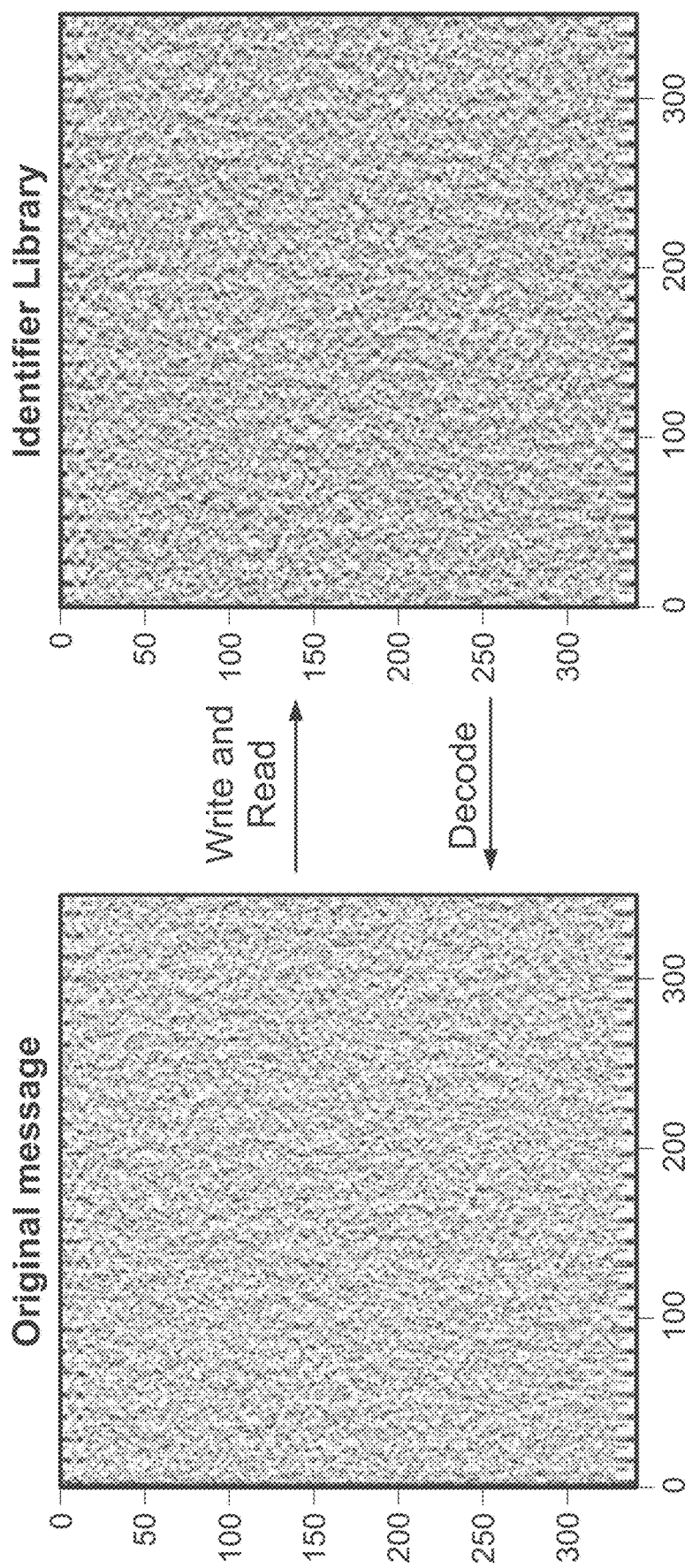
FIG. 41A shows a 341×351 reference map of an encoded message (after computational encoding).
FIG. 41B shows a heat map (341×351) of the abundances of sequences present in the identifier library as determined by sequencing.
Figure 42:
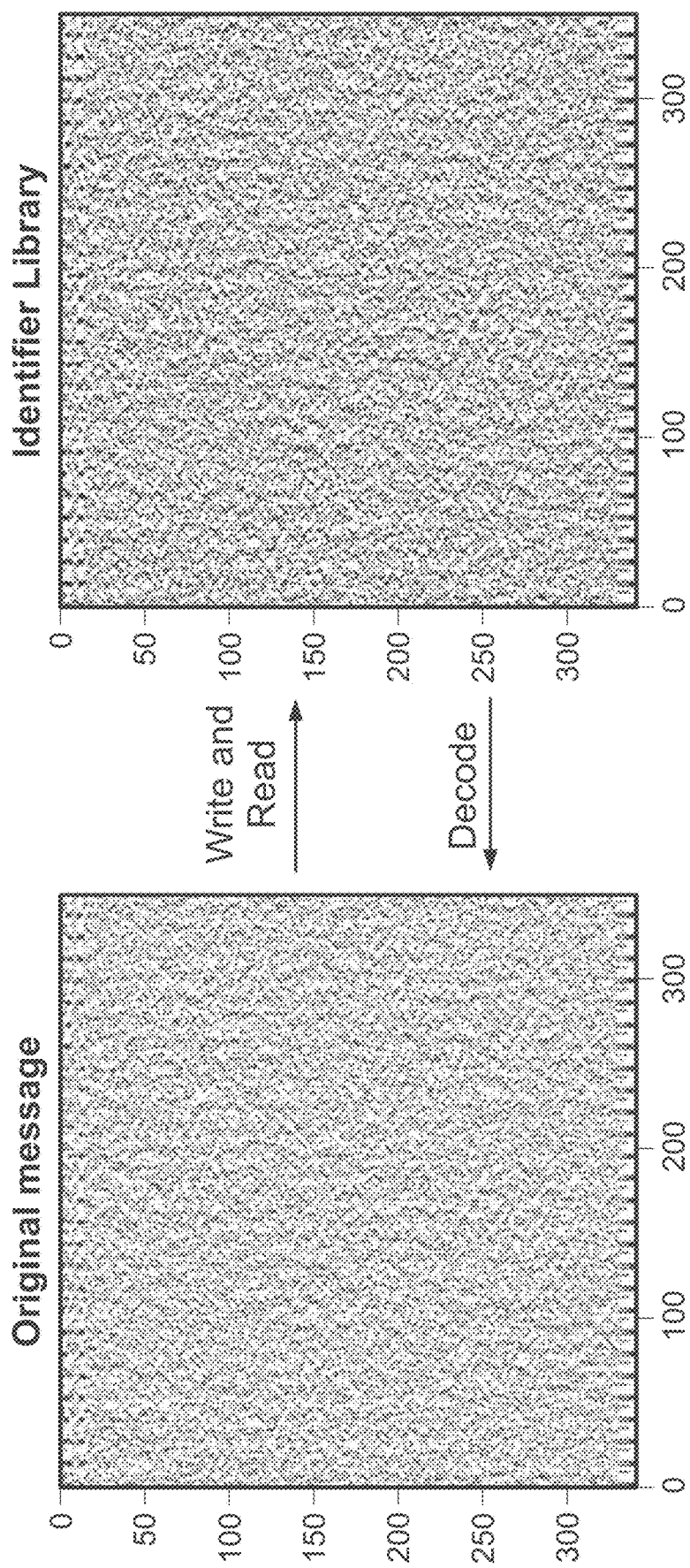
FIG. 42 shows exemplary data from a duplicate run of the entire encoding, writing, sequencing, and decoding process as shown in FIGS. 41A-B.

FIGS. 41A-B present data recovered from sequencing the identifier library that encodes the message. FIG. 41A shows a 341×351 reference map of the encoded message (after computational encoding). Dark points correspond to a '1' bit-value and white points corresponded to a '0' bit-value. The data is written in DNA by constructing identifiers corresponding to the positions of the '1' bit-values (which is possible because the identifiers have a lexicographic order). FIG. 41B shows a heat map (341×351) of the abundances of sequences present in the identifier library as determined by sequencing. Each pixel represents an identifier and the greyscale intensity at that pixel represents the relative abundance of that identifier compared to other identifiers in the row. Identifiers of each row are constructed in the same reaction. Maximum greyscale (dark) intensity is set at the average copy number for identifiers in each row. Identifiers may be interpreted as true identifiers (identifiers that represent bit values of '1') if they are within the top 3 most abundant identifiers in a contiguous string of 13 identifiers (along the rows of the map). All others are interpreted to be false identifiers (identifiers that represent bit values of '0'). Applying this decoding processing step to the data results in zero identifier errors (events where, within a codeword, a false identifier has more reads than a true identifier) and zero identifier erasures (events where the top 3 most abundant identifiers cannot be distinguished). Therefore the decoded message exactly matches the encoded message (FIG. 41A). FIG. 42 presents data from a duplicate run of the entire encoding, writing, sequencing, and decoding process. Again, the message was successfully written and read with zero errors or erasures.

Figure 43A:
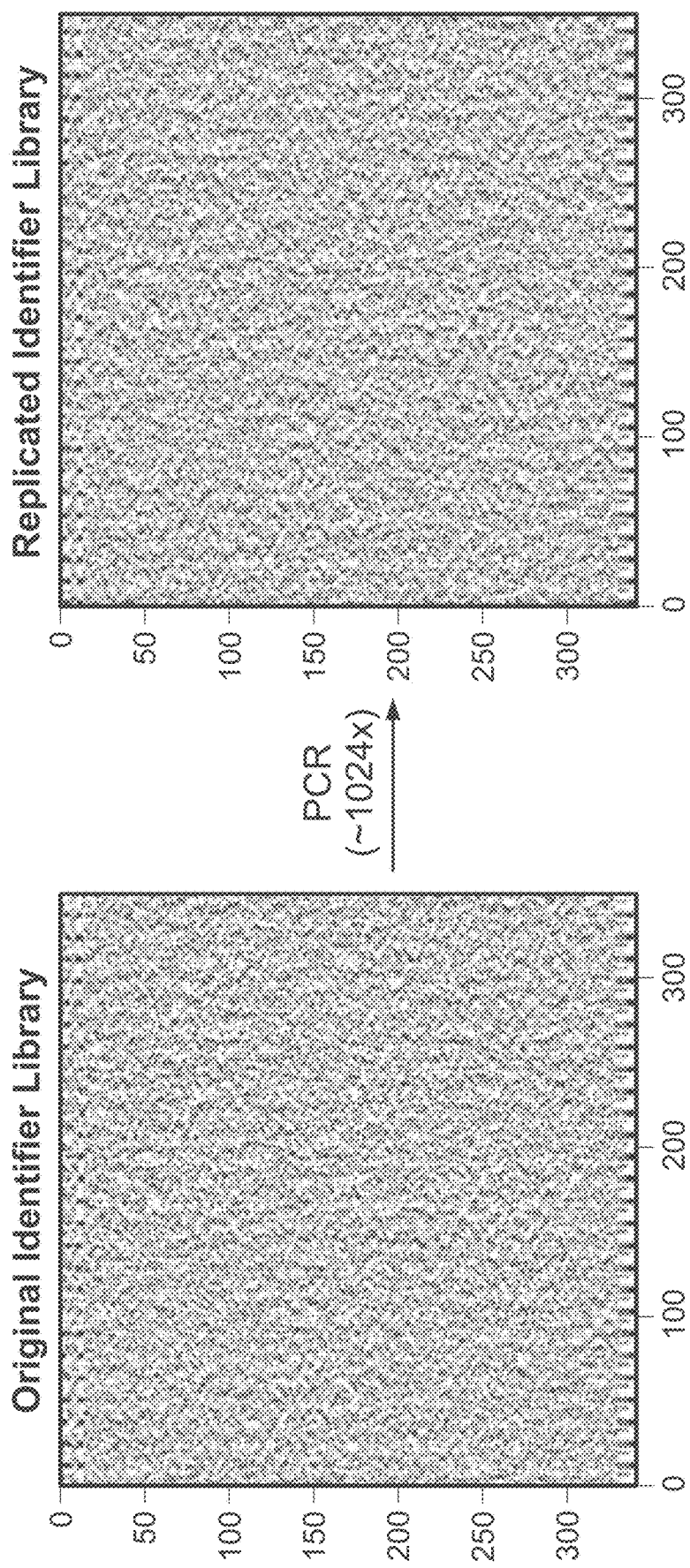
FIG. 43A shows a heat map (341×351) of the abundances of sequences present in the replicated identifier library as determined by sequencing. The data were obtained from creating multiple copies of the original identifier library containing the message from FIGS. 41A-B.
Figure 43B:
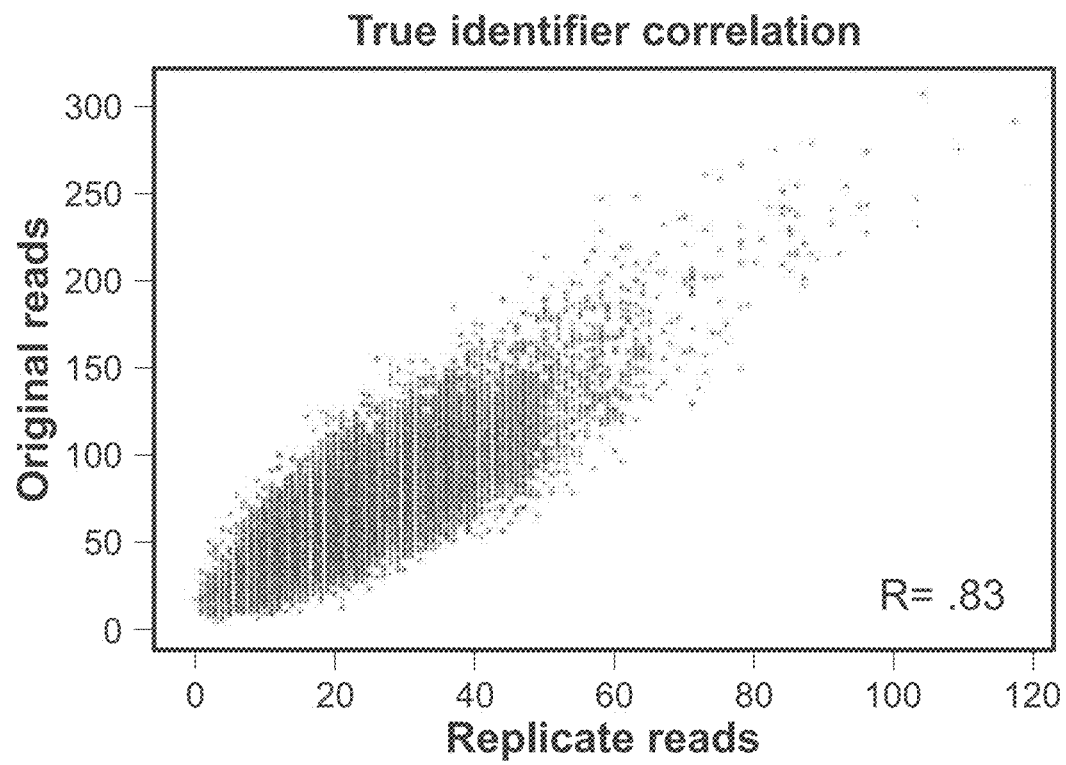
FIG. 43B shows the correlation between identifier copy numbers in the original identifier library versus the replicated identifier library.
Figure 43C:
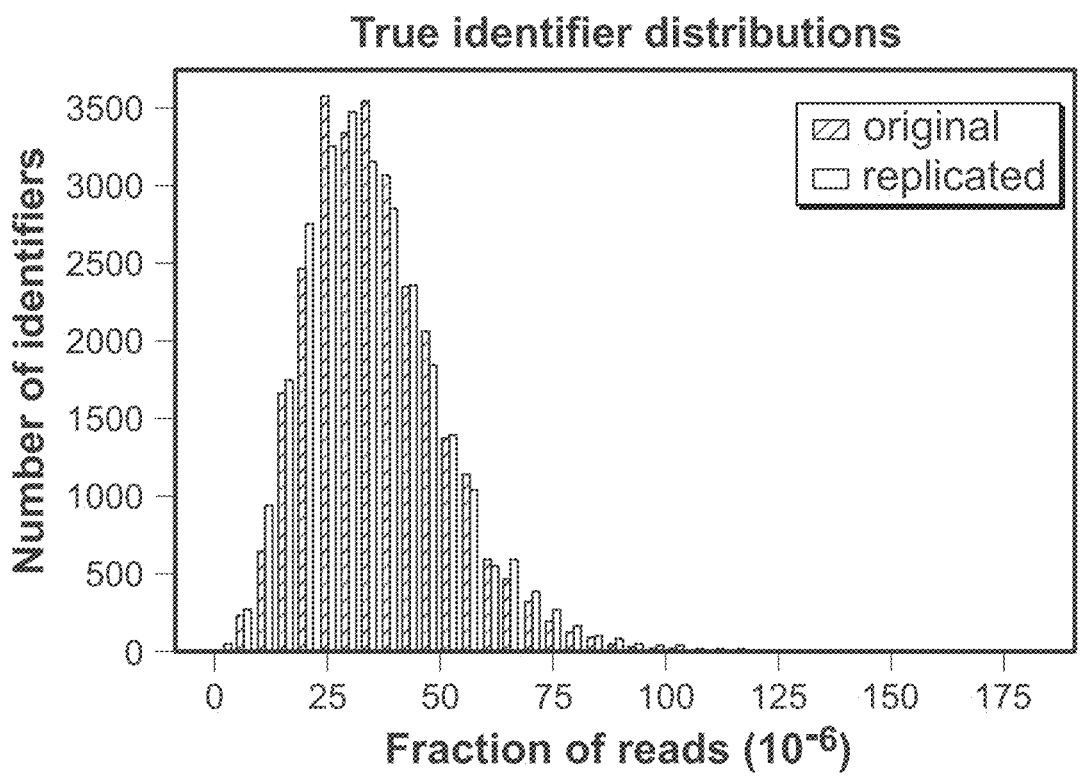
FIG. 43C shows the distribution of identifier copy numbers in the original identifier library versus the replicated identifier library.

FIGS. 43A-C present data from creating multiple copies of the original identifier library containing the message (from FIGS. 41A-B). The library was diluted 1000× and then amplified with 10 cycles of PCR with Phusion polymerase and primers that bound to the outer edges of the adapter sequences (common to all sequences in the library). The 10-cycle PCR amplified the library ~1024× back to its original concentration. FIG. 43A shows a heat map (341× 351) of the abundances of sequences present in the replicated identifier library as determined by sequencing. Each pixel represents an identifier and the greyscale intensity at that pixel represents the relative abundance of that identifier compared to other identifiers in the row. Maximum greyscale (dark) intensity is set at the average copy number for identifiers in each row. Identifiers may be interpreted to represent bit values of '1' if they are within the top 3 most abundant identifiers in a contiguous string of 13 identifiers (along the rows of the map). All others are interpreted to represent bit values of '0'. Applying this decoding processing step to the data results in zero identifier errors. There was one identifier erasure, which may be explained by small sequencing sample size (see Table 8). It was a codeword in which all false identifiers had zero reads, but one of the true identifiers also had zero reads. FIG. 43B shows the correlation between identifier copy numbers in the original identifier library versus the replicated identifier library, and FIG. 43C shows the distribution of identifier copy numbers in the original identifier library versus the replicated identifier library. Results indicate that little or no bias may occur during identifier library replication.

Figure 44A:
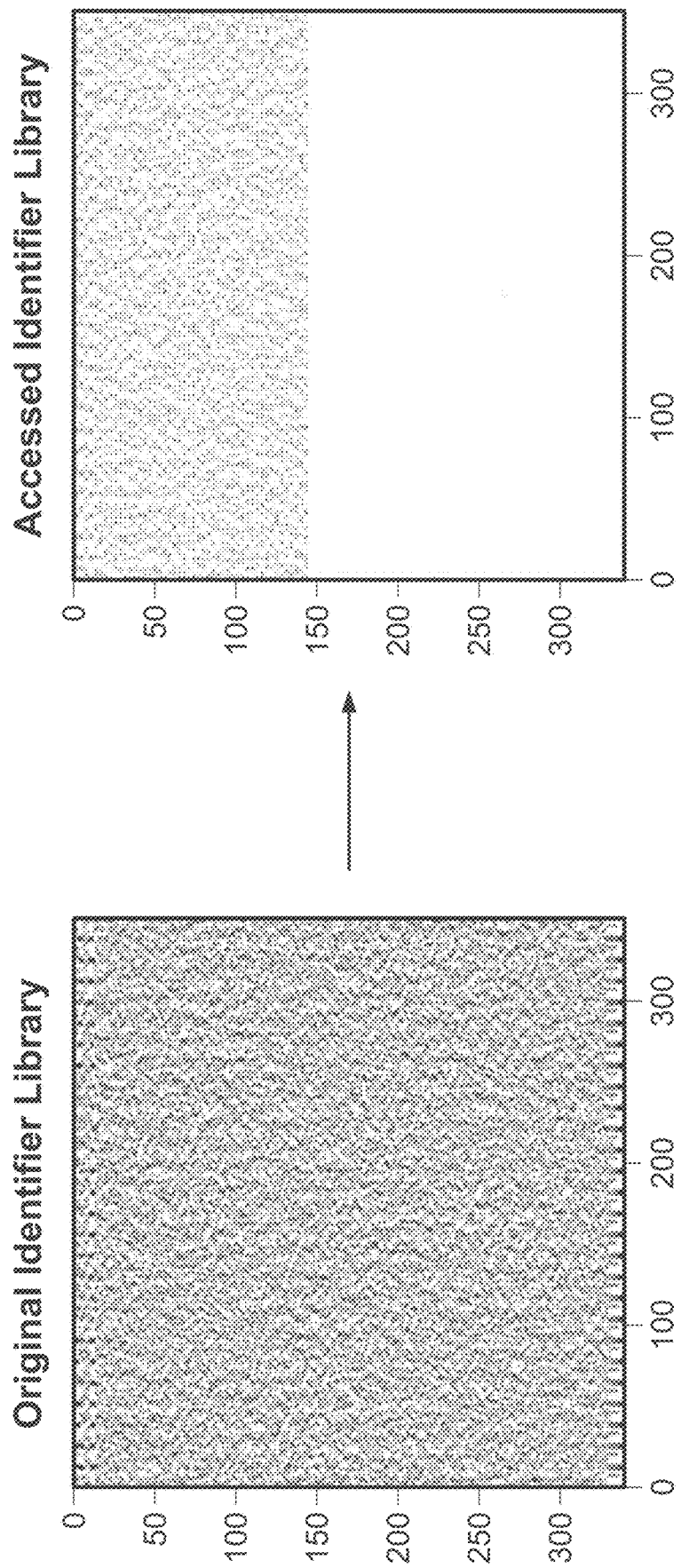
FIG. 44A shows a heat map (341×351) of the abundances of sequences present in the accessed identifier library as determined by sequencing. The data were obtained from accessing a portion of the identifier library containing the original message from FIGS. 41A-B.
Figure 44B:
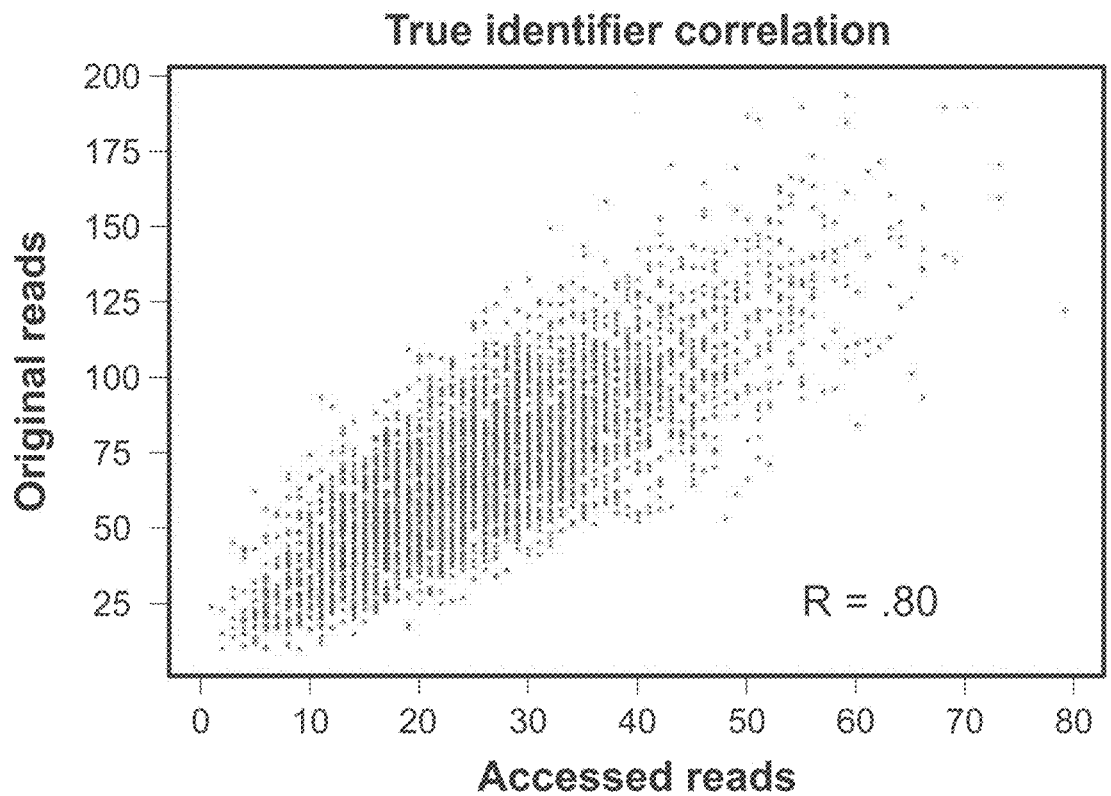
FIG. 44B shows the correlation between identifier copy numbers in the original library versus the accessed identifier library.
Figure 44C:
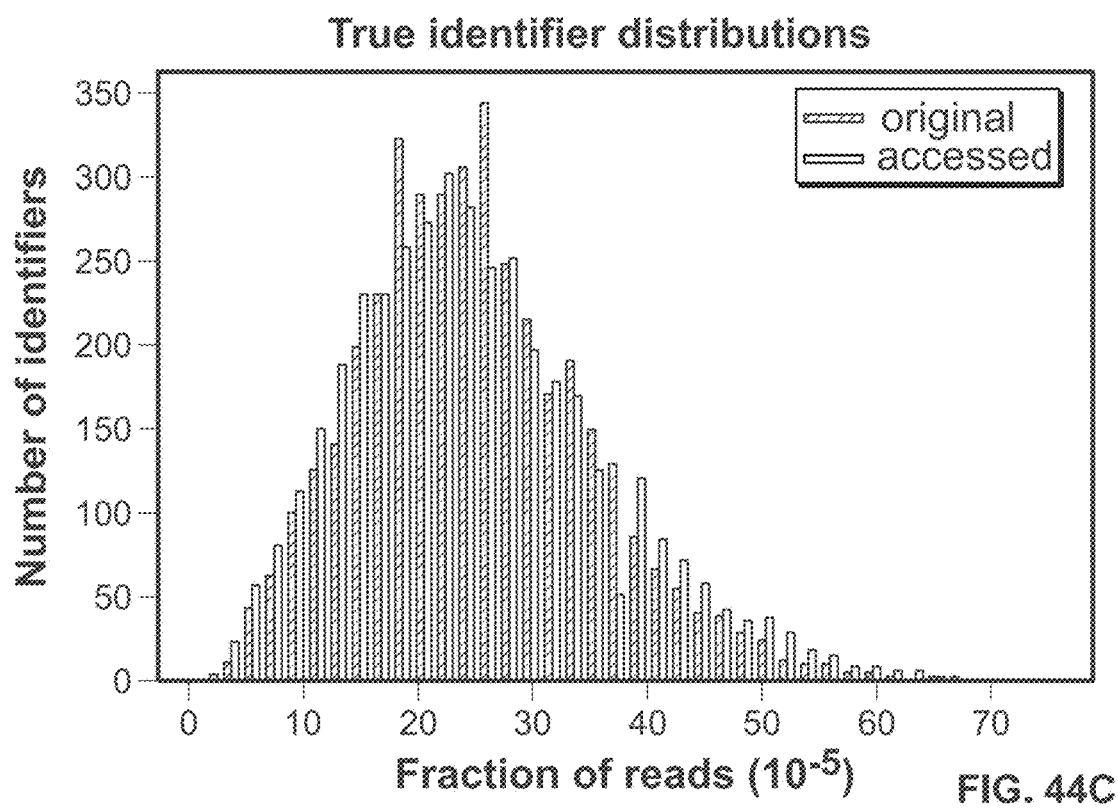
FIG. 44C shows the distribution of identifier copy numbers in the original identifier library versus the accessed identifier library.

FIGS. 44A-C present data from accessing a portion of the identifier library containing the original message (from FIGS. 41A-B). The access method was an 'AND' operation as described in FIG. 17B. The identifier library was diluted ~32000× and then amplified using PCR with primers that bound to a specific DNA component of each edge layer, thus accessing approximately $⅑^{th}$ of the library (since each layer had 3 possible components). The PCR was performed with Phusion polymerase for 15 cycles. Sequencing adapters were ligated onto the ends of the resulting sub-library, and it was sequenced on the Illumina iSeq. FIG. 44A shows a heat map (341×351) of the abundances of sequences present in the accessed identifier library as determined by sequencing. Each pixel represents an identifier and the greyscale intensity at that pixel represents the relative abundance of that identifier compared to other identifiers in the row. Maximum greyscale (dark) intensity is set at the average copy number for identifiers in each row. Identifiers may be interpreted to represent bit values of '1' if they are within the top 3 most abundant identifiers in a contiguous string of 13 identifiers (along the rows of the map). All others are interpreted to represent bit values of '0'. Applying this decoding processing step to the data results in zero identifier errors and zero identifier erasures, and therefore a dataset that exactly matches the encoded message (FIG. 41A). FIG. 44B shows the correlation between identifier copy numbers in the original library versus the accessed identifier library, and FIG. 44C shows the distribution of identifier copy numbers in the original identifier library versus the accessed identifier library. Results indicate that little or no bias may occur during identifier library access.

Figure 45A:
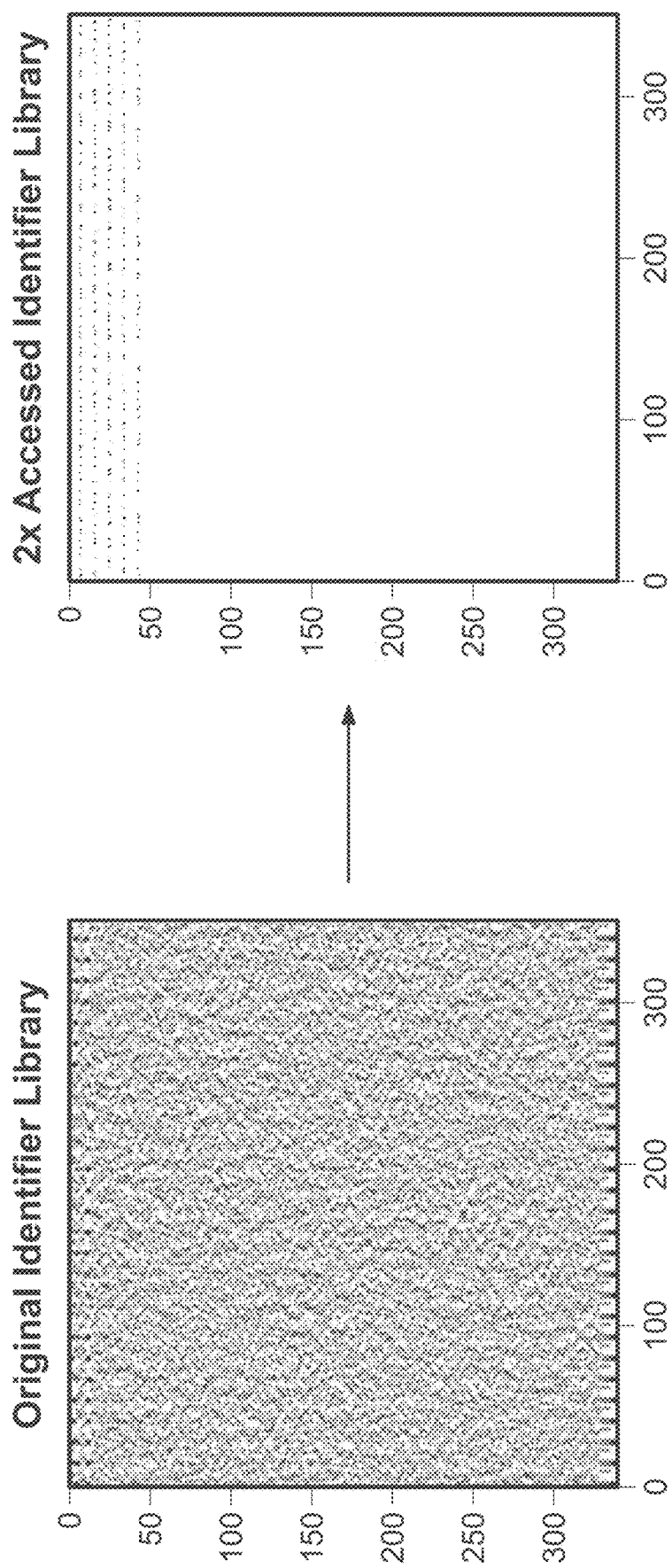
FIG. 45A shows a heat map (341×351) of the abundances of sequences present in the 2× accessed identifier library as determined by sequencing. The data were obtained from further accessing a sub-portion of the accessed identifier library from FIGS. 44A-C.
Figure 45B:
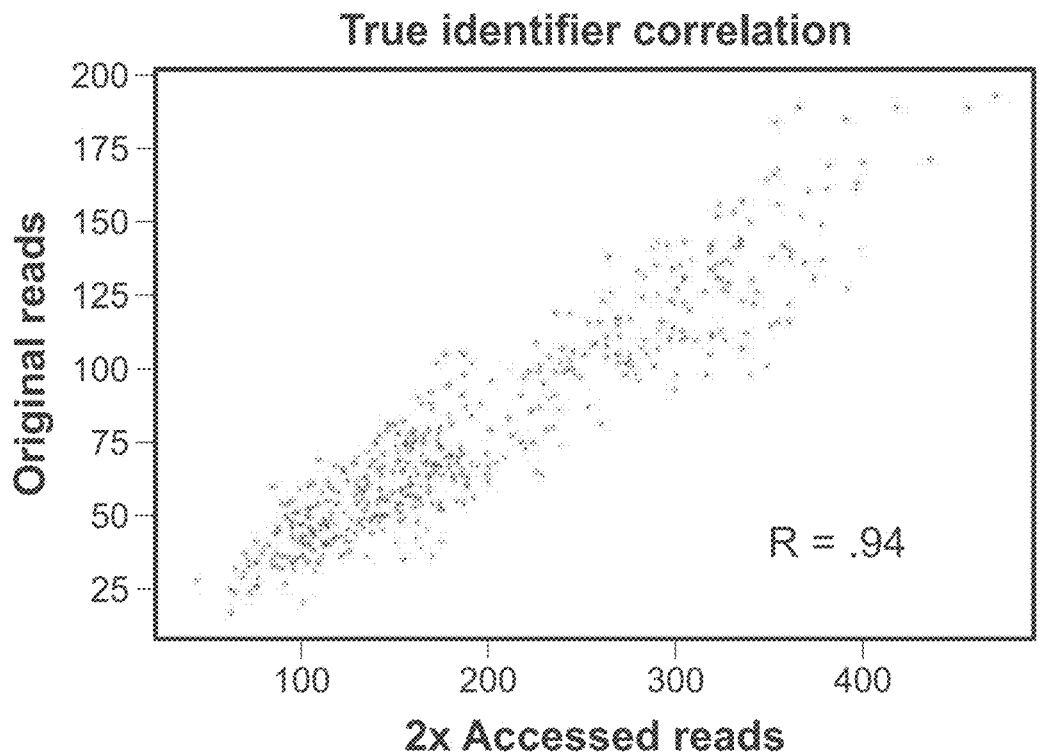
FIG. 45B shows the correlation between identifier copy numbers in the original library versus the 2× accessed identifier library.
Figure 45C:
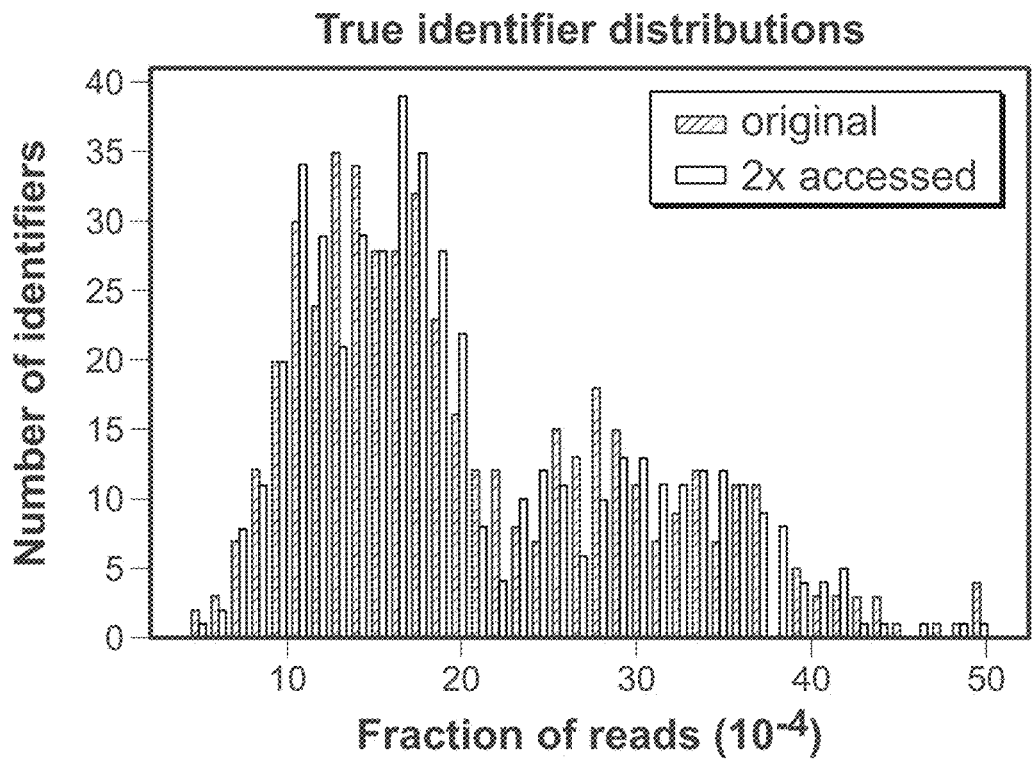
FIG. 45C shows the distribution of identifier copy numbers in the original identifier library versus the 2× accessed identifier library.

FIGS. 45A-C present data from further accessing a sub-portion of the accessed identifier library (from FIGS. 44A-C). The access method from the original identifier library was two nested 'AND' operations (where each 'AND' was as described in FIG. 17B). The original identifier library was diluted ~32000× and then amplified using PCR with primers that bound to a specific DNA component of each edge layer, thus accessing approximately $⅑^{th}$ of the library (since each layer had 3 possible components). The resulting accessed identifier library was diluted again ~32000× and then amplified using PCR with primers that bound to specific DNA components on layers one removed from each edge, thus accessing approximately $⅑^{th}$ of the accessed library (since each layer had 3 possible components), or approximately $⅛₁$ of the original library overall ($⅑^{th}$ of $⅑^{th}$). We refer to the resulting sub-library as the "2× accessed" identifier library. The PCR was performed with Phusion polymerase for 15 cycles. Sequencing adapters were ligated onto the ends of the resulting sub-library, and it was sequenced on the Illumina iSeq. FIG. 45A shows a heat map (341×351) of the abundances of sequences present in the 2× accessed identifier library as determined by sequencing. Each pixel represents an identifier and the greyscale intensity at that pixel represents the relative abundance of that identifier compared to other identifiers in the row. Maximum greyscale (dark) intensity is set at the average copy number for identifiers in each row. Identifiers may be interpreted to represent bit values of '1' if they are within the top 3 most abundant identifiers in a contiguous string of 13 identifiers (along the rows of the map). All others are interpreted to represent bit values of '0'. Applying this decoding processing step to the data results in zero identifier errors and zero identifier erasures, and therefore a dataset that exactly matches the encoded message (FIG. 41A). FIG. 45B shows the correlation between identifier copy numbers in the original library versus the 2× accessed identifier library, and FIG. 45C shows the distribution of identifier copy numbers in the original identifier library versus the 2× accessed identifier library. Results indicate that little or no bias may occur during nested identifier access methods.

Figure 46A:
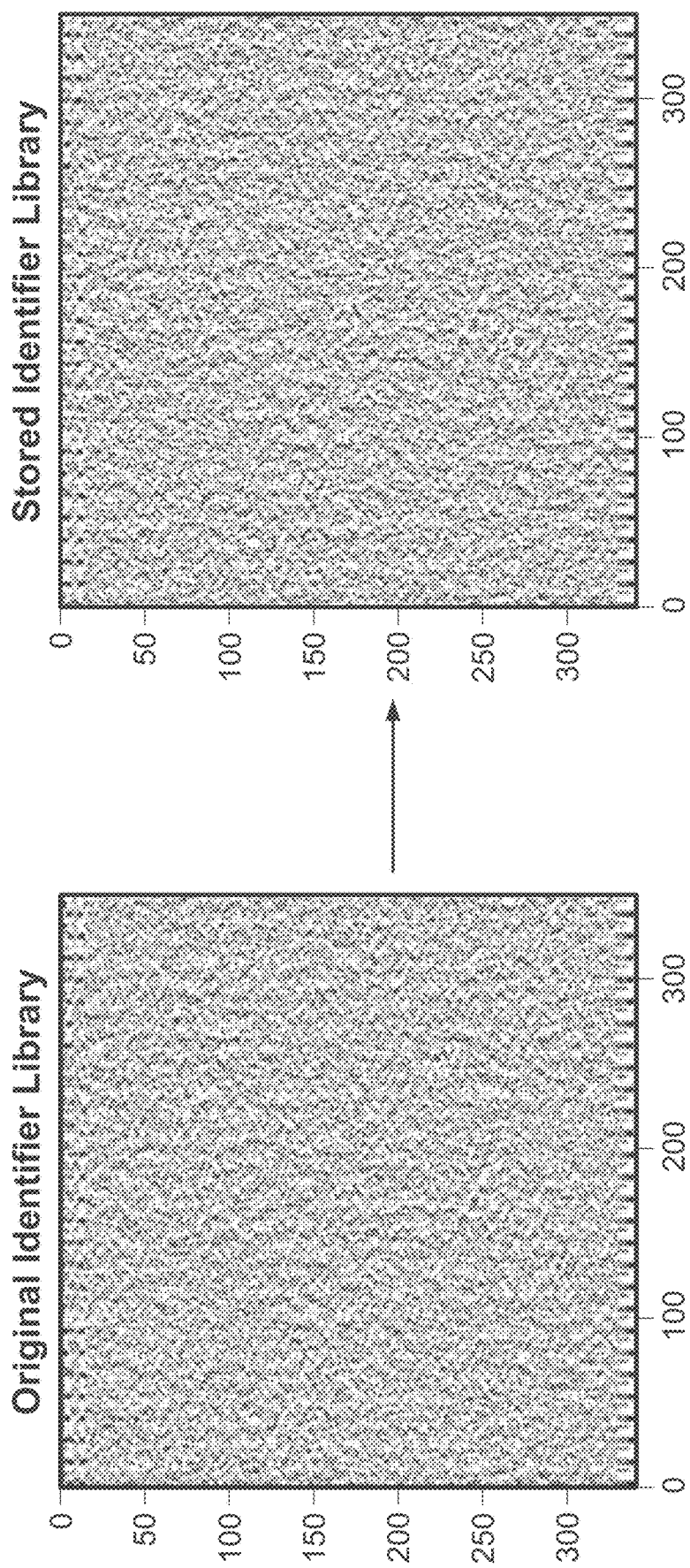
FIG. 46A shows a heat map (341×351) of the abundances of sequences present in the stored identifier library as determined by sequencing. The data were obtained from after storing the original identifier library representing the message from FIGS. 41A-B at 100° C. for 4 days.
Figure 46B:
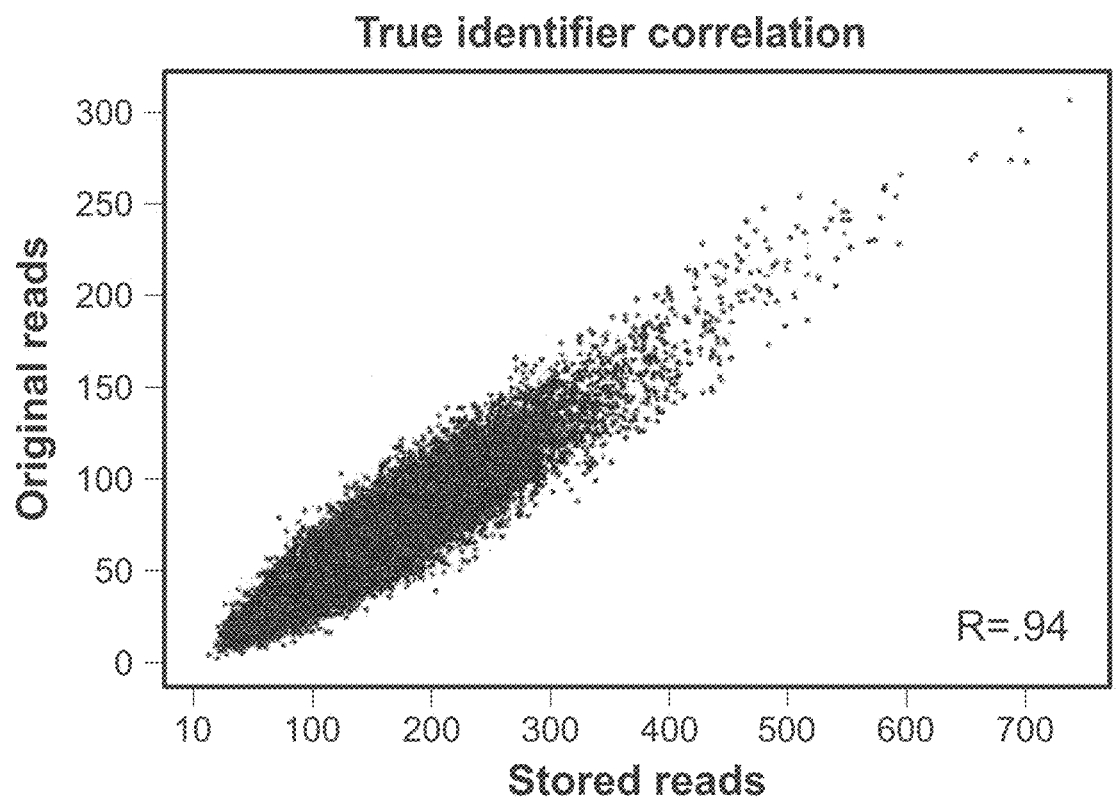
FIG. 46B shows the correlation between identifier copy numbers in the original identifier library versus the replicated identifier library.
Figure 46C:
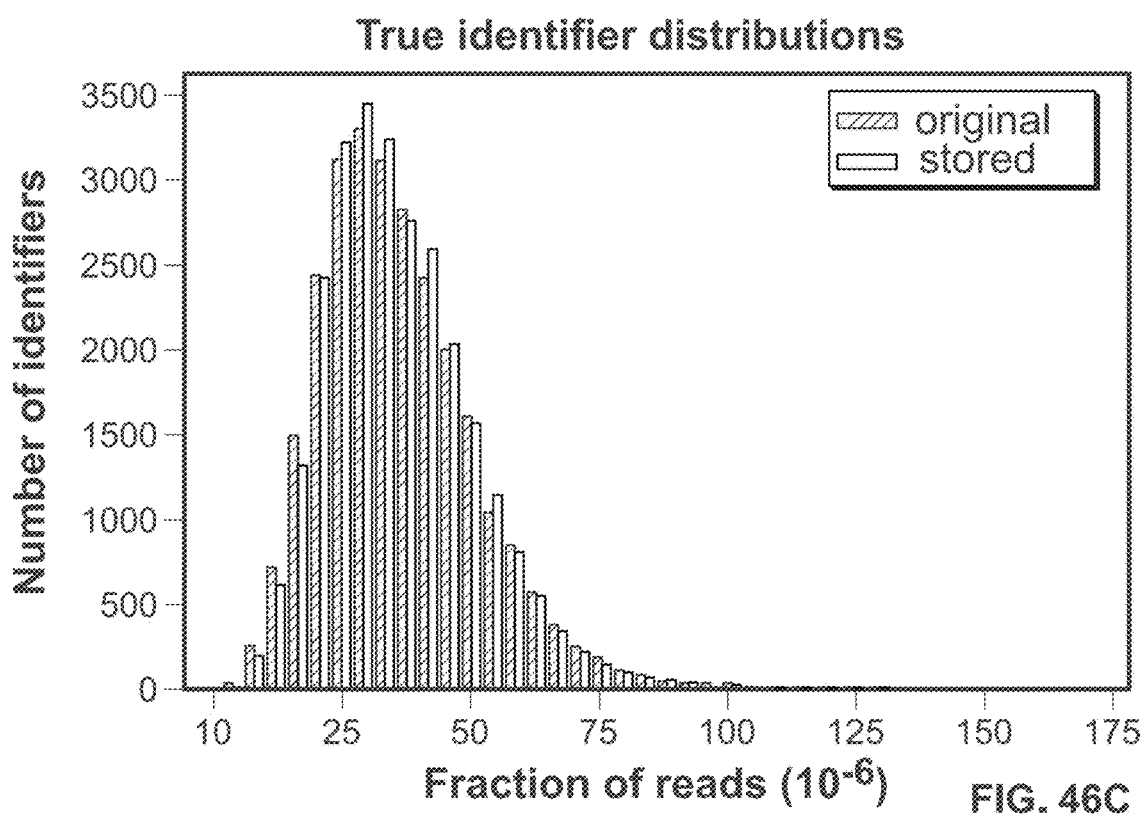
FIG. 46C shows the distribution of identifier copy numbers in the original identifier library versus the replicated identifier library.
Figure 47A:
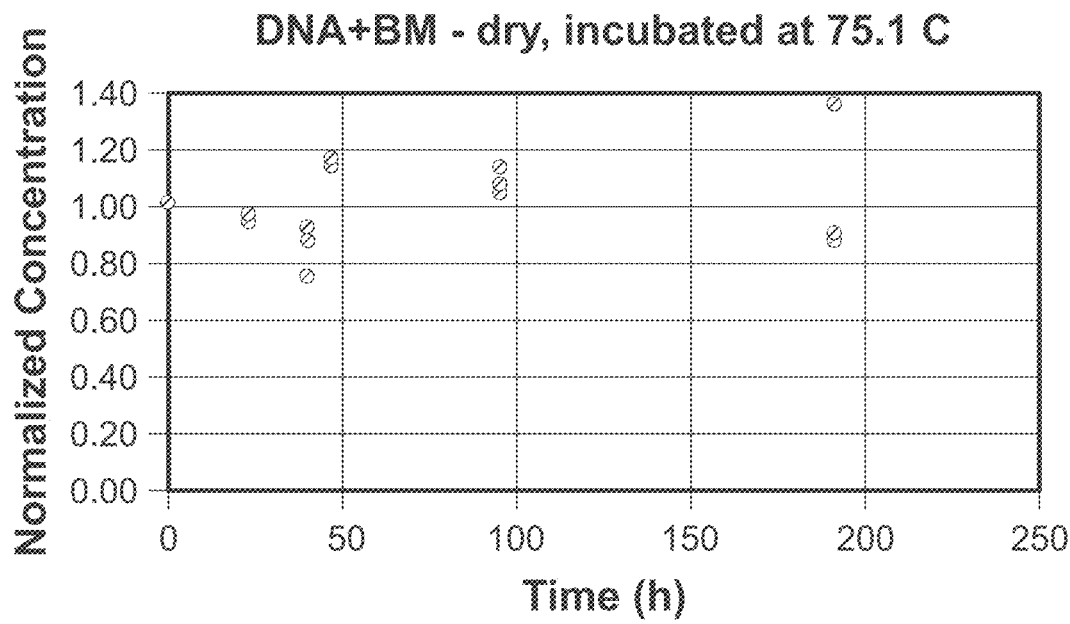
FIG. 47A shows exemplary data for DNA samples incubated for 8 days at 75.1° C.
Figure 47B:
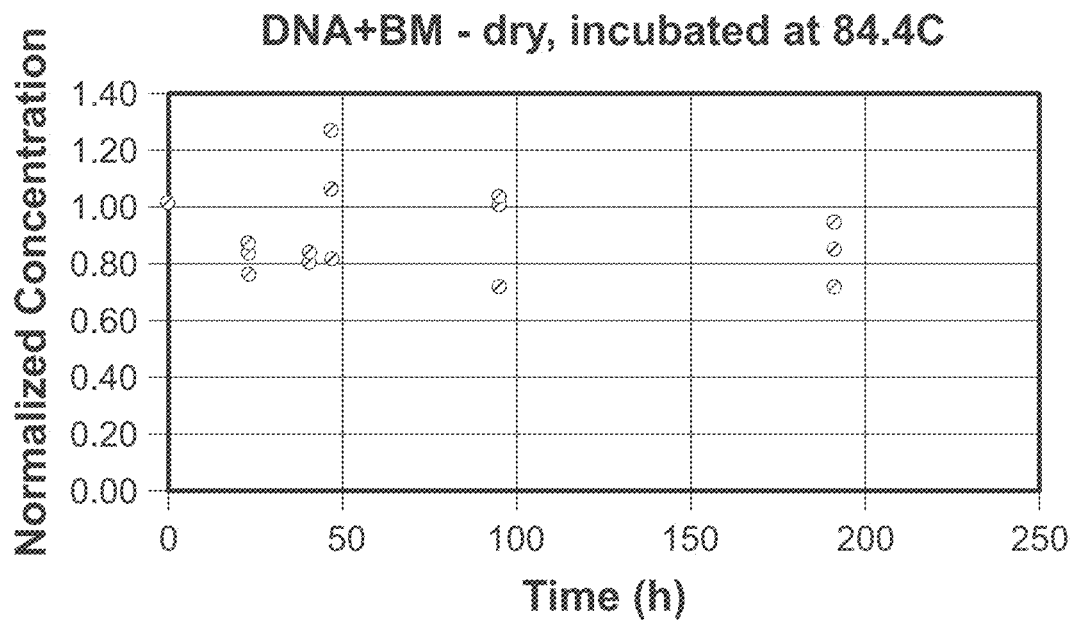
FIG. 47B shows exemplary data for DNA samples incubated for 8 days at 84.4° C.
Figure 47C:
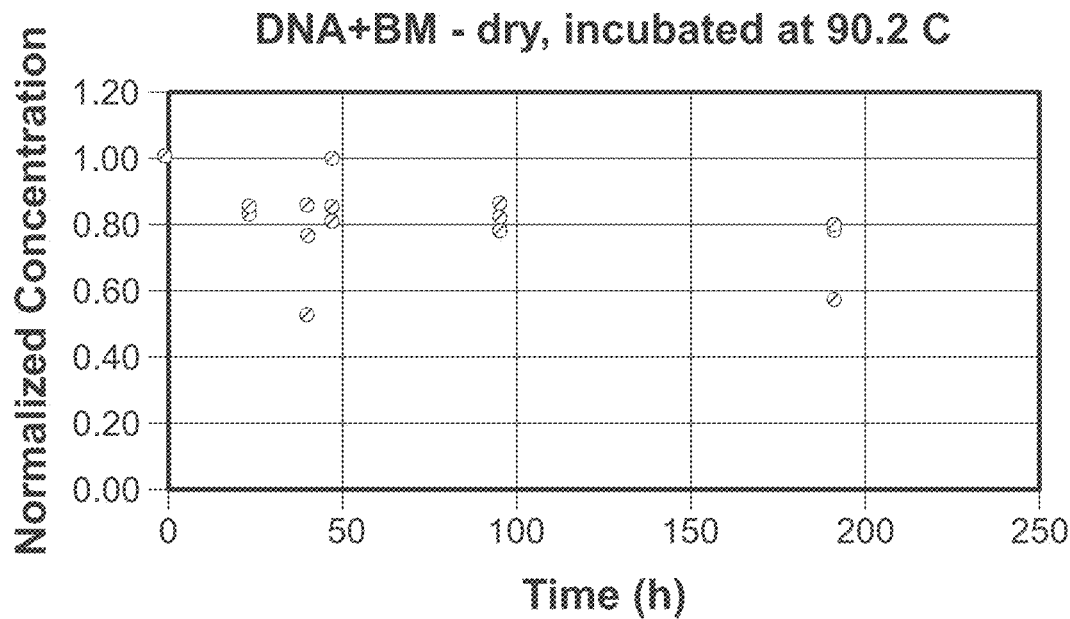
FIG. 47C shows exemplary data for DNA samples incubated for 8 days at 90.2° C.
Figure 47D:
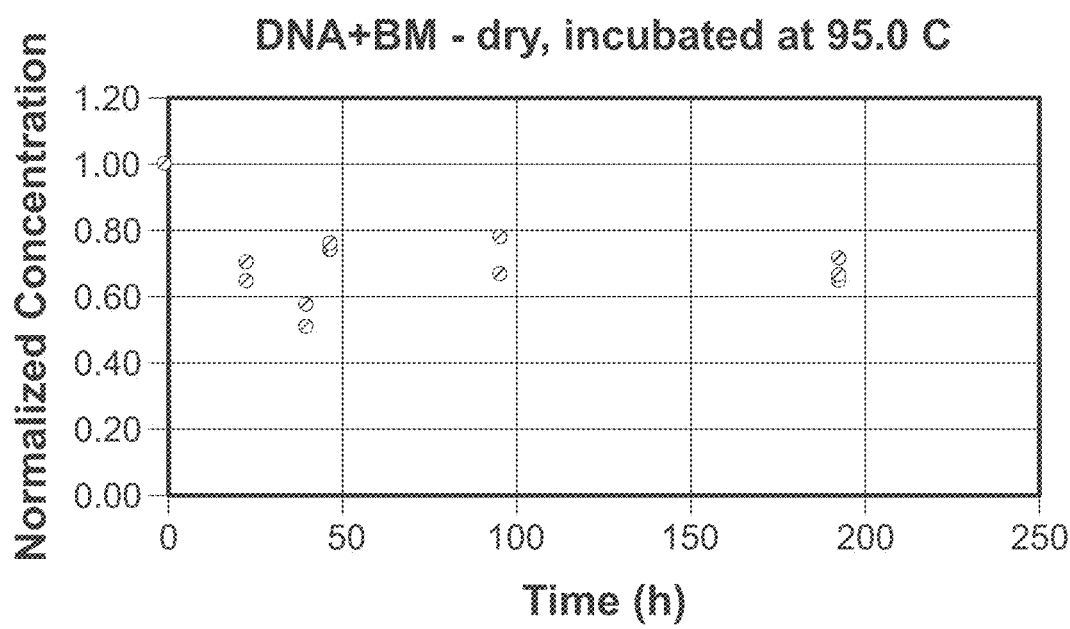
FIG. 47D shows exemplary data for DNA samples incubated for 8 days at 95.0° C.

FIGS. 46A-C present data from after storing the original identifier library representing the message (from FIG. 41) at 100° C. for 4 days. The original identifier library was dried down with a preserving additive (biostabilizing material) and kept in a thermocycler held at 100° C. for 4 days. FIG. 46A shows a heat map (341×351) of the abundances of sequences present in the stored identifier library as determined by sequencing. Each pixel represents an identifier and the greyscale intensity at that pixel represents the relative abundance of that identifier compared to other identifiers in the row. Maximum greyscale (dark) intensity is set at the average copy number for identifiers in each row. Identifiers may be interpreted to represent bit values of '1' if they are within the top 3 most abundant identifiers in a contiguous string of 13 identifiers (along the rows of the map). All others are interpreted to represent bit values of '0'. Applying this decoding processing step to the data results in zero identifier errors and zero identifier erasures, and therefore a map that exactly matches the encoded message (FIG. 41A). FIG. 46B shows the correlation between identifier copy numbers in the original identifier library versus the replicated identifier library, and FIG. 46C shows the distribution of identifier copy numbers in the original identifier library versus the replicated identifier library. Results indicate that little or no bias may occur during extreme heating of the identifier library for prolonged periods of time. Moreover, double stranded DNA quantitation (with Qubit fluorometric quantitation) yielded similar values between the original identifier library (36.4 ng/mL) and the stored identifier library (41.2 ng/mL), indicating that there may have been little to no loss of DNA during the incubation.

Table 8 presents statistics from writing and reading the identifier libraries representing the message and accessed portions of the message (from FIGS. 41-46). For each library, we report the total number of reads of identifiers that represent bit values of '0' (false identifiers), the total number of reads of identifiers that represent bit values of '1' (true identifiers), the fraction of false identifiers that were sequenced ("identifier error rate"), the total number of codewords, the number of codeword erasures, and the number of codeword errors. The distribution of identifiers in each codeword was modeled as a multinomial distribution where each of the false identifiers are identically distributed and each of the true identifiers are identically distributed, and the probability of reading (sampling) a false identifier is equivalent to the identifier error rate. Using the number of codewords represented in each library, and the number of identifiers reads from each codeword as the sample size for each codeword, we used the model to calculate the expected number of codeword erasures and codeword errors. Due to computational intractability of calculating the probability of a codeword erasure or a codeword error at a large sample size, any sample size of greater than 40 reads was bound at 40. Thus the expectation values should be considered as upper bounds. Results indicate that the erased codeword in the replicated library (FIG. 43A, FIG. 43B, and FIG. 43C) may have been expected due to intrinsic sampling noise.

TABLE 8

| Identifier library | Original | Repeated | Replicated | Accessed | 2x accessed | Stored |
|---|---|---|---|---|---|---|
| From Figure | FIG. 41 | FIG. 42 | FIG. 43 | FIG. 44 | FIG. 45 | FIG. 46 |
| True identifier reads | 1879590 | 1815322 | 641682 | 104474 | 94301 | 4327130 |
| False identifier reads | 3494 | 940 | 1117 | 221 | 205 | 8588 |
| Identifier error rate | 0.00186 | 0.00052 | 0.00174 | 0.00211 | 0.00217 | 0.00198 |
| Total codewords | 9181 | 9181 | 9181 | 1323 | 162 | 9181 |
| Codeword erasures | 0 | 0 | 1 | 0 | 0 | 0 |
| Codeword errors | 0 | 0 | 0 | 0 | 0 | 0 |
| Expected number of codeword erasures (upper bound) | 0.00812 | 0.02793 | 1.19021 | 0.09196 | 0.00014 | 0.00788 |
| Expected number of codeword errors (upper bound) | 0.00031 | 0.00099 | 0.03322 | 0.00318 | 0.00001 | 0.00030 |

Example 13: A Study of the Stability of DNA

FIGS. 47A-D presents data for DNA samples incubated for 8 days in 4 different temperatures. Multiple samples each of approximately 250 ng of ~450 base DNA (the target) was dried with preserving additive (BM represents biostabilizing material) and heated at 75.1° C. (FIG. 47A), 84.4° C. (FIG. 47B), 90.2° C. (FIG. 47C), or 95.0° C. (FIG. 47D) for 8 days. At different time points over the 8 days, samples were removed and stored at room temperature until final measurement at the end of the 8 days. At the final measurement, the relative amount of target DNA in each sample was quantified with qPCR. Quantitation values are normalized to the zero timepoint samples that were not heated. Results indicate that minimal DNA degradation may take place, even with prolonged incubation at high temperatures.

Example 14: A Study of the Effect of Glycerol on Ligation

Figure 48:
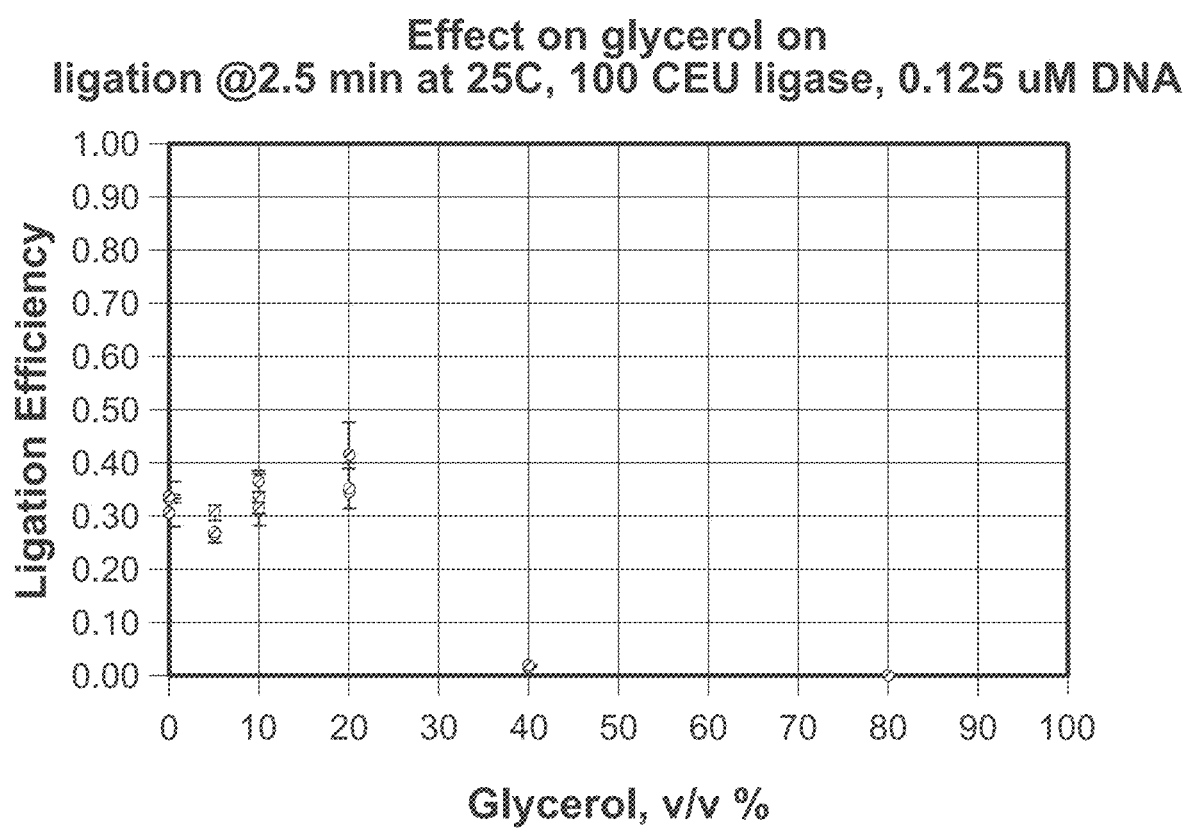
FIG. 48 shows exemplary data from ligation of four sticky-ended (with 6-base, 3' overhangs) DNA components ligated together with various amounts (in terms of percent volume-per-volume) of glycerol.

FIG. 48 presents data from ligation of 4 sticky-ended (with 6-base, 3' overhangs) DNA components ligated together with various amounts (in terms of percent volume-per-volume) of glycerol. Ligation was performed with 0.125 µM each DNA component and 5 CEU/µL T4 Ligase (100 CEU overall) at 25° C. Ligation time was 2.5 minutes. Efficiency was measured using qPCR relative to a full length control representing the fully ligated product. Results indicate that adding up to 20% or more glycerol may not affect ligation, but that adding 40% or more may be inhibitory.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for writing information into a nucleic acid sequence, comprising:
   (a) determining a string of symbols to represent said information;
   (b) constructing a plurality of components, wherein each individual component of said plurality of components is a nucleic acid molecule having the nucleic acid sequence;
   (c) generating at least one sticky end of said individual component of said plurality of components;
   (d) chemically linking together two or more components of said plurality of components via said at least one sticky end of said individual component of said two or more components, thereby generating one or more identifiers, wherein each identifier of said one or more identifiers comprises two or more components, wherein an individual identifier of said one or more identifiers corresponds to an individual symbol in said string of symbols; and
   (e) selectively capturing or amplifying an identifier library comprising at least a subset of said one or more identifiers;
   wherein said two or more components are from two or more layers,
   wherein each layer of said two or more layers comprises a distinct set of components,
   and wherein said individual identifier from said identifier library comprises a component from each layer of said two or more layers.

2. The method of claim 1, wherein each symbol in said string of symbols is one of two possible symbol values.

3. The method of claim 2, wherein one symbol value at each position of said string of symbols is represented by the absence of a distinct identifier in the identifier library.

4. The method of claim 1, wherein said two or more components are assembled in a fixed order.

5. The method of claim 1, wherein said two or more components are assembled with one or more partitioning components disposed between two components from different layers of said two or more layers.

6. The method of claim 1, wherein (c) comprises using an endonuclease to generate said at least one sticky end of said individual component of said plurality of components.

7. The method of claim 6, wherein said at least one sticky end is at a 5' end or a 3' end of said individual component.

8. The method of claim 1, wherein (c) comprises generating two sticky ends of said individual component.

9. The method of claim 1, wherein said at least one sticky end comprises the nucleic acid sequence that is selected from the group consisting of sequences listed in Table 4 or Table 5.

10. The method of claim 1, wherein said plurality of nucleic acid sequences stores metadata of said information or conceals said information.

11. The method of claim 1, further comprising:
   combining two or more identifier libraries; and
   tagging each identifier library of said two or more identifier libraries with a distinct barcode.

12. The method of claim 1, wherein each individual identifier in said identifier library comprises a distinct barcode.

13. The method of claim 12, wherein said distinct barcode of each individual identifier has a minimum hamming distance from the distinct barcode of other individual identifiers.

14. The method of claim 1, wherein chemically linking comprises ligating together two or more components of said plurality of components using a reagent comprising a ligase.

15. The method of claim 14, wherein said ligase is a T4 ligase, a T7 ligase, a T3 ligase, Taq ligase, *Chlorella* virus ligase, *Thermococcus* sp. strain 9° N ligase, or an *E. coli* ligase.

16. The method of claim 14, wherein said reagent further comprises an additive.

17. The method of claim 16, wherein said additive crowds said ligase.

18. The method of claim 16, wherein said additive comprises polyethylene glycol (PEG), dimethyl sulfoxide (DMSO), 1,2-Propanediol (1,2-Prd) glycerol, or polysorbate 20.

19. The method of claim 14, further comprising inactivating said ligase using a buffer containing EDTA or guanidine thiocyanate.

20. The method of claim 14, wherein said reagent further comprises glycerol molecules.

21. The method of claim 1, wherein chemically linking in (d) comprises using overlap-extension polymerase chain reaction (PCR).

22. The method of claim 1, further comprising dehydrating said identifier library by dehydrating each individual identifier of at least said subset of said one or more identifiers.

23. The method of claim 1, further comprising amplifying said one or more identifiers with PCR or linear amplification.

24. The method of claim 23, wherein said PCR has at least 10 cycles.

25. The method of claim 23, wherein said PCR is an emulsion PCR.

26. The method of claim 1, further comprising purifying said one or more identifiers by gel electrophoresis or affinity-tagged probes.

27. A method for writing information into a nucleic acid sequence, comprising:
  (a) determining a string of symbols to represent said information;
  (b) constructing a plurality of sticky-end components, wherein each individual component of said plurality of components comprises a nucleic acid sequence and at least one sticky end;
  (c) chemically linking together two or more components of said plurality of components via said at least one sticky end of said individual component of said two or more components, thereby generating one or more identifiers, wherein each identifier of said one or more identifiers comprises two or more components, wherein an individual identifier of said one or more identifiers corresponds to an individual symbol in said string of symbols; and
  (d) selectively capturing or amplifying an identifier library comprising at least a subset of said one or more identifiers;
    wherein said two or more components are from two or more layers,
    wherein each layer of said two or more layers comprises a distinct set of components,
    and wherein said individual identifier from said identifier library comprises a component from each layer of said two or more layers.

28. The method of claim 27, wherein (b) comprises annealing two oligonucleotides to construct each individual component such that each individual component has said at least one sticky end.

* * * * *